US010434168B2

(12) United States Patent
Peters et al.

(10) Patent No.: US 10,434,168 B2
(45) Date of Patent: Oct. 8, 2019

(54) ATTENUATED BOVINE CORONAVIRUS AND RELATED VACCINES

(71) Applicant: Intervet Inc., Madison, NJ (US)

(72) Inventors: Catherine M. Peters, Osage, IA (US); Mark W. Mellencamp, St. Joseph, MO (US); Wenzhi Xue, Overland Park, KS (US); Terri Wasmoen, Omaha, NE (US); Emilio Trigo, Lee's Summit, MO (US)

(73) Assignee: Intervet Inc., Madison, NJ (US)

( * ) Notice: Subject to any disclaimer, the term of this patent is extended or adjusted under 35 U.S.C. 154(b) by 112 days.

(21) Appl. No.: 15/506,898

(22) PCT Filed: Sep. 2, 2015

(86) PCT No.: PCT/EP2015/070006
§ 371 (c)(1),
(2) Date: Feb. 27, 2017

(87) PCT Pub. No.: WO2016/034610
PCT Pub. Date: Mar. 10, 2016

(65) Prior Publication Data

US 2017/0274065 A1 Sep. 28, 2017

Related U.S. Application Data

(60) Provisional application No. 62/045,183, filed on Sep. 3, 2014, provisional application No. 62/073,263, filed on Oct. 31, 2014.

(51) Int. Cl.

| | |
|---|---|
| ***A61K 39/215*** | (2006.01) |
| ***A61K 39/12*** | (2006.01) |
| ***C07K 14/005*** | (2006.01) |
| ***C12N 7/00*** | (2006.01) |
| ***C12Q 1/70*** | (2006.01) |
| *A61K 39/00* | (2006.01) |

(52) U.S. Cl.
CPC ............ *A61K 39/215* (2013.01); *A61K 39/12* (2013.01); *C07K 14/005* (2013.01); *C12N 7/00* (2013.01); *C12Q 1/70* (2013.01); *A61K 2039/5254* (2013.01); *A61K 2039/543* (2013.01); *A61K 2039/552* (2013.01); *C12N 2770/20011* (2013.01); *C12N 2770/20021* (2013.01); *C12N 2770/20022* (2013.01); *C12N 2770/20034* (2013.01); *C12N 2770/20064* (2013.01); *C12N 2770/20071* (2013.01)

(58) Field of Classification Search
None
See application file for complete search history.

(56) References Cited

U.S. PATENT DOCUMENTS

| | | | | |
|---|---|---|---|---|
| 3,873,422 A * | 3/1975 | Mebus | ................. | A61K 39/215 424/221.1 |
| 6,331,303 B1 | 12/2001 | Briggs et al. | | |
| 7,351,416 B2 | 4/2008 | Briggs et al. | | |
| 9,393,298 B2 | 7/2016 | Buchanan et al. | | |
| 9,480,739 B2 | 11/2016 | Eddy et al. | | |
| 2008/0044426 A1 * | 2/2008 | De Jong | .................. | C12N 7/00 424/159.1 |

FOREIGN PATENT DOCUMENTS

| | | | |
|---|---|---|---|
| WO | 1998040097 A2 | | 9/1988 |
| WO | WO 98/40097 | * | 9/1998 |
| WO | 02062382 A1 | | 8/2002 |
| WO | 2011056175 A1 | | 5/2011 |
| WO | 2013083726 A1 | | 6/2013 |
| WO | 2014140239 A1 | | 9/2014 |

OTHER PUBLICATIONS

Zhang et al. EM_STD:EF424616 from Virology 2007, vol. 363, pp. 1-10.*
Park et al., J of clinical Micro 2006 vol. 44, pp. 3178-3188 (Year: 2006).*
GenBank AB354579.1, Bovine coronavirus genomic RNA, complete genome, strain: Kakegawa, Retrieved from the internet on Aug. 16, 2018 at URL: https://www.ncbi.nlm.nih.gov/nuccore/AB354579.1/.
GenBank Accession U00735.2, Bovine coronavirus strain Mebus, complete genome, retrieved from the internet on Aug. 16, 2018 at URL: https://www.ncbi.nlm.nih.gov/nuccore/U00735.2/.
GenBank AF220295.1, Bovine coronavirus strain Quebec, complete genome, retrieved from the internet on Aug. 16, 2018 ar URL: https://www.ncbi.nlm.nih.gov/nuccore/AF220295.1/.
Park, S-J., Detection and Characterization of Bovine Coronaviruses in Fecal Specimens of Adult Cattle with Diarrhea during the Warmer Seasons, Journal of Clinical Microbiology, 2006, pp. 3178-3188, vol. 44, No. 9.
Decaro, N, et al, A candidate modified-live bovine coronavirus vaccine: safety and immunogenicity evaluation, New Microbiologica, 2009, 109-113, vol. 32.
GenPept Accession ACF21936.1, Decaro N et al., "S protein [Bovine coronavirus]" Jul. 8, 2008, [retrieved from internet Dec. 7, 2017] URL: https://www.ncbi.nim.nih.gov/protein/193795731.
Thurber et et al,, Field trial evaluation of a reo-coronavirus calf diarrhea vaccine, Canadian Journal of Comparitive Medicine, 1977, pp. 131-136, vol. 41, No. 2, CA.
Database EMBL (online), Apr. 20, 2007, "Bovine coronavirus E-AH65-TC, complete genome", CAS XP002751103, retrieved from EBI accession No. EM_STD: EF424616.

(Continued)

*Primary Examiner* — Shanon A. Foley
*Assistant Examiner* — Myron G Hill

(57) ABSTRACT

The present invention discloses novel attenuated bovine coronavirus isolates, compositions comprising these isolate, and methods of using such compositions in vaccines, including in live vaccines. The present invention further discloses the administration of such vaccines, including the intranasal administration of such vaccines, to aid in the prevention of respiratory disease caused by bovine coronavirus.

20 Claims, 1 Drawing Sheet

Specification includes a Sequence Listing.

(56) References Cited

OTHER PUBLICATIONS

Database Geneseq (online), Jun. 11, 2007, "Coronavirus Nsp11 and RdRp gene region #13", CAS XP002571104, retrieved from EBI accession No. GSN: ADV96528.
Fulton, RW, et al., Bovine coronaviruses from the respiratory tract: Antigenic and genetic diversity, Vaccine, 2013, 886-892, 31.
International Search report for PCTEP2015070006 dated Nov. 19, 2015, 5 pages.
Plummer, PJ et al., Effect of intranasal vaccination against bovine enteric coronavirus on the occurrence of respiratory tract disease in a commercial backgrounding feedlob, JAVMA, 2004, 726-731, 225(5).
Saif, Linda, Bovine Respiratory Coronavirus, Veterinary Clinics of North America: Food Animal Practice, 2010, pp. 349-364, 26(2), US.
Xinsheng Zhang et al, Quasispecies of bovine enteric and respiratory coronaviruses based on complete genome sequences and genetic changes after tissue culture adaption, Virology, May 20117, pp. 1-10, vol. 363, Issue 1, Elsevier, WO.
Office Action dated Mar. 22, 2019 for EP Patent Application 15756662.1, 9 pages.

* cited by examiner

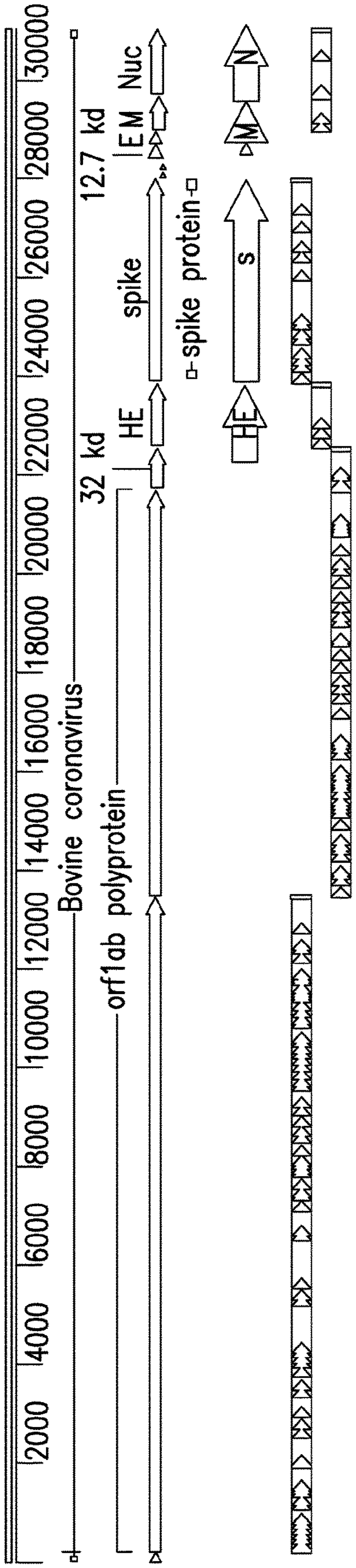
2000
4000
6000
8000
10000
12000
14000
16000
18000
20000
22000
24000
26000
28000
30000
Bovine coronavirus
32 kd
12.7 kd
orf1ab polyprotein
HE
spike
E M
Nuc
spike protein
HE
S
M
N

SEQUENCE LISTING

<160> NUMBER OF SEQ ID NOS: 25

<210> SEQ ID NO 1
<211> LENGTH: 4038
<212> TYPE: DNA
<213> ORGANISM: Bovine coronavirus

<400> SEQUENCE: 1
gatttaaagt gtactacggt tgccattaat gatgttgaca ccggtcctcc ttctattagc 60
actgatattg tcgatgttac taatggttta ggtacttatt atgttttaga tcgtgtgtat 120
ttaaatacta cgttgttgct taatggttac taccctactt caggttctac atatcgtaat 180
atggcactga agggaacttt actattgagc agactatggt ttaaaccacc ttttctttct 240
gattttatta atggtatttt tgctaaggtc aaaaatacca aggttattaa aaagggtgta 300

```
atgtatagtg agtttcctgc tataactata ggtagtactt ttgtaaatac atcctatagt    360

gtggtagtac aaccacatac taccaatttg gataataaat tacaaggtct cttagagatc    420

tctgtttgcc agtatactat gtgcgagtac ccacatacga tttgtcatcc taatctgggt    480

aatcgacgcg tagaactatg gcattgggat acaggtgttg tttcctgttt atataagcgt    540

aatttcacat atgatgtgaa tgctgattac ttgtatttcc atttttatca agaaggtggt    600

actttttatg catattttac agacactggt gttgttacta agtttctgtt taatgtttat    660

ttaggcacgg tgctttcaca ttattatgtc ctgcctttga cttgttctag tgctatgact    720

ttagaatatt gggttacacc tctcacttct aaacaatatt tactagcttt caatcaagat    780

ggtgttattt ttaatgctgt tgattgtaag agtgatttta tgagtgagat taagtgtaaa    840

acactatcta tagcaccatc tactggtgtt tatgaattaa acggttacac tgttcagcca    900

attgcagatg tttaccgacg tatacctaat cttcccgatt gtaatataga ggcttggctt    960

aatgataagt cggtgccctc tccattaaat tgggaacgta agaccttttc aaattgtaat   1020

tttaatatga gcagcctgat gtcttttatt caggcagact catttacttg taataatatt   1080

gatgctgcta agatatatgg tatgtgtttt tccagcataa ctatagataa gtttgctata   1140

cccaatggta ggaaggttga cctacaattg ggcaatttgg gctatttgca gtcttttaac   1200

tatagaattg atactactgc tacaagttgt cagttgtatt ataatttacc tgctgctaat   1260

gtttctgtta gcaggtttaa tccttctact tggaatagga gatttggttt tacagaacaa   1320

tctgttttta agcctcaacc tgcaggtgtt tttactcatc atgatgttgt ttatgcacaa   1380

cattgtttta aagctcccac aaatttctgt ccgtgtaaat tggatgggtc tttgtgtgta   1440

ggtaatggtc ctggtataga tgctggttat aaaaatagtg gtataggcac ttgtcctgca   1500

ggtactaatt atttaacttg ccataatgct gcccaatgtg attgtttgtg cactcccgac   1560

cccattacat ctaaatctac agggccttac aagtgccccc aaactaaata cttagttggc   1620

ataggtgagc actgttcggg tcttgctatt aaaagtgatt attgtggagg taatccttgt   1680

acttgccaac cacaagcatt tttgggttgg tctgctgact cttgtttaca aggggatagg   1740

tgtaatattt ttgctaattt tatttttcat gatgttaata gtggtactac ttgttctact   1800

gatttacaaa aatcaaacac agacataatt cttggtgttt gtgttaatta tgatctttat   1860

ggtattatag gccaaggtgt ttttgttgag gttaatgcga cttattataa tagttggcag   1920

aaccttttat atgattctaa tggtaatctc tatggtttta gagactactt aacaaacaga   1980

acttttatga ttcgtagttg ctatagcggt cgtgtttcag cggcctttca tgctaactct   2040

tccgaaccag cattgctatt tcggaatatt aaatgcaatt acgtttttaa taatattctt   2100

tcacgacagc tgcaacctat taactatttt gatagttatc ttggttgtgt tgtcaatgct   2160

gataatagta cttctagtgt tgttcaaaca tgtgatctca cagtaggtag tggttactgt   2220

gtggattact ctacaaaaag acgaagtcgt agagcgatta ccactggtta tcggtttact   2280

aattttgagc catttactgt taattcagta aatgatagtt tagaacctgt aggtggtttg   2340

tatgaaattc aaataccttc agagtttact ataggtaata tggaggagtt tattcaaaca   2400

agctctccta aagttactat tgattgttct gcttttgtct gtggtgatta tgcagcatgt   2460

aaatcacagt tggttgaata tggtagcttc tgtgacaata ttaatgctat actcacagaa   2520

gtaaatgaac tacttgacac tacacagttg caagtagcta atagtttaat gaatggtgtc   2580

actcttagca ctaagcttaa agatggcgtt aatttcaatg tagacgacat caatttttcc   2640
```

-continued

```
cctgtattag gttgtttagg aagcggttgt aataaaggtt ccagtagatc tgctatagag   2700
gatttacttt tttctaaagt aaagttatct gatgtcggtt tcgttgaggc ttataataat   2760
tgtactggag gtgccgaaat tagggacctc atttgtgtgc aaagttataa tggtatcaaa   2820
gtgttgcctc cactgctctc agtaaatcag atcagtggat acactttggc tgccacctct   2880
gctagtctgt ttcctccttg gtcagcagca gcaggtgtac cattttattt aaatgttcag   2940
tatcgtatta atgggcttgg tgttaccatg gatgtgttaa gtcaaaatca aaagcttatt   3000
gctaatgcat ttaacaatgc tcttgatgct attcaggaag ggtttgatgc taccaattct   3060
gctttagtta aaattcaagc tgttgttaat gcaaatgctg aagctcttaa taacttattg   3120
caacaactct ctaatagatt tggtgctata agttcttctt tacaagaaat tctatctaga   3180
ctggatgctc ttgaagcgca agctcagata gacagactta ttaatgggcg tcttaccgct   3240
cttaatgctt atgtttctca acagcttagt gattctacac tagtaaaatt tagtgcagca   3300
caagctatgg agaaggttaa tgaatgtgtc aaaagccaat catctaggat aaatttttgt   3360
ggtaatggta atcatattat atcattagtg cagaatgctc catatggttt gtattttatc   3420
cactttagct atgtccctac taagtatgtc actgcgaagg ttagtcccgg tctgtgcatt   3480
gctggtgata gaggtatagc ccctaagagt ggttattttg ttaatgtaaa taatacttgg   3540
atgttcactg gtagtggtta ttactaccct gaacccataa ctggaaataa tgttgttgtt   3600
atgagtacct gtgctgttaa ctatactaaa gcgccggatg taatgctgaa catttcaaca   3660
cccaacctcc atgattttaa ggaagagttg gatcaatggt ttaaaaacca aacatcagtg   3720
gcaccagatt tgtcacttga ttatataaat gttacattct tggacctaca agatgaaatg   3780
aataggttac aggaggcaat aaaagtttta aatcagagct acatcaatct caaggacatt   3840
ggtacatatg agtattatgt aaaatggcct tggtatgtat ggcttttaat tggctttgct   3900
ggtgtagcta tgcttgtttt actattcttc atatgctgtt gtacaggatg tgggactagt   3960
tgttttaaga tatgtggtgg ttgttgtgat gattatactg gacaccagga gttagtaatt   4020
aaaacattac atgacgac                                                 4038
```

```
<210> SEQ ID NO 2
<211> LENGTH: 1346
<212> TYPE: PRT
<213> ORGANISM: Bovine coronavirus

<400> SEQUENCE: 2

Asp Leu Lys Cys Thr Thr Val Ala Ile Asn Asp Val Asp Thr Gly Pro
1               5                   10                  15

Pro Ser Ile Ser Thr Asp Ile Val Asp Val Thr Asn Gly Leu Gly Thr
            20                  25                  30

Tyr Tyr Val Leu Asp Arg Val Tyr Leu Asn Thr Thr Leu Leu Leu Asn
        35                  40                  45

Gly Tyr Tyr Pro Thr Ser Gly Ser Thr Tyr Arg Asn Met Ala Leu Lys
    50                  55                  60

Gly Thr Leu Leu Leu Ser Arg Leu Trp Phe Lys Pro Pro Phe Leu Ser
65                  70                  75                  80

Asp Phe Ile Asn Gly Ile Phe Ala Lys Val Lys Asn Thr Lys Val Ile
                85                  90                  95

Lys Lys Gly Val Met Tyr Ser Glu Phe Pro Ala Ile Thr Ile Gly Ser
            100                 105                 110

Thr Phe Val Asn Thr Ser Tyr Ser Val Val Val Gln Pro His Thr Thr
        115                 120                 125
```

-continued

```
Asn Leu Asp Asn Lys Leu Gln Gly Leu Leu Glu Ile Ser Val Cys Gln
    130                 135                 140

Tyr Thr Met Cys Glu Tyr Pro His Thr Ile Cys His Pro Asn Leu Gly
145                 150                 155                 160

Asn Arg Arg Val Glu Leu Trp His Trp Asp Thr Gly Val Val Ser Cys
                165                 170                 175

Leu Tyr Lys Arg Asn Phe Thr Tyr Asp Val Asn Ala Asp Tyr Leu Tyr
            180                 185                 190

Phe His Phe Tyr Gln Glu Gly Gly Thr Phe Tyr Ala Tyr Phe Thr Asp
        195                 200                 205

Thr Gly Val Val Thr Lys Phe Leu Phe Asn Val Tyr Leu Gly Thr Val
    210                 215                 220

Leu Ser His Tyr Tyr Val Leu Pro Leu Thr Cys Ser Ser Ala Met Thr
225                 230                 235                 240

Leu Glu Tyr Trp Val Thr Pro Leu Thr Ser Lys Gln Tyr Leu Leu Ala
                245                 250                 255

Phe Asn Gln Asp Gly Val Ile Phe Asn Ala Val Asp Cys Lys Ser Asp
            260                 265                 270

Phe Met Ser Glu Ile Lys Cys Lys Thr Leu Ser Ile Ala Pro Ser Thr
        275                 280                 285

Gly Val Tyr Glu Leu Asn Gly Tyr Thr Val Gln Pro Ile Ala Asp Val
    290                 295                 300

Tyr Arg Arg Ile Pro Asn Leu Pro Asp Cys Asn Ile Glu Ala Trp Leu
305                 310                 315                 320

Asn Asp Lys Ser Val Pro Ser Pro Leu Asn Trp Glu Arg Lys Thr Phe
                325                 330                 335

Ser Asn Cys Asn Phe Asn Met Ser Ser Leu Met Ser Phe Ile Gln Ala
            340                 345                 350

Asp Ser Phe Thr Cys Asn Asn Ile Asp Ala Ala Lys Ile Tyr Gly Met
        355                 360                 365

Cys Phe Ser Ser Ile Thr Ile Asp Lys Phe Ala Ile Pro Asn Gly Arg
    370                 375                 380

Lys Val Asp Leu Gln Leu Gly Asn Leu Gly Tyr Leu Gln Ser Phe Asn
385                 390                 395                 400

Tyr Arg Ile Asp Thr Thr Ala Thr Ser Cys Gln Leu Tyr Tyr Asn Leu
                405                 410                 415

Pro Ala Ala Asn Val Ser Val Ser Arg Phe Asn Pro Ser Thr Trp Asn
            420                 425                 430

Arg Arg Phe Gly Phe Thr Glu Gln Ser Val Phe Lys Pro Gln Pro Ala
        435                 440                 445

Gly Val Phe Thr His His Asp Val Val Tyr Ala Gln His Cys Phe Lys
    450                 455                 460

Ala Pro Thr Asn Phe Cys Pro Cys Lys Leu Asp Gly Ser Leu Cys Val
465                 470                 475                 480

Gly Asn Gly Pro Gly Ile Asp Ala Gly Tyr Lys Asn Ser Gly Ile Gly
                485                 490                 495

Thr Cys Pro Ala Gly Thr Asn Tyr Leu Thr Cys His Asn Ala Ala Gln
            500                 505                 510

Cys Asp Cys Leu Cys Thr Pro Asp Pro Ile Thr Ser Lys Ser Thr Gly
        515                 520                 525

Pro Tyr Lys Cys Pro Gln Thr Lys Tyr Leu Val Gly Ile Gly Glu His
    530                 535                 540
```

-continued

```
Cys Ser Gly Leu Ala Ile Lys Ser Asp Tyr Cys Gly Gly Asn Pro Cys
545                 550                 555                 560

Thr Cys Gln Pro Gln Ala Phe Leu Gly Trp Ser Ala Asp Ser Cys Leu
                565                 570                 575

Gln Gly Asp Arg Cys Asn Ile Phe Ala Asn Phe Ile Phe His Asp Val
            580                 585                 590

Asn Ser Gly Thr Thr Cys Ser Thr Asp Leu Gln Lys Ser Asn Thr Asp
        595                 600                 605

Ile Ile Leu Gly Val Cys Val Asn Tyr Asp Leu Tyr Gly Ile Ile Gly
    610                 615                 620

Gln Gly Val Phe Val Glu Val Asn Ala Thr Tyr Tyr Asn Ser Trp Gln
625                 630                 635                 640

Asn Leu Leu Tyr Asp Ser Asn Gly Asn Leu Tyr Gly Phe Arg Asp Tyr
                645                 650                 655

Leu Thr Asn Arg Thr Phe Met Ile Arg Ser Cys Tyr Ser Gly Arg Val
            660                 665                 670

Ser Ala Ala Phe His Ala Asn Ser Ser Glu Pro Ala Leu Leu Phe Arg
        675                 680                 685

Asn Ile Lys Cys Asn Tyr Val Phe Asn Asn Ile Leu Ser Arg Gln Leu
    690                 695                 700

Gln Pro Ile Asn Tyr Phe Asp Ser Tyr Leu Gly Cys Val Val Asn Ala
705                 710                 715                 720

Asp Asn Ser Thr Ser Ser Val Val Gln Thr Cys Asp Leu Thr Val Gly
                725                 730                 735

Ser Gly Tyr Cys Val Asp Tyr Ser Thr Lys Arg Arg Ser Arg Arg Ala
            740                 745                 750

Ile Thr Thr Gly Tyr Arg Phe Thr Asn Phe Glu Pro Phe Thr Val Asn
        755                 760                 765

Ser Val Asn Asp Ser Leu Glu Pro Val Gly Gly Leu Tyr Glu Ile Gln
    770                 775                 780

Ile Pro Ser Glu Phe Thr Ile Gly Asn Met Glu Glu Phe Ile Gln Thr
785                 790                 795                 800

Ser Ser Pro Lys Val Thr Ile Asp Cys Ser Ala Phe Val Cys Gly Asp
                805                 810                 815

Tyr Ala Ala Cys Lys Ser Gln Leu Val Glu Tyr Gly Ser Phe Cys Asp
            820                 825                 830

Asn Ile Asn Ala Ile Leu Thr Glu Val Asn Glu Leu Leu Asp Thr Thr
        835                 840                 845

Gln Leu Gln Val Ala Asn Ser Leu Met Asn Gly Val Thr Leu Ser Thr
    850                 855                 860

Lys Leu Lys Asp Gly Val Asn Phe Asn Val Asp Asp Ile Asn Phe Ser
865                 870                 875                 880

Pro Val Leu Gly Cys Leu Gly Ser Gly Cys Asn Lys Gly Ser Ser Arg
                885                 890                 895

Ser Ala Ile Glu Asp Leu Leu Phe Ser Lys Val Lys Leu Ser Asp Val
            900                 905                 910

Gly Phe Val Glu Ala Tyr Asn Asn Cys Thr Gly Gly Ala Glu Ile Arg
        915                 920                 925

Asp Leu Ile Cys Val Gln Ser Tyr Asn Gly Ile Lys Val Leu Pro Pro
    930                 935                 940

Leu Leu Ser Val Asn Gln Ile Ser Gly Tyr Thr Leu Ala Ala Thr Ser
945                 950                 955                 960

Ala Ser Leu Phe Pro Pro Trp Ser Ala Ala Ala Gly Val Pro Phe Tyr
```

-continued

```
                965                 970                 975

Leu Asn Val Gln Tyr Arg Ile Asn Gly Leu Gly Val Thr Met Asp Val
            980                 985                 990

Leu Ser Gln Asn Gln Lys Leu Ile  Ala Asn Ala Phe Asn  Asn Ala Leu
        995                 1000                1005

Asp Ala  Ile Gln Glu Gly Phe  Asp Ala Thr Asn Ser  Ala Leu Val
    1010                 1015                1020

Lys Ile  Gln Ala Val Val Asn  Ala Asn Ala Glu Ala  Leu Asn Asn
    1025                 1030                1035

Leu Leu  Gln Gln Leu Ser Asn  Arg Phe Gly Ala Ile  Ser Ser Ser
    1040                 1045                1050

Leu Gln  Glu Ile Leu Ser Arg  Leu Asp Ala Leu Glu  Ala Gln Ala
    1055                 1060                1065

Gln Ile  Asp Arg Leu Ile Asn  Gly Arg Leu Thr Ala  Leu Asn Ala
    1070                 1075                1080

Tyr Val  Ser Gln Gln Leu Ser  Asp Ser Thr Leu Val  Lys Phe Ser
    1085                 1090                1095

Ala Ala  Gln Ala Met Glu Lys  Val Asn Glu Cys Val  Lys Ser Gln
    1100                 1105                1110

Ser Ser  Arg Ile Asn Phe Cys  Gly Asn Gly Asn His  Ile Ile Ser
    1115                 1120                1125

Leu Val  Gln Asn Ala Pro Tyr  Gly Leu Tyr Phe Ile  His Phe Ser
    1130                 1135                1140

Tyr Val  Pro Thr Lys Tyr Val  Thr Ala Lys Val Ser  Pro Gly Leu
    1145                 1150                1155

Cys Ile  Ala Gly Asp Arg Gly  Ile Ala Pro Lys Ser  Gly Tyr Phe
    1160                 1165                1170

Val Asn  Val Asn Asn Thr Trp  Met Phe Thr Gly Ser  Gly Tyr Tyr
    1175                 1180                1185

Tyr Pro  Glu Pro Ile Thr Gly  Asn Asn Val Val Val  Met Ser Thr
    1190                 1195                1200

Cys Ala  Val Asn Tyr Thr Lys  Ala Pro Asp Val Met  Leu Asn Ile
    1205                 1210                1215

Ser Thr  Pro Asn Leu His Asp  Phe Lys Glu Glu Leu  Asp Gln Trp
    1220                 1225                1230

Phe Lys  Asn Gln Thr Ser Val  Ala Pro Asp Leu Ser  Leu Asp Tyr
    1235                 1240                1245

Ile Asn  Val Thr Phe Leu Asp  Leu Gln Asp Glu Met  Asn Arg Leu
    1250                 1255                1260

Gln Glu  Ala Ile Lys Val Leu  Asn Gln Ser Tyr Ile  Asn Leu Lys
    1265                 1270                1275

Asp Ile  Gly Thr Tyr Glu Tyr  Tyr Val Lys Trp Pro  Trp Tyr Val
    1280                 1285                1290

Trp Leu  Leu Ile Gly Phe Ala  Gly Val Ala Met Leu  Val Leu Leu
    1295                 1300                1305

Phe Phe  Ile Cys Cys Cys Thr  Gly Cys Gly Thr Ser  Cys Phe Lys
    1310                 1315                1320

Ile Cys  Gly Gly Cys Cys Asp  Asp Tyr Thr Gly His  Gln Glu Leu
    1325                 1330                1335

Val Ile  Lys Thr Leu His Asp  Asp
    1340                 1345
```

<210> SEQ ID NO 3

<211> LENGTH: 1218
<212> TYPE: DNA
<213> ORGANISM: Bovine coronavirus

<400> SEQUENCE: 3

```
tttgataacc ctcctaccaa tgttgtttcg catttaaatg gagattggtt tttatttggt     60

gacagtcgtt cagattgtaa tcatgttgtt aataccaacc cccgtaatta ttcttatatg    120

gaccttaatc ctgccctgtg tgattctggt aaaatatcat ctaaagctgg caactccatt    180

tttaggagtt ttcactttac cgatttttat aattacacag gcgaaggtca acaaattatt    240

ttttatgagg gtgttaattt tacgccttat catgccttta aatgcaccac ttctggtagt    300

aatgatattt ggatgcagaa taaaggcttg ttttacactc aggtttataa gaatatggct    360

gtgtatcgca gccttacttt tgttaatgta ccatatgttt ataatggctc tgcacaatct    420

acagctcttt gtaaatctgg tagtttagtt cttaataacc ctgcatatat agctcgtgaa    480

gctaattttg gggattatta ttataaggtt gaagctgact tttatttgtc aggttgtgac    540

gagtatatcg taccactttg tatttttaac ggcaagtttt tgtcgaatac aaagtattat    600

gatgatagtc aatattattt taataaagac actggtgtta tttatggtct caattctact    660

gaaaccatta ccactggttt tgattttaat tgtcattatt tagttttacc ctctggtaat    720

tatttagcca tttcaaatga gctattgtta actgttccta cgaaagcaat ctgtcttaac    780

aagcgtaagg attttacgcc tgtacaggtt gttgattcac ggtggaacaa tgccaggcag    840

tctgataaca tgacggcggt tgcttgtcaa cccccgtact gttattttcg taattctact    900

accaactatg ttggtgttta tgatatcaat catggggatg ctggttttac tagcatactc    960

agtggtttgt tatatgattc accttgtttt tcgcagcaag gtgtttttag gtatgataat   1020

gttagcagtg tctggcctct ctattcctat ggcagatgcc ctactgctgc tggtattaat   1080

acccctgatg tacctatttg tgtgtatgat ccgctaccac ttattttgct tggcatcctt   1140

ttgggtgttg cggtcataat tattgtagtt ttgttgttat attttatggt ggataatggt   1200

actaggctgc atgatgct                                                 1218
```

<210> SEQ ID NO 4
<211> LENGTH: 406
<212> TYPE: PRT
<213> ORGANISM: Bovine coronavirus

<400> SEQUENCE: 4

```
Phe Asp Asn Pro Pro Thr Asn Val Val Ser His Leu Asn Gly Asp Trp
1               5                   10                  15

Phe Leu Phe Gly Asp Ser Arg Ser Asp Cys Asn His Val Val Asn Thr
            20                  25                  30

Asn Pro Arg Asn Tyr Ser Tyr Met Asp Leu Asn Pro Ala Leu Cys Asp
        35                  40                  45

Ser Gly Lys Ile Ser Ser Lys Ala Gly Asn Ser Ile Phe Arg Ser Phe
    50                  55                  60

His Phe Thr Asp Phe Tyr Asn Tyr Thr Gly Glu Gly Gln Gln Ile Ile
65                  70                  75                  80

Phe Tyr Glu Gly Val Asn Phe Thr Pro Tyr His Ala Phe Lys Cys Thr
                85                  90                  95

Thr Ser Gly Ser Asn Asp Ile Trp Met Gln Asn Lys Gly Leu Phe Tyr
            100                 105                 110

Thr Gln Val Tyr Lys Asn Met Ala Val Tyr Arg Ser Leu Thr Phe Val
        115                 120                 125
```

-continued

```
Asn Val Pro Tyr Val Tyr Asn Gly Ser Ala Gln Ser Thr Ala Leu Cys
    130                 135                 140

Lys Ser Gly Ser Leu Val Leu Asn Asn Pro Ala Tyr Ile Ala Arg Glu
145                 150                 155                 160

Ala Asn Phe Gly Asp Tyr Tyr Tyr Lys Val Glu Ala Asp Phe Tyr Leu
                165                 170                 175

Ser Gly Cys Asp Glu Tyr Ile Val Pro Leu Cys Ile Phe Asn Gly Lys
            180                 185                 190

Phe Leu Ser Asn Thr Lys Tyr Tyr Asp Asp Ser Gln Tyr Tyr Phe Asn
        195                 200                 205

Lys Asp Thr Gly Val Ile Tyr Gly Leu Asn Ser Thr Glu Thr Ile Thr
    210                 215                 220

Thr Gly Phe Asp Phe Asn Cys His Tyr Leu Val Leu Pro Ser Gly Asn
225                 230                 235                 240

Tyr Leu Ala Ile Ser Asn Glu Leu Leu Leu Thr Val Pro Thr Lys Ala
                245                 250                 255

Ile Cys Leu Asn Lys Arg Lys Asp Phe Thr Pro Val Gln Val Val Asp
            260                 265                 270

Ser Arg Trp Asn Asn Ala Arg Gln Ser Asp Asn Met Thr Ala Val Ala
        275                 280                 285

Cys Gln Pro Pro Tyr Cys Tyr Phe Arg Asn Ser Thr Thr Asn Tyr Val
    290                 295                 300

Gly Val Tyr Asp Ile Asn His Gly Asp Ala Gly Phe Thr Ser Ile Leu
305                 310                 315                 320

Ser Gly Leu Leu Tyr Asp Ser Pro Cys Phe Ser Gln Gln Gly Val Phe
                325                 330                 335

Arg Tyr Asp Asn Val Ser Ser Val Trp Pro Leu Tyr Ser Tyr Gly Arg
            340                 345                 350

Cys Pro Thr Ala Ala Gly Ile Asn Thr Pro Asp Val Pro Ile Cys Val
        355                 360                 365

Tyr Asp Pro Leu Pro Leu Ile Leu Leu Gly Ile Leu Leu Gly Val Ala
    370                 375                 380

Val Ile Ile Ile Val Val Leu Leu Leu Tyr Phe Met Val Asp Asn Gly
385                 390                 395                 400

Thr Arg Leu His Asp Ala
                405


<210> SEQ ID NO 5
<211> LENGTH: 693
<212> TYPE: DNA
<213> ORGANISM: Bovine coronavirus

<400> SEQUENCE: 5

atgagtagtg taactacacc agcaccagtt tacacctgga ctgctgatga agctattaaa      60

ttcctaaagg aatggaactt ttctttgggt attatactac tttttattac aatcatattg     120

caatttggat atacaagtcg cagtatgttt gtttatgtta ttaagatgat cattttgtgg     180

cttatgtggc cccttactat catcttaact attttcaatt gcgtgtatgc gttgaataat     240

gtgtatcttg gcttttctat agttttcact atagtggcca ttatcatgtg gattgtgtat     300

tttgtgaata gtatcaggtt gtttattaga actggaagtt ggtggagttt caacccagaa     360

acaaacaact tgatgtgtat agatatgaag ggaaggatgt atgttaggcc gataattgag     420

gactaccata cccttacggt cacaataata cgtggtcatc tttacatgca aggtataaaa     480
```

```
ctaggtactg gctattcttt gtcagatttg ccagcttatg tgactgttgc taaggtctca    540

cacctgctca cgtataagcg tggttttctt gacaagatag gcgatactag tggttttgct    600

gtttatgtta agtccaaagt cggtaattac cgactgccat caacccaaaa gggttctggc    660

atggacaccg cattgttgag aaatataatc taa                                 693


<210> SEQ ID NO 6
<211> LENGTH: 230
<212> TYPE: PRT
<213> ORGANISM: Bovine coronavirus

<400> SEQUENCE: 6

Met Ser Ser Val Thr Thr Pro Ala Pro Val Tyr Thr Trp Thr Ala Asp
1               5                   10                  15

Glu Ala Ile Lys Phe Leu Lys Glu Trp Asn Phe Ser Leu Gly Ile Ile
            20                  25                  30

Leu Leu Phe Ile Thr Ile Ile Leu Gln Phe Gly Tyr Thr Ser Arg Ser
        35                  40                  45

Met Phe Val Tyr Val Ile Lys Met Ile Ile Leu Trp Leu Met Trp Pro
    50                  55                  60

Leu Thr Ile Ile Leu Thr Ile Phe Asn Cys Val Tyr Ala Leu Asn Asn
65                  70                  75                  80

Val Tyr Leu Gly Phe Ser Ile Val Phe Thr Ile Val Ala Ile Ile Met
                85                  90                  95

Trp Ile Val Tyr Phe Val Asn Ser Ile Arg Leu Phe Ile Arg Thr Gly
            100                 105                 110

Ser Trp Trp Ser Phe Asn Pro Glu Thr Asn Asn Leu Met Cys Ile Asp
        115                 120                 125

Met Lys Gly Arg Met Tyr Val Arg Pro Ile Ile Glu Asp Tyr His Thr
    130                 135                 140

Leu Thr Val Thr Ile Ile Arg Gly His Leu Tyr Met Gln Gly Ile Lys
145                 150                 155                 160

Leu Gly Thr Gly Tyr Ser Leu Ser Asp Leu Pro Ala Tyr Val Thr Val
                165                 170                 175

Ala Lys Val Ser His Leu Leu Thr Tyr Lys Arg Gly Phe Leu Asp Lys
            180                 185                 190

Ile Gly Asp Thr Ser Gly Phe Ala Val Tyr Val Lys Ser Lys Val Gly
        195                 200                 205

Asn Tyr Arg Leu Pro Ser Thr Gln Lys Gly Ser Gly Met Asp Thr Ala
    210                 215                 220

Leu Leu Arg Asn Ile Ile
225                 230


<210> SEQ ID NO 7
<211> LENGTH: 255
<212> TYPE: DNA
<213> ORGANISM: Bovine coronavirus

<400> SEQUENCE: 7

atgtttatgg ctgatgctta ttttgcagac actgtgtggt atgtggggca aataattttt     60

atagttgcca tttgtttatt ggttataata gttgtagtgg catttttggc aacttttaaa    120

ttgtgtattc aactttgcgg tatgtgtaat accttagtac tgtccccttc tatttatgtg    180

tttaatagag gtaggcagtt ttatgagttt tacaacgatg taaaaccacc agttcttgat    240

gtggatgacg tttag                                                     255
```

<210> SEQ ID NO 8
<211> LENGTH: 84
<212> TYPE: PRT
<213> ORGANISM: Bovine coronavirus

<400> SEQUENCE: 8

```
Met Phe Met Ala Asp Ala Tyr Phe Ala Asp Thr Val Trp Tyr Val Gly
1               5                   10                  15

Gln Ile Ile Phe Ile Val Ala Ile Cys Leu Leu Val Ile Ile Val Val
            20                  25                  30

Val Ala Phe Leu Ala Thr Phe Lys Leu Cys Ile Gln Leu Cys Gly Met
        35                  40                  45

Cys Asn Thr Leu Val Leu Ser Pro Ser Ile Tyr Val Phe Asn Arg Gly
    50                  55                  60

Arg Gln Phe Tyr Glu Phe Tyr Asn Asp Val Lys Pro Pro Val Leu Asp
65                  70                  75                  80

Val Asp Asp Val
```

<210> SEQ ID NO 9
<211> LENGTH: 1347
<212> TYPE: DNA
<213> ORGANISM: Bovine coronavirus

<400> SEQUENCE: 9

```
atgtctttta ctcctggtaa gcaatccagt agtagagcgt cctctggaaa tcgttctggt     60

aatggcatcc ttaagtgggc cgatcagtcc gaccaatcta gaaatgttca aaccaggggt    120

agaagagctc aacccaagca aactgctact tctcagctac catcaggagg gaatgttgta    180

ccctactatt cttggttctc tggaattact cagtttcaaa aaggaaagga gtttgaattt    240

gcagagggac aaggtgtgcc tattgcacca ggagtcccag ctactgaagc taaggggtac    300

tggtacagac acaacagacg ttcttttaaa acagccgatg gcaaccagcg tcaactgctg    360

ccacgatggt atttttacta tcttggaaca ggaccgcatg ccaaagacca gtatggcacc    420

gatattgacg gtgtcttctg ggtcgctagt aaccaggctg atgtcaatac ccccgctgac    480

attctcgatc gggacccaag tagcgatgag gctattccga ctaggtttcc gcctggcacg    540

gtactccctc agggttacta tattgaaggc tcaggaaggt ctgctcctaa ttccagatct    600

acttcacgcg catccagtag agcctctagt gcaggatcgc gtagtagagc caattctggc    660

aacagaaccc ctacctctgg tgtaacacct gatatggctg atcaaattgc tagtcttgtt    720

ctggcaaaac ttggcaagga tgccactaag ccacagcaag taactaagca gactgccaaa    780

gaaatcagac agaaaatttt gaataagccc cgccagaaga ggagccccaa taaacaatgc    840

actgttcagc agtgttttgg gaagagaggc cccaatcaga attttggtgg tggagaaatg    900

ttaaaacttg gaactagtga cccacagttc cccattcttg cagaactcgc acccacagct    960

ggtgcgtttt tctttggatc aagattagag ttggccaaag tgcagaattt gtctgggaat   1020

cttgacgagc cccagaagga tgtttatgaa ttgcgctata atggtgcaat tagatttgac   1080

agtacacttt caggttttga gaccataatg aaggtgttga atgagaattt gaatgcatat   1140

caacaacaag atggtatgat gaatatgagt ccaaaaccac agcgtcagcg tggtcagaag   1200

aatggacaag gagaaaatga taatataagt gttgcagcgc ctaaaagccg tgtgcagcaa   1260

aataagagta gagagttgac tgcagaggac atcagccttc ttaagaagat ggatgagccc   1320

tatactgaag acacctcaga aatataa                                       1347
```

<210> SEQ ID NO 10
<211> LENGTH: 448
<212> TYPE: PRT
<213> ORGANISM: Bovine coronavirus

<400> SEQUENCE: 10

```
Met Ser Phe Thr Pro Gly Lys Gln Ser Ser Ser Arg Ala Ser Ser Gly
1               5                   10                  15

Asn Arg Ser Gly Asn Gly Ile Leu Lys Trp Ala Asp Gln Ser Asp Gln
            20                  25                  30

Ser Arg Asn Val Gln Thr Arg Gly Arg Arg Ala Gln Pro Lys Gln Thr
        35                  40                  45

Ala Thr Ser Gln Leu Pro Ser Gly Gly Asn Val Val Pro Tyr Tyr Ser
    50                  55                  60

Trp Phe Ser Gly Ile Thr Gln Phe Gln Lys Gly Lys Glu Phe Glu Phe
65                  70                  75                  80

Ala Glu Gly Gln Gly Val Pro Ile Ala Pro Gly Val Pro Ala Thr Glu
                85                  90                  95

Ala Lys Gly Tyr Trp Tyr Arg His Asn Arg Arg Ser Phe Lys Thr Ala
            100                 105                 110

Asp Gly Asn Gln Arg Gln Leu Leu Pro Arg Trp Tyr Phe Tyr Tyr Leu
        115                 120                 125

Gly Thr Gly Pro His Ala Lys Asp Gln Tyr Gly Thr Asp Ile Asp Gly
    130                 135                 140

Val Phe Trp Val Ala Ser Asn Gln Ala Asp Val Asn Thr Pro Ala Asp
145                 150                 155                 160

Ile Leu Asp Arg Asp Pro Ser Ser Asp Glu Ala Ile Pro Thr Arg Phe
                165                 170                 175

Pro Pro Gly Thr Val Leu Pro Gln Gly Tyr Tyr Ile Glu Gly Ser Gly
            180                 185                 190

Arg Ser Ala Pro Asn Ser Arg Ser Thr Ser Arg Ala Ser Ser Arg Ala
        195                 200                 205

Ser Ser Ala Gly Ser Arg Ser Arg Ala Asn Ser Gly Asn Arg Thr Pro
    210                 215                 220

Thr Ser Gly Val Thr Pro Asp Met Ala Asp Gln Ile Ala Ser Leu Val
225                 230                 235                 240

Leu Ala Lys Leu Gly Lys Asp Ala Thr Lys Pro Gln Gln Val Thr Lys
                245                 250                 255

Gln Thr Ala Lys Glu Ile Arg Gln Lys Ile Leu Asn Lys Pro Arg Gln
            260                 265                 270

Lys Arg Ser Pro Asn Lys Gln Cys Thr Val Gln Gln Cys Phe Gly Lys
        275                 280                 285

Arg Gly Pro Asn Gln Asn Phe Gly Gly Gly Glu Met Leu Lys Leu Gly
    290                 295                 300

Thr Ser Asp Pro Gln Phe Pro Ile Leu Ala Glu Leu Ala Pro Thr Ala
305                 310                 315                 320

Gly Ala Phe Phe Phe Gly Ser Arg Leu Glu Leu Ala Lys Val Gln Asn
                325                 330                 335

Leu Ser Gly Asn Leu Asp Glu Pro Gln Lys Asp Val Tyr Glu Leu Arg
            340                 345                 350

Tyr Asn Gly Ala Ile Arg Phe Asp Ser Thr Leu Ser Gly Phe Glu Thr
        355                 360                 365

Ile Met Lys Val Leu Asn Glu Asn Leu Asn Ala Tyr Gln Gln Gln Asp
    370                 375                 380
```

```
Gly Met Met Asn Met Ser Pro Lys Pro Gln Arg Gln Arg Gly Gln Lys
385                 390                 395                 400

Asn Gly Gln Gly Glu Asn Asp Asn Ile Ser Val Ala Ala Pro Lys Ser
                405                 410                 415

Arg Val Gln Gln Asn Lys Ser Arg Glu Leu Thr Ala Glu Asp Ile Ser
            420                 425                 430

Leu Leu Lys Lys Met Asp Glu Pro Tyr Thr Glu Asp Thr Ser Glu Ile
        435                 440                 445


<210> SEQ ID NO 11
<211> LENGTH: 21284
<212> TYPE: DNA
<213> ORGANISM: Bovine coronavirus

<400> SEQUENCE: 11

atgtcgaaga tcaacaaata cggtctcgaa ctacactggg ctccagaatt tccatggatg      60

tttgaggacg cagaggagaa gttggataac cctagtagtt cagaggtgga tatagtatgc     120

tccaccactg cgcaaaagct ggaaacaggc ggaatttgtc ctgaaaatca tgtgatggtg     180

gattgtcgcc gacttcttaa acaagagtgt tgtgtgcagt ctagcctaat acgtgaaatt     240

gttatgaata cacgtccata tgatttggag gtgctacttc aagatgcttt gcagtcctgc     300

gaagcagttt tggttacacc ccctctaggt atgtctctgg aggcatgcta tgtgagaggt     360

tgtaatccta atggatggac catgggtttg tttcggcgta gaagtgtgtg taacactggt     420

cgttgcgctg ttaacaagca tgtggcctat cagctatata tgattgatcc tgcgggtgtc     480

tgttttggtg caggtcaatt tgtgggttgg gttataccct tagcctttat gcctgtgcaa     540

tcccggaaat ttattgttcc tagggttatg tacttgcgta agtgtggcga aaagggtgcc     600

tacaataaag atcataaacg tggcggtttt gaacacgttt ataattttaa agttgaggat     660

gcttacgacc tggttcatga tgagcctaag ggtaagtttt ctaagaaggc ttatgcttta     720

attagaggat accgtggtgt taaaccgctt ctctatgtag accagtatgg ttgtgattat     780

actggtggtc ttgcagatgg cttagaggct tatgctgata agacattgca agaaatgaag     840

gcattatttc ctatttggag ccaggaactc ccttttgatg taactgtggc atggcacgtt     900

gtgcgtgatc cacgttatgt tatgagactg cagagtgctt ctactatacg tagtgttgca     960

tatgttgcta accctactga agacttgtgt gatggttctg ttgttataaa ggaacctgtg    1020

catgtttatg cggatgactc tattatttta cgtcaacata atttagttga cattatgagt    1080

tgtttttata tggaggcaga tgcagttgta aatgcttttt atggtgttga tttgaaagat    1140

tgtggttttg ttatgcagtt tggttatatt gactgcgaac aagacttgtg tgattttaaa    1200

ggttgggttc ctggtaatat gatagatggt tttgcttgca ctacttgtgg tcatgtttat    1260

gagacaggtg atttgctagc acaatcttca ggtgttttgc ctgttaatcc tgtattgcat    1320

actaagagtg cagcaggtta tggtggtttt ggttgtaagg attcttttac cctgtatggc    1380

caaactgtag tttattttgg aggttgtgtg tattggagtc cagcacgtaa tatatggatt    1440

cctatattaa aatcttctgt taagtcttat gacggtttgg tttatactgg agttgtaggt    1500

tgcaaggcta ttgtaaagga aacaaatctc atttgcaaag cgttgtacct tgattatgtt    1560

caacacaagt gtggcaattt acaccagcgg gagttgctag gtgtgtcaga tgtgtggcat    1620

aaacaattgt tattaaatag aggtgtgtac aaacctcttt tagagaatat tgattatttt    1680

aatatgcggc gcgctaaatt tagtttagaa acttttactg tttgtgcaga tggttttatg    1740
```

-continued

```
ccttttcttt tagatgattt ggttccgcgc gcatattatt tggcagtaag tggtcaagca   1800
ttttgtgact acgcaggtaa aatctgccat gctgttgtgt ctaagagtaa agagttactt   1860
gatgtgtctc tggattcttt aggtgcagct atacattatt tgaattctaa aattgttgat   1920
ttggctcaac attttagtga ttttggaaca agtttcgttt ctaaaattgt tcatttcttt   1980
aagactttta ctactagcac tgctcttgca tttgcatggg ttttatttca tgttttgcat   2040
ggtgcttata tagtagtgga gagtgatata tattttgtta aaaacattcc tcgttatgct   2100
agtgctgttg cacaagcatt tcggagtgtt gctaaagttg tactggactc tttaagagtt   2160
acttttattg atggcctttc ttgttttaag attggacgta gaagaatttg tctttcaggc   2220
agtaaaattt atgaagttga gcgtggcttg ttacattcat ctcaattgcc attagatgtt   2280
tatgatttaa ccatgcctag tcaagttcag aaaaccaagc aaaaacctat ttatttaaaa   2340
ggttctggtt ctgatttttc attagcggat agtgtagttg aagttgttac aacttcactt   2400
acaccatgtg gttattctga accacctaaa gttgcagata aaatttgcat tgtggataat   2460
gtttatatgg ccaaggctgg tgacaaatat taccctgttg tggttgatgg tcatgttgga   2520
cttttggatc aagcatggag ggttccttgt gctggaaggc gtgttacatt taaggaacag   2580
cctacagtaa atgagattgc aagcacgcct aagactatta aagtttttta tgagcttgac   2640
aaagatttta atactatttt aaacactgca tgtggagtgt ttgaagtgga tgatactgtg   2700
gatatggagg aattttatgc tgtggtgatt gatgccatag aagagaaact ttctccatgt   2760
aaggagcttg aaggtgtagg tgctaaagtt agtgcctttt tacagaaatt agaggataat   2820
tccctatttt tatttgatga ggctggtgag gaagttcttg ctcctaaatt gtattgtgct   2880
tttacagctc ctgaagatga tgactttctt gaagaaagtg gtgttgaaga agatgatgta   2940
gaaggtgagg aaactgattt aactgtcaca agtgctggag agccttgtgt tgccagtgaa   3000
caggaggagt cttctgaaat cttagaggac actttggatg atggtccatg tgtggagaca   3060
tctgattcac aagttgaaga agatgtacaa atgtcggatt ttgttgatct tgaatctgtg   3120
attcaggatt atgaaaatgt ttgttttgag ttttatacta cagaaccaga atttgttaaa   3180
gttttggatc tgtatgttcc taaagcaact cgcaacaatt gctggttgcg atcagttttg   3240
gcagtgatgc agaaactgcc ctgtcaattt aaagataaaa atttgcagga tctttgggtg   3300
ttatataagc aacagtatag tcagttgttt gttgatacct tggttaataa gatacctgct   3360
aatattgtag ttccacaagg tggttatgtt gctgattttg catattggtt cttaacctta   3420
tgtgattggc agtgtgttgc atactggaaa tgcattaaat gtgatttagc tcttaagctt   3480
aaaggcttgg atgctatgtt cttttatggt gatgttgtct cacatgtgtg caagtgtggt   3540
gagtctatgg tacttattga tgttgatgtg ccatttacag cccactttgc tcttaaagat   3600
aagttgtttt gtgcatttat tactaagcgt agtgtgtata aagcagcttg tgttgtggct   3660
gttaatgata gtcattctat ggctgttgtt gatggtaaac aaattgatga tcattgtatc   3720
actagtatta ctagtgataa gtttgatttt attattgggc atggtatgtc attttcaatg   3780
actacttttg aaattgccca attgtatggt tcttgtataa cacctaatgt atgttttgtt   3840
aaaggtgata taattaaagt ttctaagcgt gttaaagcag aagtcgttgt aaatcctgct   3900
aatggccata tggcacatgg tggtggtgtt gcaaaggcta ttgcagtagc agctggacag   3960
cagtttgtta aagagaccac cgatatggtt aagtctaaag gagtttgtgc tactggagat   4020
tgttatgtct ctacaggggg caaattatgt aaaactgtgc ttaatgttgt tggacctgat   4080
gcgaggacac agggtaaaca aagttatgca ttgttagagc gtgtttataa acatcttaac   4140
```

aaatatgatt gtgttgttac aactttgatc tcagctggta tatttagtgt gccttctgat 4200
gtgtctttaa catatctact tggtactgct aagaaacaag ttgttcttgt tagcaataat 4260
caagaggatt ttgatcttat ttctaagtgt cagataactg ccgttgaggg cactaagaaa 4320
ttggcagagc gtctttcttt taatgttggg cgttctatcg tttacgaaac agatgctaat 4380
aagttgattt taagcaatga cgttgcattt gtttcgacat ttaatgtctt acaggatgtt 4440
ttatccttaa gacatgatat agcacttgat gatgatgcac gaacctttgt tcagagcaat 4500
gttgatgttg tacctgaggg ttggcgtgtt gtcaataagt tttatcaaat taatggtgtt 4560
agaaccgtta agtattttga gtgtcccggg ggcatagata tatgcagcca ggataaagtt 4620
tttggttatg tacagcaggg tagttttaat aaggctactg ttgctcaaat taaagccttg 4680
tttttggata aagtggacat cttgctaact gttgatggtg ttaatttcac taacaggttt 4740
gtgcctgtag gtgaaagttt tggtaagagt ctaggaaatg tgttttgtga tggagttaat 4800
gtcacgaaac ataagtgtga tataaattat aaaggtaaag tctttttcca gtttgataat 4860
ctttctagtg aagatttaaa ggctgtaaga agttctttta attttgatca gaaggaattg 4920
cttgcctact acaacatgct tgttaattgt tctaagtggc aggttgtttt taatggtaag 4980
tatttcactt ttaagcaagc taataacaat tgttttgtta atgtttcttg cttaatgctc 5040
cagagtttga atctgaaatt taaaattgtt caatggcagg aggcgtggct tgaatttcgt 5100
tctggccgcc ctgctagatt tgtatctttg gttttggcta aaggtgggtt taaatttggg 5160
gatcctgctg attctagaga tttcttgcgt gttgtgttta gtcaagttga tttgacaggg 5220
gcaatatgtg attttgaaat tgcatgtaaa tgtggtgtaa agcaggaaca gcgtactggt 5280
gtggacgctg ttatgcattt tggtacattg agtcgtgaag atcttgagat tggttacacc 5340
gtggattgtt cttgcggtaa aaagctaatt cattgtgtac gatttgatgt accattttta 5400
atttgcagta atacacctgc tagtgtaaaa ttacctaagg gtgtaggaag tgcaaatatt 5460
tttaaaggtg ataaggttgg tcattatgtt catgttaagt gtgaacagtc ttatcagctt 5520
tatgatgctt ctaatgttaa gaaggttaca gacgttactg gcaatttgtc agattgtttg 5580
tatcttaaaa atttgaaaca aacttttaaa tcggtgttaa ccacctatta tttggatgat 5640
gttaagaaaa ttgagtataa acctgacttg tcacaatatt attgtgacgg aggtaagtat 5700
tatactcagc gtattattaa agcccaattt aaaacatttg agaaagtaga tggtgtgtat 5760
actaatttta aattgatagg acacaccgtc tgtgatattc ttaatgctaa gttgggtttt 5820
gatagctcta aagagtttgt tgaatataag gttactgagt ggccaacagc tacaggtgat 5880
gtggtgttgg ctactgatga tttgtatgtt aagagatatg aaaggggttg tattactttt 5940
ggtaaacctg ttatatggtt aagccatgag caagcttccc tcaattcttt aacatatttt 6000
aatagacctt tattggttga tgagaataaa tttgatgttt taaaagtgga tgatgttgac 6060
gatggtggtg atatctcaga gagtgatgct aaagaaccca aagaaatcaa cattattaag 6120
ttaagtggtg ttaaaaaacc atttaaggtt gaagatagtg tcattgttaa tgatgatact 6180
agtgaaatca aatatgttaa gagtttgtct atagttgatg tgtatgatat gtggcttaca 6240
ggttgtaggt gtgttgttag gactgctaat gctttgagca gagcagttaa cgtacctaca 6300
atacgtaagt ttataaaatt tggtatgact cttgttagta taccaattga tttgttaaat 6360
ttaagagaga ttaagcctgt ttttaatgtg gttaaagctg tgcgaaataa aatttctgca 6420
tgctttaatt ttattaaatg gctttttgtc ttattatttg gctggattaa aatatccgct 6480

-continued gataataaag taatttacac cacagaagtt gcatcaaagc ttacgtgtaa gcttgtagct 6540
ttagctttta aaaatgcatt tttgacattt aagtggagtg tggttgctag aggtgcttgc 6600
attatagcga ctatatttct attgtggttt aattttatat atgccaatgt aatttttagt 6660
gatttttatt tgcctaaaat cggtttcttg ccgacttttg ttggtaagat cgcacagtgg 6720
attaagaaca cttttagtct tgtaactatt tgtgatctat attccattca ggatgtgggt 6780
tttaagaatc agtattgtaa tggaagtatc gcatgtcagt tctgcttggc aggatttgat 6840
atgttagata attataaagc cattgatgta gtacagtatg aagctgatag gcgagcattt 6900
gttgattata caggtgtgtt aaagattgtc attgaattga tagttagtta cgccctgtat 6960
acggcatggt tttacccatt gtttgctctt attagtattc agatcttgac cacttggctg 7020
cctgagcttt ttatgcttag tacattacat tggagtgtta ggttgctggt gtctttagct 7080
aatatgttac cagcacatgt gtttatgagg ttttatatta ttattgcctc ttttattaag 7140
ctgtttagct tgtttaggca tgttgcctat ggttgtagta aatctggttg tttgttttgt 7200
tacaagagga atcgtagtct acgtgttaaa tgtagtacta ttgttggtgg catgatacgc 7260
tattacgatg ttatggctaa tggtggcact ggcttttgtt caaaacatca atggaattgc 7320
attgattgtg attcttataa accaggtaat actttttatta ctgttgaggc cgctcttgat 7380
ttatctaagg aattgaaacg gcctattcag cctacagatg ttgcttatca tacggttacg 7440
gatgttaagc aagttggttg ttatatgcgc ttgttctatg atcgtgatgg acagcgcaca 7500
tatgatgatg ttaatgctag tttgtttgtg gattatagta atttgctaca ttctaaggtt 7560
aagagtgtgc ctaatatgca tgttgtggta gtggaaaatg atgccgataa agctaatttt 7620
cttaatgctg ctgtatttta tgcacagtct ttgtttagac ctattttaat ggttgataaa 7680
aatctgataa ctactgctaa tactggtacg tctgttacag aaactatgtt tgatgtttat 7740
gtggatacat ttttgtctat gtttgatgtg gataaaaaga gtcttaatgc tttaatagca 7800
actgcgcatt cttctataaa acagggtacg cagatctgta aagttttgga taccttttta 7860
agctgtgctc gtaaaagttg ttctattgat tcagatgttg atactaagtg tttagctgat 7920
tctgtcatgt ctgctgtatc ggcaggcctt gaattgacgg atgaaagttg taataacttg 7980
gtgccaacat atttgaaggg tgataacatt gtggcagctg atttaggtgt tctgattcaa 8040
aattctgcta agcatgtgca gggtaatgtt gctaaaatag ccggtgtttc ctgtatatgg 8100
tctgtggatg cttttaatca gcttagttct gatttccagc ataaattgaa gaaagcatgt 8160
tgtaaaacta gtttgaaact gaagcttact tataataagc agatggctaa tgtctctgtt 8220
ttaactacac cctttagtct taaagggggt gcagttttta gttattttgt ttatgtatgt 8280
tttgtgttga gtttggtttg ttttattgga ttgtggtgct taatgcccac ttacacagta 8340
cacaaatcag attttcagct tcccgtttat gccagttata aagttttaga taatggtgtt 8400
attagagatg ttagcgttga agatgtttgt ttcgctaaca aatttgaaca atttgatcaa 8460
tggtatgagt ctacatttgg tctaagttat tatagtaaca gtatggcttg tcccattgtt 8520
gttgctgtag tagaccagga ttttggctct actgtgttta atgtccctac caaagtgtta 8580
cgatatggtt accatgtgtt gcactttatt acacatgcac tttctgctga tggagtgcag 8640
tgttatacgc cacatagtca aatatcgtat tctaattttt atgctagtgg ctgtgtgctt 8700
tcctctgctt gcactatgtt tgcaatggcc gatggtagtc cacaacctta ttgttataca 8760
gatgggctta tgcagaatgc ttctctgtat agttcattgg tacctcatgt gcggtataat 8820
cttgctaatg ctaaaggttt tatccgtttt ccagaagtgt tgcgagaagg acttgtgcgt 8880

-continued

```
attgtgcgta ctcgttctat gtcgtattgc agagttggat tatgtgagga agctgatgag   8940
ggtatatgct ttaattttaa tggttcttgg gtgcttaata atgattatta tagatcattg   9000
cctgggacct tttgtggtag agatgttttt gacttaattt atcagctgtt taaaggttta   9060
gcacagcctg tggatttctt ggcattgact gctagttcca ttgctggtgc tatacttgct   9120
gtaattgttg ttttggtgtt ttattactta ataaagctta aacgtgcttt tggtgattac   9180
accagtattg tttttgttaa tgtgattgtg tggtgtgtaa attttatgat gctttttgtg   9240
tttcaagttt accctacact ttcttgtgta tatgctattt gttattttta tgccacgctt   9300
tatttccctt cggagataag tgtgataatg catttacaat ggctagttat gtatggcact   9360
attatgcctt tatggttttg tttgctatat atatctgttg ttgtttcaaa tcatgctttt   9420
tgggtatttt cttactgcag acagcttggt acttctgttc gtagtgatgg tacatttgaa   9480
gaaatggctc ttactacttt tatgattaca aaagattctt attgtaagct taagaattct   9540
ttgtctgatg ttgcttttaa tagatatttg agtttgtata ataaatatag gtattacagc   9600
ggtaaaatgg atactgctgc atatagggag gctgcttgtt ctcagttggc taaagcaatg   9660
gatacattta ccaataataa tggtagtgat gtgctttacc aaccgcctac tgcttccgtt   9720
tcaacttcat tcttgcaatc tggtattgtg aaaatggtta atcctacttc taaggtagaa   9780
ccatgtattg tcagtgttac ctatggtaat atgacattga atggtttatg gttggatgat   9840
aaggtctact gtcccagaca tgtgatatgt tctgcttcag atatgactta tccagattat   9900
acaaatttgt tgtgtagagt aacatcaagt gattttactg tattgtttga tcgtctaagc   9960
cttacagtga tgtcttatca aatgcagggt tgtatgcttg ttcttacagt gaccctgcaa  10020
aattctcgta cgccaaaata tacatttggt gtggttaaac ctggtgagac ttttactgtt  10080
ttagctgctt ataacggcaa accacaagga gcctttcatg tgactatgcg tagtagttat  10140
accattaagg gttccttttt atgcggatct tgtggatctg ttggttatgt aataatgggt  10200
gattgtgtta aatttgtgta tatgcatcaa ttggagctta gtactggttg tcatactggt  10260
actgatttca atggggattt ttatggtcct tataaggatg ctcaggttgt ccaattgccc  10320
gttcaggatt atatacaatc tgttaatttt gtagcatggc tttatgctgc tatacttaat  10380
aattgtaatt ggtttgtaca aagtgataag tgttctgttg aagattttaa tgtgtgggct  10440
ttgtctaatg ggtttagcca agttaagtct gatcttgtta tagatgcttt agcttctatg  10500
actggtgtgt ctttggaaac actattggct gctattaagc gtcttaagaa tggttttcaa  10560
ggacgtcaga ttatgggtag ttgctccttt gaggatgaat tgacacctag cgatgtttat  10620
caacaactcg ctggtatcaa gttacaatca aagcgtacta gattggttaa aggcattgtt  10680
tgttggatta tggcttctac atttttgttt agttgtataa ttacagcatt tgtgaaatgg  10740
actatgttta tgtatgtaac tactaatatg cttagtatta cgttttgtgc actttgtgtt  10800
ataagtttgg ccatgttgtt ggttaaacat aagcatcttt atttgactat gtatataatt  10860
cctgtgcttt ttacactgct gtataacaac tatttggttg tgtacaagca gacatttaga  10920
ggctatgttt atgcatggct atcatattat gttccatcag ttgagtatac ttatactgat  10980
gaagtaattt atggcatgtt attgcttata ggaatggtct ttgttacatt acgtagcatt  11040
aaccatgatt tgttctcttt tataatgttt gttggtcgtg tgatttctgt tgtctctttg  11100
tggtacatgg gttctaactt agaggaagaa attcttctta tgttggcttc tctttttggt  11160
acttacacat ggacaacagc tttatctatg gctgcagcaa aggttattgc taagtgggtt  11220
```

```
gctgtgaatg ttttgtattt cacagatata cctcaaatta agatagtgct tgtatgctat  11280
ttgtttatag gttatattat tagctgttat tggggtttgt tttccttgat gaacagtttg  11340
tttagaatgc ctttgggtgt ttataattat aaaatttcag tacaggaatt aagatatatg  11400
aatgctaatg gattgcgccc tcctaagaat agttttgaag ccctcatgct taattttaag  11460
cttttgggta ttggaggtgt gccaattatt gaagtatctc aatttcaatc aaaattgact  11520
gatgttaaat gtgctaatgt tgtcttgctt aattgcttgc aacatttgca tgttgcttct  11580
aactctaagt tgtggcaata ttgtagcact ttgcacaatg aaatacttgc cacttctgat  11640
ctgggtgttg cttttgaaaa gcttgctcag ttgttaattg ttttgtttgc taatccagct  11700
gctgtggata gcaagtgcct gactagtatt gaagaagttt gcgacgatta cgcaaaggac  11760
aatactgttt tgcaggcttt acagagtgaa tttgttaata tggctagctt cgttgaatat  11820
gaagttgcta agaaaaatct tgatgaggcg tgttctagtg gttctgctaa tcgacagcag  11880
ttaaaacagc tagagaaagc ctgtaatatt gctaaatctg cttatgaacg cgaccgtgct  11940
gtagcaagaa agttggagcg tatggcagat ttggctctca ctaatatgta taaagaagct  12000
agaattaatg ataagaagag taaggttgtt tctgccttgc aaactatgct tttagtatg   12060
gtgcgtaagt tagataatca agctctgaat tcaatattag ataatgctgt gaagggttgt  12120
gtaccattga atgcaatccc ttcattggca gcaaatactc tgactataat tgtaccagat  12180
aaaagtgttt atgatcaggt agttgacaat gtctatgtta cctatgcggg taatgtatgg  12240
cagattcaaa ctatccaaga ttcagatggt acaaataagc agttgaatga gatatctgat  12300
gattgtaact ggccactagt tattattgca aatcggcata atgaggtatc tgctaccgtt  12360
ttgcaaaata atgaattaat gcctgctaag ttgaaaactc aggttgttaa tagtggtcca  12420
gatcagactt gtaatacacc tactcaatgt tactataata atagttacaa tgggaagatt  12480
gtttatgcta tacttagtga tgttgatggt cttaagtata caaaaattct taaagatgat  12540
ggcaattttg ttgttttgga gttagatcct ccttgtaaat ttactgttca agatgttaaa  12600
ggtcttaaaa ttaagtacct ttattttgta aaaggttgta acacactagc aagaggctgg  12660
gttgttggta caatttcttc tacagttaga ttgcaagctg gaactgctac tgagtatgct  12720
tccaactcat ctatattatc tttatgtgcg ttttctgtag atcctaagaa aacgtattta  12780
gattttatac aacagggagg aacacctatt gccaattgtg ttaaaatgtt gtgtgaccat  12840
gctggtaccg gtatggccat tactgttaaa cccgatgcta ccactagtca ggattcatat  12900
ggtggtgcgt ctgtttgtat atattgccgc gcacgagttg aacacccaga tgttgatggg  12960
ttgtgcaaat tacgcggcaa gtttgtacaa gtgcctgtag gtataaaaga tcctgtgtct  13020
tatgttttga cacatgatgt ttgtcaagtt tgtggatttt ggcgggatgg aagctgttca  13080
tgtgttagca ctgacactac tgttcagtca aaagatacta attttttaaa cgggttcggg  13140
gtacgagtgt agatgcccgt ctcgtaccct gtgccagtgg tttatctact gatgtacaat  13200
taagggcatt tgatatttgc aatgctagtg ttgctggcat tggtttacat ttaaaagtta  13260
attgctgccg ttttcagcgt gttgatgaga acggtgataa attagatcag ttctttgttg  13320
ttaagaggac agatctgact atatataata gagagatgga atgctatgag cgtgtaaaag  13380
attgtaagtt tgtggctgaa cacgatttct ttacatttga tgtagaaggt agtcgtgtgc  13440
cacacattgt acgcaaggat ttaacaaagt atactatgtt ggatctttgc tatgcattgc  13500
gacattttga tcgcaatgat tgcatgctgc tttgtgacat tctctctata tatgctggtt  13560
gtgaacaatc ctactttact aagaaggatt ggtatgattt tgttgaaaat cctgatatta  13620
```

-continued

```
ttaatgttta taaaaagcta ggacctattt ttaatagagc cctagttagc gctactgagt  13680
ttgcagacaa attggtggag gtaggcttag taggcatttt aacacttgat aaccaagatt  13740
taaatggtaa atggtatgat tttggtgact atgttattgc agccccaggg tgtggtgttg  13800
ctatagcaga ctcttattat tcttatatga tgcctatgct gaccatgtgt catgcattgg  13860
attgtgaatt gtatgtgaat aatgcttata gactatttga tcttgtacag tatgatttta  13920
ctgattacaa gctcgaattg tttaataagt attttaagca ctggagtatg ccataccatc  13980
ctaacacggt tgattgtcag gatgatcggt gtatcataca ttgtgctaat tttaacatac  14040
tttttagtat ggttttacct aatacatgtt ttgggcctct tgttaggcaa atttttgtgg  14100
atggtgtgcc ttttgttgtt tcaattggct accattataa agaacttggt attgtgatga  14160
acatggatgt ggatacacat cgttatcgct tgtctttaaa agacttgctt ttatatgctg  14220
ctgatccagc tttgcatgta gcttctgcta gtgcattgta tgatttacgc acttgctgtt  14280
ttagtgttgc ggctataaca agcggtgtaa aatttcaaac agttaaacct ggtaatttta  14340
atcaggattt ttatgatttt attttaagta agggcctgct taaagagggt agttcagttg  14400
atctgaagca ctttttcttt acgcaggatg gtaatgctgc tattactgat tataattatt  14460
ataagtacaa tttgcccacc atggtggaca ttaagcagtt gttgtttgtt ttggaagttg  14520
tttataagta ttttgagatt tatgatggtg ggtgtatacc ggcatcacaa gtcattgtta  14580
ataattatga taagagtgct ggctatccat ttaataaatt tggaaaagcc aggctctatt  14640
atgaagcatt atcatttgag gagcaggatg aaatttacgc ctatactaag cgcaatgtcc  14700
tgccaacact tactcaaatg aatttgaaat atgctattag tgctaagaat agagcccgca  14760
ctgttgctgg tgtttccata cttagtacta tgactggcag aatgtttcat caaaaatgtt  14820
tgaaaagtat agcagctaca cgtggtgttc ctgttgttat aggcaccact aagttttatg  14880
gcggctggga tgatatgtta cgtcgcctta ttaaagatgt tgataatcct gtacttatgg  14940
gttgggatta tcctaagtgt gatcgtgcta tgccaaacat actacgtatt gttagtagtc  15000
tggtcttggc ccgaaaacat gaggcatgtt gttcgcaaag cgataggttt tatcgacttg  15060
cgaatgaatg cgcacaagtt ctgagtgaaa ttgttatgtg tggtggctgt tattatgtta  15120
agcctggtgg cactagtagt ggtgatgcaa ctactgcttt tgctaattca gtttttaaca  15180
tatgtcaagc tgtttcagcc aatgtatgtg ctttaatgtc atgcaatggt aataagattg  15240
aagatttgag tatacgtgct cttcagaagc gcttatactc acatgtgtat agaagtgata  15300
tggttgattc aacctttgtc acagaatatt atgaattttt aaataagcat tttagtatga  15360
tgattttgag tgatgatggc gttgtgtgtt ataattctga ttatgcgtcc aaagggtata  15420
ttgctaatat aagtgccttt caacaggtat tgtattatca aaataacgtt tttatgtcag  15480
aatccaaatg ttgggttgaa aatgacataa acaatggacc tcatgaattt tgttcacaac  15540
atacaatgct tgtaaagatg gatggggacg atgtctatct tccatatcct gatcctagtc  15600
gtatattagg agctggatgt tttgtagatg atttgttaaa gactgatagt gttcttttaa  15660
tagaacgatt tgtaagtctt gcaatagatg cttatccact tgtgtaccac gaaaatgaag  15720
aataccaaaa ggtttttcgt gtttatttgg agtatataaa gaagttgtac aatgacctgg  15780
gtaatcagat cttggatagc tacagtgtta ttttaagtac ttgtgatgga caaaagttta  15840
ctgatgagtc cttttacaag aacatgtatt taagaagtgc agttatgcag agtgttggag  15900
cttgcgtggt ctgctcttcc caaacatcat tacgttgtgg cagttgcatc agaaagcctc  15960
```

-continued

```
ttctttgctg caagtgttgt tacgatcatg ttatggcaac tgatcataaa tatgttttga  16020
gtgtttcacc atatgtgtgt aacgcaccag gatgtgatgt aaatgatgtt accaaattgt  16080
atctaggtgg tatgtcatat tattgtgaag atcataagcc acaatattcg tttaagttgg  16140
taatgaatgg tatggttttt ggtctatata aacaatcttg tacaggatct ccgtacatag  16200
atgattttaa tcgtatagct agttgtaaat ggactgatgt tgatgattac atactggcta  16260
atgaatgtac agagcgcttg aaattgtttg ctgcagaaac gcaaaaggcg actgaggaag  16320
cctttaagca gagttatgca tcagcaacaa tacaagagat tgttagtgag cgcgaattga  16380
tcctctcttg ggagattgga aaagtgaagc caccacttaa taaaaattat gtttttactg  16440
gctaccattt tactaaaaat ggcaagacag ttttaggtga gtatgttttt gataagagtg  16500
agttgactaa tggtgtgtat tatcgcgcca caaccactta taagctatct gtaggagatg  16560
tttttgtttt aacctctcat tcagtagcta atttaagtgc tcctacgctt gtgccgcagg  16620
agaattatag tagtattaga tttgctagtg tttatagtgt gcttgagaca tttcagaaca  16680
atgttgtgaa ctatcaacac attggtatga aacgttattg caccgtgcaa ggacctcctg  16740
gtacaggaaa gtcacatctt gctattggtc ttgctgtata ttattgtaca gcacgtgtag  16800
tatacactgc ggccagccat gcagctgttg acgcattgtg tgaaaaagca tacaaatttt  16860
tgaatataaa tgattgcact cgtattgttc ctgccaaggt cagggtggag tgctatgata  16920
agtttaaaat taatgacacc actcgtaagt atgtgtttac tactataaat gcattacctg  16980
agatggtgac tgatattgtt gttgtagatg aagttagtat gcttaccaat tatgagcttt  17040
ctgttattaa tgctcgtatt cgcgctaagc attatgttta tattggtgat cctgctcaat  17100
tgccagcacc acgtgtgtta ttgagcaagg gtacacttga acctaaatat tttaacactg  17160
ttactaagct tatgtgttgc ttagggccag acatttttct tggtacatgt tatagatgtc  17220
ctaaggaaat cgttgataca gtgtctgcct tggtttatga aaataagctt aaggctaaga  17280
atgaaagtag ttcattgtgt tttaaggtct attataaagg cgttacaaca catgaaagtt  17340
ctagtgctgt aaatatgcag cagatttatt tgattaataa gtttttgaag gttaaccctt  17400
tgtggcataa agccgttttt attagcccat ataatagtca gaactttgca gctaagcgcg  17460
ttttgggttt gcaaacccaa accgtggatt ctgcgcaagg ttctgaatat gattatgtta  17520
tatattcaca gactgcagaa acagcgcatt ctgtaaatgt taatcgcttc aatgttgcta  17580
ttactcgagc caagaaaggt attctttgcg ttatgagtaa tatgcagttg tttgaagcat  17640
tacagtttac tacattgacc gtagataaag tgccacaggc cgttgaaacg agagttcaat  17700
gtagtaccaa tttatttaaa gattgtagca agagttatag tggttaccac ccagctcatg  17760
ctccttcatt tttggcagta gatgacaaat ataaggcaac tggcgattta gccgtgtgtc  17820
ttggtattgg agattctgct gttacatatt caagattaat atcactcatg ggttttaaac  17880
tggatgttac ccttgatggg tattgtaagc tttttataac taaagaagaa gctgttaaac  17940
gcgtgcgtgc ttgggttggc tttgatgctg aaggtgctca tgccacgcgt gatagcattg  18000
ggacaaattt cccacttcaa ttagggtttt ccacaggaat tgattttgtt gtggaagcca  18060
ctggtttgtt tgctgataga gatggttaca gctttaaaaa ggctgtggct aaagctcctc  18120
ctggtgaaca atttaagcat ctcatccctt tgatgacgag aggtcagcgc tgggatgttg  18180
ttagacctag aatagtacaa atgtttgcag atcatttaat tgatctgtct gattgtgttg  18240
tgctagttac atgggcagcc aactttgagc tcacttgtct ccgctacttt gcaaaagtag  18300
gtcgtgagat ctcttgtaat gtgtgcacta aacgtgccac agcttacaat tctagaactg  18360
```

-continued gttactatgg ttgttggcgc catagtgtta catgtgatta cttgtataat ccacttattg 18420
ttgatattca acagtgggga tatattggtt ctttatcaag taatcatgat ttatattgta 18480
gtgtccataa aggagcacat gttgcctcct ctgatgctat aatgacacgg tgtttggccg 18540
tttatgattg tttttgcaat aatattaatt ggaatgtgga gtatcccatc atttcaaatg 18600
agttaagtat taatacctct tgtagggtct tgcagcgtgt tatgcttaaa gctgccatgc 18660
tctgcaacag atatactttg tgttatgata ttggcaatcc aaaagcgatt gcctgtgtca 18720
aagattttga ttttaagttc tatgatgccc aaccaattgt taagtctgtc aagactcttt 18780
tgtatttttt tgaggcacat aaggactctt ttaaagatgg tttgtgtatg ttttggaact 18840
gtaatgtgga taagtatcca ccgaatgcag ttgtatgtag atttgacacg agagtgttga 18900
ataatttaaa tcttcctggc tgtaatggag gtagtttgta tgttaacaaa catgcattcc 18960
acactaaacc cttttctagg gcagcctttg agcatttgaa gcctatgcca tttttctatt 19020
attcagatac gccttgcgtg tatatggatg gcatggatgc taagcaggtt gattatgtac 19080
ctttgaaatc cgccacttgc atcacaagat gcaatttagg tggtgcagtt tgtttaaaac 19140
atgctgaaga gtatcgtgag tacctagagt cttacaatac agctactaca gcaggtttta 19200
ctttttgggt ctataagaca tttgattttt ataatttgtg gaatacgttc accaagctac 19260
aaagcttgga gaatgttgta tataatttag tcaagactgg tcattataca ggacaggctg 19320
gtgaaatgcc ttgtgccatt ataaatgata aagttgtggc taagatcgat aaggaggatg 19380
ttgtcatttt tattaataat acaacatatc ctactaatgt ggctgttgaa ttatttgcca 19440
agcgcagtat tcgacaccat ccagagctta agctctttag aaatttgaat atagacgtgt 19500
gctggaagca cgtcatttgg gattatgcta gagaaagtat attttgcagt aatacctatg 19560
gtgtctgcat gtatacagat ttaaagttca ttgataaatt gaatgtcctt tttgatggtc 19620
gtgataatgg tgctcttgaa gcttttaaac gctctaataa tggcgtttac atttccacga 19680
caaaagttaa gagtctttcg atgataagag gtccaccgcg tgctgaatta aatggcgtag 19740
tggtggacaa ggttggagac acagattgtg tgttttattt tgctgtgcgt aaagagggtc 19800
aggatgtcat cttcagccaa ttcgacagcc tgagagtcag ctctaaccag agcccacaag 19860
gtaatctggg gagtaatgaa cccggtaatg tcggtggtaa tgatgctctg gcaacctcca 19920
ctatctttac acaaagccgt gttattagct cttttacatg tcgtactgat atggaaaaag 19980
attttatagc tttagatcaa gatgtgttta ttcagaagta tggtttggag gactatgcct 20040
ttgaacacat tgtttatggt aatttcaacc agaagattat tggtggtttg catttgttaa 20100
taggcttgta ccgaagacag caaacttcca atttggttat tcaggagttt gtttcatacg 20160
actccagcat acactcttat tttatcactg atgagaagag tggtggtagt aagagtgttt 20220
gcactgttat agatattttg ttggatgatt ttgtggctct tgtcaagtca cttaatctta 20280
actgtgtgag taaggttgtt aatgttaatg ttgattttaa agattttcag ttcatgcttt 20340
ggtgtaacga tgagaaagtt atgactttct atcctcgttt gcaagctgca tctgactgga 20400
agcctggtta ttctatgcct gtattatata agtatttgaa ttccccaatg gaaagagtta 20460
gtctctggaa ttatgggaag ccagttactt tgcctacagg ctgtatgatg aatgttgcta 20520
agtatactca gttatgtcaa tatctgaata ctacaacatt agctgtacct gttaatatgc 20580
gagttttgca tttaggtgca ggttcagaaa aaggagtagc accgggttct gcagttctta 20640
ggcagtggtt gcctgctggt actattcttg tagataatga tttataccca tttgtgagtg 20700

```
acagtgtcgc tacatatttt ggggattgta taaccttacc ctttgattgt caatgggatt  20760

tgataatctc tgatatgtat gaccctatta ctaagaacat aggggagtac aatgtaagta  20820

aagatggttt ctttacatac atttgtcata tgattcgcga caagttagct ctgggtggca  20880

gtgttgctat aaaaataaca gagttttctt ggaatgcaga attatataag ttaatggggt  20940

attttgcatt ttggacggtt ttctgcacaa atgcaaatgc ttcttctagt gaagggtttt  21000

taattggcat aaattatttg ggtaagccca aggttgagat agatggaaat gttatgcatg  21060

ccaattattt gttttggaga aattccacag tttggaacgg gggtgcttat agcctgtttg  21120

atatggctaa attcccgctt aagttggctg gtactgccgt aataaattta agagcagacc  21180

agattaatga tatggtttat tcccttcttg aaaagggtaa actacttgtt agagatacaa  21240

ataaagaagt tttgttggt gacagtatgg ttaatgtaat ctaa                    21284


<210> SEQ ID NO 12
<211> LENGTH: 7094
<212> TYPE: PRT
<213> ORGANISM: Bovine coronavirus

<400> SEQUENCE: 12

Met Ser Lys Ile Asn Lys Tyr Gly Leu Glu Leu His Trp Ala Pro Glu
1               5                   10                  15

Phe Pro Trp Met Phe Glu Asp Ala Glu Glu Lys Leu Asp Asn Pro Ser
            20                  25                  30

Ser Ser Glu Val Asp Ile Val Cys Ser Thr Thr Ala Gln Lys Leu Glu
        35                  40                  45

Thr Gly Gly Ile Cys Pro Glu Asn His Val Met Val Asp Cys Arg Arg
    50                  55                  60

Leu Leu Lys Gln Glu Cys Cys Val Gln Ser Ser Leu Ile Arg Glu Ile
65                  70                  75                  80

Val Met Asn Thr Arg Pro Tyr Asp Leu Glu Val Leu Leu Gln Asp Ala
                85                  90                  95

Leu Gln Ser Cys Glu Ala Val Leu Val Thr Pro Pro Leu Gly Met Ser
            100                 105                 110

Leu Glu Ala Cys Tyr Val Arg Gly Cys Asn Pro Asn Gly Trp Thr Met
        115                 120                 125

Gly Leu Phe Arg Arg Arg Ser Val Cys Asn Thr Gly Arg Cys Ala Val
    130                 135                 140

Asn Lys His Val Ala Tyr Gln Leu Tyr Met Ile Asp Pro Ala Gly Val
145                 150                 155                 160

Cys Phe Gly Ala Gly Gln Phe Val Gly Trp Val Ile Pro Leu Ala Phe
                165                 170                 175

Met Pro Val Gln Ser Arg Lys Phe Ile Val Pro Arg Val Met Tyr Leu
            180                 185                 190

Arg Lys Cys Gly Glu Lys Gly Ala Tyr Asn Lys Asp His Lys Arg Gly
        195                 200                 205

Gly Phe Glu His Val Tyr Asn Phe Lys Val Glu Asp Ala Tyr Asp Leu
    210                 215                 220

Val His Asp Glu Pro Lys Gly Lys Phe Ser Lys Lys Ala Tyr Ala Leu
225                 230                 235                 240

Ile Arg Gly Tyr Arg Gly Val Lys Pro Leu Leu Tyr Val Asp Gln Tyr
                245                 250                 255

Gly Cys Asp Tyr Thr Gly Gly Leu Ala Asp Gly Leu Glu Ala Tyr Ala
            260                 265                 270
```

Asp Lys Thr Leu Gln Glu Met Lys Ala Leu Phe Pro Ile Trp Ser Gln
        275                 280                 285

Glu Leu Pro Phe Asp Val Thr Val Ala Trp His Val Val Arg Asp Pro
    290                 295                 300

Arg Tyr Val Met Arg Leu Gln Ser Ala Ser Thr Ile Arg Ser Val Ala
305                 310                 315                 320

Tyr Val Ala Asn Pro Thr Glu Asp Leu Cys Asp Gly Ser Val Val Ile
                325                 330                 335

Lys Glu Pro Val His Val Tyr Ala Asp Asp Ser Ile Ile Leu Arg Gln
            340                 345                 350

His Asn Leu Val Asp Ile Met Ser Cys Phe Tyr Met Glu Ala Asp Ala
        355                 360                 365

Val Val Asn Ala Phe Tyr Gly Val Asp Leu Lys Asp Cys Gly Phe Val
    370                 375                 380

Met Gln Phe Gly Tyr Ile Asp Cys Glu Gln Asp Leu Cys Asp Phe Lys
385                 390                 395                 400

Gly Trp Val Pro Gly Asn Met Ile Asp Gly Phe Ala Cys Thr Thr Cys
                405                 410                 415

Gly His Val Tyr Glu Thr Gly Asp Leu Leu Ala Gln Ser Ser Gly Val
            420                 425                 430

Leu Pro Val Asn Pro Val Leu His Thr Lys Ser Ala Ala Gly Tyr Gly
        435                 440                 445

Gly Phe Gly Cys Lys Asp Ser Phe Thr Leu Tyr Gly Gln Thr Val Val
    450                 455                 460

Tyr Phe Gly Gly Cys Val Tyr Trp Ser Pro Ala Arg Asn Ile Trp Ile
465                 470                 475                 480

Pro Ile Leu Lys Ser Ser Val Lys Ser Tyr Asp Gly Leu Val Tyr Thr
                485                 490                 495

Gly Val Val Gly Cys Lys Ala Ile Val Lys Glu Thr Asn Leu Ile Cys
            500                 505                 510

Lys Ala Leu Tyr Leu Asp Tyr Val Gln His Lys Cys Gly Asn Leu His
        515                 520                 525

Gln Arg Glu Leu Leu Gly Val Ser Asp Val Trp His Lys Gln Leu Leu
    530                 535                 540

Leu Asn Arg Gly Val Tyr Lys Pro Leu Leu Glu Asn Ile Asp Tyr Phe
545                 550                 555                 560

Asn Met Arg Arg Ala Lys Phe Ser Leu Glu Thr Phe Thr Val Cys Ala
                565                 570                 575

Asp Gly Phe Met Pro Phe Leu Leu Asp Asp Leu Val Pro Arg Ala Tyr
            580                 585                 590

Tyr Leu Ala Val Ser Gly Gln Ala Phe Cys Asp Tyr Ala Gly Lys Ile
        595                 600                 605

Cys His Ala Val Val Ser Lys Ser Lys Glu Leu Leu Asp Val Ser Leu
    610                 615                 620

Asp Ser Leu Gly Ala Ala Ile His Tyr Leu Asn Ser Lys Ile Val Asp
625                 630                 635                 640

Leu Ala Gln His Phe Ser Asp Phe Gly Thr Ser Phe Val Ser Lys Ile
                645                 650                 655

Val His Phe Phe Lys Thr Phe Thr Thr Ser Thr Ala Leu Ala Phe Ala
            660                 665                 670

Trp Val Leu Phe His Val Leu His Gly Ala Tyr Ile Val Val Glu Ser
        675                 680                 685

Asp Ile Tyr Phe Val Lys Asn Ile Pro Arg Tyr Ala Ser Ala Val Ala

-continued

```
    690                 695                 700

Gln Ala Phe Arg Ser Val Ala Lys Val Val Leu Asp Ser Leu Arg Val
705                 710                 715                 720

Thr Phe Ile Asp Gly Leu Ser Cys Phe Lys Ile Gly Arg Arg Arg Ile
                725                 730                 735

Cys Leu Ser Gly Ser Lys Ile Tyr Glu Val Glu Arg Gly Leu Leu His
            740                 745                 750

Ser Ser Gln Leu Pro Leu Asp Val Tyr Asp Leu Thr Met Pro Ser Gln
        755                 760                 765

Val Gln Lys Thr Lys Gln Lys Pro Ile Tyr Leu Lys Gly Ser Gly Ser
    770                 775                 780

Asp Phe Ser Leu Ala Asp Ser Val Val Glu Val Val Thr Thr Ser Leu
785                 790                 795                 800

Thr Pro Cys Gly Tyr Ser Glu Pro Pro Lys Val Ala Asp Lys Ile Cys
                805                 810                 815

Ile Val Asp Asn Val Tyr Met Ala Lys Ala Gly Asp Lys Tyr Tyr Pro
            820                 825                 830

Val Val Val Asp Gly His Val Gly Leu Leu Asp Gln Ala Trp Arg Val
        835                 840                 845

Pro Cys Ala Gly Arg Arg Val Thr Phe Lys Glu Gln Pro Thr Val Asn
    850                 855                 860

Glu Ile Ala Ser Thr Pro Lys Thr Ile Lys Val Phe Tyr Glu Leu Asp
865                 870                 875                 880

Lys Asp Phe Asn Thr Ile Leu Asn Thr Ala Cys Gly Val Phe Glu Val
                885                 890                 895

Asp Asp Thr Val Asp Met Glu Glu Phe Tyr Ala Val Val Ile Asp Ala
            900                 905                 910

Ile Glu Glu Lys Leu Ser Pro Cys Lys Glu Leu Glu Gly Val Gly Ala
        915                 920                 925

Lys Val Ser Ala Phe Leu Gln Lys Leu Glu Asp Asn Ser Leu Phe Leu
    930                 935                 940

Phe Asp Glu Ala Gly Glu Glu Val Leu Ala Pro Lys Leu Tyr Cys Ala
945                 950                 955                 960

Phe Thr Ala Pro Glu Asp Asp Asp Phe Leu Glu Glu Ser Gly Val Glu
                965                 970                 975

Glu Asp Asp Val Glu Gly Glu Glu Thr Asp Leu Thr Val Thr Ser Ala
            980                 985                 990

Gly Glu Pro Cys Val Ala Ser Glu  Gln Glu Glu Ser Ser  Glu Ile Leu
        995                 1000                1005

Glu Asp  Thr Leu Asp Asp Gly  Pro Cys Val Glu Thr  Ser Asp Ser
    1010                1015                1020

Gln Val  Glu Glu Asp Val Gln  Met Ser Asp Phe Val  Asp Leu Glu
    1025                1030                1035

Ser Val  Ile Gln Asp Tyr Glu  Asn Val Cys Phe Glu  Phe Tyr Thr
    1040                1045                1050

Thr Glu  Pro Glu Phe Val Lys  Val Leu Asp Leu Tyr  Val Pro Lys
    1055                1060                1065

Ala Thr  Arg Asn Asn Cys Trp  Leu Arg Ser Val Leu  Ala Val Met
    1070                1075                1080

Gln Lys  Leu Pro Cys Gln Phe  Lys Asp Lys Asn Leu  Gln Asp Leu
    1085                1090                1095

Trp Val  Leu Tyr Lys Gln Gln  Tyr Ser Gln Leu Phe  Val Asp Thr
    1100                1105                1110
```

-continued

```
Leu Val  Asn Lys Ile Pro Ala  Asn Ile Val Val Pro  Gln Gly Gly
    1115                 1120                 1125

Tyr Val  Ala Asp Phe Ala Tyr  Trp Phe Leu Thr Leu  Cys Asp Trp
    1130                 1135                 1140

Gln Cys  Val Ala Tyr Trp Lys  Cys Ile Lys Cys Asp  Leu Ala Leu
    1145                 1150                 1155

Lys Leu  Lys Gly Leu Asp Ala  Met Phe Phe Tyr Gly  Asp Val Val
    1160                 1165                 1170

Ser His  Val Cys Lys Cys Gly  Glu Ser Met Val Leu  Ile Asp Val
    1175                 1180                 1185

Asp Val  Pro Phe Thr Ala His  Phe Ala Leu Lys Asp  Lys Leu Phe
    1190                 1195                 1200

Cys Ala  Phe Ile Thr Lys Arg  Ser Val Tyr Lys Ala  Ala Cys Val
    1205                 1210                 1215

Val Ala  Val Asn Asp Ser His  Ser Met Ala Val Val  Asp Gly Lys
    1220                 1225                 1230

Gln Ile  Asp Asp His Cys Ile  Thr Ser Ile Thr Ser  Asp Lys Phe
    1235                 1240                 1245

Asp Phe  Ile Ile Gly His Gly  Met Ser Phe Ser Met  Thr Thr Phe
    1250                 1255                 1260

Glu Ile  Ala Gln Leu Tyr Gly  Ser Cys Ile Thr Pro  Asn Val Cys
    1265                 1270                 1275

Phe Val  Lys Gly Asp Ile Ile  Lys Val Ser Lys Arg  Val Lys Ala
    1280                 1285                 1290

Glu Val  Val Val Asn Pro Ala  Asn Gly His Met Ala  His Gly Gly
    1295                 1300                 1305

Gly Val  Ala Lys Ala Ile Ala  Val Ala Ala Gly Gln  Gln Phe Val
    1310                 1315                 1320

Lys Glu  Thr Thr Asp Met Val  Lys Ser Lys Gly Val  Cys Ala Thr
    1325                 1330                 1335

Gly Asp  Cys Tyr Val Ser Thr  Gly Gly Lys Leu Cys  Lys Thr Val
    1340                 1345                 1350

Leu Asn  Val Val Gly Pro Asp  Ala Arg Thr Gln Gly  Lys Gln Ser
    1355                 1360                 1365

Tyr Ala  Leu Leu Glu Arg Val  Tyr Lys His Leu Asn  Lys Tyr Asp
    1370                 1375                 1380

Cys Val  Val Thr Thr Leu Ile  Ser Ala Gly Ile Phe  Ser Val Pro
    1385                 1390                 1395

Ser Asp  Val Ser Leu Thr Tyr  Leu Leu Gly Thr Ala  Lys Lys Gln
    1400                 1405                 1410

Val Val  Leu Val Ser Asn Asn  Gln Glu Asp Phe Asp  Leu Ile Ser
    1415                 1420                 1425

Lys Cys  Gln Ile Thr Ala Val  Glu Gly Thr Lys Lys  Leu Ala Glu
    1430                 1435                 1440

Arg Leu  Ser Phe Asn Val Gly  Arg Ser Ile Val Tyr  Glu Thr Asp
    1445                 1450                 1455

Ala Asn  Lys Leu Ile Leu Ser  Asn Asp Val Ala Phe  Val Ser Thr
    1460                 1465                 1470

Phe Asn  Val Leu Gln Asp Val  Leu Ser Leu Arg His  Asp Ile Ala
    1475                 1480                 1485

Leu Asp  Asp Asp Ala Arg Thr  Phe Val Gln Ser Asn  Val Asp Val
    1490                 1495                 1500
```

-continued

Val Pro Glu Gly Trp Arg Val Val Asn Lys Phe Tyr Gln Ile Asn
    1505                1510                1515

Gly Val Arg Thr Val Lys Tyr Phe Glu Cys Pro Gly Gly Ile Asp
    1520                1525                1530

Ile Cys Ser Gln Asp Lys Val Phe Gly Tyr Val Gln Gln Gly Ser
    1535                1540                1545

Phe Asn Lys Ala Thr Val Ala Gln Ile Lys Ala Leu Phe Leu Asp
    1550                1555                1560

Lys Val Asp Ile Leu Leu Thr Val Asp Gly Val Asn Phe Thr Asn
    1565                1570                1575

Arg Phe Val Pro Val Gly Glu Ser Phe Gly Lys Ser Leu Gly Asn
    1580                1585                1590

Val Phe Cys Asp Gly Val Asn Val Thr Lys His Lys Cys Asp Ile
    1595                1600                1605

Asn Tyr Lys Gly Lys Val Phe Phe Gln Phe Asp Asn Leu Ser Ser
    1610                1615                1620

Glu Asp Leu Lys Ala Val Arg Ser Ser Phe Asn Phe Asp Gln Lys
    1625                1630                1635

Glu Leu Leu Ala Tyr Tyr Asn Met Leu Val Asn Cys Ser Lys Trp
    1640                1645                1650

Gln Val Val Phe Asn Gly Lys Tyr Phe Thr Phe Lys Gln Ala Asn
    1655                1660                1665

Asn Asn Cys Phe Val Asn Val Ser Cys Leu Met Leu Gln Ser Leu
    1670                1675                1680

Asn Leu Lys Phe Lys Ile Val Gln Trp Gln Glu Ala Trp Leu Glu
    1685                1690                1695

Phe Arg Ser Gly Arg Pro Ala Arg Phe Val Ser Leu Val Leu Ala
    1700                1705                1710

Lys Gly Gly Phe Lys Phe Gly Asp Pro Ala Asp Ser Arg Asp Phe
    1715                1720                1725

Leu Arg Val Val Phe Ser Gln Val Asp Leu Thr Gly Ala Ile Cys
    1730                1735                1740

Asp Phe Glu Ile Ala Cys Lys Cys Gly Val Lys Gln Glu Gln Arg
    1745                1750                1755

Thr Gly Val Asp Ala Val Met His Phe Gly Thr Leu Ser Arg Glu
    1760                1765                1770

Asp Leu Glu Ile Gly Tyr Thr Val Asp Cys Ser Cys Gly Lys Lys
    1775                1780                1785

Leu Ile His Cys Val Arg Phe Asp Val Pro Phe Leu Ile Cys Ser
    1790                1795                1800

Asn Thr Pro Ala Ser Val Lys Leu Pro Lys Gly Val Gly Ser Ala
    1805                1810                1815

Asn Ile Phe Lys Gly Asp Lys Val Gly His Tyr Val His Val Lys
    1820                1825                1830

Cys Glu Gln Ser Tyr Gln Leu Tyr Asp Ala Ser Asn Val Lys Lys
    1835                1840                1845

Val Thr Asp Val Thr Gly Asn Leu Ser Asp Cys Leu Tyr Leu Lys
    1850                1855                1860

Asn Leu Lys Gln Thr Phe Lys Ser Val Leu Thr Thr Tyr Tyr Leu
    1865                1870                1875

Asp Asp Val Lys Lys Ile Glu Tyr Lys Pro Asp Leu Ser Gln Tyr
    1880                1885                1890

Tyr Cys Asp Gly Gly Lys Tyr Tyr Thr Gln Arg Ile Ile Lys Ala

-continued

```
    1895                1900                1905

Gln Phe  Lys Thr Phe Glu Lys  Val Asp Gly Val Tyr  Thr Asn Phe
    1910                1915                1920

Lys Leu  Ile Gly His Thr Val  Cys Asp Ile Leu Asn  Ala Lys Leu
    1925                1930                1935

Gly Phe  Asp Ser Ser Lys Glu  Phe Val Glu Tyr Lys  Val Thr Glu
    1940                1945                1950

Trp Pro  Thr Ala Thr Gly Asp  Val Val Leu Ala Thr  Asp Asp Leu
    1955                1960                1965

Tyr Val  Lys Arg Tyr Glu Arg  Gly Cys Ile Thr Phe  Gly Lys Pro
    1970                1975                1980

Val Ile  Trp Leu Ser His Glu  Gln Ala Ser Leu Asn  Ser Leu Thr
    1985                1990                1995

Tyr Phe  Asn Arg Pro Leu Leu  Val Asp Glu Asn Lys  Phe Asp Val
    2000                2005                2010

Leu Lys  Val Asp Asp Val Asp  Asp Gly Gly Asp Ile  Ser Glu Ser
    2015                2020                2025

Asp Ala  Lys Glu Pro Lys Glu  Ile Asn Ile Ile Lys  Leu Ser Gly
    2030                2035                2040

Val Lys  Lys Pro Phe Lys Val  Glu Asp Ser Val Ile  Val Asn Asp
    2045                2050                2055

Asp Thr  Ser Glu Ile Lys Tyr  Val Lys Ser Leu Ser  Ile Val Asp
    2060                2065                2070

Val Tyr  Asp Met Trp Leu Thr  Gly Cys Arg Cys Val  Val Arg Thr
    2075                2080                2085

Ala Asn  Ala Leu Ser Arg Ala  Val Asn Val Pro Thr  Ile Arg Lys
    2090                2095                2100

Phe Ile  Lys Phe Gly Met Thr  Leu Val Ser Ile Pro  Ile Asp Leu
    2105                2110                2115

Leu Asn  Leu Arg Glu Ile Lys  Pro Val Phe Asn Val  Val Lys Ala
    2120                2125                2130

Val Arg  Asn Lys Ile Ser Ala  Cys Phe Asn Phe Ile  Lys Trp Leu
    2135                2140                2145

Phe Val  Leu Leu Phe Gly Trp  Ile Lys Ile Ser Ala  Asp Asn Lys
    2150                2155                2160

Val Ile  Tyr Thr Thr Glu Val  Ala Ser Lys Leu Thr  Cys Lys Leu
    2165                2170                2175

Val Ala  Leu Ala Phe Lys Asn  Ala Phe Leu Thr Phe  Lys Trp Ser
    2180                2185                2190

Val Val  Ala Arg Gly Ala Cys  Ile Ile Ala Thr Ile  Phe Leu Leu
    2195                2200                2205

Trp Phe  Asn Phe Ile Tyr Ala  Asn Val Ile Phe Ser  Asp Phe Tyr
    2210                2215                2220

Leu Pro  Lys Ile Gly Phe Leu  Pro Thr Phe Val Gly  Lys Ile Ala
    2225                2230                2235

Gln Trp  Ile Lys Asn Thr Phe  Ser Leu Val Thr Ile  Cys Asp Leu
    2240                2245                2250

Tyr Ser  Ile Gln Asp Val Gly  Phe Lys Asn Gln Tyr  Cys Asn Gly
    2255                2260                2265

Ser Ile  Ala Cys Gln Phe Cys  Leu Ala Gly Phe Asp  Met Leu Asp
    2270                2275                2280

Asn Tyr  Lys Ala Ile Asp Val  Val Gln Tyr Glu Ala  Asp Arg Arg
    2285                2290                2295
```

```
Ala Phe  Val Asp Tyr Thr Gly  Val Leu Lys Ile Val  Ile Glu Leu
    2300                 2305                 2310

Ile Val  Ser Tyr Ala Leu Tyr  Thr Ala Trp Phe Tyr  Pro Leu Phe
    2315                 2320                 2325

Ala Leu  Ile Ser Ile Gln Ile  Leu Thr Thr Trp Leu  Pro Glu Leu
    2330                 2335                 2340

Phe Met  Leu Ser Thr Leu His  Trp Ser Val Arg Leu  Leu Val Ser
    2345                 2350                 2355

Leu Ala  Asn Met Leu Pro Ala  His Val Phe Met Arg  Phe Tyr Ile
    2360                 2365                 2370

Ile Ile  Ala Ser Phe Ile Lys  Leu Phe Ser Leu Phe  Arg His Val
    2375                 2380                 2385

Ala Tyr  Gly Cys Ser Lys Ser  Gly Cys Leu Phe Cys  Tyr Lys Arg
    2390                 2395                 2400

Asn Arg  Ser Leu Arg Val Lys  Cys Ser Thr Ile Val  Gly Gly Met
    2405                 2410                 2415

Ile Arg  Tyr Tyr Asp Val Met  Ala Asn Gly Gly Thr  Gly Phe Cys
    2420                 2425                 2430

Ser Lys  His Gln Trp Asn Cys  Ile Asp Cys Asp Ser  Tyr Lys Pro
    2435                 2440                 2445

Gly Asn  Thr Phe Ile Thr Val  Glu Ala Ala Leu Asp  Leu Ser Lys
    2450                 2455                 2460

Glu Leu  Lys Arg Pro Ile Gln  Pro Thr Asp Val Ala  Tyr His Thr
    2465                 2470                 2475

Val Thr  Asp Val Lys Gln Val  Gly Cys Tyr Met Arg  Leu Phe Tyr
    2480                 2485                 2490

Asp Arg  Asp Gly Gln Arg Thr  Tyr Asp Asp Val Asn  Ala Ser Leu
    2495                 2500                 2505

Phe Val  Asp Tyr Ser Asn Leu  Leu His Ser Lys Val  Lys Ser Val
    2510                 2515                 2520

Pro Asn  Met His Val Val Val  Val Glu Asn Asp Ala  Asp Lys Ala
    2525                 2530                 2535

Asn Phe  Leu Asn Ala Ala Val  Phe Tyr Ala Gln Ser  Leu Phe Arg
    2540                 2545                 2550

Pro Ile  Leu Met Val Asp Lys  Asn Leu Ile Thr Thr  Ala Asn Thr
    2555                 2560                 2565

Gly Thr  Ser Val Thr Glu Thr  Met Phe Asp Val Tyr  Val Asp Thr
    2570                 2575                 2580

Phe Leu  Ser Met Phe Asp Val  Asp Lys Lys Ser Leu  Asn Ala Leu
    2585                 2590                 2595

Ile Ala  Thr Ala His Ser Ser  Ile Lys Gln Gly Thr  Gln Ile Cys
    2600                 2605                 2610

Lys Val  Leu Asp Thr Phe Leu  Ser Cys Ala Arg Lys  Ser Cys Ser
    2615                 2620                 2625

Ile Asp  Ser Asp Val Asp Thr  Lys Cys Leu Ala Asp  Ser Val Met
    2630                 2635                 2640

Ser Ala  Val Ser Ala Gly Leu  Glu Leu Thr Asp Glu  Ser Cys Asn
    2645                 2650                 2655

Asn Leu  Val Pro Thr Tyr Leu  Lys Gly Asp Asn Ile  Val Ala Ala
    2660                 2665                 2670

Asp Leu  Gly Val Leu Ile Gln  Asn Ser Ala Lys His  Val Gln Gly
    2675                 2680                 2685
```

```
Asn Val  Ala Lys Ile Ala Gly  Val Ser Cys Ile Trp  Ser Val Asp
    2690                 2695                 2700

Ala Phe  Asn Gln Leu Ser Ser  Asp Phe Gln His Lys  Leu Lys Lys
    2705                 2710                 2715

Ala Cys  Cys Lys Thr Ser Leu  Lys Leu Lys Leu Thr  Tyr Asn Lys
    2720                 2725                 2730

Gln Met  Ala Asn Val Ser Val  Leu Thr Thr Pro Phe  Ser Leu Lys
    2735                 2740                 2745

Gly Gly  Ala Val Phe Ser Tyr  Phe Val Tyr Val Cys  Phe Val Leu
    2750                 2755                 2760

Ser Leu  Val Cys Phe Ile Gly  Leu Trp Cys Leu Met  Pro Thr Tyr
    2765                 2770                 2775

Thr Val  His Lys Ser Asp Phe  Gln Leu Pro Val Tyr  Ala Ser Tyr
    2780                 2785                 2790

Lys Val  Leu Asp Asn Gly Val  Ile Arg Asp Val Ser  Val Glu Asp
    2795                 2800                 2805

Val Cys  Phe Ala Asn Lys Phe  Glu Gln Phe Asp Gln  Trp Tyr Glu
    2810                 2815                 2820

Ser Thr  Phe Gly Leu Ser Tyr  Tyr Ser Asn Ser Met  Ala Cys Pro
    2825                 2830                 2835

Ile Val  Val Ala Val Val Asp  Gln Asp Phe Gly Ser  Thr Val Phe
    2840                 2845                 2850

Asn Val  Pro Thr Lys Val Leu  Arg Tyr Gly Tyr His  Val Leu His
    2855                 2860                 2865

Phe Ile  Thr His Ala Leu Ser  Ala Asp Gly Val Gln  Cys Tyr Thr
    2870                 2875                 2880

Pro His  Ser Gln Ile Ser Tyr  Ser Asn Phe Tyr Ala  Ser Gly Cys
    2885                 2890                 2895

Val Leu  Ser Ser Ala Cys Thr  Met Phe Ala Met Ala  Asp Gly Ser
    2900                 2905                 2910

Pro Gln  Pro Tyr Cys Tyr Thr  Asp Gly Leu Met Gln  Asn Ala Ser
    2915                 2920                 2925

Leu Tyr  Ser Ser Leu Val Pro  His Val Arg Tyr Asn  Leu Ala Asn
    2930                 2935                 2940

Ala Lys  Gly Phe Ile Arg Phe  Pro Glu Val Leu Arg  Glu Gly Leu
    2945                 2950                 2955

Val Arg  Ile Val Arg Thr Arg  Ser Met Ser Tyr Cys  Arg Val Gly
    2960                 2965                 2970

Leu Cys  Glu Glu Ala Asp Glu  Gly Ile Cys Phe Asn  Phe Asn Gly
    2975                 2980                 2985

Ser Trp  Val Leu Asn Asn Asp  Tyr Tyr Arg Ser Leu  Pro Gly Thr
    2990                 2995                 3000

Phe Cys  Gly Arg Asp Val Phe  Asp Leu Ile Tyr Gln  Leu Phe Lys
    3005                 3010                 3015

Gly Leu  Ala Gln Pro Val Asp  Phe Leu Ala Leu Thr  Ala Ser Ser
    3020                 3025                 3030

Ile Ala  Gly Ala Ile Leu Ala  Val Ile Val Val Leu  Val Phe Tyr
    3035                 3040                 3045

Tyr Leu  Ile Lys Leu Lys Arg  Ala Phe Gly Asp Tyr  Thr Ser Ile
    3050                 3055                 3060

Val Phe  Val Asn Val Ile Val  Trp Cys Val Asn Phe  Met Met Leu
    3065                 3070                 3075

Phe Val  Phe Gln Val Tyr Pro  Thr Leu Ser Cys Val  Tyr Ala Ile
```

```
    3080                3085                3090

Cys Tyr  Phe Tyr Ala Thr Leu  Tyr Phe Pro Ser Glu  Ile Ser Val
    3095                3100                3105

Ile Met  His Leu Gln Trp Leu  Val Met Tyr Gly Thr  Ile Met Pro
    3110                3115                3120

Leu Trp  Phe Cys Leu Leu Tyr  Ile Ser Val Val Val  Ser Asn His
    3125                3130                3135

Ala Phe  Trp Val Phe Ser Tyr  Cys Arg Gln Leu Gly  Thr Ser Val
    3140                3145                3150

Arg Ser  Asp Gly Thr Phe Glu  Glu Met Ala Leu Thr  Thr Phe Met
    3155                3160                3165

Ile Thr  Lys Asp Ser Tyr Cys  Lys Leu Lys Asn Ser  Leu Ser Asp
    3170                3175                3180

Val Ala  Phe Asn Arg Tyr Leu  Ser Leu Tyr Asn Lys  Tyr Arg Tyr
    3185                3190                3195

Tyr Ser  Gly Lys Met Asp Thr  Ala Ala Tyr Arg Glu  Ala Ala Cys
    3200                3205                3210

Ser Gln  Leu Ala Lys Ala Met  Asp Thr Phe Thr Asn  Asn Asn Gly
    3215                3220                3225

Ser Asp  Val Leu Tyr Gln Pro  Pro Thr Ala Ser Val  Ser Thr Ser
    3230                3235                3240

Phe Leu  Gln Ser Gly Ile Val  Lys Met Val Asn Pro  Thr Ser Lys
    3245                3250                3255

Val Glu  Pro Cys Ile Val Ser  Val Thr Tyr Gly Asn  Met Thr Leu
    3260                3265                3270

Asn Gly  Leu Trp Leu Asp Asp  Lys Val Tyr Cys Pro  Arg His Val
    3275                3280                3285

Ile Cys  Ser Ala Ser Asp Met  Thr Tyr Pro Asp Tyr  Thr Asn Leu
    3290                3295                3300

Leu Cys  Arg Val Thr Ser Ser  Asp Phe Thr Val Leu  Phe Asp Arg
    3305                3310                3315

Leu Ser  Leu Thr Val Met Ser  Tyr Gln Met Gln Gly  Cys Met Leu
    3320                3325                3330

Val Leu  Thr Val Thr Leu Gln  Asn Ser Arg Thr Pro  Lys Tyr Thr
    3335                3340                3345

Phe Gly  Val Val Lys Pro Gly  Glu Thr Phe Thr Val  Leu Ala Ala
    3350                3355                3360

Tyr Asn  Gly Lys Pro Gln Gly  Ala Phe His Val Thr  Met Arg Ser
    3365                3370                3375

Ser Tyr  Thr Ile Lys Gly Ser  Phe Leu Cys Gly Ser  Cys Gly Ser
    3380                3385                3390

Val Gly  Tyr Val Ile Met Gly  Asp Cys Val Lys Phe  Val Tyr Met
    3395                3400                3405

His Gln  Leu Glu Leu Ser Thr  Gly Cys His Thr Gly  Thr Asp Phe
    3410                3415                3420

Asn Gly  Asp Phe Tyr Gly Pro  Tyr Lys Asp Ala Gln  Val Val Gln
    3425                3430                3435

Leu Pro  Val Gln Asp Tyr Ile  Gln Ser Val Asn Phe  Val Ala Trp
    3440                3445                3450

Leu Tyr  Ala Ala Ile Leu Asn  Asn Cys Asn Trp Phe  Val Gln Ser
    3455                3460                3465

Asp Lys  Cys Ser Val Glu Asp  Phe Asn Val Trp Ala  Leu Ser Asn
    3470                3475                3480
```

```
Gly Phe Ser Gln Val Lys Ser Asp Leu Val Ile Asp Ala Leu Ala
    3485                3490                3495

Ser Met Thr Gly Val Ser Leu Glu Thr Leu Leu Ala Ala Ile Lys
    3500                3505                3510

Arg Leu Lys Asn Gly Phe Gln Gly Arg Gln Ile Met Gly Ser Cys
    3515                3520                3525

Ser Phe Glu Asp Glu Leu Thr Pro Ser Asp Val Tyr Gln Gln Leu
    3530                3535                3540

Ala Gly Ile Lys Leu Gln Ser Lys Arg Thr Arg Leu Val Lys Gly
    3545                3550                3555

Ile Val Cys Trp Ile Met Ala Ser Thr Phe Leu Phe Ser Cys Ile
    3560                3565                3570

Ile Thr Ala Phe Val Lys Trp Thr Met Phe Met Tyr Val Thr Thr
    3575                3580                3585

Asn Met Leu Ser Ile Thr Phe Cys Ala Leu Cys Val Ile Ser Leu
    3590                3595                3600

Ala Met Leu Leu Val Lys His Lys His Leu Tyr Leu Thr Met Tyr
    3605                3610                3615

Ile Ile Pro Val Leu Phe Thr Leu Leu Tyr Asn Asn Tyr Leu Val
    3620                3625                3630

Val Tyr Lys Gln Thr Phe Arg Gly Tyr Val Tyr Ala Trp Leu Ser
    3635                3640                3645

Tyr Tyr Val Pro Ser Val Glu Tyr Thr Tyr Thr Asp Glu Val Ile
    3650                3655                3660

Tyr Gly Met Leu Leu Leu Ile Gly Met Val Phe Val Thr Leu Arg
    3665                3670                3675

Ser Ile Asn His Asp Leu Phe Ser Phe Ile Met Phe Val Gly Arg
    3680                3685                3690

Val Ile Ser Val Val Ser Leu Trp Tyr Met Gly Ser Asn Leu Glu
    3695                3700                3705

Glu Glu Ile Leu Leu Met Leu Ala Ser Leu Phe Gly Thr Tyr Thr
    3710                3715                3720

Trp Thr Thr Ala Leu Ser Met Ala Ala Ala Lys Val Ile Ala Lys
    3725                3730                3735

Trp Val Ala Val Asn Val Leu Tyr Phe Thr Asp Ile Pro Gln Ile
    3740                3745                3750

Lys Ile Val Leu Val Cys Tyr Leu Phe Ile Gly Tyr Ile Ile Ser
    3755                3760                3765

Cys Tyr Trp Gly Leu Phe Ser Leu Met Asn Ser Leu Phe Arg Met
    3770                3775                3780

Pro Leu Gly Val Tyr Asn Tyr Lys Ile Ser Val Gln Glu Leu Arg
    3785                3790                3795

Tyr Met Asn Ala Asn Gly Leu Arg Pro Pro Lys Asn Ser Phe Glu
    3800                3805                3810

Ala Leu Met Leu Asn Phe Lys Leu Leu Gly Ile Gly Gly Val Pro
    3815                3820                3825

Ile Ile Glu Val Ser Gln Phe Gln Ser Lys Leu Thr Asp Val Lys
    3830                3835                3840

Cys Ala Asn Val Val Leu Leu Asn Cys Leu Gln His Leu His Val
    3845                3850                3855

Ala Ser Asn Ser Lys Leu Trp Gln Tyr Cys Ser Thr Leu His Asn
    3860                3865                3870
```

-continued

```
Glu Ile  Leu Ala Thr Ser Asp  Leu Gly Val Ala Phe  Glu Lys Leu
    3875                 3880                 3885

Ala Gln  Leu Leu Ile Val Leu  Phe Ala Asn Pro Ala  Ala Val Asp
    3890                 3895                 3900

Ser Lys  Cys Leu Thr Ser Ile  Glu Glu Val Cys Asp  Asp Tyr Ala
    3905                 3910                 3915

Lys Asp  Asn Thr Val Leu Gln  Ala Leu Gln Ser Glu  Phe Val Asn
    3920                 3925                 3930

Met Ala  Ser Phe Val Glu Tyr  Glu Val Ala Lys Lys  Asn Leu Asp
    3935                 3940                 3945

Glu Ala  Cys Ser Ser Gly Ser  Ala Asn Arg Gln Gln  Leu Lys Gln
    3950                 3955                 3960

Leu Glu  Lys Ala Cys Asn Ile  Ala Lys Ser Ala Tyr  Glu Arg Asp
    3965                 3970                 3975

Arg Ala  Val Ala Arg Lys Leu  Glu Arg Met Ala Asp  Leu Ala Leu
    3980                 3985                 3990

Thr Asn  Met Tyr Lys Glu Ala  Arg Ile Asn Asp Lys  Lys Ser Lys
    3995                 4000                 4005

Val Val  Ser Ala Leu Gln Thr  Met Leu Phe Ser Met  Val Arg Lys
    4010                 4015                 4020

Leu Asp  Asn Gln Ala Leu Asn  Ser Ile Leu Asp Asn  Ala Val Lys
    4025                 4030                 4035

Gly Cys  Val Pro Leu Asn Ala  Ile Pro Ser Leu Ala  Ala Asn Thr
    4040                 4045                 4050

Leu Thr  Ile Ile Val Pro Asp  Lys Ser Val Tyr Asp  Gln Val Val
    4055                 4060                 4065

Asp Asn  Val Tyr Val Thr Tyr  Ala Gly Asn Val Trp  Gln Ile Gln
    4070                 4075                 4080

Thr Ile  Gln Asp Ser Asp Gly  Thr Asn Lys Gln Leu  Asn Glu Ile
    4085                 4090                 4095

Ser Asp  Asp Cys Asn Trp Pro  Leu Val Ile Ile Ala  Asn Arg His
    4100                 4105                 4110

Asn Glu  Val Ser Ala Thr Val  Leu Gln Asn Asn Glu  Leu Met Pro
    4115                 4120                 4125

Ala Lys  Leu Lys Thr Gln Val  Val Asn Ser Gly Pro  Asp Gln Thr
    4130                 4135                 4140

Cys Asn  Thr Pro Thr Gln Cys  Tyr Tyr Asn Asn Ser  Tyr Asn Gly
    4145                 4150                 4155

Lys Ile  Val Tyr Ala Ile Leu  Ser Asp Val Asp Gly  Leu Lys Tyr
    4160                 4165                 4170

Thr Lys  Ile Leu Lys Asp Asp  Gly Asn Phe Val Val  Leu Glu Leu
    4175                 4180                 4185

Asp Pro  Pro Cys Lys Phe Thr  Val Gln Asp Val Lys  Gly Leu Lys
    4190                 4195                 4200

Ile Lys  Tyr Leu Tyr Phe Val  Lys Gly Cys Asn Thr  Leu Ala Arg
    4205                 4210                 4215

Gly Trp  Val Val Gly Thr Ile  Ser Ser Thr Val Arg  Leu Gln Ala
    4220                 4225                 4230

Gly Thr  Ala Thr Glu Tyr Ala  Ser Asn Ser Ser Ile  Leu Ser Leu
    4235                 4240                 4245

Cys Ala  Phe Ser Val Asp Pro  Lys Lys Thr Tyr Leu  Asp Phe Ile
    4250                 4255                 4260

Gln Gln  Gly Gly Thr Pro Ile  Ala Asn Cys Val Lys  Met Leu Cys
```

```
    4265                4270                4275

Asp His  Ala Gly Thr Gly Met  Ala Ile Thr Val Lys  Pro Asp Ala
    4280                4285                4290

Thr Thr  Ser Gln Asp Ser Tyr  Gly Gly Ala Ser Val  Cys Ile Tyr
    4295                4300                4305

Cys Arg  Ala Arg Val Glu His  Pro Asp Val Asp Gly  Leu Cys Lys
    4310                4315                4320

Leu Arg  Gly Lys Phe Val Gln  Val Pro Val Gly Ile  Lys Asp Pro
    4325                4330                4335

Val Ser  Tyr Val Leu Thr His  Asp Val Cys Gln Val  Cys Gly Phe
    4340                4345                4350

Trp Arg  Asp Gly Ser Cys Ser  Cys Val Ser Thr Asp  Thr Thr Val
    4355                4360                4365

Gln Ser  Lys Asp Thr Asn Phe  Leu Asn Arg Val Arg  Gly Thr Ser
    4370                4375                4380

Val Asp  Ala Arg Leu Val Pro  Cys Ala Ser Gly Leu  Ser Thr Asp
    4385                4390                4395

Val Gln  Leu Arg Ala Phe Asp  Ile Cys Asn Ala Ser  Val Ala Gly
    4400                4405                4410

Ile Gly  Leu His Leu Lys Val  Asn Cys Cys Arg Phe  Gln Arg Val
    4415                4420                4425

Asp Glu  Asn Gly Asp Lys Leu  Asp Gln Phe Phe Val  Val Lys Arg
    4430                4435                4440

Thr Asp  Leu Thr Ile Tyr Asn  Arg Glu Met Glu Cys  Tyr Glu Arg
    4445                4450                4455

Val Lys  Asp Cys Lys Phe Val  Ala Glu His Asp Phe  Phe Thr Phe
    4460                4465                4470

Asp Val  Glu Gly Ser Arg Val  Pro His Ile Val Arg  Lys Asp Leu
    4475                4480                4485

Thr Lys  Tyr Thr Met Leu Asp  Leu Cys Tyr Ala Leu  Arg His Phe
    4490                4495                4500

Asp Arg  Asn Asp Cys Met Leu  Leu Cys Asp Ile Leu  Ser Ile Tyr
    4505                4510                4515

Ala Gly  Cys Glu Gln Ser Tyr  Phe Thr Lys Lys Asp  Trp Tyr Asp
    4520                4525                4530

Phe Val  Glu Asn Pro Asp Ile  Ile Asn Val Tyr Lys  Lys Leu Gly
    4535                4540                4545

Pro Ile  Phe Asn Arg Ala Leu  Val Ser Ala Thr Glu  Phe Ala Asp
    4550                4555                4560

Lys Leu  Val Glu Val Gly Leu  Val Gly Ile Leu Thr  Leu Asp Asn
    4565                4570                4575

Gln Asp  Leu Asn Gly Lys Trp  Tyr Asp Phe Gly Asp  Tyr Val Ile
    4580                4585                4590

Ala Ala  Pro Gly Cys Gly Val  Ala Ile Ala Asp Ser  Tyr Tyr Ser
    4595                4600                4605

Tyr Met  Met Pro Met Leu Thr  Met Cys His Ala Leu  Asp Cys Glu
    4610                4615                4620

Leu Tyr  Val Asn Asn Ala Tyr  Arg Leu Phe Asp Leu  Val Gln Tyr
    4625                4630                4635

Asp Phe  Thr Asp Tyr Lys Leu  Glu Leu Phe Asn Lys  Tyr Phe Lys
    4640                4645                4650

His Trp  Ser Met Pro Tyr His  Pro Asn Thr Val Asp  Cys Gln Asp
    4655                4660                4665
```

```
Asp Arg Cys Ile Ile His Cys Ala Asn Phe Asn Ile Leu Phe Ser
    4670                4675                4680

Met Val Leu Pro Asn Thr Cys Phe Gly Pro Leu Val Arg Gln Ile
    4685                4690                4695

Phe Val Asp Gly Val Pro Phe Val Val Ser Ile Gly Tyr His Tyr
    4700                4705                4710

Lys Glu Leu Gly Ile Val Met Asn Met Asp Val Asp Thr His Arg
    4715                4720                4725

Tyr Arg Leu Ser Leu Lys Asp Leu Leu Leu Tyr Ala Ala Asp Pro
    4730                4735                4740

Ala Leu His Val Ala Ser Ala Ser Ala Leu Tyr Asp Leu Arg Thr
    4745                4750                4755

Cys Cys Phe Ser Val Ala Ala Ile Thr Ser Gly Val Lys Phe Gln
    4760                4765                4770

Thr Val Lys Pro Gly Asn Phe Asn Gln Asp Phe Tyr Asp Phe Ile
    4775                4780                4785

Leu Ser Lys Gly Leu Leu Lys Glu Gly Ser Ser Val Asp Leu Lys
    4790                4795                4800

His Phe Phe Phe Thr Gln Asp Gly Asn Ala Ala Ile Thr Asp Tyr
    4805                4810                4815

Asn Tyr Tyr Lys Tyr Asn Leu Pro Thr Met Val Asp Ile Lys Gln
    4820                4825                4830

Leu Leu Phe Val Leu Glu Val Val Tyr Lys Tyr Phe Glu Ile Tyr
    4835                4840                4845

Asp Gly Gly Cys Ile Pro Ala Ser Gln Val Ile Val Asn Asn Tyr
    4850                4855                4860

Asp Lys Ser Ala Gly Tyr Pro Phe Asn Lys Phe Gly Lys Ala Arg
    4865                4870                4875

Leu Tyr Tyr Glu Ala Leu Ser Phe Glu Glu Gln Asp Glu Ile Tyr
    4880                4885                4890

Ala Tyr Thr Lys Arg Asn Val Leu Pro Thr Leu Thr Gln Met Asn
    4895                4900                4905

Leu Lys Tyr Ala Ile Ser Ala Lys Asn Arg Ala Arg Thr Val Ala
    4910                4915                4920

Gly Val Ser Ile Leu Ser Thr Met Thr Gly Arg Met Phe His Gln
    4925                4930                4935

Lys Cys Leu Lys Ser Ile Ala Ala Thr Arg Gly Val Pro Val Val
    4940                4945                4950

Ile Gly Thr Thr Lys Phe Tyr Gly Gly Trp Asp Asp Met Leu Arg
    4955                4960                4965

Arg Leu Ile Lys Asp Val Asp Asn Pro Val Leu Met Gly Trp Asp
    4970                4975                4980

Tyr Pro Lys Cys Asp Arg Ala Met Pro Asn Ile Leu Arg Ile Val
    4985                4990                4995

Ser Ser Leu Val Leu Ala Arg Lys His Glu Ala Cys Cys Ser Gln
    5000                5005                5010

Ser Asp Arg Phe Tyr Arg Leu Ala Asn Glu Cys Ala Gln Val Leu
    5015                5020                5025

Ser Glu Ile Val Met Cys Gly Gly Cys Tyr Tyr Val Lys Pro Gly
    5030                5035                5040

Gly Thr Ser Ser Gly Asp Ala Thr Thr Ala Phe Ala Asn Ser Val
    5045                5050                5055
```

-continued

```
Phe Asn Ile Cys Gln Ala Val Ser Ala Asn Val Cys Ala Leu Met
    5060                5065                5070

Ser Cys Asn Gly Asn Lys Ile Glu Asp Leu Ser Ile Arg Ala Leu
    5075                5080                5085

Gln Lys Arg Leu Tyr Ser His Val Tyr Arg Ser Asp Met Val Asp
    5090                5095                5100

Ser Thr Phe Val Thr Glu Tyr Tyr Glu Phe Leu Asn Lys His Phe
    5105                5110                5115

Ser Met Met Ile Leu Ser Asp Asp Gly Val Val Cys Tyr Asn Ser
    5120                5125                5130

Asp Tyr Ala Ser Lys Gly Tyr Ile Ala Asn Ile Ser Ala Phe Gln
    5135                5140                5145

Gln Val Leu Tyr Tyr Gln Asn Asn Val Phe Met Ser Glu Ser Lys
    5150                5155                5160

Cys Trp Val Glu Asn Asp Ile Asn Asn Gly Pro His Glu Phe Cys
    5165                5170                5175

Ser Gln His Thr Met Leu Val Lys Met Asp Gly Asp Asp Val Tyr
    5180                5185                5190

Leu Pro Tyr Pro Asp Pro Ser Arg Ile Leu Gly Ala Gly Cys Phe
    5195                5200                5205

Val Asp Asp Leu Leu Lys Thr Asp Ser Val Leu Leu Ile Glu Arg
    5210                5215                5220

Phe Val Ser Leu Ala Ile Asp Ala Tyr Pro Leu Val Tyr His Glu
    5225                5230                5235

Asn Glu Glu Tyr Gln Lys Val Phe Arg Val Tyr Leu Glu Tyr Ile
    5240                5245                5250

Lys Lys Leu Tyr Asn Asp Leu Gly Asn Gln Ile Leu Asp Ser Tyr
    5255                5260                5265

Ser Val Ile Leu Ser Thr Cys Asp Gly Gln Lys Phe Thr Asp Glu
    5270                5275                5280

Ser Phe Tyr Lys Asn Met Tyr Leu Arg Ser Ala Val Met Gln Ser
    5285                5290                5295

Val Gly Ala Cys Val Val Cys Ser Ser Gln Thr Ser Leu Arg Cys
    5300                5305                5310

Gly Ser Cys Ile Arg Lys Pro Leu Leu Cys Cys Lys Cys Cys Tyr
    5315                5320                5325

Asp His Val Met Ala Thr Asp His Lys Tyr Val Leu Ser Val Ser
    5330                5335                5340

Pro Tyr Val Cys Asn Ala Pro Gly Cys Asp Val Asn Asp Val Thr
    5345                5350                5355

Lys Leu Tyr Leu Gly Gly Met Ser Tyr Tyr Cys Glu Asp His Lys
    5360                5365                5370

Pro Gln Tyr Ser Phe Lys Leu Val Met Asn Gly Met Val Phe Gly
    5375                5380                5385

Leu Tyr Lys Gln Ser Cys Thr Gly Ser Pro Tyr Ile Asp Asp Phe
    5390                5395                5400

Asn Arg Ile Ala Ser Cys Lys Trp Thr Asp Val Asp Asp Tyr Ile
    5405                5410                5415

Leu Ala Asn Glu Cys Thr Glu Arg Leu Lys Leu Phe Ala Ala Glu
    5420                5425                5430

Thr Gln Lys Ala Thr Glu Glu Ala Phe Lys Gln Ser Tyr Ala Ser
    5435                5440                5445

Ala Thr Ile Gln Glu Ile Val Ser Glu Arg Glu Leu Ile Leu Ser
```

-continued

```
    5450                5455                5460

Trp Glu Ile Gly Lys Val Lys Pro Pro Leu Asn Lys Asn Tyr Val
    5465                5470                5475

Phe Thr Gly Tyr His Phe Thr Lys Asn Gly Lys Thr Val Leu Gly
    5480                5485                5490

Glu Tyr Val Phe Asp Lys Ser Glu Leu Thr Asn Gly Val Tyr Tyr
    5495                5500                5505

Arg Ala Thr Thr Thr Tyr Lys Leu Ser Val Gly Asp Val Phe Val
    5510                5515                5520

Leu Thr Ser His Ser Val Ala Asn Leu Ser Ala Pro Thr Leu Val
    5525                5530                5535

Pro Gln Glu Asn Tyr Ser Ser Ile Arg Phe Ala Ser Val Tyr Ser
    5540                5545                5550

Val Leu Glu Thr Phe Gln Asn Asn Val Val Asn Tyr Gln His Ile
    5555                5560                5565

Gly Met Lys Arg Tyr Cys Thr Val Gln Gly Pro Pro Gly Thr Gly
    5570                5575                5580

Lys Ser His Leu Ala Ile Gly Leu Ala Val Tyr Tyr Cys Thr Ala
    5585                5590                5595

Arg Val Val Tyr Thr Ala Ala Ser His Ala Ala Val Asp Ala Leu
    5600                5605                5610

Cys Glu Lys Ala Tyr Lys Phe Leu Asn Ile Asn Asp Cys Thr Arg
    5615                5620                5625

Ile Val Pro Ala Lys Val Arg Val Glu Cys Tyr Asp Lys Phe Lys
    5630                5635                5640

Ile Asn Asp Thr Thr Arg Lys Tyr Val Phe Thr Thr Ile Asn Ala
    5645                5650                5655

Leu Pro Glu Met Val Thr Asp Ile Val Val Val Asp Glu Val Ser
    5660                5665                5670

Met Leu Thr Asn Tyr Glu Leu Ser Val Ile Asn Ala Arg Ile Arg
    5675                5680                5685

Ala Lys His Tyr Val Tyr Ile Gly Asp Pro Ala Gln Leu Pro Ala
    5690                5695                5700

Pro Arg Val Leu Leu Ser Lys Gly Thr Leu Glu Pro Lys Tyr Phe
    5705                5710                5715

Asn Thr Val Thr Lys Leu Met Cys Cys Leu Gly Pro Asp Ile Phe
    5720                5725                5730

Leu Gly Thr Cys Tyr Arg Cys Pro Lys Glu Ile Val Asp Thr Val
    5735                5740                5745

Ser Ala Leu Val Tyr Glu Asn Lys Leu Lys Ala Lys Asn Glu Ser
    5750                5755                5760

Ser Ser Leu Cys Phe Lys Val Tyr Tyr Lys Gly Val Thr Thr His
    5765                5770                5775

Glu Ser Ser Ser Ala Val Asn Met Gln Gln Ile Tyr Leu Ile Asn
    5780                5785                5790

Lys Phe Leu Lys Val Asn Pro Leu Trp His Lys Ala Val Phe Ile
    5795                5800                5805

Ser Pro Tyr Asn Ser Gln Asn Phe Ala Ala Lys Arg Val Leu Gly
    5810                5815                5820

Leu Gln Thr Gln Thr Val Asp Ser Ala Gln Gly Ser Glu Tyr Asp
    5825                5830                5835

Tyr Val Ile Tyr Ser Gln Thr Ala Glu Thr Ala His Ser Val Asn
    5840                5845                5850
```

-continued

```
Val Asn Arg Phe Asn Val Ala Ile Thr Arg Ala Lys Lys Gly Ile
    5855                5860                5865

Leu Cys Val Met Ser Asn Met Gln Leu Phe Glu Ala Leu Gln Phe
    5870                5875                5880

Thr Thr Leu Thr Val Asp Lys Val Pro Gln Ala Val Glu Thr Arg
    5885                5890                5895

Val Gln Cys Ser Thr Asn Leu Phe Lys Asp Cys Ser Lys Ser Tyr
    5900                5905                5910

Ser Gly Tyr His Pro Ala His Ala Pro Ser Phe Leu Ala Val Asp
    5915                5920                5925

Asp Lys Tyr Lys Ala Thr Gly Asp Leu Ala Val Cys Leu Gly Ile
    5930                5935                5940

Gly Asp Ser Ala Val Thr Tyr Ser Arg Leu Ile Ser Leu Met Gly
    5945                5950                5955

Phe Lys Leu Asp Val Thr Leu Asp Gly Tyr Cys Lys Leu Phe Ile
    5960                5965                5970

Thr Lys Glu Glu Ala Val Lys Arg Val Arg Ala Trp Val Gly Phe
    5975                5980                5985

Asp Ala Glu Gly Ala His Ala Thr Arg Asp Ser Ile Gly Thr Asn
    5990                5995                6000

Phe Pro Leu Gln Leu Gly Phe Ser Thr Gly Ile Asp Phe Val Val
    6005                6010                6015

Glu Ala Thr Gly Leu Phe Ala Asp Arg Asp Gly Tyr Ser Phe Lys
    6020                6025                6030

Lys Ala Val Ala Lys Ala Pro Pro Gly Glu Gln Phe Lys His Leu
    6035                6040                6045

Ile Pro Leu Met Thr Arg Gly Gln Arg Trp Asp Val Val Arg Pro
    6050                6055                6060

Arg Ile Val Gln Met Phe Ala Asp His Leu Ile Asp Leu Ser Asp
    6065                6070                6075

Cys Val Val Leu Val Thr Trp Ala Ala Asn Phe Glu Leu Thr Cys
    6080                6085                6090

Leu Arg Tyr Phe Ala Lys Val Gly Arg Glu Ile Ser Cys Asn Val
    6095                6100                6105

Cys Thr Lys Arg Ala Thr Ala Tyr Asn Ser Arg Thr Gly Tyr Tyr
    6110                6115                6120

Gly Cys Trp Arg His Ser Val Thr Cys Asp Tyr Leu Tyr Asn Pro
    6125                6130                6135

Leu Ile Val Asp Ile Gln Gln Trp Gly Tyr Ile Gly Ser Leu Ser
    6140                6145                6150

Ser Asn His Asp Leu Tyr Cys Ser Val His Lys Gly Ala His Val
    6155                6160                6165

Ala Ser Ser Asp Ala Ile Met Thr Arg Cys Leu Ala Val Tyr Asp
    6170                6175                6180

Cys Phe Cys Asn Asn Ile Asn Trp Asn Val Glu Tyr Pro Ile Ile
    6185                6190                6195

Ser Asn Glu Leu Ser Ile Asn Thr Ser Cys Arg Val Leu Gln Arg
    6200                6205                6210

Val Met Leu Lys Ala Ala Met Leu Cys Asn Arg Tyr Thr Leu Cys
    6215                6220                6225

Tyr Asp Ile Gly Asn Pro Lys Ala Ile Ala Cys Val Lys Asp Phe
    6230                6235                6240
```

Asp Phe Lys Phe Tyr Asp Ala Gln Pro Ile Val Lys Ser Val Lys
6245 6250 6255

Thr Leu Leu Tyr Phe Phe Glu Ala His Lys Asp Ser Phe Lys Asp
6260 6265 6270

Gly Leu Cys Met Phe Trp Asn Cys Asn Val Asp Lys Tyr Pro Pro
6275 6280 6285

Asn Ala Val Val Cys Arg Phe Asp Thr Arg Val Leu Asn Asn Leu
6290 6295 6300

Asn Leu Pro Gly Cys Asn Gly Gly Ser Leu Tyr Val Asn Lys His
6305 6310 6315

Ala Phe His Thr Lys Pro Phe Ser Arg Ala Ala Phe Glu His Leu
6320 6325 6330

Lys Pro Met Pro Phe Phe Tyr Tyr Ser Asp Thr Pro Cys Val Tyr
6335 6340 6345

Met Asp Gly Met Asp Ala Lys Gln Val Asp Tyr Val Pro Leu Lys
6350 6355 6360

Ser Ala Thr Cys Ile Thr Arg Cys Asn Leu Gly Gly Ala Val Cys
6365 6370 6375

Leu Lys His Ala Glu Glu Tyr Arg Glu Tyr Leu Glu Ser Tyr Asn
6380 6385 6390

Thr Ala Thr Thr Ala Gly Phe Thr Phe Trp Val Tyr Lys Thr Phe
6395 6400 6405

Asp Phe Tyr Asn Leu Trp Asn Thr Phe Thr Lys Leu Gln Ser Leu
6410 6415 6420

Glu Asn Val Val Tyr Asn Leu Val Lys Thr Gly His Tyr Thr Gly
6425 6430 6435

Gln Ala Gly Glu Met Pro Cys Ala Ile Ile Asn Asp Lys Val Val
6440 6445 6450

Ala Lys Ile Asp Lys Glu Asp Val Val Ile Phe Ile Asn Asn Thr
6455 6460 6465

Thr Tyr Pro Thr Asn Val Ala Val Glu Leu Phe Ala Lys Arg Ser
6470 6475 6480

Ile Arg His His Pro Glu Leu Lys Leu Phe Arg Asn Leu Asn Ile
6485 6490 6495

Asp Val Cys Trp Lys His Val Ile Trp Asp Tyr Ala Arg Glu Ser
6500 6505 6510

Ile Phe Cys Ser Asn Thr Tyr Gly Val Cys Met Tyr Thr Asp Leu
6515 6520 6525

Lys Phe Ile Asp Lys Leu Asn Val Leu Phe Asp Gly Arg Asp Asn
6530 6535 6540

Gly Ala Leu Glu Ala Phe Lys Arg Ser Asn Asn Gly Val Tyr Ile
6545 6550 6555

Ser Thr Thr Lys Val Lys Ser Leu Ser Met Ile Arg Gly Pro Pro
6560 6565 6570

Arg Ala Glu Leu Asn Gly Val Val Val Asp Lys Val Gly Asp Thr
6575 6580 6585

Asp Cys Val Phe Tyr Phe Ala Val Arg Lys Glu Gly Gln Asp Val
6590 6595 6600

Ile Phe Ser Gln Phe Asp Ser Leu Arg Val Ser Ser Asn Gln Ser
6605 6610 6615

Pro Gln Gly Asn Leu Gly Ser Asn Glu Pro Gly Asn Val Gly Gly
6620 6625 6630

Asn Asp Ala Leu Ala Thr Ser Thr Ile Phe Thr Gln Ser Arg Val

```
    6635                6640                6645

Ile Ser  Ser Phe Thr Cys Arg  Thr Asp Met Glu Lys  Asp Phe Ile
    6650                6655                6660

Ala Leu  Asp Gln Asp Val Phe  Ile Gln Lys Tyr Gly  Leu Glu Asp
    6665                6670                6675

Tyr Ala  Phe Glu His Ile Val  Tyr Gly Asn Phe Asn  Gln Lys Ile
    6680                6685                6690

Ile Gly  Gly Leu His Leu Leu  Ile Gly Leu Tyr Arg  Arg Gln Gln
    6695                6700                6705

Thr Ser  Asn Leu Val Ile Gln  Glu Phe Val Ser Tyr  Asp Ser Ser
    6710                6715                6720

Ile His  Ser Tyr Phe Ile Thr  Asp Glu Lys Ser Gly  Gly Ser Lys
    6725                6730                6735

Ser Val  Cys Thr Val Ile Asp  Ile Leu Leu Asp Asp  Phe Val Ala
    6740                6745                6750

Leu Val  Lys Ser Leu Asn Leu  Asn Cys Val Ser Lys  Val Val Asn
    6755                6760                6765

Val Asn  Val Asp Phe Lys Asp  Phe Gln Phe Met Leu  Trp Cys Asn
    6770                6775                6780

Asp Glu  Lys Val Met Thr Phe  Tyr Pro Arg Leu Gln  Ala Ala Ser
    6785                6790                6795

Asp Trp  Lys Pro Gly Tyr Ser  Met Pro Val Leu Tyr  Lys Tyr Leu
    6800                6805                6810

Asn Ser  Pro Met Glu Arg Val  Ser Leu Trp Asn Tyr  Gly Lys Pro
    6815                6820                6825

Val Thr  Leu Pro Thr Gly Cys  Met Met Asn Val Ala  Lys Tyr Thr
    6830                6835                6840

Gln Leu  Cys Gln Tyr Leu Asn  Thr Thr Thr Leu Ala  Val Pro Val
    6845                6850                6855

Asn Met  Arg Val Leu His Leu  Gly Ala Gly Ser Glu  Lys Gly Val
    6860                6865                6870

Ala Pro  Gly Ser Ala Val Leu  Arg Gln Trp Leu Pro  Ala Gly Thr
    6875                6880                6885

Ile Leu  Val Asp Asn Asp Leu  Tyr Pro Phe Val Ser  Asp Ser Val
    6890                6895                6900

Ala Thr  Tyr Phe Gly Asp Cys  Ile Thr Leu Pro Phe  Asp Cys Gln
    6905                6910                6915

Trp Asp  Leu Ile Ile Ser Asp  Met Tyr Asp Pro Ile  Thr Lys Asn
    6920                6925                6930

Ile Gly  Glu Tyr Asn Val Ser  Lys Asp Gly Phe Phe  Thr Tyr Ile
    6935                6940                6945

Cys His  Met Ile Arg Asp Lys  Leu Ala Leu Gly Gly  Ser Val Ala
    6950                6955                6960

Ile Lys  Ile Thr Glu Phe Ser  Trp Asn Ala Glu Leu  Tyr Lys Leu
    6965                6970                6975

Met Gly  Tyr Phe Ala Phe Trp  Thr Val Phe Cys Thr  Asn Ala Asn
    6980                6985                6990

Ala Ser  Ser Ser Glu Gly Phe  Leu Ile Gly Ile Asn  Tyr Leu Gly
    6995                7000                7005

Lys Pro  Lys Val Glu Ile Asp  Gly Asn Val Met His  Ala Asn Tyr
    7010                7015                7020

Leu Phe  Trp Arg Asn Ser Thr  Val Trp Asn Gly Gly  Ala Tyr Ser
    7025                7030                7035
```

-continued

Leu Phe Asp Met Ala Lys Phe Pro Leu Lys Leu Ala Gly Thr Ala
    7040                7045                7050

Val Ile Asn Leu Arg Ala Asp Gln Ile Asn Asp Met Val Tyr Ser
    7055                7060                7065

Leu Leu Glu Lys Gly Lys Leu Leu Val Arg Asp Thr Asn Lys Glu
    7070                7075                7080

Val Phe Val Gly Asp Ser Met Val Asn Val Ile
    7085                7090

<210> SEQ ID NO 13
<211> LENGTH: 837
<212> TYPE: DNA
<213> ORGANISM: Bovine coronavirus

<400> SEQUENCE: 13
atggcagttg cttatgcaaa caagcctaat cactttatta attttccact tacccagttt 60
gagggttttg tgttaaatta taaaggttta caatttcaac ttctcgatga aggagtggat 120
tgtaaaatac aaacagcgcc gcacattagt cttgttatgc tggatattca gcctgaagac 180
tatagaagtg ttgatgttgc tattcaagaa gttattgatg acatgcattg ggtgagggc 240 tttcagatta aatttgataa cccccatatc ctaggaagat gcatagtttt agatgttaaa 300
ggtgtagaag aattgcatga tgatttagtt aattacattc gtgataaagg ttgtgttgct 360
gaccaatcca ggaaatggat tggacattgc accatagccc aactcacgga tgctgcactt 420
tccattaagg aaaatgttga tttcataaac agcatgcaat tcaattataa aatcactatc 480
aacccctcat caccggctag acttgaaata gttaagcttg gtgctgaaaa gaaagatggt 540
ttttatgaaa ccatagttag ccactggatg ggaattcgtt ttgaatataa tccacccact 600
gataagctag ctatgattat gggttattgt tgtttagaag tggtgcgtaa agagctagaa 660
gaaggtgatc ttcccgagaa tgatgatgat gcttggttta agctatcgta ccattatgaa 720
aacaattctt ggttctttcg acatgtctac aggaaaagtt cttatttccg taagtcttgt 780
caaaatttag attgtaattg tttggggttt tatgaatctc cagttgaaga agactaa 837

<210> SEQ ID NO 14
<211> LENGTH: 278
<212> TYPE: PRT
<213> ORGANISM: Bovine coronavirus

<400> SEQUENCE: 14

Met Ala Val Ala Tyr Ala Asn Lys Pro Asn His Phe Ile Asn Phe Pro
1               5                   10                  15

Leu Thr Gln Phe Glu Gly Phe Val Leu Asn Tyr Lys Gly Leu Gln Phe
            20                  25                  30

Gln Leu Leu Asp Glu Gly Val Asp Cys Lys Ile Gln Thr Ala Pro His
        35                  40                  45

Ile Ser Leu Val Met Leu Asp Ile Gln Pro Glu Asp Tyr Arg Ser Val
    50                  55                  60

Asp Val Ala Ile Gln Glu Val Ile Asp Asp Met His Trp Gly Glu Gly
65                  70                  75                  80

Phe Gln Ile Lys Phe Asp Asn Pro His Ile Leu Gly Arg Cys Ile Val
                85                  90                  95

Leu Asp Val Lys Gly Val Glu Glu Leu His Asp Asp Leu Val Asn Tyr
            100                 105                 110

Ile Arg Asp Lys Gly Cys Val Ala Asp Gln Ser Arg Lys Trp Ile Gly

```
        115                 120                 125

His Cys Thr Ile Ala Gln Leu Thr Asp Ala Ala Leu Ser Ile Lys Glu
    130                 135                 140

Asn Val Asp Phe Ile Asn Ser Met Gln Phe Asn Tyr Lys Ile Thr Ile
145                 150                 155                 160

Asn Pro Ser Ser Pro Ala Arg Leu Glu Ile Val Lys Leu Gly Ala Glu
                165                 170                 175

Lys Lys Asp Gly Phe Tyr Glu Thr Ile Val Ser His Trp Met Gly Ile
            180                 185                 190

Arg Phe Glu Tyr Asn Pro Pro Thr Asp Lys Leu Ala Met Ile Met Gly
        195                 200                 205

Tyr Cys Cys Leu Glu Val Val Arg Lys Glu Leu Glu Glu Gly Asp Leu
    210                 215                 220

Pro Glu Asn Asp Asp Asp Ala Trp Phe Lys Leu Ser Tyr His Tyr Glu
225                 230                 235                 240

Asn Asn Ser Trp Phe Phe Arg His Val Tyr Arg Lys Ser Ser Tyr Phe
                245                 250                 255

Arg Lys Ser Cys Gln Asn Leu Asp Cys Asn Cys Leu Gly Phe Tyr Glu
            260                 265                 270

Ser Pro Val Glu Glu Asp
        275


<210> SEQ ID NO 15
<211> LENGTH: 132
<212> TYPE: DNA
<213> ORGANISM: Bovine coronavirus

<400> SEQUENCE: 15

atgacgacta agttcgtctt tgatttattg gctcctgacg atatattaca tcccttcaat      60

catgtgaagc taattataag acccattgag gtcgagcata ttataatagc taccacaatg     120

cctgctgttt ag                                                         132


<210> SEQ ID NO 16
<211> LENGTH: 43
<212> TYPE: PRT
<213> ORGANISM: Bovine coronavirus

<400> SEQUENCE: 16

Met Thr Thr Lys Phe Val Phe Asp Leu Leu Ala Pro Asp Asp Ile Leu
1               5                   10                  15

His Pro Phe Asn His Val Lys Leu Ile Ile Arg Pro Ile Glu Val Glu
            20                  25                  30

His Ile Ile Ile Ala Thr Thr Met Pro Ala Val
        35                  40


<210> SEQ ID NO 17
<211> LENGTH: 138
<212> TYPE: DNA
<213> ORGANISM: Bovine coronavirus

<400> SEQUENCE: 17

atgccaatgg ctacaaccat tgacggtaca gattatacta atattatgcc tagtactgtt      60

tctacaacag tttatttagg ctgttctata ggtattgaca ctagcaccac tggttttacc     120

tgtttttcac ggtactag                                                   138


<210> SEQ ID NO 18
```

<211> LENGTH: 45
<212> TYPE: PRT
<213> ORGANISM: Bovine coronavirus

<400> SEQUENCE: 18

Met Pro Met Ala Thr Thr Ile Asp Gly Thr Asp Tyr Thr Asn Ile Met
1 5 10 15

Pro Ser Thr Val Ser Thr Thr Val Tyr Leu Gly Cys Ser Ile Gly Ile
20 25 30

Asp Thr Ser Thr Thr Gly Phe Thr Cys Phe Ser Arg Tyr
35 40 45

<210> SEQ ID NO 19
<211> LENGTH: 330
<212> TYPE: DNA
<213> ORGANISM: Bovine coronavirus

<400> SEQUENCE: 19
atggacatct ggagacctga gattaaatat ctccgttata ttaacggttt taatgtctca 60
gaattagaag atgcttgttt taaatttaac tataaatttc ctaaagtagg atattgtaga 120
gttcctagtc atgcttggtg ccgtaatcaa ggtagctttt gtgctacact cactctttat 180
ggcaaatcca aacattatga taaatatttt ggagtaataa ctggttttac agcattcgct 240
aatactgtag aggaggctgt taacaaactg gttttcttag ctgttgactt tattacctgg 300
cggagacagg agttaaatgt ttatggctga 330

<210> SEQ ID NO 20
<211> LENGTH: 109
<212> TYPE: PRT
<213> ORGANISM: Bovine coronavirus

<400> SEQUENCE: 20

Met Asp Ile Trp Arg Pro Glu Ile Lys Tyr Leu Arg Tyr Ile Asn Gly
1 5 10 15

Phe Asn Val Ser Glu Leu Glu Asp Ala Cys Phe Lys Phe Asn Tyr Lys
20 25 30

Phe Pro Lys Val Gly Tyr Cys Arg Val Pro Ser His Ala Trp Cys Arg
35 40 45

Asn Gln Gly Ser Phe Cys Ala Thr Leu Thr Leu Tyr Gly Lys Ser Lys
50 55 60

His Tyr Asp Lys Tyr Phe Gly Val Ile Thr Gly Phe Thr Ala Phe Ala
65 70 75 80

Asn Thr Val Glu Glu Ala Val Asn Lys Leu Val Phe Leu Ala Val Asp
85 90 95

Phe Ile Thr Trp Arg Arg Gln Glu Leu Asn Val Tyr Gly
100 105

<210> SEQ ID NO 21
<211> LENGTH: 4092
<212> TYPE: DNA
<213> ORGANISM: Bovine coronavirus

<400> SEQUENCE: 21
atgtttttga tacttttaat ttccttacca atggcttttg ctgttatagg agatttaaag 60
tgtactacgg ttgccattaa tgatgttgac accggtcctc cttctattag cactgatatt 120
gtcgatgtta ctaatggttt aggtacttat tatgttttag atcgtgtgta tttaaatact 180
acgttgttgc ttaatggtta ctaccctact tcaggttcta catatcgtaa tatggcactg 240

```
aagggaactt tactattgag cagactatgg tttaaaccac cttttctttc tgattttatt    300
aatggtattt ttgctaaggt caaaaatacc aaggttatta aaaagggtgt aatgtatagt    360
gagtttcctg ctataactat aggtagtact tttgtaaata catcctatag tgtggtagta    420
caaccacata ctaccaattt ggataataaa ttacaaggtc tcttagagat ctctgtttgc    480
cagtatacta tgtgcgagta cccacatacg atttgtcatc ctaatctggg taatcgacgc    540
gtagaactat ggcattggga tacaggtgtt gtttcctgtt tatataagcg taatttcaca    600
tatgatgtga atgctgatta cttgtatttc catttttatc aagaaggtgg tactttttat    660
gcatatttta cagacactgg tgttgttact aagtttctgt ttaatgttta tttaggcacg    720
gtgctttcac attattatgt cctgcctttg acttgttcta gtgctatgac tttagaatat    780
tgggttacac ctctcacttc taaacaatat ttactagctt tcaatcaaga tggtgttatt    840
tttaatgctg ttgattgtaa gagtgatttt atgagtgaga ttaagtgtaa aacactatct    900
atagcaccat ctactggtgt ttatgaatta aacggttaca ctgttcagcc aattgcagat    960
gtttaccgac gtatacctaa tcttcccgat tgtaatatag aggcttggct taatgataag   1020
tcggtgccct ctccattaaa ttgggaacgt aagacctttt caaattgtaa ttttaatatg   1080
agcagcctga tgtcttttat tcaggcagac tcatttactt gtaataatat tgatgctgct   1140
aagatatatg gtatgtgttt ttccagcata actatagata agtttgctat acccaatggt   1200
aggaaggttg acctacaatt gggcaatttg ggctatttgc agtcttttaa ctatagaatt   1260
gatactactg ctacaagttg tcagttgtat tataatttac ctgctgctaa tgtttctgtt   1320
agcaggttta atccttctac ttggaatagg agatttggtt ttacagaaca atctgttttt   1380
aagcctcaac ctgcaggtgt ttttactcat catgatgttg tttatgcaca acattgtttt   1440
aaagctccca caaatttctg tccgtgtaaa ttggatgggt ctttgtgtgt aggtaatggt   1500
cctggtatag atgctggtta taaaaatagt ggtataggca cttgtcctgc aggtactaat   1560
tatttaactt gccataatgc tgcccaatgt gattgtttgt gcactcccga ccccattaca   1620
tctaaatcta cagggcctta caagtgcccc caaactaaat acttagttgg cataggtgag   1680
cactgttcgg gtcttgctat taaaagtgat tattgtggag gtaatccttg tacttgccaa   1740
ccacaagcat tttgggttgg gtctgctgac tcttgtttac aaggggatag gtgtaatatt   1800
tttgctaatt ttatttttca tgatgttaat agtggtacta cttgttctac tgatttacaa   1860
aaatcaaaca cagacataat tcttggtgtt tgtgttaatt atgatcttta tggtattata   1920
ggccaaggtg tttttgttga ggttaatgcg acttattata atagttggca gaacctttta   1980
tatgattcta atggtaatct ctatggtttt agagactact taacaaacag aacttttatg   2040
attcgtagtt gctatagcgg tcgtgtttca gcggcctttc atgctaactc ttccgaacca   2100
gcattgctat ttcggaatat taaatgcaat tacgttttta ataatattct ttcacgacag   2160
ctgcaaccta ttaactattt tgatagttat cttggttgtg ttgtcaatgc tgataatagt   2220
acttctagtg ttgttcaaac atgtgatctc acagtaggta gtggttactg tgtggattac   2280
tctacaaaaa gacgaagtcg tagagcgatt accactggtt atcggtttac taattttgag   2340
ccatttactg ttaattcagt aaatgatagt ttagaacctg taggtggttt gtatgaaatt   2400
caaatacctt cagagtttac tataggtaat atggaggagt ttattcaaac aagctctcct   2460
aaagttacta ttgattgttc tgcttttgtc tgtggtgatt atgcagcatg taaatcacag   2520
ttggttgaat atggtagctt ctgtgacaat attaatgcta tactcacaga agtaaatgaa   2580
```

```
ctacttgaca ctacacagtt gcaagtagct aatagtttaa tgaatggtgt cactcttagc   2640
actaagctta aagatggcgt taatttcaat gtagacgaca tcaatttttc ccctgtatta   2700
ggttgtttag gaagcggttg taataaaggt tccagtagat ctgctataga ggatttactt   2760
ttttctaaag taaagttatc tgatgtcggt ttcgttgagg cttataataa ttgtactgga   2820
ggtgccgaaa ttagggacct catttgtgtg caaagttata atggtatcaa agtgttgcct   2880
ccactgctct cagtaaatca gatcagtgga tacactttgg ctgccacctc tgctagtctg   2940
tttcctcctt ggtcagcagc agcaggtgta ccattttatt taaatgttca gtatcgtatt   3000
aatgggcttg gtgttaccat ggatgtgtta agtcaaaatc aaaagcttat tgctaatgca   3060
tttaacaatg ctcttgatgc tattcaggaa gggtttgatg ctaccaattc tgctttagtt   3120
aaaattcaag ctgttgttaa tgcaaatgct gaagctctta ataacttatt gcaacaactc   3180
tctaatagat ttggtgctat aagttcttct ttacaagaaa ttctatctag actggatgct   3240
cttgaagcgc aagctcagat agacagactt attaatgggc gtcttaccgc tcttaatgct   3300
tatgtttctc aacagcttag tgattctaca ctagtaaaat ttagtgcagc acaagctatg   3360
gagaaggtta atgaatgtgt caaaagccaa tcatctagga taaatttttg tggtaatggt   3420
aatcatatta tatcattagt gcagaatgct ccatatggtt tgtattttat ccactttagc   3480
tatgtcccta ctaagtatgt cactgcgaag gttagtcccg gtctgtgcat tgctggtgat   3540
agaggtatag cccctaagag tggttatttt gttaatgtaa ataatacttg gatgttcact   3600
ggtagtggtt attactaccc tgaacccata actggaaata atgttgttgt tatgagtacc   3660
tgtgctgtta actatactaa agcgccggat gtaatgctga acatttcaac acccaacctc   3720
catgatttta aggaagagtt ggatcaatgg tttaaaaacc aaacatcagt ggcaccagat   3780
ttgtcacttg attatataaa tgttacattc ttggacctac aagatgaaat gaataggtta   3840
caggaggcaa taaaagtttt aaatcagagc tacatcaatc tcaaggacat tggtacatat   3900
gagtattatg taaaatggcc ttggtatgta tggcttttaa ttggctttgc tggtgtagct   3960
atgcttgttt tactattctt catatgctgt tgtacaggat gtgggactag ttgttttaag   4020
atatgtggtg gttgttgtga tgattatact ggacaccagg agttagtaat taaaacatta   4080
catgacgact aa                                                       4092
```

<210> SEQ ID NO 22
<211> LENGTH: 1363
<212> TYPE: PRT
<213> ORGANISM: Bovine coronavirus

<400> SEQUENCE: 22

```
Met Phe Leu Ile Leu Leu Ile Ser Leu Pro Met Ala Phe Ala Val Ile
1               5                   10                  15

Gly Asp Leu Lys Cys Thr Thr Val Ala Ile Asn Asp Val Asp Thr Gly
            20                  25                  30

Pro Pro Ser Ile Ser Thr Asp Ile Val Asp Val Thr Asn Gly Leu Gly
        35                  40                  45

Thr Tyr Tyr Val Leu Asp Arg Val Tyr Leu Asn Thr Thr Leu Leu Leu
    50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Arg Leu Trp Phe Lys Pro Pro Phe Leu
                85                  90                  95

Ser Asp Phe Ile Asn Gly Ile Phe Ala Lys Val Lys Asn Thr Lys Val
```

-continued

```
            100                 105                 110

Ile Lys Lys Gly Val Met Tyr Ser Glu Phe Pro Ala Ile Thr Ile Gly
        115                 120                 125

Ser Thr Phe Val Asn Thr Ser Tyr Ser Val Val Val Gln Pro His Thr
    130                 135                 140

Thr Asn Leu Asp Asn Lys Leu Gln Gly Leu Leu Glu Ile Ser Val Cys
145                 150                 155                 160

Gln Tyr Thr Met Cys Glu Tyr Pro His Thr Ile Cys His Pro Asn Leu
                165                 170                 175

Gly Asn Arg Arg Val Glu Leu Trp His Trp Asp Thr Gly Val Val Ser
            180                 185                 190

Cys Leu Tyr Lys Arg Asn Phe Thr Tyr Asp Val Asn Ala Asp Tyr Leu
        195                 200                 205

Tyr Phe His Phe Tyr Gln Glu Gly Gly Thr Phe Tyr Ala Tyr Phe Thr
    210                 215                 220

Asp Thr Gly Val Val Thr Lys Phe Leu Phe Asn Val Tyr Leu Gly Thr
225                 230                 235                 240

Val Leu Ser His Tyr Tyr Val Leu Pro Leu Thr Cys Ser Ser Ala Met
                245                 250                 255

Thr Leu Glu Tyr Trp Val Thr Pro Leu Thr Ser Lys Gln Tyr Leu Leu
            260                 265                 270

Ala Phe Asn Gln Asp Gly Val Ile Phe Asn Ala Val Asp Cys Lys Ser
        275                 280                 285

Asp Phe Met Ser Glu Ile Lys Cys Lys Thr Leu Ser Ile Ala Pro Ser
    290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
        355                 360                 365

Ala Asp Ser Phe Thr Cys Asn Asn Ile Asp Ala Ala Lys Ile Tyr Gly
    370                 375                 380

Met Cys Phe Ser Ser Ile Thr Ile Asp Lys Phe Ala Ile Pro Asn Gly
385                 390                 395                 400

Arg Lys Val Asp Leu Gln Leu Gly Asn Leu Gly Tyr Leu Gln Ser Phe
                405                 410                 415

Asn Tyr Arg Ile Asp Thr Thr Ala Thr Ser Cys Gln Leu Tyr Tyr Asn
            420                 425                 430

Leu Pro Ala Ala Asn Val Ser Val Ser Arg Phe Asn Pro Ser Thr Trp
        435                 440                 445

Asn Arg Arg Phe Gly Phe Thr Glu Gln Ser Val Phe Lys Pro Gln Pro
    450                 455                 460

Ala Gly Val Phe Thr His His Asp Val Val Tyr Ala Gln His Cys Phe
465                 470                 475                 480

Lys Ala Pro Thr Asn Phe Cys Pro Cys Lys Leu Asp Gly Ser Leu Cys
                485                 490                 495

Val Gly Asn Gly Pro Gly Ile Asp Ala Gly Tyr Lys Asn Ser Gly Ile
            500                 505                 510

Gly Thr Cys Pro Ala Gly Thr Asn Tyr Leu Thr Cys His Asn Ala Ala
        515                 520                 525
```

```
Gln Cys Asp Cys Leu Cys Thr Pro Asp Pro Ile Thr Ser Lys Ser Thr
    530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Gln Ala Phe Leu Gly Trp Ser Ala Asp Ser Cys
            580                 585                 590

Leu Gln Gly Asp Arg Cys Asn Ile Phe Ala Asn Phe Ile Phe His Asp
        595                 600                 605

Val Asn Ser Gly Thr Thr Cys Ser Thr Asp Leu Gln Lys Ser Asn Thr
    610                 615                 620

Asp Ile Ile Leu Gly Val Cys Val Asn Tyr Asp Leu Tyr Gly Ile Ile
625                 630                 635                 640

Gly Gln Gly Val Phe Val Glu Val Asn Ala Thr Tyr Tyr Asn Ser Trp
                645                 650                 655

Gln Asn Leu Leu Tyr Asp Ser Asn Gly Asn Leu Tyr Gly Phe Arg Asp
            660                 665                 670

Tyr Leu Thr Asn Arg Thr Phe Met Ile Arg Ser Cys Tyr Ser Gly Arg
        675                 680                 685

Val Ser Ala Ala Phe His Ala Asn Ser Ser Glu Pro Ala Leu Leu Phe
    690                 695                 700

Arg Asn Ile Lys Cys Asn Tyr Val Phe Asn Asn Ile Leu Ser Arg Gln
705                 710                 715                 720

Leu Gln Pro Ile Asn Tyr Phe Asp Ser Tyr Leu Gly Cys Val Val Asn
                725                 730                 735

Ala Asp Asn Ser Thr Ser Ser Val Val Gln Thr Cys Asp Leu Thr Val
            740                 745                 750

Gly Ser Gly Tyr Cys Val Asp Tyr Ser Thr Lys Arg Arg Ser Arg Arg
        755                 760                 765

Ala Ile Thr Thr Gly Tyr Arg Phe Thr Asn Phe Glu Pro Phe Thr Val
    770                 775                 780

Asn Ser Val Asn Asp Ser Leu Glu Pro Val Gly Gly Leu Tyr Glu Ile
785                 790                 795                 800

Gln Ile Pro Ser Glu Phe Thr Ile Gly Asn Met Glu Glu Phe Ile Gln
                805                 810                 815

Thr Ser Ser Pro Lys Val Thr Ile Asp Cys Ser Ala Phe Val Cys Gly
            820                 825                 830

Asp Tyr Ala Ala Cys Lys Ser Gln Leu Val Glu Tyr Gly Ser Phe Cys
        835                 840                 845

Asp Asn Ile Asn Ala Ile Leu Thr Glu Val Asn Glu Leu Leu Asp Thr
    850                 855                 860

Thr Gln Leu Gln Val Ala Asn Ser Leu Met Asn Gly Val Thr Leu Ser
865                 870                 875                 880

Thr Lys Leu Lys Asp Gly Val Asn Phe Asn Val Asp Asp Ile Asn Phe
                885                 890                 895

Ser Pro Val Leu Gly Cys Leu Gly Ser Gly Cys Asn Lys Gly Ser Ser
            900                 905                 910

Arg Ser Ala Ile Glu Asp Leu Leu Phe Ser Lys Val Lys Leu Ser Asp
        915                 920                 925

Val Gly Phe Val Glu Ala Tyr Asn Asn Cys Thr Gly Gly Ala Glu Ile
    930                 935                 940
```

-continued

```
Arg Asp Leu Ile Cys Val Gln Ser Tyr Asn Gly Ile Lys Val Leu Pro
945                 950                 955                 960

Pro Leu Leu Ser Val Asn Gln Ile Ser Gly Tyr Thr Leu Ala Ala Thr
                965                 970                 975

Ser Ala Ser Leu Phe Pro Pro Trp Ser Ala Ala Ala Gly Val Pro Phe
            980                 985                 990

Tyr Leu Asn Val Gln Tyr Arg Ile  Asn Gly Leu Gly Val  Thr Met Asp
        995                 1000                 1005

Val Leu  Ser Gln Asn Gln Lys  Leu Ile Ala Asn Ala  Phe Asn Asn
    1010                 1015                 1020

Ala Leu  Asp Ala Ile Gln Glu  Gly Phe Asp Ala Thr  Asn Ser Ala
    1025                 1030                 1035

Leu Val  Lys Ile Gln Ala Val  Val Asn Ala Asn Ala  Glu Ala Leu
    1040                 1045                 1050

Asn Asn  Leu Leu Gln Gln Leu  Ser Asn Arg Phe Gly  Ala Ile Ser
    1055                 1060                 1065

Ser Ser  Leu Gln Glu Ile Leu  Ser Arg Leu Asp Ala  Leu Glu Ala
    1070                 1075                 1080

Gln Ala  Gln Ile Asp Arg Leu  Ile Asn Gly Arg Leu  Thr Ala Leu
    1085                 1090                 1095

Asn Ala  Tyr Val Ser Gln Gln  Leu Ser Asp Ser Thr  Leu Val Lys
    1100                 1105                 1110

Phe Ser  Ala Ala Gln Ala Met  Glu Lys Val Asn Glu  Cys Val Lys
    1115                 1120                 1125

Ser Gln  Ser Ser Arg Ile Asn  Phe Cys Gly Asn Gly  Asn His Ile
    1130                 1135                 1140

Ile Ser  Leu Val Gln Asn Ala  Pro Tyr Gly Leu Tyr  Phe Ile His
    1145                 1150                 1155

Phe Ser  Tyr Val Pro Thr Lys  Tyr Val Thr Ala Lys  Val Ser Pro
    1160                 1165                 1170

Gly Leu  Cys Ile Ala Gly Asp  Arg Gly Ile Ala Pro  Lys Ser Gly
    1175                 1180                 1185

Tyr Phe  Val Asn Val Asn Asn  Thr Trp Met Phe Thr  Gly Ser Gly
    1190                 1195                 1200

Tyr Tyr  Tyr Pro Glu Pro Ile  Thr Gly Asn Asn Val  Val Val Met
    1205                 1210                 1215

Ser Thr  Cys Ala Val Asn Tyr  Thr Lys Ala Pro Asp  Val Met Leu
    1220                 1225                 1230

Asn Ile  Ser Thr Pro Asn Leu  His Asp Phe Lys Glu  Glu Leu Asp
    1235                 1240                 1245

Gln Trp  Phe Lys Asn Gln Thr  Ser Val Ala Pro Asp  Leu Ser Leu
    1250                 1255                 1260

Asp Tyr  Ile Asn Val Thr Phe  Leu Asp Leu Gln Asp  Glu Met Asn
    1265                 1270                 1275

Arg Leu  Gln Glu Ala Ile Lys  Val Leu Asn Gln Ser  Tyr Ile Asn
    1280                 1285                 1290

Leu Lys  Asp Ile Gly Thr Tyr  Glu Tyr Tyr Val Lys  Trp Pro Trp
    1295                 1300                 1305

Tyr Val  Trp Leu Leu Ile Gly  Phe Ala Gly Val Ala  Met Leu Val
    1310                 1315                 1320

Leu Leu  Phe Phe Ile Cys Cys  Cys Thr Gly Cys Gly  Thr Ser Cys
    1325                 1330                 1335

Phe Lys  Ile Cys Gly Gly Cys  Cys Asp Asp Tyr Thr  Gly His Gln
```

1340 1345 1350

Glu Leu Val Ile Lys Thr Leu His Asp Asp
1355 1360

<210> SEQ ID NO 23
<211> LENGTH: 1275
<212> TYPE: DNA
<213> ORGANISM: Bovine coronavirus

<400> SEQUENCE: 23

```
atgtttttgc ttcttagatt tgttctagtt agctgcataa ttggtagcct aggttttgat      60

aaccctccta ccaatgttgt ttcgcattta aatggagatt ggtttttatt tggtgacagt     120

cgttcagatt gtaatcatgt tgttaatacc aacccccgta attattctta tatggacctt     180

aatcctgccc tgtgtgattc tggtaaaata tcatctaaag ctggcaactc catttttagg     240

agttttcact ttaccgattt ttataattac acaggcgaag gtcaacaaat tatttttat      300

gagggtgtta attttacgcc ttatcatgcc tttaaatgca ccacttctgg tagtaatgat     360

atttggatgc agaataaagg cttgttttac actcaggttt ataagaatat ggctgtgtat     420

cgcagcctta cttttgttaa tgtaccatat gtttataatg gctctgcaca atctacagct     480

ctttgtaaat ctggtagttt agttcttaat aaccctgcat atatagctcg tgaagctaat     540

tttggggatt attattataa ggttgaagct gacttttatt tgtcaggttg tgacgagtat     600

atcgtaccac tttgtatttt taacggcaag tttttgtcga atacaaagta ttatgatgat     660

agtcaatatt attttaataa agacactggt gttatttatg gtctcaattc tactgaaacc     720

attaccactg gttttgattt taattgtcat tatttagttt taccctctgg taattattta     780

gccatttcaa atgagctatt gttaactgtt cctacgaaag caatctgtct taacaagcgt     840

aaggatttta cgcctgtaca ggttgttgat tcacggtgga acaatgccag gcagtctgat     900

aacatgacgg cggttgcttg tcaacccccg tactgttatt ttcgtaattc tactaccaac     960

tatgttggtg tttatgatat caatcatggg gatgctggtt ttactagcat actcagtggt    1020

ttgttatatg attcaccttg tttttcgcag caaggtgttt ttaggtatga taatgttagc    1080

agtgtctggc ctctctattc ctatggcaga tgccctactg ctgctggtat taatacccct    1140

gatgtaccta tttgtgtgta tgatccgcta ccacttattt tgcttggcat ccttttgggt    1200

gttgcggtca taattattgt agttttgttg ttatatttta tggtggataa tggtactagg    1260

ctgcatgatg cttag                                                     1275
```

<210> SEQ ID NO 24
<211> LENGTH: 424
<212> TYPE: PRT
<213> ORGANISM: Bovine coronavirus

<400> SEQUENCE: 24

```
Met Phe Leu Leu Leu Arg Phe Val Leu Val Ser Cys Ile Ile Gly Ser
1               5                   10                  15

Leu Gly Phe Asp Asn Pro Pro Thr Asn Val Val Ser His Leu Asn Gly
            20                  25                  30

Asp Trp Phe Leu Phe Gly Asp Ser Arg Ser Asp Cys Asn His Val Val
        35                  40                  45

Asn Thr Asn Pro Arg Asn Tyr Ser Tyr Met Asp Leu Asn Pro Ala Leu
    50                  55                  60

Cys Asp Ser Gly Lys Ile Ser Ser Lys Ala Gly Asn Ser Ile Phe Arg
65                  70                  75                  80
```

-continued

```
Ser Phe His Phe Thr Asp Phe Tyr Asn Tyr Thr Gly Glu Gly Gln Gln
                85                  90                  95

Ile Ile Phe Tyr Glu Gly Val Asn Phe Thr Pro Tyr His Ala Phe Lys
            100                 105                 110

Cys Thr Thr Ser Gly Ser Asn Asp Ile Trp Met Gln Asn Lys Gly Leu
        115                 120                 125

Phe Tyr Thr Gln Val Tyr Lys Asn Met Ala Val Tyr Arg Ser Leu Thr
    130                 135                 140

Phe Val Asn Val Pro Tyr Val Tyr Asn Gly Ser Ala Gln Ser Thr Ala
145                 150                 155                 160

Leu Cys Lys Ser Gly Ser Leu Val Leu Asn Asn Pro Ala Tyr Ile Ala
                165                 170                 175

Arg Glu Ala Asn Phe Gly Asp Tyr Tyr Tyr Lys Val Glu Ala Asp Phe
            180                 185                 190

Tyr Leu Ser Gly Cys Asp Glu Tyr Ile Val Pro Leu Cys Ile Phe Asn
        195                 200                 205

Gly Lys Phe Leu Ser Asn Thr Lys Tyr Tyr Asp Asp Ser Gln Tyr Tyr
    210                 215                 220

Phe Asn Lys Asp Thr Gly Val Ile Tyr Gly Leu Asn Ser Thr Glu Thr
225                 230                 235                 240

Ile Thr Thr Gly Phe Asp Phe Asn Cys His Tyr Leu Val Leu Pro Ser
                245                 250                 255

Gly Asn Tyr Leu Ala Ile Ser Asn Glu Leu Leu Leu Thr Val Pro Thr
            260                 265                 270

Lys Ala Ile Cys Leu Asn Lys Arg Lys Asp Phe Thr Pro Val Gln Val
        275                 280                 285

Val Asp Ser Arg Trp Asn Asn Ala Arg Gln Ser Asp Asn Met Thr Ala
    290                 295                 300

Val Ala Cys Gln Pro Pro Tyr Cys Tyr Phe Arg Asn Ser Thr Thr Asn
305                 310                 315                 320

Tyr Val Gly Val Tyr Asp Ile Asn His Gly Asp Ala Gly Phe Thr Ser
                325                 330                 335

Ile Leu Ser Gly Leu Leu Tyr Asp Ser Pro Cys Phe Ser Gln Gln Gly
            340                 345                 350

Val Phe Arg Tyr Asp Asn Val Ser Ser Val Trp Pro Leu Tyr Ser Tyr
        355                 360                 365

Gly Arg Cys Pro Thr Ala Ala Gly Ile Asn Thr Pro Asp Val Pro Ile
    370                 375                 380

Cys Val Tyr Asp Pro Leu Pro Leu Ile Leu Leu Gly Ile Leu Leu Gly
385                 390                 395                 400

Val Ala Val Ile Ile Ile Val Val Leu Leu Leu Tyr Phe Met Val Asp
                405                 410                 415

Asn Gly Thr Arg Leu His Asp Ala
            420


<210> SEQ ID NO 25
<211> LENGTH: 31028
<212> TYPE: DNA
<213> ORGANISM: Bovine coronavirus
<220> FEATURE:
<221> NAME/KEY: misc_feature
<222> LOCATION: (1)..(6)
<223> OTHER INFORMATION: n is a, c, g, or t

<400> SEQUENCE: 25
```

-continued

```
nnnnnngagc gatttgcgtg cgtgcatccc gcttctctga tctcttgtta gatcttttta     60
taatctaaac tttataaaaa catccactcc ctgtattcta tgcttgtggg cgtagatttt    120
tcatagtggt gtctatattc atttctgctg ttaacagctt tcagccaggg acgtgttgta    180
tcctaggcag tggcccaccc ataggtcaca atgtcgaaga tcaacaaata cggtctcgaa    240
ctacactggg ctccagaatt tccatggatg tttgaggacg cagaggagaa gttggataac    300
cctagtagtt cagaggtgga tatagtatgc tccaccactg cgcaaaagct ggaaacaggc    360
ggaatttgtc ctgaaaatca tgtgatggtg gattgtcgcc gacttcttaa acaagagtgt    420
tgtgtgcagt ctagcctaat acgtgaaatt gttatgaata cacgtccata tgatttggag    480
gtgctacttc aagatgcttt gcagtcctgc gaagcagttt tggttacacc ccctctaggt    540
atgtctctgg aggcatgcta tgtgagaggt tgtaatccta atggatggac catgggtttg    600
tttcggcgta gaagtgtgtg taacactggt cgttgcgctg ttaacaagca tgtggcctat    660
cagctatata tgattgatcc tgcgggtgtc tgttttggtg caggtcaatt tgtgggttgg    720
gttataccct tagcctttat gcctgtgcaa tcccggaaat ttattgttcc tagggttatg    780
tacttgcgta agtgtggcga aaagggtgcc tacaataaag atcataaacg tggcggtttt    840
gaacacgttt ataattttaa agttgaggat gcttacgacc tggttcatga tgagcctaag    900
ggtaagtttt ctaagaaggc ttatgcttta attagaggat accgtggtgt taaaccgctt    960
ctctatgtag accagtatgg ttgtgattat actggtggtc ttgcagatgg cttagaggct   1020
tatgctgata agacattgca agaaatgaag gcattatttc ctatttggag ccaggaactc   1080
ccttttgatg taactgtggc atggcacgtt gtgcgtgatc cacgttatgt tatgagactg   1140
cagagtgctt ctactatacg tagtgttgca tatgttgcta accctactga agacttgtgt   1200
gatggttctg ttgttataaa ggaacctgtg catgtttatg cggatgactc tattatttta   1260
cgtcaacata atttagttga cattatgagt tgtttttata tggaggcaga tgcagttgta   1320
aatgcttttt atggtgttga tttgaaagat tgtggttttg ttatgcagtt tggttatatt   1380
gactgcgaac aagacttgtg tgattttaaa ggttgggttc ctggtaatat gatagatggt   1440
tttgcttgca ctacttgtgg tcatgtttat gagacaggtg atttgctagc acaatcttca   1500
ggtgttttgc ctgttaatcc tgtattgcat actaagagtg cagcaggtta tggtggtttt   1560
ggttgtaagg attcttttac cctgtatggc caaactgtag tttattttgg aggttgtgtg   1620
tattggagtc cagcacgtaa tatatggatt cctatattaa aatcttctgt taagtcttat   1680
gacggtttgg tttatactgg agttgtaggt tgcaaggcta ttgtaaagga aacaaatctc   1740
atttgcaaag cgttgtacct tgattatgtt caacacaagt gtggcaattt acaccagcgg   1800
gagttgctag gtgtgtcaga tgtgtggcat aaacaattgt tattaaatag aggtgtgtac   1860
aaacctcttt tagagaatat tgattatttt aatatgcggc gcgctaaatt tagtttagaa   1920
acttttactg tttgtgcaga tggttttatg ccttttcttt tagatgattt ggttccgcgc   1980
gcatattatt tggcagtaag tggtcaagca ttttgtgact acgcaggtaa aatctgccat   2040
gctgttgtgt ctaagagtaa agagttactt gatgtgtctc tggattcttt aggtgcagct   2100
atacattatt tgaattctaa aattgttgat ttggctcaac attttagtga ttttggaaca   2160
agtttcgttt ctaaaattgt tcatttcttt aagactttta ctactagcac tgctcttgca   2220
tttgcatggg ttttatttca tgttttgcat ggtgcttata tagtagtgga gagtgatata   2280
tattttgtta aaaacattcc tcgttatgct agtgctgttg cacaagcatt tcggagtgtt   2340
gctaaagttg tactggactc tttaagagtt acttttattg atggcctttc ttgttttaag   2400
```

```
attggacgta gaagaatttg tctttcaggc agtaaaattt atgaagttga gcgtggcttg   2460
ttacattcat ctcaattgcc attagatgtt tatgatttaa ccatgcctag tcaagttcag   2520
aaaaccaagc aaaaacctat ttatttaaaa ggttctggtt ctgatttttc attagcggat   2580
agtgtagttg aagttgttac aacttcactt acaccatgtg gttattctga accacctaaa   2640
gttgcagata aaatttgcat tgtggataat gtttatatgg ccaaggctgg tgacaaatat   2700
taccctgttg tggttgatgg tcatgttgga cttttggatc aagcatggag ggttccttgt   2760
gctggaaggc gtgttacatt taaggaacag cctacagtaa atgagattgc aagcacgcct   2820
aagactatta aagtttttta tgagcttgac aaagatttta atactatttt aaacactgca   2880
tgtggagtgt ttgaagtgga tgatactgtg gatatggagg aattttatgc tgtggtgatt   2940
gatgccatag aagagaaact ttctccatgt aaggagcttg aaggtgtagg tgctaaagtt   3000
agtgcctttt tacagaaatt agaggataat tccctatttt tatttgatga ggctggtgag   3060
gaagttcttg ctcctaaatt gtattgtgct tttacagctc ctgaagatga tgactttctt   3120
gaagaaagtg gtgttgaaga agatgatgta gaaggtgagg aaactgattt aactgtcaca   3180
agtgctggag agccttgtgt tgccagtgaa caggaggagt cttctgaaat cttagaggac   3240
actttggatg atggtccatg tgtggagaca tctgattcac aagttgaaga agatgtacaa   3300
atgtcggatt ttgttgatct tgaatctgtg attcaggatt atgaaaatgt ttgttttgag   3360
ttttatacta cagaaccaga atttgttaaa gttttggatc tgtatgttcc taaagcaact   3420
cgcaacaatt gctggttgcg atcagttttg gcagtgatgc agaaactgcc ctgtcaattt   3480
aaagataaaa atttgcagga tctttgggtg ttatataagc aacagtatag tcagttgttt   3540
gttgatacct tggttaataa gatacctgct aatattgtag ttccacaagg tggttatgtt   3600
gctgattttg catattggtt cttaacctta tgtgattggc agtgtgttgc atactggaaa   3660
tgcattaaat gtgatttagc tcttaagctt aaaggcttgg atgctatgtt cttttatggt   3720
gatgttgtct cacatgtgtg caagtgtggt gagtctatgg tacttattga tgttgatgtg   3780
ccatttacag cccactttgc tcttaaagat aagttgtttt gtgcatttat tactaagcgt   3840
agtgtgtata aagcagcttg tgttgtggct gttaatgata gtcattctat ggctgttgtt   3900
gatggtaaac aaattgatga tcattgtatc actagtatta ctagtgataa gtttgatttt   3960
attattgggc atggtatgtc attttcaatg actacttttg aaattgccca attgtatggt   4020
tcttgtataa cacctaatgt atgttttgtt aaaggtgata taattaaagt ttctaagcgt   4080
gttaaagcag aagtcgttgt aaatcctgct aatggccata tggcacatgg tggtggtgtt   4140
gcaaaggcta ttgcagtagc agctggacag cagtttgtta aagagaccac cgatatggtt   4200
aagtctaaag gagtttgtgc tactggagat tgttatgtct ctacaggggg caaattatgt   4260
aaaactgtgc ttaatgttgt tggacctgat gcgaggacac agggtaaaca aagttatgca   4320
ttgttagagc gtgtttataa acatcttaac aaatatgatt gtgttgttac aactttgatc   4380
tcagctggta tatttagtgt gccttctgat gtgtctttaa catatctact tggtactgct   4440
aagaaacaag ttgttcttgt tagcaataat caagaggatt ttgatcttat ttctaagtgt   4500
cagataactg ccgttgaggg cactaagaaa ttggcagagc gtctttcttt taatgttggg   4560
cgttctatcg tttacgaaac agatgctaat aagttgattt taagcaatga cgttgcattt   4620
gtttcgacat ttaatgtctt acaggatgtt ttatccttaa gacatgatat agcacttgat   4680
gatgatgcac gaacctttgt tcagagcaat gttgatgttg tacctgaggg ttggcgtgtt   4740
```

```
gtcaataagt tttatcaaat taatggtgtt agaaccgtta agtattttga gtgtcccggg   4800
ggcatagata tatgcagcca ggataaagtt tttggttatg tacagcaggg tagttttaat   4860
aaggctactg ttgctcaaat taaagccttg tttttggata aagtggacat cttgctaact   4920
gttgatggtg ttaatttcac taacaggttt gtgcctgtag gtgaaagttt tggtaagagt   4980
ctaggaaatg tgttttgtga tggagttaat gtcacgaaac ataagtgtga tataaattat   5040
aaaggtaaag tctttttcca gtttgataat ctttctagtg aagatttaaa ggctgtaaga   5100
agttctttta attttgatca gaaggaattg cttgcctact acaacatgct tgttaattgt   5160
tctaagtggc aggttgtttt taatggtaag tatttcactt ttaagcaagc taataacaat   5220
tgttttgtta atgtttcttg cttaatgctc cagagtttga atctgaaatt taaaattgtt   5280
caatggcagg aggcgtggct tgaatttcgt tctggccgcc ctgctagatt tgtatctttg   5340
gttttggcta aaggtgggtt taaatttggg gatcctgctg attctagaga tttcttgcgt   5400
gttgtgttta gtcaagttga tttgacaggg gcaatatgtg attttgaaat tgcatgtaaa   5460
tgtggtgtaa agcaggaaca gcgtactggt gtggacgctg ttatgcattt tggtacattg   5520
agtcgtgaag atcttgagat tggttacacc gtggattgtt cttgcggtaa aaagctaatt   5580
cattgtgtac gatttgatgt accattttta atttgcagta atacacctgc tagtgtaaaa   5640
ttacctaagg gtgtaggaag tgcaaatatt tttaaaggtg ataaggttgg tcattatgtt   5700
catgttaagt gtgaacagtc ttatcagctt tatgatgctt ctaatgttaa gaaggttaca   5760
gacgttactg gcaatttgtc agattgtttg tatcttaaaa atttgaaaca aacttttaaa   5820
tcggtgttaa ccacctatta tttggatgat gttaagaaaa ttgagtataa acctgacttg   5880
tcacaatatt attgtgacgg aggtaagtat tatactcagc gtattattaa agcccaattt   5940
aaaacatttg agaaagtaga tggtgtgtat actaatttta aattgatagg acacaccgtc   6000
tgtgatattc ttaatgctaa gttgggtttt gatagctcta aagagtttgt tgaatataag   6060
gttactgagt ggccaacagc tacaggtgat gtggtgttgg ctactgatga tttgtatgtt   6120
aagagatatg aaaggggttg tattactttt ggtaaacctg ttatatggtt aagccatgag   6180
caagcttccc tcaattcttt aacatatttt aatagacctt tattggttga tgagaataaa   6240
tttgatgttt taaaagtgga tgatgttgac gatggtggtg atatctcaga gagtgatgct   6300
aaagaaccca aagaaatcaa cattattaag ttaagtggtg ttaaaaaacc atttaaggtt   6360
gaagatagtg tcattgttaa tgatgatact agtgaaatca aatatgttaa gagtttgtct   6420
atagttgatg tgtatgatat gtggcttaca ggttgtaggt gtgttgttag gactgctaat   6480
gctttgagca gagcagttaa cgtacctaca atacgtaagt ttataaaatt tggtatgact   6540
cttgttagta taccaattga tttgttaaat ttaagagaga ttaagcctgt ttttaatgtg   6600
gttaaagctg tgcgaaataa aatttctgca tgctttaatt ttattaaatg gctttttgtc   6660
ttattatttg gctggattaa aatatccgct gataataaag taatttacac cacagaagtt   6720
gcatcaaagc ttacgtgtaa gcttgtagct ttagctttta aaaatgcatt tttgacattt   6780
aagtggagtg tggttgctag aggtgcttgc attatagcga ctatatttct attgtggttt   6840
aattttatat atgccaatgt aatttttagt gatttttatt tgcctaaaat cggtttcttg   6900
ccgacttttg ttggtaagat cgcacagtgg attaagaaca cttttagtct tgtaactatt   6960
tgtgatctat attccattca ggatgtgggt tttaagaatc agtattgtaa tggaagtatc   7020
gcatgtcagt tctgcttggc aggatttgat atgttagata attataaagc cattgatgta   7080
gtacagtatg aagctgatag gcgagcattt gttgattata caggtgtgtt aaagattgtc   7140
```

```
attgaattga tagttagtta cgccctgtat acggcatggt tttacccatt gtttgctctt   7200
attagtattc agatcttgac cacttggctg cctgagcttt ttatgcttag tacattacat   7260
tggagtgtta ggttgctggt gtctttagct aatatgttac cagcacatgt gtttatgagg   7320
ttttatatta ttattgcctc ttttattaag ctgtttagct tgtttaggca tgttgcctat   7380
ggttgtagta aatctggttg tttgttttgt tacaagagga atcgtagtct acgtgttaaa   7440
tgtagtacta ttgttggtgg catgatacgc tattacgatg ttatggctaa tggtggcact   7500
ggcttttgtt caaaacatca atggaattgc attgattgtg attcttataa accaggtaat   7560
acttttatta ctgttgaggc cgctcttgat ttatctaagg aattgaaacg gcctattcag   7620
cctacagatg ttgcttatca tacggttacg gatgttaagc aagttggttg ttatatgcgc   7680
ttgttctatg atcgtgatgg acagcgcaca tatgatgatg ttaatgctag tttgtttgtg   7740
gattatagta atttgctaca ttctaaggtt aagagtgtgc ctaatatgca tgttgtggta   7800
gtggaaaatg atgccgataa agctaatttt cttaatgctg ctgtatttta tgcacagtct   7860
ttgtttagac ctattttaat ggttgataaa aatctgataa ctactgctaa tactggtacg   7920
tctgttacag aaactatgtt tgatgtttat gtggatacat tttgtctat  gtttgatgtg   7980
gataaaaaga gtcttaatgc tttaatagca actgcgcatt cttctataaa acagggtacg   8040
cagatctgta aagttttgga taccttttta agctgtgctc gtaaaagttg ttctattgat   8100
tcagatgttg atactaagtg tttagctgat tctgtcatgt ctgctgtatc ggcaggcctt   8160
gaattgacgg atgaaagttg taataacttg gtgccaacat atttgaaggg tgataacatt   8220
gtggcagctg atttaggtgt tctgattcaa aattctgcta agcatgtgca gggtaatgtt   8280
gctaaaatag ccggtgtttc ctgtatatgg tctgtggatg cttttaatca gcttagttct   8340
gatttccagc ataaattgaa gaaagcatgt tgtaaaacta gtttgaaact gaagcttact   8400
tataataagc agatggctaa tgtctctgtt ttaactacac cctttagtct taaagggggt   8460
gcagttttta gttattttgt ttatgtatgt tttgtgttga gtttggtttg ttttattgga   8520
ttgtggtgct taatgcccac ttacacagta cacaaatcag attttcagct tcccgtttat   8580
gccagttata aagttttaga taatggtgtt attagagatg ttagcgttga agatgtttgt   8640
ttcgctaaca aatttgaaca atttgatcaa tggtatgagt ctacatttgg tctaagttat   8700
tatagtaaca gtatggcttg tcccattgtt gttgctgtag tagaccagga ttttggctct   8760
actgtgttta atgtccctac caaagtgtta cgatatggtt accatgtgtt gcactttatt   8820
acacatgcac tttctgctga tggagtgcag tgttatacgc cacatagtca aatatcgtat   8880
tctaattttt atgctagtgg ctgtgtgctt tcctctgctt gcactatgtt tgcaatggcc   8940
gatggtagtc cacaacctta ttgttataca gatgggctta tgcagaatgc ttctctgtat   9000
agttcattgg tacctcatgt gcggtataat cttgctaatg ctaaaggttt tatccgtttt   9060
ccagaagtgt tgcgagaagg acttgtgcgt attgtgcgta ctcgttctat gtcgtattgc   9120
agagttggat tatgtgagga agctgatgag ggtatatgct ttaattttaa tggttcttgg   9180
gtgcttaata atgattatta tagatcattg cctgggacct tttgtggtag agatgttttt   9240
gacttaattt atcagctgtt taaaggttta gcacagcctg tggatttctt ggcattgact   9300
gctagttcca ttgctggtgc tatacttgct gtaattgttg ttttggtgtt ttattactta   9360
ataaagctta aacgtgcttt tggtgattac accagtattg tttttgttaa tgtgattgtg   9420
tggtgtgtaa attttatgat gctttttgtg tttcaagttt accctacact ttcttgtgta   9480
```

```
tatgctattt gttattttta tgccacgctt tatttccctt cggagataag tgtgataatg   9540
catttacaat ggctagttat gtatggcact attatgcctt tatggttttg tttgctatat   9600
atatctgttg ttgtttcaaa tcatgctttt tgggtatttt cttactgcag acagcttggt   9660
acttctgttc gtagtgatgg tacatttgaa gaaatggctc ttactacttt tatgattaca   9720
aaagattctt attgtaagct taagaattct ttgtctgatg ttgcttttaa tagatatttg   9780
agtttgtata ataaatatag gtattacagc ggtaaaatgg atactgctgc atatagggag   9840
gctgcttgtt ctcagttggc taaagcaatg gatacattta ccaataataa tggtagtgat   9900
gtgctttacc aaccgcctac tgcttccgtt tcaacttcat tcttgcaatc tggtattgtg   9960
aaaatggtta atcctacttc taaggtagaa ccatgtattg tcagtgttac ctatggtaat  10020
atgacattga atggtttatg gttggatgat aaggtctact gtcccagaca tgtgatatgt  10080
tctgcttcag atatgactta tccagattat acaaatttgt tgtgtagagt aacatcaagt  10140
gattttactg tattgtttga tcgtctaagc cttacagtga tgtcttatca aatgcagggt  10200
tgtatgcttg ttcttacagt gaccctgcaa aattctcgta cgccaaaata tacatttggt  10260
gtggttaaac ctggtgagac ttttactgtt ttagctgctt ataacggcaa accacaagga  10320
gcctttcatg tgactatgcg tagtagttat accattaagg gttccttttt atgcggatct  10380
tgtggatctg ttggttatgt aataatgggt gattgtgtta aatttgtgta tatgcatcaa  10440
ttggagctta gtactggttg tcatactggt actgatttca atggggattt ttatggtcct  10500
tataaggatg ctcaggttgt ccaattgccc gttcaggatt atatacaatc tgttaatttt  10560
gtagcatggc tttatgctgc tatacttaat aattgtaatt ggtttgtaca aagtgataag  10620
tgttctgttg aagattttaa tgtgtgggct ttgtctaatg ggtttagcca agttaagtct  10680
gatcttgtta tagatgcttt agcttctatg actggtgtgt ctttggaaac actattggct  10740
gctattaagc gtcttaagaa tggttttcaa ggacgtcaga ttatgggtag ttgctccttt  10800
gaggatgaat tgacacctag cgatgtttat caacaactcg ctggtatcaa gttacaatca  10860
aagcgtacta gattggttaa aggcattgtt tgttggatta tggcttctac atttttgttt  10920
agttgtataa ttacagcatt tgtgaaatgg actatgttta tgtatgtaac tactaatatg  10980
cttagtatta cgttttgtgc actttgtgtt ataagtttgg ccatgttgtt ggttaaacat  11040
aagcatcttt atttgactat gtatataatt cctgtgcttt ttacactgct gtataacaac  11100
tatttggttg tgtacaagca gacatttaga ggctatgttt atgcatggct atcatattat  11160
gttccatcag ttgagtatac ttatactgat gaagtaattt atggcatgtt attgcttata  11220
ggaatggtct ttgttacatt acgtagcatt aaccatgatt tgttctcttt tataatgttt  11280
gttggtcgtg tgatttctgt tgtctctttg tggtacatgg gttctaactt agaggaagaa  11340
attcttctta tgttggcttc tctttttggt acttacacat ggacaacagc tttatctatg  11400
gctgcagcaa aggttattgc taagtgggtt gctgtgaatg ttttgtattt cacagatata  11460
cctcaaatta agatagtgct tgtatgctat ttgtttatag gttatattat tagctgttat  11520
tggggtttgt tttccttgat gaacagtttg tttagaatgc ctttgggtgt ttataattat  11580
aaaatttcag tacaggaatt aagatatatg aatgctaatg gattgcgccc tcctaagaat  11640
agttttgaag ccctcatgct taattttaag cttttgggta ttggaggtgt gccaattatt  11700
gaagtatctc aatttcaatc aaaattgact gatgttaaat gtgctaatgt tgtcttgctt  11760
aattgcttgc aacatttgca tgttgcttct aactctaagt tgtggcaata ttgtagcact  11820
ttgcacaatg aaatacttgc cacttctgat ctgggtgttg cttttgaaaa gcttgctcag  11880
```

```
ttgttaattg ttttgtttgc taatccagct gctgtggata gcaagtgcct gactagtatt  11940
gaagaagttt gcgacgatta cgcaaaggac aatactgttt tgcaggcttt acagagtgaa  12000
tttgttaata tggctagctt cgttgaatat gaagttgcta agaaaaatct tgatgaggcg  12060
tgttctagtg gttctgctaa tcgacagcag ttaaaacagc tagagaaagc ctgtaatatt  12120
gctaaatctg cttatgaacg cgaccgtgct gtagcaagaa agttggagcg tatggcagat  12180
ttggctctca ctaatatgta taaagaagct agaattaatg ataagaagag taaggttgtt  12240
tctgccttgc aaactatgct ttttagtatg gtgcgtaagt tagataatca agctctgaat  12300
tcaatattag ataatgctgt gaagggttgt gtaccattga atgcaatccc ttcattggca  12360
gcaaatactc tgactataat tgtaccagat aaaagtgttt atgatcaggt agttgacaat  12420
gtctatgtta cctatgcggg taatgtatgg cagattcaaa ctatccaaga ttcagatggt  12480
acaaataagc agttgaatga gatatctgat gattgtaact ggccactagt tattattgca  12540
aatcggcata atgaggtatc tgctaccgtt ttgcaaaata atgaattaat gcctgctaag  12600
ttgaaaactc aggttgttaa tagtggtcca gatcagactt gtaatacacc tactcaatgt  12660
tactataata atagttacaa tgggaagatt gtttatgcta tacttagtga tgttgatggt  12720
cttaagtata caaaaattct taaagatgat ggcaattttg ttgttttgga gttagatcct  12780
ccttgtaaat ttactgttca agatgttaaa ggtcttaaaa ttaagtacct ttattttgta  12840
aaaggttgta acacactagc aagaggctgg gttgttggta caatttcttc tacagttaga  12900
ttgcaagctg gaactgctac tgagtatgct tccaactcat ctatattatc tttatgtgcg  12960
ttttctgtag atcctaagaa aacgtattta gattttatac aacagggagg aacacctatt  13020
gccaattgtg ttaaaatgtt gtgtgaccat gctggtaccg gtatggccat tactgttaaa  13080
cccgatgcta ccactagtca ggattcatat ggtggtgcgt ctgtttgtat atattgccgc  13140
gcacgagttg aacacccaga tgttgatggg ttgtgcaaat tacgcggcaa gtttgtacaa  13200
gtgcctgtag gtataaaaga tcctgtgtct tatgttttga cacatgatgt ttgtcaagtt  13260
tgtggatttt ggcgggatgg aagctgttca tgtgttagca ctgacactac tgttcagtca  13320
aaagatacta attttttaaa cgggttcggg gtacgagtgt agatgcccgt ctcgtaccct  13380
gtgccagtgg tttatctact gatgtacaat taagggcatt tgatatttgc aatgctagtg  13440
ttgctggcat tggtttacat ttaaaagtta attgctgccg ttttcagcgt gttgatgaga  13500
acggtgataa attagatcag ttctttgttg ttaagaggac agatctgact atatataata  13560
gagagatgga atgctatgag cgtgtaaaag attgtaagtt tgtggctgaa cacgatttct  13620
ttacatttga tgtagaaggt agtcgtgtgc cacacattgt acgcaaggat ttaacaaagt  13680
atactatgtt ggatctttgc tatgcattgc gacattttga tcgcaatgat tgcatgctgc  13740
tttgtgacat tctctctata tatgctggtt gtgaacaatc ctactttact aagaaggatt  13800
ggtatgattt tgttgaaaat cctgatatta ttaatgttta taaaaagcta ggacctattt  13860
ttaatagagc cctagttagc gctactgagt ttgcagacaa attggtggag gtaggcttag  13920
taggcatttt aacacttgat aaccaagatt taaatggtaa atggtatgat tttggtgact  13980
atgttattgc agccccaggg tgtggtgttg ctatagcaga ctcttattat tcttatatga  14040
tgcctatgct gaccatgtgt catgcattgg attgtgaatt gtatgtgaat aatgcttata  14100
gactatttga tcttgtacag tatgatttta ctgattacaa gctcgaattg tttaataagt  14160
attttaagca ctggagtatg ccataccatc ctaacacggt tgattgtcag gatgatcggt  14220
```

-continued

```
gtatcataca ttgtgctaat tttaacatac tttttagtat ggttttacct aatacatgtt  14280
ttgggcctct tgttaggcaa atttttgtgg atggtgtgcc ttttgttgtt tcaattggct  14340
accattataa agaacttggt attgtgatga acatggatgt ggatacacat cgttatcgct  14400
tgtctttaaa agacttgctt ttatatgctg ctgatccagc tttgcatgta gcttctgcta  14460
gtgcattgta tgatttacgc acttgctgtt ttagtgttgc ggctataaca agcggtgtaa  14520
aatttcaaac agttaaacct ggtaatttta atcaggattt ttatgatttt attttaagta  14580
agggcctgct taaagagggt agttcagttg atctgaagca ctttttcttt acgcaggatg  14640
gtaatgctgc tattactgat tataattatt ataagtacaa tttgcccacc atggtggaca  14700
ttaagcagtt gttgtttgtt ttggaagttg tttataagta ttttgagatt tatgatggtg  14760
ggtgtatacc ggcatcacaa gtcattgtta ataattatga taagagtgct ggctatccat  14820
ttaataaatt tggaaaagcc aggctctatt atgaagcatt atcatttgag gagcaggatg  14880
aaatttacgc ctatactaag cgcaatgtcc tgccaacact tactcaaatg aatttgaaat  14940
atgctattag tgctaagaat agagcccgca ctgttgctgg tgtttccata cttagtacta  15000
tgactggcag aatgtttcat caaaaatgtt tgaaaagtat agcagctaca cgtggtgttc  15060
ctgttgttat aggcaccact aagttttatg gcggctggga tgatatgtta cgtcgcctta  15120
ttaaagatgt tgataatcct gtacttatgg gttgggatta tcctaagtgt gatcgtgcta  15180
tgccaaacat actacgtatt gttagtagtc tggtcttggc ccgaaaacat gaggcatgtt  15240
gttcgcaaag cgataggttt tatcgacttg cgaatgaatg cgcacaagtt ctgagtgaaa  15300
ttgttatgtg tggtggctgt tattatgtta agcctggtgg cactagtagt ggtgatgcaa  15360
ctactgcttt tgctaattca gtttttaaca tatgtcaagc tgtttcagcc aatgtatgtg  15420
ctttaatgtc atgcaatggt aataagattg aagatttgag tatacgtgct cttcagaagc  15480
gcttatactc acatgtgtat agaagtgata tggttgattc aacctttgtc acagaatatt  15540
atgaattttt aaataagcat tttagtatga tgattttgag tgatgatggc gttgtgtgtt  15600
ataattctga ttatgcgtcc aaagggtata ttgctaatat aagtgccttt caacaggtat  15660
tgtattatca aaataacgtt tttatgtcag aatccaaatg ttgggttgaa aatgacataa  15720
acaatggacc tcatgaattt tgttcacaac atacaatgct tgtaaagatg gatggggacg  15780
atgtctatct tccatatcct gatcctagtc gtatattagg agctggatgt tttgtagatg  15840
atttgttaaa gactgatagt gttcttttaa tagaacgatt tgtaagtctt gcaatagatg  15900
cttatccact tgtgtaccac gaaaatgaag aataccaaaa ggtttttcgt gtttatttgg  15960
agtatataaa gaagttgtac aatgacctgg gtaatcagat cttggatagc tacagtgtta  16020
ttttaagtac ttgtgatgga caaaagttta ctgatgagtc cttttacaag aacatgtatt  16080
taagaagtgc agttatgcag agtgttggag cttgcgtggt ctgctcttcc caaacatcat  16140
tacgttgtgg cagttgcatc agaaagcctc ttctttgctg caagtgttgt tacgatcatg  16200
ttatggcaac tgatcataaa tatgttttga gtgtttcacc atatgtgtgt aacgcaccag  16260
gatgtgatgt aaatgatgtt accaaattgt atctaggtgg tatgtcatat tattgtgaag  16320
atcataagcc acaatattcg tttaagttgg taatgaatgg tatggttttt ggtctatata  16380
aacaatcttg tacaggatct ccgtacatag atgattttaa tcgtatagct agttgtaaat  16440
ggactgatgt tgatgattac atactggcta atgaatgtac agagcgcttg aaattgtttg  16500
ctgcagaaac gcaaaaggcg actgaggaag cctttaagca gagttatgca tcagcaacaa  16560
tacaagagat tgttagtgag cgcgaattga tcctctcttg ggagattgga aaagtgaagc  16620
```

caccacttaa taaaaattat gtttttactg gctaccattt tactaaaaat ggcaagacag 16680
ttttaggtga gtatgttttt gataagagtg agttgactaa tggtgtgtat tatcgcgcca 16740
caaccactta taagctatct gtaggagatg tttttgtttt aacctctcat tcagtagcta 16800
atttaagtgc tcctacgctt gtgccgcagg agaattatag tagtattaga tttgctagtg 16860
tttatagtgt gcttgagaca tttcagaaca atgttgtgaa ctatcaacac attggtatga 16920
aacgttattg caccgtgcaa ggacctcctg gtacaggaaa gtcacatctt gctattggtc 16980
ttgctgtata ttattgtaca gcacgtgtag tatacactgc ggccagccat gcagctgttg 17040
acgcattgtg tgaaaaagca tacaaatttt tgaatataaa tgattgcact cgtattgttc 17100
ctgccaaggt cagggtggag tgctatgata agtttaaaat taatgacacc actcgtaagt 17160
atgtgtttac tactataaat gcattacctg agatggtgac tgatattgtt gttgtagatg 17220
aagttagtat gcttaccaat tatgagcttt ctgttattaa tgctcgtatt cgcgctaagc 17280
attatgttta tattggtgat cctgctcaat tgccagcacc acgtgtgtta ttgagcaagg 17340
gtacacttga acctaaatat tttaacactg ttactaagct tatgtgttgc ttagggccag 17400
acatttttct tggtacatgt tatagatgtc ctaaggaaat cgttgataca gtgtctgcct 17460
tggtttatga aaataagctt aaggctaaga atgaaagtag ttcattgtgt tttaaggtct 17520
attataaagg cgttacaaca catgaaagtt ctagtgctgt aaatatgcag cagatttatt 17580
tgattaataa gtttttgaag gttaaccctt tgtggcataa agccgttttt attagcccat 17640
ataatagtca gaactttgca gctaagcgcg ttttgggttt gcaaacccaa accgtggatt 17700
ctgcgcaagg ttctgaatat gattatgtta tatattcaca gactgcagaa acagcgcatt 17760
ctgtaaatgt taatcgcttc aatgttgcta ttactcgagc caagaaaggt attctttgcg 17820
ttatgagtaa tatgcagttg tttgaagcat tacagtttac tacattgacc gtagataaag 17880
tgccacaggc cgttgaaacg agagttcaat gtagtaccaa tttatttaaa gattgtagca 17940
agagttatag tggttaccac ccagctcatg ctccttcatt tttggcagta gatgacaaat 18000
ataaggcaac tggcgattta gccgtgtgtc ttggtattgg agattctgct gttacatatt 18060
caagattaat atcactcatg ggttttaaac tggatgttac ccttgatggg tattgtaagc 18120
tttttataac taaagaagaa gctgttaaac gcgtgcgtgc ttgggttggc tttgatgctg 18180
aaggtgctca tgccacgcgt gatagcattg ggacaaattt cccacttcaa ttagggtttt 18240
ccacaggaat tgattttgtt gtggaagcca ctggtttgtt tgctgataga gatggttaca 18300
gctttaaaaa ggctgtggct aaagctcctc ctggtgaaca atttaagcat ctcatccctt 18360
tgatgacgag aggtcagcgc tgggatgttg ttagacctag aatagtacaa atgtttgcag 18420
atcatttaat tgatctgtct gattgtgttg tgctagttac atgggcagcc aactttgagc 18480
tcacttgtct ccgctacttt gcaaaagtag gtcgtgagat ctcttgtaat gtgtgcacta 18540
aacgtgccac agcttacaat tctagaactg gttactatgg ttgttggcgc catagtgtta 18600
catgtgatta cttgtataat ccacttattg ttgatattca acagtgggga tatattggtt 18660
ctttatcaag taatcatgat ttatattgta gtgtccataa aggagcacat gttgcctcct 18720
ctgatgctat aatgacacgg tgtttggccg tttatgattg tttttgcaat aatattaatt 18780
ggaatgtgga gtatcccatc atttcaaatg agttaagtat taatacctct tgtagggtct 18840
tgcagcgtgt tatgcttaaa gctgccatgc tctgcaacag atatactttg tgttatgata 18900
ttggcaatcc aaaagcgatt gcctgtgtca aagattttga ttttaagttc tatgatgccc 18960

-continued

```
aaccaattgt taagtctgtc aagactcttt tgtatttttt tgaggcacat aaggactctt  19020
ttaaagatgg tttgtgtatg ttttggaact gtaatgtgga taagtatcca ccgaatgcag  19080
ttgtatgtag atttgacacg agagtgttga ataatttaaa tcttcctggc tgtaatggag  19140
gtagtttgta tgttaacaaa catgcattcc acactaaacc cttttctagg gcagcctttg  19200
agcatttgaa gcctatgcca tttttctatt attcagatac gccttgcgtg tatatggatg  19260
gcatggatgc taagcaggtt gattatgtac ctttgaaatc cgccacttgc atcacaagat  19320
gcaatttagg tggtgcagtt tgtttaaaac atgctgaaga gtatcgtgag tacctagagt  19380
cttacaatac agctactaca gcaggtttta ctttttgggt ctataagaca tttgattttt  19440
ataatttgtg gaatacgttc accaagctac aaagcttgga gaatgttgta tataatttag  19500
tcaagactgg tcattataca ggacaggctg gtgaaatgcc ttgtgccatt ataaatgata  19560
aagttgtggc taagatcgat aaggaggatg ttgtcatttt tattaataat acaacatatc  19620
ctactaatgt ggctgttgaa ttatttgcca agcgcagtat tcgacaccat ccagagctta  19680
agctctttag aaatttgaat atagacgtgt gctggaagca cgtcatttgg gattatgcta  19740
gagaaagtat attttgcagt aatacctatg gtgtctgcat gtatacagat ttaaagttca  19800
ttgataaatt gaatgtcctt tttgatggtc gtgataatgg tgctcttgaa gcttttaaac  19860
gctctaataa tggcgtttac atttccacga caaaagttaa gagtctttcg atgataagag  19920
gtccaccgcg tgctgaatta aatggcgtag tggtggacaa ggttggagac acagattgtg  19980
tgttttattt tgctgtgcgt aaagagggtc aggatgtcat cttcagccaa ttcgacagcc  20040
tgagagtcag ctctaaccag agcccacaag gtaatctggg gagtaatgaa cccggtaatg  20100
tcggtggtaa tgatgctctg gcaacctcca ctatctttac acaaagccgt gttattagct  20160
cttttacatg tcgtactgat atggaaaaag attttatagc tttagatcaa gatgtgttta  20220
ttcagaagta tggtttggag gactatgcct ttgaacacat tgtttatggt aatttcaacc  20280
agaagattat tggtggtttg catttgttaa taggcttgta ccgaagacag caaacttcca  20340
atttggttat tcaggagttt gtttcatacg actccagcat acactcttat tttatcactg  20400
atgagaagag tggtggtagt aagagtgttt gcactgttat agatattttg ttggatgatt  20460
ttgtggctct tgtcaagtca cttaatctta actgtgtgag taaggttgtt aatgttaatg  20520
ttgattttaa agattttcag ttcatgcttt ggtgtaacga tgagaaagtt atgactttct  20580
atcctcgttt gcaagctgca tctgactgga agcctggtta ttctatgcct gtattatata  20640
agtatttgaa ttccccaatg gaaagagtta gtctctggaa ttatgggaag ccagttactt  20700
tgcctacagg ctgtatgatg aatgttgcta agtatactca gttatgtcaa tatctgaata  20760
ctacaacatt agctgtacct gttaatatgc gagttttgca tttaggtgca ggttcagaaa  20820
aaggagtagc accgggttct gcagttctta ggcagtggtt gcctgctggt actattcttg  20880
tagataatga tttataccca tttgtgagtg acagtgtcgc tacatatttt ggggattgta  20940
taaccttacc ctttgattgt caatgggatt tgataatctc tgatatgtat gaccctatta  21000
ctaagaacat aggggagtac aatgtaagta aagatggttt ctttacatac atttgtcata  21060
tgattcgcga caagttagct ctgggtggca gtgttgctat aaaaataaca gagttttctt  21120
ggaatgcaga attatataag ttaatggggt attttgcatt ttggacggtt ttctgcacaa  21180
atgcaaatgc ttcttctagt gaagggtttt taattggcat aaattatttg ggtaagccca  21240
aggttgagat agatggaaat gttatgcatg ccaattattt gttttggaga aattccacag  21300
tttggaacgg gggtgcttat agcctgtttg atatggctaa attcccgctt aagttggctg  21360
```

gtactgccgt aataaattta agagcagacc agattaatga tatggtttat tcccttcttg 21420
aaaagggtaa actacttgtt agagatacaa ataaagaagt tttgttggt gacagtatgg 21480 ttaatgtaat ctaaacttta agaatggcag ttgcttatgc aaacaagcct aatcacttta 21540
ttaattttcc acttacccag tttgagggtt ttgtgttaaa ttataaaggt ttacaatttc 21600
aacttctcga tgaaggagtg gattgtaaaa tacaaacagc gccgcacatt agtcttgtta 21660
tgctggatat tcagcctgaa gactatagaa gtgttgatgt tgctattcaa gaagttattg 21720
atgacatgca ttggggtgag ggctttcaga ttaaatttga taaccccat atcctaggaa 21780 gatgcatagt tttagatgtt aaaggtgtag aagaattgca tgatgattta gttaattaca 21840
ttcgtgataa aggttgtgtt gctgaccaat ccaggaaatg gattggacat tgcaccatag 21900
cccaactcac ggatgctgca ctttccatta aggaaaatgt tgatttcata aacagcatgc 21960
aattcaatta taaaatcact atcaacccct catcaccggc tagacttgaa atagttaagc 22020
ttggtgctga aaagaaagat ggtttttatg aaaccatagt tagccactgg atgggaattc 22080
gttttgaata taatccaccc actgataagc tagctatgat tatgggttat tgttgtttag 22140
aagtggtgcg taaagagcta gaagaaggtg atcttcccga gaatgatgat gatgcttggt 22200
ttaagctatc gtaccattat gaaaacaatt cttggttctt tcgacatgtc tacaggaaaa 22260
gttcttattt ccgtaagtct tgtcaaaatt tagattgtaa ttgtttgggg ttttatgaat 22320
ctccagttga agaagactaa actcagtgaa aatgtttttg cttcttagat ttgttctagt 22380
tagctgcata attggtagcc taggttttga taaccctcct accaatgttg tttcgcattt 22440
aaatggagat tggtttttat ttggtgacag tcgttcagat tgtaatcatg ttgttaatac 22500
caacccccgt aattattctt atatggacct taatcctgcc ctgtgtgatt ctggtaaaat 22560
atcatctaaa gctggcaact ccatttttag gagttttcac tttaccgatt tttataatta 22620
cacaggcgaa ggtcaacaaa ttattttta tgagggtgtt aattttacgc cttatcatgc 22680
ctttaaatgc accacttctg gtagtaatga tatttggatg cagaataaag gcttgtttta 22740
cactcaggtt tataagaata tggctgtgta tcgcagcctt acttttgtta atgtaccata 22800
tgtttataat ggctctgcac aatctacagc tctttgtaaa tctggtagtt tagttcttaa 22860
taaccctgca tatatagctc gtgaagctaa ttttggggat tattattata aggttgaagc 22920
tgacttttat ttgtcaggtt gtgacgagta tatcgtacca ctttgtattt ttaacggcaa 22980
gtttttgtcg aatacaaagt attatgatga tagtcaatat tattttaata aagacactgg 23040
tgttatttat ggtctcaatt ctactgaaac cattaccact ggttttgatt ttaattgtca 23100
ttatttagtt ttaccctctg gtaattattt agccatttca aatgagctat tgttaactgt 23160
tcctacgaaa gcaatctgtc ttaacaagcg taaggatttt acgcctgtac aggttgttga 23220
ttcacggtgg aacaatgcca ggcagtctga taacatgacg gcggttgctt gtcaaccccc 23280
gtactgttat tttcgtaatt ctactaccaa ctatgttggt gtttatgata tcaatcatgg 23340
ggatgctggt tttactagca tactcagtgg tttgttatat gattcacctt gtttttcgca 23400
gcaaggtgtt tttaggtatg ataatgttag cagtgtctgg cctctctatt cctatggcag 23460
atgccctact gctgctggta ttaatacccc tgatgtacct atttgtgtgt atgatccgct 23520
accacttatt ttgcttggca tccttttggg tgttgcggtc ataattattg tagttttgtt 23580
gttatatttt atggtggata atggtactag gctgcatgat gcttagacca taatctaaac 23640
atgtttttga tacttttaat ttccttacca atggcttttg ctgttatagg agatttaaag 23700

```
tgtactacgg ttgccattaa tgatgttgac accggtcctc cttctattag cactgatatt  23760
gtcgatgtta ctaatggttt aggtacttat tatgttttag atcgtgtgta tttaaatact  23820
acgttgttgc ttaatggtta ctaccctact tcaggttcta catatcgtaa tatggcactg  23880
aagggaactt tactattgag cagactatgg tttaaaccac cttttctttc tgattttatt  23940
aatggtattt ttgctaaggt caaaaatacc aaggttatta aaaagggtgt aatgtatagt  24000
gagtttcctg ctataactat aggtagtact tttgtaaata catcctatag tgtggtagta  24060
caaccacata ctaccaattt ggataataaa ttacaaggtc tcttagagat ctctgtttgc  24120
cagtatacta tgtgcgagta cccacatacg atttgtcatc ctaatctggg taatcgacgc  24180
gtagaactat ggcattggga tacaggtgtt gtttcctgtt tatataagcg taatttcaca  24240
tatgatgtga atgctgatta cttgtatttc catttttatc aagaaggtgg tactttttat  24300
gcatatttta cagacactgg tgttgttact aagtttctgt ttaatgttta tttaggcacg  24360
gtgctttcac attattatgt cctgcctttg acttgttcta gtgctatgac tttagaatat  24420
tgggttacac ctctcacttc taaacaatat ttactagctt tcaatcaaga tggtgttatt  24480
tttaatgctg ttgattgtaa gagtgatttt atgagtgaga ttaagtgtaa aacactatct  24540
atagcaccat ctactggtgt ttatgaatta aacggttaca ctgttcagcc aattgcagat  24600
gtttaccgac gtatacctaa tcttcccgat tgtaatatag aggcttggct taatgataag  24660
tcggtgccct ctccattaaa ttgggaacgt aagacctttt caaattgtaa ttttaatatg  24720
agcagcctga tgtcttttat tcaggcagac tcatttactt gtaataatat tgatgctgct  24780
aagatatatg gtatgtgttt ttccagcata actatagata agtttgctat acccaatggt  24840
aggaaggttg acctacaatt gggcaatttg ggctatttgc agtcttttaa ctatagaatt  24900
gatactactg ctacaagttg tcagttgtat tataatttac ctgctgctaa tgtttctgtt  24960
agcaggttta atccttctac ttggaatagg agatttggtt ttacagaaca atctgttttt  25020
aagcctcaac ctgcaggtgt ttttactcat catgatgttg tttatgcaca acattgtttt  25080
aaagctccca caaatttctg tccgtgtaaa ttggatgggt ctttgtgtgt aggtaatggt  25140
cctggtatag atgctggtta taaaaatagt ggtataggca cttgtcctgc aggtactaat  25200
tatttaactt gccataatgc tgcccaatgt gattgtttgt gcactcccga ccccattaca  25260
tctaaatcta cagggcctta caagtgcccc caaactaaat acttagttgg cataggtgag  25320
cactgttcgg gtcttgctat taaaagtgat tattgtggag gtaatccttg tacttgccaa  25380
ccacaagcat ttttgggttg gtctgctgac tcttgtttac aaggggatag gtgtaatatt  25440
tttgctaatt ttatttttca tgatgttaat agtggtacta cttgttctac tgatttacaa  25500
aaatcaaaca cagacataat tcttggtgtt tgtgttaatt atgatcttta tggtattata  25560
ggccaaggtg tttttgttga ggttaatgcg acttattata atagttggca gaacctttta  25620
tatgattcta atggtaatct ctatggtttt agagactact taacaaacag aacttttatg  25680
attcgtagtt gctatagcgg tcgtgtttca gcggcctttc atgctaactc ttccgaacca  25740
gcattgctat ttcggaatat taaatgcaat tacgttttta ataatattct ttcacgacag  25800
ctgcaaccta ttaactattt tgatagttat cttggttgtg ttgtcaatgc tgataatagt  25860
acttctagtg ttgttcaaac atgtgatctc acagtaggta gtggttactg tgtggattac  25920
tctacaaaaa gacgaagtcg tagagcgatt accactggtt atcggtttac taattttgag  25980
ccatttactg ttaattcagt aaatgatagt ttagaacctg taggtggttt gtatgaaatt  26040
caaatacctt cagagtttac tataggtaat atggaggagt ttattcaaac aagctctcct  26100
```

-continued

```
aaagttacta ttgattgttc tgcttttgtc tgtggtgatt atgcagcatg taaatcacag  26160
ttggttgaat atggtagctt ctgtgacaat attaatgcta tactcacaga agtaaatgaa  26220
ctacttgaca ctacacagtt gcaagtagct aatagtttaa tgaatggtgt cactcttagc  26280
actaagctta aagatggcgt taatttcaat gtagacgaca tcaatttttc ccctgtatta  26340
ggttgtttag gaagcggttg taataaaggt tccagtagat ctgctataga ggatttactt  26400
ttttctaaag taaagttatc tgatgtcggt ttcgttgagg cttataataa ttgtactgga  26460
ggtgccgaaa ttagggacct catttgtgtg caaagttata atggtatcaa agtgttgcct  26520
ccactgctct cagtaaatca gatcagtgga tacactttgg ctgccacctc tgctagtctg  26580
tttcctcctt ggtcagcagc agcaggtgta ccattttatt taaatgttca gtatcgtatt  26640
aatgggcttg gtgttaccat ggatgtgtta agtcaaaatc aaaagcttat tgctaatgca  26700
tttaacaatg ctcttgatgc tattcaggaa gggtttgatg ctaccaattc tgctttagtt  26760
aaaattcaag ctgttgttaa tgcaaatgct gaagctctta ataacttatt gcaacaactc  26820
tctaatagat ttggtgctat aagttcttct ttacaagaaa ttctatctag actggatgct  26880
cttgaagcgc aagctcagat agacagactt attaatgggc gtcttaccgc tcttaatgct  26940
tatgtttctc aacagcttag tgattctaca ctagtaaaat ttagtgcagc acaagctatg  27000
gagaaggtta atgaatgtgt caaaagccaa tcatctagga taaatttttg tggtaatggt  27060
aatcatatta tatcattagt gcagaatgct ccatatggtt tgtattttat ccactttagc  27120
tatgtcccta ctaagtatgt cactgcgaag gttagtcccg gtctgtgcat tgctggtgat  27180
agaggtatag cccctaagag tggttatttt gttaatgtaa ataatacttg gatgttcact  27240
ggtagtggtt attactaccc tgaacccata actggaaata atgttgttgt tatgagtacc  27300
tgtgctgtta actatactaa agcgccggat gtaatgctga acatttcaac acccaacctc  27360
catgatttta aggaagagtt ggatcaatgg tttaaaaacc aaacatcagt ggcaccagat  27420
ttgtcacttg attatataaa tgttacattc ttggacctac aagatgaaat gaataggtta  27480
caggaggcaa taaaagtttt aaatcagagc tacatcaatc tcaaggacat tggtacatat  27540
gagtattatg taaaatggcc ttggtatgta tggcttttaa ttggctttgc tggtgtagct  27600
atgcttgttt tactattctt catatgctgt tgtacaggat gtgggactag ttgttttaag  27660
atatgtggtg gttgttgtga tgattatact ggacaccagg agttagtaat taaaacatta  27720
catgacgact aagttcgtct ttgatttatt ggctcctgac gatatattac atcccttcaa  27780
tcatgtgaag ctaattataa gacccattga ggtcgagcat attataatag ctaccacaat  27840
gcctgctgtt tagtgggtac tgtgtcttat ataactagta aacctgtaat gccaatggct  27900
acaaccattg acggtacaga ttatactaat attatgccta gtactgtttc tacaacagtt  27960
tatttaggct gttctatagg tattgacact agcaccactg gttttacctg tttttcacgg  28020
tactagttcc aaaccatatt ataatttagg tagaccttat aactttaagc attattgcca  28080
aagttcctaa ggtcacgccc tagtaatgga catctggaga cctgagatta aatatctccg  28140
ttatattaac ggttttaatg tctcagaatt agaagatgct tgttttaaat ttaactataa  28200
atttcctaaa gtaggatatt gtagagttcc tagtcatgct tggtgccgta atcaaggtag  28260
cttttgtgct acactcactc tttatggcaa atccaaacat tatgataaat attttggagt  28320
aataactggt tttacagcat tcgctaatac tgtagaggag gctgttaaca aactggtttt  28380
cttagctgtt gactttatta cctggcggag acaggagtta aatgtttatg gctgatgctt  28440
```

-continued

```
attttgcaga cactgtgtgg tatgtggggc aaataatttt tatagttgcc atttgtttat  28500
tggttataat agttgtagtg gcatttttgg caacttttaa attgtgtatt caactttgcg  28560
gtatgtgtaa taccttagta ctgtcccctt ctatttatgt gtttaataga ggtaggcagt  28620
tttatgagtt ttacaacgat gtaaaaccac cagttcttga tgtggatgac gtttagttaa  28680
tccaaacatt atgagtagtg taactacacc agcaccagtt tacacctgga ctgctgatga  28740
agctattaaa ttcctaaagg aatggaactt ttctttgggt attatactac tttttattac  28800
aatcatattg caatttggat atacaagtcg cagtatgttt gtttatgtta ttaagatgat  28860
cattttgtgg cttatgtggc cccttactat catcttaact attttcaatt gcgtgtatgc  28920
gttgaataat gtgtatcttg gcttttctat agttttcact atagtggcca ttatcatgtg  28980
gattgtgtat tttgtgaata gtatcaggtt gtttattaga actggaagtt ggtggagttt  29040
caacccagaa acaaacaact tgatgtgtat agatatgaag ggaaggatgt atgttaggcc  29100
gataattgag gactaccata cccttacggt cacaataata cgtggtcatc tttacatgca  29160
aggtataaaa ctaggtactg gctattcttt gtcagatttg ccagcttatg tgactgttgc  29220
taaggtctca cacctgctca cgtataagcg tggttttctt gacaagatag gcgatactag  29280
tggttttgct gtttatgtta agtccaaagt cggtaattac cgactgccat caacccaaaa  29340
gggttctggc atggacaccg cattgttgag aaatataatc taaactttaa ggatgtcttt  29400
tactcctggt aagcaatcca gtagtagagc gtcctctgga aatcgttctg gtaatggcat  29460
ccttaagtgg gccgatcagt ccgaccaatc tagaaatgtt caaaccaggg gtagaagagc  29520
tcaacccaag caaactgcta cttctcagct accatcagga gggaatgttg taccctacta  29580
ttcttggttc tctggaatta ctcagtttca aaaaggaaag gagtttgaat ttgcagaggg  29640
acaaggtgtg cctattgcac caggagtccc agctactgaa gctaaggggt actggtacag  29700
acacaacaga cgttctttta aaacagccga tggcaaccag cgtcaactgc tgccacgatg  29760
gtatttttac tatcttggaa caggaccgca tgccaaagac cagtatggca ccgatattga  29820
cggtgtcttc tgggtcgcta gtaaccaggc tgatgtcaat accccggctg acattctcga  29880
tcgggaccca agtagcgatg aggctattcc gactaggttt ccgcctggca cggtactccc  29940
tcagggttac tatattgaag gctcaggaag gtctgctcct aattccagat ctacttcacg  30000
cgcatccagt agagcctcta gtgcaggatc gcgtagtaga gccaattctg gcaacagaac  30060
ccctacctct ggtgtaacac ctgatatggc tgatcaaatt gctagtcttg ttctggcaaa  30120
acttggcaag gatgccacta agccacagca agtaactaag cagactgcca aagaaatcag  30180
acagaaaatt ttgaataagc cccgccagaa gaggagcccc aataaacaat gcactgttca  30240
gcagtgtttt gggaagagag gccccaatca gaattttggt ggtggagaaa tgttaaaact  30300
tggaactagt gacccacagt tccccattct tgcagaactc gcacccacag ctggtgcgtt  30360
tttctttgga tcaagattag agttggccaa agtgcagaat ttgtctggga atcttgacga  30420
gccccagaag gatgtttatg aattgcgcta taatggtgca attagatttg acagtacact  30480
ttcaggtttt gagaccataa tgaaggtgtt gaatgagaat ttgaatgcat atcaacaaca  30540
agatggtatg atgaatatga gtccaaaacc acagcgtcag cgtggtcaga agaatggaca  30600
aggagaaaat gataatataa gtgttgcagc gcctaaaagc cgtgtgcagc aaaataagag  30660
tagagagttg actgcagagg acatcagcct tcttaagaag atggatgagc cctatactga  30720
agacacctca gaaatataag agaatgaacc ttatgtcggc acctggtggt aagccctcgc  30780
aggaaagtcg ggataaggca ctctctatca gaatggatgt cttgctgcta taatagatag  30840
```

-continued

```
agaaggttat agcagactat agattaatta gttgaaagtt ttgtgtggta atgtatagtg  30900

ttggagaaag tgaaagactt gcggaagtaa ttgccgacaa gtgcccaagg ggaagagcca  30960

gcatgttaag ttaccaccca gtaattagta aatgaatgaa gttaattatg gccaattgga  31020

agaatcac                                                           31028
```

ATTENUATED BOVINE CORONAVIRUS AND RELATED VACCINES

CROSS-REFERENCE TO RELATED APPLICATIONS

This application is a national stage entry under 35 U.S.C. § 371 of PCT/EP 2015/070006 filed on Sep. 2, 2015, which claims priority to US Application No. 62/073,263 filed on Oct. 31, 2014 and US Application No. 62/045,183 filed on Sep. 3, 2014. The content of PCT/EP 2015/070006 is hereby incorporated by reference in its entirety.

FIELD OF THE INVENTION

The present invention relates to novel attenuated bovine coronavirus isolates, to compositions comprising these isolates, and methods of using such compositions in vaccines, including in live vaccines that aid in the protection against respiratory disease caused by coronavirus. The present invention further relates to the administration of such vaccines, including the intranasal administration of such vaccines.

BACKGROUND OF THE INVENTION

A member of the Coronaviridae family, Nidovirales order, and *Coronavirus* genus, bovine coronavirus (BCoV) is an enveloped, single stranded, nonsegmented, positive sense RNA virus that encodes: (i) a spike protein (S protein), which is a large surface glycoprotein that comprises an S1 domain and an S2 domain; (ii) a hemagglutinin-esterase protein (HE), (iii) an integral membrane protein (M); (iv) a small membrane protein (E); and (v) a nucleocapsid protein (N) [Fulton et al., *Vaccine* 31:886-892 (2013)]. BCoV was initially associated with a neonatal enteric disease in calves, as well as winter dysentery in adult cattle [Fulton et al., *Vaccine* 31:886-892 (2013)]. Subsequently, BCoV was implicated in respiratory infections in both recently weaned calves and feedlot calves [Plummer et al., *JAVMA* 225(5): 726-731 (2004)]. Accordingly, BCoV has been found to be a pneumoenteric virus that can infect the intestine and upper and lower respiratory tract of cattle, with the bovine enteric coronavirus and the bovine respiratory coronavirus being reported to comprise only minor genetic differences. Consistently, there is an absence of any consistent antigenic or genetic markers that distinguish BCoV isolates according to their different clinical syndromes, as well as a report of a high level of cross-protection between bovine enteric coronavirus and the bovine respiratory coronavirus isolates following an in vivo challenge [Saif, *Vet. Clin. North Am Food Anim Pract.* 210(26):349-364 (2010)].

In addition, there are a significant number of other viruses and bacteria that can infect cattle. Viruses include bovine viral diarrhea virus types 1 and 2, (BVDV1, or alternatively BVD1; and BVDV2, or alternatively BVD2), infectious bovine rinotracheitis (IBR) virus, parainfluenza type 3 virus (PI3), bovine respiratory syncytial virus (BRSV), and Rift Valley fever virus (RVFV). Bacteria that can infect cattle include *Pasteurella multocida, Mannheimia haemolytica, Histophilus somni*, and *Mycoplasma bovis.*

It is now widely accepted that the best way of preventing disease due to bacterial or virus infections in bovine is to vaccinate them against these pathogens. Moreover, multivalent live attenuated viral or bacterial vaccines can be safely administered that limit the number of vaccine injections required. Accordingly, multivalent live virus vaccines that protect against BVDV1 and BVDV2, IBR, PI3, and/or BRSV are commercially available. Surprisingly however, heretofore no commercial vaccines have contained a live attenuated bovine coronavirus that has been shown to aid in the protection against both respiratory disease and enteric disease caused by coronavirus. Therefore, there remains a need to obtain a bovine coronavirus suitable for a vaccine (or multivalent vaccine) to aid in the protection of calves and cattle from both respiratory infections and enteric infections due to BCoV.

The citation of any reference herein should not be construed as an admission that such reference is available as "prior art" to the instant application.

SUMMARY OF THE INVENTION

The present invention provides attenuated bovine coronaviruses (BCoV). In certain embodiments the attenuated BCoV encodes one or more of the following: a spike protein that has 95% or greater identity with the amino acid sequence of SEQ ID NO: 2 (or SEQ ID NO: 22), a hemagglutinin-esterase glycoprotein (HE) that has 95% or greater identity with the amino acid sequence of SEQ ID NO: 4 (or SEQ ID NO: 24), an integral membrane protein (M) that has 95% or greater identity with the amino acid sequence of SEQ ID NO: 6, a small membrane protein (E) that has 95% or greater identity with the amino acid sequence of SEQ ID NO: 8, a nucleocapsid protein (N) that has 95% or greater identity with the amino acid sequence of SEQ ID NO: 10, an Orf 1 ab protein that has 95% or greater identity with the amino acid sequence of SEQ ID NO: 12, an Orf 2a protein that has 95% or greater identity with the amino acid sequence of SEQ ID NO: 14, a 4.9 kDa protein that has 95% or greater identity with the amino acid sequence of SEQ ID NO: 16, or a 4.8 kDa protein that has 95% or greater identity with the amino acid sequence of SEQ ID NO: 18.

In particular embodiments the attenuated BCoV encodes one or more of the following: a spike protein that has 98% or greater identity with the amino acid sequence of SEQ ID NO: 2 (or SEQ ID NO: 22), a hemagglutinin-esterase glycoprotein (HE) that has 98% or greater identity with the amino acid sequence of SEQ ID NO: 4 (or SEQ ID NO: 24), an integral membrane protein (M) that has 98% or greater identity with the amino acid sequence of SEQ ID NO: 6, a small membrane protein (E) that has 98% or greater identity with the amino acid sequence of SEQ ID NO: 8, a nucleocapsid protein (N) that has 98% or greater identity with the amino acid sequence of SEQ ID NO: 10, an Orf 1 ab protein that has 98% or greater identity with the amino acid sequence of SEQ ID NO: 12, an Orf 2a protein that has 98% or greater identity with the amino acid sequence of SEQ ID NO: 14, a 4.9 kDa protein that has 98% or greater identity with the amino acid sequence of SEQ ID NO: 16, or a 4.8 kDa protein that has 98% or greater identity with the amino acid sequence of SEQ ID NO: 18.

In yet other embodiments the attenuated BCoV encodes one or more of the following: a spike protein that has 99% or greater identity with the amino acid sequence of SEQ ID NO: 2 (or SEQ ID NO: 22), a hemagglutinin-esterase glycoprotein (HE) that has 99% or greater identity with the amino acid sequence of SEQ ID NO: 4 (or SEQ ID NO: 24), an integral membrane protein (M) that has 99% or greater identity with the amino acid sequence of SEQ ID NO: 6, a small membrane protein (E) that has 99% or greater identity with the amino acid sequence of SEQ ID NO: 8, a nucleocapsid protein (N) that has 99% or greater identity with the amino acid sequence of SEQ ID NO: 10, an Orf 1 ab protein that has 99% or greater identity with the amino acid sequence of SEQ ID NO: 12, an Orf 2a protein that has 99% or greater identity with the amino acid sequence of SEQ ID NO: 14, a 4.9 kDa protein that has 99% or greater identity with the amino acid sequence of SEQ ID NO: 16, or a 4.8 kDa protein that has 99% or greater identity with the amino acid sequence of SEQ ID NO: 18.

In still other embodiments the attenuated BCoV encodes one or more of the following: a spike protein that comprises the amino acid sequence of SEQ ID NO: 2 (or SEQ ID NO: 22), a hemagglutinin-esterase glycoprotein (HE) that comprises the amino acid sequence of SEQ ID NO: 4 (or SEQ ID NO: 24), an integral membrane protein (M) that comprises the amino acid sequence of SEQ ID NO: 6, a small membrane protein (E) that comprises the amino acid sequence of SEQ ID NO: 8, a nucleocapsid protein (N) that comprises the amino acid sequence of SEQ ID NO: 10, an Orf 1 ab protein that comprises the amino acid sequence of SEQ ID NO: 12, an Orf 2a protein that comprises the amino acid sequence of SEQ ID NO: 14, a 4.9 kDa protein that comprises the amino acid sequence of SEQ ID NO: 16, or a 4.8 kDa protein that comprises the amino acid sequence of SEQ ID NO: 18. In a more specific embodiment, the attenuated BCoV comprises the nucleotide sequence of SEQ ID NO: 25.

Accordingly, in certain embodiments the attenuated BCoV encodes a spike protein that has 95% or greater identity with the amino acid sequence of SEQ ID NO: 2. In particular embodiments the attenuated BCoV encodes a spike protein that has 98% or greater identity with the amino acid sequence of SEQ ID NO: 2. In more particular embodiments the attenuated BCoV encodes a spike protein that has 99% or greater identity with the amino acid sequence of SEQ ID NO: 2. In still more particular embodiments the attenuated BCoV encodes a spike protein that comprises the amino acid sequence of SEQ ID NO: 2. In yet more particular embodiments the spike protein of the attenuated BCoV is encoded by the nucleotide sequence of SEQ ID NO: 1.

In certain embodiments the attenuated BCoV encodes a hemagglutinin-esterase glycoprotein (HE) that has 95% or greater identity with the amino acid sequence of SEQ ID NO: 4. In particular embodiments the attenuated BCoV encodes a hemagglutinin-esterase glycoprotein that has 98% or greater identity with the amino acid sequence of SEQ ID NO: 4. In more particular embodiments the attenuated BCoV encodes a hemagglutinin-esterase glycoprotein that has 99% or greater identity with the amino acid sequence of SEQ ID NO: 4. In still more particular embodiments the attenuated BCoV encodes a hemagglutinin-esterase glycoprotein that comprises the amino acid sequence of SEQ ID NO: 4. In yet more particular embodiments the hemagglutinin-esterase glycoprotein of the attenuated BCoV is encoded by the nucleotide sequence of SEQ ID NO: 3.

In certain embodiments the attenuated BCoV encodes an integral membrane protein (M) that has 95% or greater identity with the amino acid sequence of SEQ ID NO: 6. In particular embodiments the attenuated BCoV encodes an integral membrane protein that has 98% or greater identity with the amino acid sequence of SEQ ID NO: 6. In more particular embodiments the attenuated BCoV encodes an integral membrane protein that has 99% or greater identity with the amino acid sequence of SEQ ID NO: 6. In still more particular embodiments the attenuated BCoV encodes an integral membrane protein that comprises the amino acid sequence of SEQ ID NO: 6. In yet more particular embodiments the integral membrane protein of the attenuated BCoV is encoded by the nucleotide sequence of SEQ ID NO: 5.

In certain embodiments the attenuated BCoV encodes a small membrane protein (E) that has 95% or greater identity with the amino acid sequence of SEQ ID NO: 8. In particular embodiments the attenuated BCoV encodes a small membrane protein that has 98% or greater identity with the amino acid sequence of SEQ ID NO: 8. In more particular embodiments the attenuated BCoV encodes a small membrane protein that has 99% or greater identity with the amino acid sequence of SEQ ID NO: 8. In still more particular embodiments the attenuated BCoV encodes a small membrane protein that comprises the amino acid sequence of SEQ ID NO: 8. In yet more particular embodiments the small membrane protein of the attenuated BCoV is encoded by the nucleotide sequence of SEQ ID NO: 7.

In certain embodiments the attenuated BCoV encodes a nucleocapsid protein (N) that has 95% or greater identity with the amino acid sequence of SEQ ID NO: 10. In particular embodiments the attenuated BCoV encodes a nucleocapsid protein that has 98% or greater identity with the amino acid sequence of SEQ ID NO: 10. In more particular embodiments the attenuated BCoV encodes a nucleocapsid protein that has 99% or greater identity with the amino acid sequence of SEQ ID NO: 10. In still more particular embodiments the attenuated BCoV encodes a nucleocapsid protein that comprises the amino acid sequence of SEQ ID NO: 10. In yet more particular embodiments the nucleocapsid protein of the attenuated BCoV is encoded by the nucleotide sequence of SEQ ID NO: 9.

In specific embodiments the attenuated BCoV comprises the immunogenic and/or physical and/or genetic characteristics of the attenuated bovine coronavirus having the ATCC deposit number PTA-121515. In related embodiments the attenuated BCoV is derived from an isolate having the ATCC deposit number PTA-121515. In other related embodiments the attenuated BCoV is the progeny of an isolate having the ATCC deposit number PTA-121515. In more specific embodiments the attenuated BCoV is an isolate having the ATCC deposit number PTA-121515. All of the attenuated bovine coronaviruses (BCoVs) of the present invention are also provided as isolated BCoVs.

In a related aspect, the present invention provides immunogenic compositions and vaccines comprising one or more of the attenuated BCoVs of the present invention. In particular embodiments the immunogenic compositions and vaccines comprise a live attenuated BCoV. In certain embodiments the vaccine aids in prevention of respiratory disease caused by BCoV. In particular embodiments the vaccine aids in prevention of enteric disease caused by BCoV. In still other embodiments the vaccine aids in prevention of both respiratory disease and enteric disease caused by BCoV. In certain embodiments the vaccine is stored frozen prior to thawing before use. In alternative embodiments the vaccine is lyophilized, which is rehydrated prior to administration. In other embodiments the vaccine is stored as a liquid stable vaccine.

The present invention further provides multivalent vaccines. In particular embodiments a multivalent vaccine comprises an attenuated BCoV of the present invention along with one or more additional viruses such as bovine viral diarrhea virus (BVDV), infectious bovine rinotracheitis virus (IBR), parainfluenza type 3 virus (PI3), bovine respiratory syncytial virus (BRSV), Rift Valley fever virus (RVFV), or any combination thereof. In specific embodiments the multivalent vaccine comprises BVDV1. In other embodiments the multivalent vaccine comprises BVDV2. In still other embodiments the multivalent vaccine comprises both BVDV1 and BVDV2. In certain embodiments the vaccine comprises both a live attenuated BCoV of the present invention and one or more of the additional live attenuated viruses, e.g., a live attenuated bovine viral diarrhea virus (BVDV), a live attenuated infectious bovine rinotracheitis virus (IBR), a live attenuated parainfluenza type 3 virus (PI3), a live attenuated bovine respiratory syncytial virus (BRSV), a live attenuated Rift Valley fever virus (RVFV), or any combination thereof.

A vaccine of the present invention can further comprise one or more bacterial antigens. In certain embodiments, the bacterial antigen is a *Pasteurella multocida*. In particular embodiments, the bacterial antigen is a *Mannheimia haemolytica*. In other embodiments, the bacterial antigen is a *Histophilus somni*. In yet other embodiments, the bacterial antigen is a *Mycoplasma bovis*. In still other embodiments, the vaccine comprises two or more of these bacterial antigens. In yet other embodiments, one or more of the bacterial antigens of the vaccine is a live attenuated bacterium. In certain embodiments, one or more of the bacterial antigens of the vaccine is a killed bacterium.

The present invention further provides methods of vaccinating a bovine (e.g., a calf) with a vaccine of the present invention. In particular embodiments the method of vaccinating the bovine comprises administering the vaccine intranasally. In certain alternative embodiments the method of vaccinating the bovine comprises administering the vaccine orally.

In another aspect of the present invention, an isolated and/or recombinant protein antigen obtained from the attenuated bovine coronavirus isolates of the present invention is provided. Included in the present invention are novel antigenic fragments of such proteins of the invention. In a related aspect, isolated and/or recombinant nucleic acids encoding the proteins and/or encoding antigenic fragments of the proteins are provided. In a further aspect, the present invention provides recombinant vectors, including recombinant virus vectors that comprise and/or express such nucleic acids and host cells that comprise such vectors or that have been genetically modified to encode the nucleic acids of the present invention.

BRIEF DESCRIPTION OF THE DRAWINGS

FIG. 1 is a schematic representation of the genome map of BCoV as annotated in Example 2 below.

DETAILED DESCRIPTION OF THE INVENTION

The present invention provides attenuated bovine coronaviruses (BCoVs). In one aspect of the present invention, all of the attenuated BCoVs are also provided as isolated BCoVs. An attenuated BCoV of the present invention can be included in safe and efficacious bovine vaccines (including multivalent bovine vaccines). Surprisingly such BCoV vaccines provide cross-protection against both enteric and respiratory disease. Accordingly, the present invention provides vaccines that aid in the protection of calves and cattle from both enteric and respiratory coronavirus infections.

In a particular aspect of the invention, the safe and efficacious BCoV bovine vaccines are for intranasal administration. Administering a vaccine intranasally has several advantages over other routes. For example, both maternal antibodies and antibodies from prior exposure to a pathogen can neutralize a modified live virus vaccine if the vaccine is administered by a parenteral route to the animal subject. However, intranasal administration can bypass the maternal antibodies and stimulate an immune response in a naïve animal. Furthermore, it can booster the immune response in an animal with antibodies from previous exposure. Therefore, the present invention further provides methods of administering the safe and efficacious BCoV bovine vaccines by an intranasal route.

The use of singular terms for convenience in the description is in no way intended to be so limiting. Thus, for example, reference to a "virus" includes reference to one or more of such viruses, unless otherwise specified. The use of plural terms is also not intended to be limiting, unless otherwise specified.

As used herein, the term, "approximately," is used interchangeably with the term "about" and generally signifies that a value is within twenty-five percent of the indicated value, unless otherwise indicated, e.g., a concentration of "about" 2 mM EDTA can be 1.5 mM to 2.5 mM EDTA.

As used herein, a "vaccine" is a composition that is suitable for application to an animal (e.g., cattle) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines.

As used herein, a "multivalent vaccine" is a vaccine that comprises two or more different antigens. In a particular embodiment of this type, the multivalent vaccine stimulates the immune system of the recipient against two or more different pathogens.

As used herein, a "liquid stable" vaccine is a vaccine maintained as a liquid (including a liquid multivalent vaccine) that remains efficacious for at least one year when stored at or below 7° C. (e.g., in a standard refrigerator, and/or at 0° C.-7° C.). In particular embodiments a liquid stable vaccine remains efficacious when stored at or below 7° C. for at least 1.5 years. In more particular embodiments a liquid stable vaccine remains efficacious when stored at or below 7° C. for at least 2 years. In still more particular embodiments a liquid stable vaccine remains efficacious when stored at or below 7° C. for at least 2.5 to 3 years. Examples of liquid stable vaccines are provided in U.S. application Ser. No. 14/202,454 filed on Mar. 10, 2014, and U.S. application Ser. No. 14/202,194 filed on Mar. 10, 2014, the contents of both of which are hereby incorporated by reference in their entireties.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The term "prophylactically-effective amount" refers to the amount of a composition that when administered to bovine significantly reduces the likelihood and/or extent of an infection/infestation due to a given pathogen.

"Metaphylaxis" is the timely mass medication of an entire group of animals to eliminate or minimize an expected outbreak of disease, e.g. in one or more animals at high risk of infection/infestation. In one particular embodiment, high risk calves are light weight, commingled, long haul cattle with unknown health histories.

The term "chemoprophylaxis" refers to the administration of a medication/treatment, e.g., one or more prophylactic compositions, for the purpose of preventing or reducing viral, bacterial, and/or parasitic infection/infestation; and/or preventing or reducing disease and/or symptoms related to that infection/infestation.

The term "prophylactic composition" refers to any agent used singularly or in combination with other agents that significantly reduces the likelihood and/or extent of an infection/infestation due to a given pathogen in bovine. In one such embodiment the bovine are at high risk of developing bovine respiratory disease, following commingling, transportation, changes in weather, changes in nutrition, and/or other stressors that can initiate a symptom and/or a disease related to the presence of the viral, bacterial, or parasitic pathogens commonly associated with bovine, targeted by the agent or combination of agents.

As used herein, the term "therapeutically effective amount" is an amount of a given antigen, e.g., a live attenuated bovine virus, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen. An "efficacious" vaccine retains sufficient titer for a given antigen to be compliant with the regulatory requirements for that antigen for the jurisdiction where the vaccine is administered, e.g., the administration of a vaccine in the United States is governed by the United States Department of Agriculture (USDA).

As used herein, an "immune response" refers to the subject animal's active immunity due to having received one or more vaccines. The immune response can include the production of antibodies to the antigen or immunogen present in the vaccine "Immune response" in a subject refers to the development of a humoral immune response, a cellular immune response, or a humoral and a cellular immune response to an antigen Immune responses may be measured using standard immunoassays and neutralization assays, which are known in the art.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous sugar, e.g., dextrose and/or glycerol solutions can be employed as carriers, particularly for injectable solutions. In addition, the carrier can be and/or comprise a hydrocolloid and/or polymer solution e.g., to thicken the bovine vaccines that are to be sprayed onto the cattle, e.g., calves.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein "intranasal administration" of a vaccine to an animal subject or "intranasally administering" a vaccine to an animal subject refers to applying or administering that vaccine to/through the nose and/or nasal cavity.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

Multivalent Vaccines:

The present invention provides monovalent and multivalent bovine vaccines that comprise the attenuated BCoV of the present invention. Accordingly, the multivalent bovine vaccines of the present invention comprise an attenuated BCoV and further include one or more additional bovine virus such as BVDV1, BVDV2, PI3, IBR, BRSV, and/or RVFV. As noted above, a multivalent vaccine that comprises a live attenuated BCoV of the present invention can also include one or more of the following live attenuated viruses: BVDV1, BVDV2, PI3, IBR, BRSV, and/or RVFV, along with one or more killed bovine viruses.

In addition, any multivalent bovine vaccine that comprises the attenuated BCoV of the present invention can further include one or more live attenuated or killed bacterial antigens. In certain embodiments that only virus antigen in such multivalent bovine vaccines is BCoV. In related embodiments, a bovine virus vaccine that comprises the attenuated BCoV of the present invention vaccine can be combined with one or more live attenuated or killed bacterial antigens and/or viral antigens. In particular embodiments of this type, the combination of the bovine virus vaccine with one or more live attenuated or killed bacterial antigens and/or viral antigens is made sometime prior to administration, but subsequent to storage. In specific embodiments of this type, the bacterial antigen(s) is comprised by a vaccine (either monovalent or multivalent) and that bovine bacterial vaccine is combined with a live, attenuated bovine virus vaccine of the present invention prior to administration. In a more specific embodiment, the live, attenuated bovine virus vaccine can be used to liquefy/solubilize a freeze-dried bovine bacterial vaccine prior to the administration of the combined vaccine to the animal subject. In an alternative specific embodiment, a bovine bacterial vaccine can be used to liquefy/solubilize a freeze-dried live, attenuated bovine virus vaccine (e.g., a BCoV vaccine) prior to the administration of the combined vaccine to the animal subject. In still other embodiments, the live, attenuated bovine virus vaccine and the attenuated and/or killed bovine bacterial vaccine are administered sequentially. In specific embodiments, the live, attenuated bovine virus vaccine is a liquid stable vaccine. In alternative embodiments, the live, attenuated bovine virus vaccine (e.g., a BCoV vaccine) is a lyophilized vaccine.

Accordingly, a bovine virus vaccine that comprises a live, attenuated BCoV of the present invention can be combined with one or more live attenuated or killed bacterial vaccines comprising an antigen such as *Pasteurella multocida, Mannheimia haemolytica, Histophilus somni*, and *Mycoplasma bovis* prior to administration to the animal subject. Therefore, in certain embodiments the attenuated bacterial vaccine comprises an attenuated *Mannheimia hemolytica*. In particular embodiments of this type the attenuated *Mannheimia hemolytica* is a leukotoxin deletant. In a specific embodiment of this type, the attenuated *Mannheimia hemolytica* is an avirulent, live *Mannheimia haemolytica* in which the gene encoding leukotoxin A was modified to be missing the nucleotide sequence that encodes amino acids 34-378 of the leukotoxin A protein [see, U.S. Pat. No. 6,331,303 B1, hereby incorporated by reference in its entirety].

In yet other embodiments the attenuated bacterial vaccine comprises an attenuated *Pasteurella multocida*. In more particular embodiments the *Pasteurella multocida* comprises a deletion in its hyaE gene. In a specific embodiment of this type, the attenuated *Pasteurella multocida* is a live, avirulent, *Pasteurella multocida* in which the gene encoding the hyaE protein was modified to be missing the nucleotide sequence that encodes amino acids 239-359 of the hyaE protein, and/or missing nucleotides 718-1084 [see, U.S. Pat. No. 7,351,416 B2, hereby incorporated by reference in its entirety]. In yet other embodiments the attenuated bacterial vaccine comprises an attenuated *Histophilus somni*. In more particular embodiments the *Histophilus somni* is live, avirulent *Histophilus somni* that is an aroA mutant.

In particular embodiments of the methods of the present invention, the attenuated bacterial vaccine comprises both an attenuated *Mannheimia hemolytica* and an attenuated *Pasteurella multocida*. In a more specific embodiment, the antibacterial composition is an attenuated bacterial vaccine comprising an avirulent, live *Mannheimia haemolytica* in which the gene encoding leukotoxin A was modified to be missing the nucleotide sequence that encodes amino acids 34-378 of the leukotoxin A protein, and an avirulent, live *Pasteurella multocida* in which the gene encoding the hyaE protein was modified to be missing the nucleotide sequence that encodes amino acids 239-359 of the hyaE protein and/or missing nucleotides 718-1084. In more particular embodiments of the methods of the present invention, the attenuated bacterial vaccine comprises an attenuated *Mannheimia hemolytica*, an attenuated *Pasteurella multocida*, and an avirulent *Histophilus somni.*

Vaccine Administration:

The bovine virus vaccines of the present invention may be administered by any conventional means, for example, by systemic administration, including by parenteral administration such as, without limitation, subcutaneous or intramuscular administration. The bovine virus vaccines of the present invention also may be administered by mucosal administration, such as by intranasal, oral, intratracheal, rectal, and/or ocular administration. Alternatively, the vaccines may be administered via a skin patch, in a delayed release implant, scarification, or topical administration. It is contemplated that a bovine virus vaccine of the present invention also may be administered via the drinking water and/or food of the recipient bovine. In a preferred embodiment, a bovine virus vaccine of the present invention comprising a live attenuated BCoV of the present invention is administered intranasally.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

In certain embodiments of the methods of the present invention, a bovine virus vaccine comprising a live attenuated BCoV of the present invention that is suitable for intranasal administration further comprises an attenuated IBR. In more particular embodiments the bovine virus vaccine comprising a live attenuated BCoV of the present invention that is suitable for intranasal administration comprises one or more, or all of the following; a live attenuated IBR, a live attenuated BVDV1, a live attenuated BVDV2, a live attenuated PI3, and a live attenuated BRSV.

The immunogenicity level may be determined experimentally by vaccine dose titration and challenge study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the breed of a bovine, age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.1 mL (typical for intradermal or transdermal application) and 5.0 mL. A typical range for the administration volume is between 0.2 and 2.0 mL. In specific embodiments a range for the administration volume is about 1.0 to 2.0 mL for intramuscular or subcutaneous administration. In alternative specific embodiments a range for the administration volume is about 0.5 to 2.0 for intranasal administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose. In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

Adjuvants & Immunostimulants

An adjuvant in general is a substance that boosts the immune response of the target in a non-specific manner. Many different adjuvants are known in the art. Non-limiting examples of adjuvants that may be used in the formulation of a vaccine made with material according to the present invention include aluminum salts (e.g., alum, aluminum hydroxide, aluminum phosphate, aluminum oxide), cholesterol, monophosphoryl lipid A adjuvants, amphigen, tocophenols, monophosphenyl lipid A, muramyl dipeptide, oil emulsions, glucans, carbomers, block copolymers, Avridine lipid-amine adjuvant, heat-labile enterotoxin from *E. coli* (recombinant or otherwise), cholera toxin, muramyl dipeptide, Freund's Complete and-Incomplete adjuvant, vitamin E, non-ionic block polymers and polyamines such as dextransulphate, carbopol, pyran, saponins and saponin derivatives, block co-polymers, and adjuvants such as those identified in U.S. Pat. Nos. 4,578,269, 4,744,983, 5,254,339, which are all herein fully incorporated by reference. Non-limiting examples of peptides that can serve as adjuvants include muramyldipeptides, dimethylglycine, or tuftsin. Non-limiting examples of oils that can serve as adjuvants include mineral oils, vegetable oils, animal oils and emulsions thereof.

Vaccines made from material according to the present invention may be formulated as oil-in water emulsions, as water-in-oil emulsions or as water-in-oil-in-water emulsions. Non-limiting examples of oil-in-water emulsions include paraffin oil-in-water emulsions, or emulsions made from one or more of squalene, block copolymers of ethylene oxide and propylene oxide, polysorbate surfactants, and/or threonyl analogs of muramyl dipeptide.

Oils used as adjuvants may be metabolizable by the subject receiving the vaccine such as vegetable or animal oils. Such oils typically consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues.

Adjuvants may also consist of components that cannot be metabolized by the body of the animal subject to which the emulsion is administered. Non-metabolizable oils suitable for use in the emulsions of the present invention include alkanes, alkenes, alkynes, and their corresponding acids and alcohols, the ethers and esters thereof, and mixtures thereof. The individual compounds of the oil may be light hydrocarbon compounds, e.g., compounds having 6 to 30 carbon atoms. The oil may be synthetically prepared or purified from petroleum products. Non-limiting examples of non-metabolizable oils for use in the preparation of vaccines based upon material cultured according to the present invention include mineral oil, paraffin oil, and cycloparaffins, for example. The term "mineral oil" refers to a non-metabolizable adjuvant oil that is a mixture of liquid hydrocarbons obtained from petrolatum via a distillation technique. The term is synonymous with "liquefied paraffin," "liquid petrolatum" and "white mineral oil." The term is also intended to include "light mineral oil," i.e., oil which is similarly obtained by distillation of petrolatum, but which has a slightly lower specific gravity than white mineral oil.

Other compounds capable of enhancing a humoral immunity response that may be used in the formulation of vaccines based upon material cultured according to the present invention include, without limitation, ethylene maleic anhydrate (EMA) copolymer, latex emulsions of a copolymer of styrene with a mixture of acrylic acid and methacrylic acid.

In addition to the adjuvant, a vaccine based upon material cultured according to the present invention can include immunomodulatory agents such as, e.g., interleukins, interferons, or other cytokines (e.g., Th1-related cytokines, such as interleukin-12 (IL-12), interleukin-18 (IL-18), or gamma interferon). The amount of adjuvant or immunostimulant added in a vaccine formulation based upon material cultured according to the present invention depends on the nature of the adjuvant or immunostimulant itself. The skilled artisan is capable of selecting an amount that is sufficient to enhance an immune response to the bacterial immunizing agent.

Carriers

Pharmaceutically acceptable carriers suitable for use in vaccines comprising material according to the present invention may be any conventional liquid carrier suitable for veterinary pharmaceutical compositions, including balanced salt solutions suitable for use in tissue culture media. Pharmaceutically acceptable carriers are understood to be compounds that do not adversely affect the health of the animal to be vaccinated, at least not to the extent that the adverse effect is worse than the effects seen when the animal is not vaccinated. Suitable carriers also include sterile water, saline, aqueous buffers such as PBS, solvents, diluents, isotonic agents, buffering agents, dextrose, ethanol, mannitol, sorbitol, lactose and glycerol, and the like.

Vehicle

Vaccines formulated from material according to the present invention may also comprise a vehicle. A vehicle is a compound to which the host cells, bacterial cells, or proteins, protein fragments, nucleic acids or parts thereof adhere, without being covalently bound to it. Non-limiting examples of such vehicles include bio-microcapsules, micro-alginates, liposomes and macrosols. Some materials that serve as adjuvants can also serve as vehicles such as aluminum-hydroxide, aluminum phosphate, aluminum sulphate or aluminum oxide, silica, kaolin, and bentonite, all known in the art.

Stabilizers

Often, a vaccine is mixed with stabilizers, e.g., to protect degradation-prone components from being degraded, to enhance the shelf-life of the vaccine, or to improve freeze-drying efficiency. Non-limiting examples of stabilizers that may be added to vaccine formulations based upon material cultured according to the present invention include SPGA, skimmed milk, gelatins, bovine serum albumin, carbohydrates (e.g., sorbitol, mannitol, trehalose, starch, sucrose, dextran or glucose), proteins (e.g., albumin, casein or degradation products thereof), non-animal origin stabilizers, and buffers (e.g., alkali metal phosphates).

Freeze-Drying/Reconstitution

For reasons of stability or economy, vaccines based upon material cultured according to the present invention may be freeze-dried. In general this will enable prolonged storage at temperatures above 0° C., e.g., at 4° C. Procedures for freeze-drying are known to persons skilled in the art. Equipment for freeze-drying at different scales is available commercially. To reconstitute the freeze-dried vaccine, it may be suspended in a physiologically acceptable diluent. Such diluents may be as simple as sterile water, a physiological salt solution or other carrier as discussed above.

Biological Deposit

Cultures of the following biological material have been deposited with the following international depository: American Type Culture Collection (ATCC) 10801 University Boulevard, Manassas, Va. 20110-2209, U.S.A., under conditions that satisfy the requirements of the Budapest Treaty. All restrictions imposed by the depositor on the availability to the public of the deposited material will be irrevocably removed upon granting of a patent.

| Organism | Accession No. | Date of Deposit |
|---|---|---|
| *Bovine Coronavirus* (BCV-Des MSV Lot# 9068110M01) | PTA-121515 | Aug. 28, 2014 |

TABLE 1

SEQUENCE LISTING

| SEQ ID NO: | | Type |
|---|---|---|
| 1 | Spike Protein# (S Protein) | NA |
| 2 | Spike Protein# (S Protein) | AA |
| 3 | Hemagglutinin-esterase glycoprotein# (HE) | NA |
| 4 | Hemagglutinin-esterase glycoprotein# (HE) | AA |
| 5 | Integral membrane protein (M) | NA |
| 6 | Integral membrane protein (M) | AA |
| 7 | Small membrane protein (E) | NA |
| 8 | Small membrane protein (E) | AA |
| 9 | Nucleocapsid protein (N) | NA |
| 10 | Nucleocapsid protein (N) | AA |
| 11 | Orf lab | NA |
| 12 | Orf lab | AA |
| 13 | Orf 2a | NA |
| 14 | Orf 2a | AA |
| 15 | 4.9 kDa protein | NA |
| 16 | 4.9 kDa protein | AA |
| 17 | 4.8 kDa protein | NA |
| 18 | 4.8 kDa protein | AA |
| 19 | 12.7 kDa protein | NA |
| 20 | 12.7 kDa protein | AA |
| 21 | *Spike Protein (S Protein) | NA |
| 22 | *Spike Protein (S Protein) | AA |
| 23 | *Hemagglutinin-esterase glycoprotein (HE) | NA |
| 24 | *Hemagglutinin-esterase glycoprotein (HE) | AA |
| 25 | Full Genome | NA |

AA is an amino acid sequence; NA is a nucleic acid sequence.
#Sequences that are provided without the signal sequence.
*Sequences that are provided with the signal sequence.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

Safe and Efficacious Attenuated Bovine Coronavirus Vaccines

Origin and Isolation of a BCoV Isolate:

A fecal sample was obtained from a calf in Idaho that had diarrhea. The fecal material was centrifuged at 6,500 rpm for 20 minutes. The supernatant then was layered onto a sucrose cushion and centrifuged at 28,000 rpm for 1.5 hours. The pellet was resuspended in cell culture medium and inoculated into culture vessels containing a monolayer of bovine kidney cells. The cells that showed evidence of cytopathic effect were reacted with a BCoV specific monoclonal antibody allowing the cells that were positive for BCoV to be identified.

Attenuation Process:

One BCoV isolate identified in the bovine kidney cells was subjected to 56 passages on bovine kidney cells to attenuate the virus. Limiting dilution cloning was performed on passages 4, 5, 10, 15, and 25, to obtain a pure virus isolate. The BCoV material obtained from the previous passage was inoculated onto a monolayer of bovine kidney cells for each passage. Virus fluids were harvested at each passage when a cytopathic effect was observed in the cells. The amount of BCoV in the fluids was determined by titration in a cell culture assay and the virus was detected by staining with a BCoV specific monoclonal antibody. Passage 56 was used to make a master stock of the modified live attenuated BCoV i.e., BCV-Des MSV Lot#9068110M01, which was deposited with the ATCC on Aug. 28, 2014. All studies regarding the modified live attenuated BCoV below were performed with BCoV from this master stock.

Vaccination/Challenge Study, the Evaluation of the Efficacy of the Modified Live BCoV:

A lyophilized vaccine composed of the modified live BCoV was rehydrated with sterile diluent and used to vaccinate twenty-two (22) calves, which were three to five days of age and that had been colostrum deprived. Each calf was vaccinated one time with a 2 mL dose of vaccine by the intranasal route. A second group of twenty-two (22) calves, also three to five days of age and that had been colostrum deprived, were vaccinated one time with a 2 mL dose of a placebo vaccine. Nineteen to twenty-one days after vaccination all calves were challenged with a heterologous virulent strain of BCoV that causes both respiratory and enteric disease. The calves were monitored for 14 days post challenge for signs of respiratory disease that included nasal discharge, coughing, and ocular discharge. The calves also were monitored for 14 days post challenge for signs of enteric disease (as evaluated by severity of diarrhea). The calves were further observed for depression, dehydration, and inappetence. Nasal and fecal samples were collected to test for virus shedding. Blood for serological evaluation was collected before and after vaccination, and again after the challenge.

Whereas, 86% (19 out of 22) of the placebo-vaccinated control calves were affected with moderate or severe respiratory disease, only 25% (5 out of 20) of those vaccinated with the BCoV vaccine exhibited such symptoms. The severity of respiratory disease was reduced in vaccinates (p=0.0001) compared to placebo controls and the duration of respiratory disease was reduced in vaccinates (p=0.0066) compared to the placebo controls. In the case of respiratory disease, the prevented fraction was 0.71 with a 95% confidence interval of (0.41, 0.89). Therefore these results, at the minimum, support a claim of "aids in prevention" of respiratory disease caused by BCoV [see, Table 2 below]. There also was a reduction in the severity and duration of nasal shedding in vaccinates (p=0.0063 for both) compared to the placebo controls.

TABLE 2

Protection Against Respiratory Disease

| Treatment Group | N | Proportion of Affected Animals | p = value | Prevented Fraction Estimate | Prevented Fraction 95% Conf. Interval |
|---|---|---|---|---|---|
| Control | 22 | 19/22 = 0.86 | <0.0001 | 0.71 | 0.41, 0.89 |
| Vaccinates | 20 | 5/20 = .25 | | | |

* Two calves were not enrolled in the study due to prior health reasons.

Sixteen of the twenty-two placebo-vaccinated control calves, i.e., 73%, were affected with moderate or severe enteric disease compared to eight of the twenty calves vaccinated with the BCoV vaccine, i.e., 40%. The severity of enteric disease was reduced in vaccinates (p=0.0009) compared to placebo controls and the duration of enteric disease was reduced in vaccinates (p=0.0017) compared to placebo controls. In the case of enteric disease, the prevented fraction was 0.45 with a 95% confidence interval of (0.01, 0.73). Therefore these results, at the minimum, support a claim of "aids in prevention" of enteric disease caused by BCoV [see, Table 3 below]. Moreover, the data demonstrate that the modified live BCoV vaccine is protective for both respiratory and enteric disease following a challenge with heterologous virulent BCoV.

TABLE 3

Protection Against Enteric Disease

| Treatment Group | N | Proportion of Affected Animals | p = value | Prevented Fraction Estimate | Prevented Fraction 95% Conf. Interval |
|---|---|---|---|---|---|
| Control | 22 | 16/22 = 0.73 | <0.0461 | 0.45 | 0.01, 0.73 |
| Vaccinates | 20 | 8/20 = 0.40 | | | |

* Two calves were not enrolled in the study due to prior health reasons.

Modified Live BCoV does not Revert to Virulence when Passaged Through the Host Animal and Retains a Stable Phenotype:

Newborn colostrum deprived calves in the first passage were inoculated with the modified live BCoV, equally administered by the oral and intranasal routes. One newborn colostrum deprived calf was used as a sentinel control in each passage. The calves were observed daily for 14 days for respiratory and enteric disease. Nasal and fecal samples were collected post inoculation. All of the calves remained healthy for the 14 day observation period and no abnormal findings were noted at necropsy on day 14. BCoV was not recovered by culture of fecal samples from any of the calves in passage 1, but was recovered in nasal samples from two calves (one for one day each). The original nasal sample material from the two calves was pooled and administered to three newborn colostrum deprived calves for the second passage. All of the calves remained healthy for the 14-day observation period and no abnormal findings were noted at necropsy on day 14. BCoV was not recovered from nasal or fecal samples from any of the calves in passage 2. A confirmation passage was conducted in which 10 newborn colostrum deprived calves were inoculated with the pool of the original nasal material from the two calves in passage 1. The calves were observed for twenty-one days. All of the calves remained healthy for the twenty-one day observation period. BCoV was not recovered from nasal or fecal samples from any of the calves in the confirmation passage. Small lesions were detected in two inoculated calves and the one sentinel control calf at necropsy, but BCoV was not recovered by culture. These data indicate that the modified live BCoV does not cause clinical signs of respiratory or enteric disease consistent with BCoV infection when passaged through the host animal. Moreover, the modified live BCoV is phenotypically stable.

Evaluation of the Shed, Spread, and Dissemination of the Modified Live BCoV when Administered to Newborn Calves at a Dose that is Greater than the Expected Final Release Level in a Vaccine:

Thirteen newborn, colostrum deprived calves were inoculated by the intranasal route with a dose of the modified live BCoV that is ≥10× the expected release level in a vaccine and was ≥100× the level of BCoV used in the vaccination/challenge study. Six newborn, colostrum deprived calves were used as un-inoculated controls. The calves were observed for respiratory and enteric disease caused by BCoV. Nasal and fecal samples were collected from all of the calves. A necropsy was performed on seven of the inoculated calves after seven days observation and a necropsy was performed on the remaining six inoculated calves after a 14-day observation. A necropsy was performed on all control calves after the 14-day observation. At necropsy, samples of the trachea, mesenteric lymph nodes, intestine tonsil, turbinate, and lung were collected and tested for BCoV. Clinical signs of respiratory or enteric disease caused by BCoV was not observed in any of the inoculated or controls calves. The BCoV was isolated in 4 of 13 inoculated calves on one or two days, but BCoV was not isolated in fecal samples from any of the calves. BCoV was detected by PCR in one or more samples of tissues collected from 11 of 13 inoculate calves, but not in any of the control calves. These data demonstrated that the modified live BCoV is shed from inoculated calves and disseminates in tissues of inoculated calves, which is a good thing because the virus goes to the necessary tissues to elicit the appropriate immune response, but does not spread to un-inoculated control calves. This study therefore confirmed the safety of the modified live BCoV. Therefore, the modified live BCoV protects calves from both respiratory and enteric disease, and moreover, substantially reduces virus shedding.

Example 2

Genetic Analysis of BCoV

The genome map of the attenuated BCoV described in Example 1 above is depicted in FIG. 1 and annotated in Table 2 below.

TABLE 2

GENOME MAP

| Position (nucleotides) | Description | #AA | #NA |
|---|---|---|---|
| 1-210 | 5' UTR | | |
| 211-13341, 13341-21494 | Orf1ab polyprotein | 11 | 12 |
| 21504 . . . 22340 | 32 kDa protein (also known as Orf 2a) | 13 | 14 |
| 22352 . . . 23626 | Hemagglutinin-esterase pre-cursor (HE gene) | 3 | 4 |
| (22352 . . . 22405) | signal peptide | | |
| (22406 . . . 23623) | mature peptide | | |
| 23641 . . . 27732 | Spike protein precursor (S gene) | 1 | 2 |
| (23641 . . . 23691) | signal peptide | | |
| (23692 . . . 27729) | mature peptide | | |
| 27722 . . . 27853 | 4.9 kDa protein | 15 | 16 |
| 27889 . . . 28026 | 4.8 kDA protein | 17 | 18 |
| 28106 . . . 28435 | 12.7 kDa protein | 19 | 20 |
| 28422 . . . 28676 | Small envelope protein (E gene) | 7 | 8 |
| 28691 . . . 29383 | Multispanning envelope protein (M gene) | 5 | 6 |
| 29393 . . . 30739 | Nucleocapsid protein (N gene) | 9 | 10 |

#SEQ ID NOs. for amino acid sequences (AA) and nucleotide sequences (NA) which are further delineated in Table 1 above.

The nucleotide and amino acid sequences for the BCoV are provided below:

```
Complete Genome of BCoV (31,028 nucleotides): SEQ ID NO: 25
nnnnnnGAGCGATTTGCGTGCGTGCATCCCGCTTCTCTGATCTCTTGTTAGATCTTTTTATAATCTAAACTTTATAAAAA

CATCCACTCCCTGTATTCTATGCTTGTGGGCGTAGATTTTTCATAGTGGTGTCTATATTCATTTCTGCTGTTAACAGCTT

TCAGCCAGGGACGTGTTGTATCCTAGGCAGTGGCCCACCCATAGGTCACAATGTCGAAGATCAACAAATACGGTCTCGAA

CTACACTGGGCTCCAGAATTTCCATGGATGTTTGAGGACGCAGAGGAGAAGTTGGATAACCCTAGTAGTTCAGAGGTGGA

TATAGTATGCTCCACCACTGCGCAAAAGCTGGAAACAGGCGGAATTTGTCCTGAAAATCATGTGATGGTGGATTGTCGCC

GACTTCTTAAACAAGAGTGTTGTGTGCAGTCTAGCCTAATACGTGAAATTGTTATGAATACACGTCCATATGATTTGGAG

GTGCTACTTCAAGATGCTTTGCAGTCCTGCGAAGCAGTTTTGGTTACACCCCCTCTAGGTATGTCTCTGGAGGCATGCTA

TGTGAGAGGTTGTAATCCTAATGGATGGACCATGGGTTTGTTTCGGCGTAGAAGTGTGTGTAACACTGGTCGTTGCGCTG

TTAACAAGCATGTGGCCTATCAGCTATATATGATTGATCCTGCGGGTGTCTGTTTTGGTGCAGGTCAATTTGTGGGTTGG

GTTATACCCTTAGCCTTTATGCCTGTGCAATCCCGGAAATTTATTGTTCCTAGGGTTATGTACTTGCGTAAGTGTGGCGA

AAAGGGTGCCTACAATAAAGATCATAAACGTGGCGGTTTTGAACACGTTTATAATTTTAAAGTTGAGGATGCTTACGACC

TGGTTCATGATGAGCCTAAGGGTAAGTTTTCTAAGAAGGCTTATGCTTTAATTAGAGGATACCGTGGTGTTAAACCGCTT

CTCTATGTAGACCAGTATGGTTGTGATTATACTGGTGGTCTTGCAGATGGCTTAGAGGCTTATGCTGATAAGACATTGCA

AGAAATGAAGGCATTATTTCCTATTTGGAGCCAGGAACTCCCTTTTGATGTAACTGTGGCATGGCACGTTGTGCGTGATC

CACGTTATGTTATGAGACTGCAGAGTGCTTCTACTATACGTAGTGTTGCATATGTTGCTAACCCTACTGAAGACTTGTGT

GATGGTTCTGTTGTTATAAAGGAACCTGTGCATGTTTATGCGGATGACTCTATTATTTTACGTCAACATAATTTAGTTGA

CATTATGAGTTGTTTTTATATGGAGGCAGATGCAGTTGTAAATGCTTTTTATGGTGTTGATTTGAAAGATTGTGGTTTTG

TTATGCAGTTTGGTTATATTGACTGCGAACAAGACTTGTGTGATTTTAAAGGTTGGGTTCCTGGTAATATGATAGATGGT

TTTGCTTGCACTACTTGTGGTCATGTTTATGAGACAGGTGATTTGCTAGCACAATCTTCAGGTGTTTTGCCTGTTAATCC

TGTATTGCATACTAAGAGTGCAGCAGGTTATGGTGGTTTTGGTTGTAAGGATTCTTTTACCCTGTATGGCCAAACTGTAG

TTTATTTTGGAGGTTGTGTGTATTGGAGTCCAGCACGTAATATATGGATTCCTATATTAAAATCTTCTGTTAAGTCTTAT

GACGGTTTGGTTTATACTGGAGTTGTAGGTTGCAAGGCTATTGTAAAGGAAACAAATCTCATTTGCAAAGCGTTGTACCT

TGATTATGTTCAACACAAGTGTGGCAATTTACACCAGCGGGAGTTGCTAGGTGTGTCAGATGTGTGGCATAAACAATTGT

TATTAAATAGAGGTGTGTACAAACCTCTTTTAGAGAATATTGATTATTTTAATATGCGGCGCGCTAAATTTAGTTTAGAA

ACTTTTACTGTTTGTGCAGATGGTTTTATGCCTTTTCTTTTAGATGATTTGGTTCCGCGCGCATATTATTTGGCAGTAAG
```

-continued

TGGTCAAGCATTTTGTGACTACGCAGGTAAAATCTGCCATGCTGTTGTGTCTAAGAGTAAAGAGTTACTTGATGTGTCTC

TGGATTCTTTAGGTGCAGCTATACATTATTTGAATTCTAAAATTGTTGATTTGGCTCAACATTTTAGTGATTTTGGAACA

AGTTTCGTTTCTAAAATTGTTCATTTCTTTAAGACTTTTACTACTAGCACTGCTCTTGCATTTGCATGGGTTTTATTTCA

TGTTTTGCATGGTGCTTATATAGTAGTGGAGAGTGATATATATTTTGTTAAAAACATTCCTCGTTATGCTAGTGCTGTTG

CACAAGCATTTCGGAGTGTTGCTAAAGTTGTACTGGACTCTTTAAGAGTTACTTTTATTGATGGCCTTTCTTGTTTTAAG

ATTGGACGTAGAAGAATTTGTCTTTCAGGCAGTAAAATTTATGAAGTTGAGCGTGGCTTGTTACATTCATCTCAATTGCC

ATTAGATGTTTATGATTTAACCATGCCTAGTCAAGTTCAGAAAACCAAGCAAAAACCTATTTATTTAAAAGGTTCTGGTT

CTGATTTTTCATTAGCGGATAGTGTAGTTGAAGTTGTTACAACTTCACTTACACCATGTGGTTATTCTGAACCACCTAAA

GTTGCAGATAAAATTTGCATTGTGGATAATGTTTATATGGCCAAGGCTGGTGACAAATATTACCCTGTTGTGGTTGATGG

TCATGTTGGACTTTTGGATCAAGCATGGAGGGTTCCTTGTGCTGGAAGGCGTGTTACATTTAAGGAACAGCCTACAGTAA

ATGAGATTGCAAGCACGCCTAAGACTATTAAAGTTTTTTATGAGCTTGACAAAGATTTTAATACTATTTTAAACACTGCA

TGTGGAGTGTTTGAAGTGGATGATACTGTGGATATGGAGGAATTTTATGCTGTGGTGATTGATGCCATAGAAGAGAAACT

TTCTCCATGTAAGGAGCTTGAAGGTGTAGGTGCTAAAGTTAGTGCCTTTTTACAGAAATTAGAGGATAATTCCCTATTTT

TATTTGATGAGGCTGGTGAGGAAGTTCTTGCTCCTAAATTGTATTGTGCTTTTACAGCTCCTGAAGATGATGACTTTCTT

GAAGAAAGTGGTGTTGAAGAAGATGATGTAGAAGGTGAGGAAACTGATTTAACTGTCACAAGTGCTGGAGAGCCTTGTGT

TGCCAGTGAACAGGAGGAGTCTTCTGAAATCTTAGAGGACACTTTGGATGATGGTCCATGTGTGGAGACATCTGATTCAC

AAGTTGAAGAAGATGTACAAATGTCGGATTTTGTTGATCTTGAATCTGTGATTCAGGATTATGAAAATGTTTGTTTTGAG

TTTTATACTACAGAACCAGAATTTGTTAAAGTTTTGGATCTGTATGTTCCTAAAGCAACTCGCAACAATTGCTGGTTGCG

ATCAGTTTTGGCAGTGATGCAGAAACTGCCCTGTCAATTTAAAGATAAAAATTTGCAGGATCTTTGGGTGTTATATAAGC

AACAGTATAGTCAGTTGTTTGTTGATACCTTGGTTAATAAGATACCTGCTAATATTGTAGTTCCACAAGGTGGTTATGTT

GCTGATTTTGCATATTGGTTCTTAACCTTATGTGATTGGCAGTGTGTTGCATACTGGAAATGCATTAAATGTGATTTAGC

TCTTAAGCTTAAAGGCTTGGATGCTATGTTCTTTTATGGTGATGTTGTCTCACATGTGTGCAAGTGTGGTGAGTCTATGG

TACTTATTGATGTTGATGTGCCATTTACAGCCCACTTTGCTCTTAAAGATAAGTTGTTTTGTGCATTTATTACTAAGCGT

AGTGTGTATAAAGCAGCTTGTGTTGTGGCTGTTAATGATAGTCATTCTATGGCTGTTGTTGATGGTAAACAAATTGATGA

TCATTGTATCACTAGTATTACTAGTGATAAGTTTGATTTTATTATTGGGCATGGTATGTCATTTTCAATGACTACTTTTG

AAATTGCCCAATTGTATGGTTCTTGTATAACACCTAATGTATGTTTTGTTAAAGGTGATATAATTAAAGTTTCTAAGCGT

GTTAAAGCAGAAGTCGTTGTAAATCCTGCTAATGGCCATATGGCACATGGTGGTGGTGTTGCAAAGGCTATTGCAGTAGC

AGCTGGACAGCAGTTTGTTAAAGAGACCACCGATATGGTTAAGTCTAAAGGAGTTTGTGCTACTGGAGATTGTTATGTCT

CTACAGGGGGCAAATTATGTAAAACTGTGCTTAATGTTGTTGGACCTGATGCGAGGACACAGGGTAAACAAAGTTATGCA

TTGTTAGAGCGTGTTTATAAACATCTTAACAAATATGATTGTGTTGTTACAACTTTGATCTCAGCTGGTATATTTAGTGT

GCCTTCTGATGTGTCTTTAACATATCTACTTGGTACTGCTAAGAAACAAGTTGTTCTTGTTAGCAATAATCAAGAGGATT

TTGATCTTATTTCTAAGTGTCAGATAACTGCCGTTGAGGGCACTAAGAAATTGGCAGAGCGTCTTTCTTTTAATGTTGGG

CGTTCTATCGTTTACGAAACAGATGCTAATAAGTTGATTTTAAGCAATGACGTTGCATTTGTTTCGACATTTAATGTCTT

ACAGGATGTTTTATCCTTAAGACATGATATAGCACTTGATGATGATGCACGAACCTTTGTTCAGAGCAATGTTGATGTTG

TACCTGAGGGTTGGCGTGTTGTCAATAAGTTTTATCAAATTAATGGTGTTAGAACCGTTAAGTATTTTGAGTGTCCCGGG

GGCATAGATATATGCAGCCAGGATAAAGTTTTTGGTTATGTACAGCAGGGTAGTTTTAATAAGGCTACTGTTGCTCAAAT

TAAAGCCTTGTTTTTGGATAAAGTGGACATCTTGCTAACTGTTGATGGTGTTAATTTCACTAACAGGTTTGTGCCTGTAG

GTGAAAGTTTTGGTAAGAGTCTAGGAAATGTGTTTTGTGATGGAGTTAATGTCACGAAACATAAGTGTGATATAAATTAT

AAAGGTAAAGTCTTTTTCCAGTTTGATAATCTTTCTAGTGAAGATTTAAAGGCTGTAAGAAGTTCTTTTAATTTTGATCA

GAAGGAATTGCTTGCCTACTACAACATGCTTGTTAATTGTTCTAAGTGGCAGGTTGTTTTTAATGGTAAGTATTTCACTT

-continued

TTAAGCAAGCTAATAACAATTGTTTTGTTAATGTTTCTTGCTTAATGCTCCAGAGTTTGAATCTGAAATTTAAAATTGTT

CAATGGCAGGAGGCGTGGCTTGAATTTCGTTCTGGCCGCCCTGCTAGATTTGTATCTTTGGTTTTGGCTAAAGGTGGGTT

TAAATTTGGGGATCCTGCTGATTCTAGAGATTTCTTGCGTGTTGTGTTTAGTCAAGTTGATTTGACAGGGGCAATATGTG

ATTTTGAAATTGCATGTAAATGTGGTGTAAAGCAGGAACAGCGTACTGGTGTGGACGCTGTTATGCATTTTGGTACATTG

AGTCGTGAAGATCTTGAGATTGGTTACACCGTGGATTGTTCTTGCGGTAAAAAGCTAATTCATTGTGTACGATTTGATGT

ACCATTTTTAATTTGCAGTAATACACCTGCTAGTGTAAAATTACCTAAGGGTGTAGGAAGTGCAAATATTTTTAAAGGTG

ATAAGGTTGGTCATTATGTTCATGTTAAGTGTGAACAGTCTTATCAGCTTTATGATGCTTCTAATGTTAAGAAGGTTACA

GACGTTACTGGCAATTTGTCAGATTGTTTGTATCTTAAAAATTTGAAACAAACTTTTAAATCGGTGTTAACCACCTATTA

TTTGGATGATGTTAAGAAAATTGAGTATAAACCTGACTTGTCACAATATTATTGTGACGGAGGTAAGTATTATACTCAGC

GTATTATTAAAGCCCAATTTAAAACATTTGAGAAAGTAGATGGTGTGTATACTAATTTTAAATTGATAGGACACACCGTC

TGTGATATTCTTAATGCTAAGTTGGGTTTTGATAGCTCTAAAGAGTTTGTTGAATATAAGGTTACTGAGTGGCCAACAGC

TACAGGTGATGTGGTGTTGGCTACTGATGATTTGTATGTTAAGAGATATGAAAGGGGTTGTATTACTTTTGGTAAACCTG

TTATATGGTTAAGCCATGAGCAAGCTTCCCTCAATTCTTTAACATATTTTAATAGACCTTTATTGGTTGATGAGAATAAA

TTTGATGTTTTAAAAGTGGATGATGTTGACGATGGTGGTGATATCTCAGAGAGTGATGCTAAAGAACCCAAAGAAATCAA

CATTATTAAGTTAAGTGGTGTTAAAAAACCATTTAAGGTTGAAGATAGTGTCATTGTTAATGATGATACTAGTGAAATCA

AATATGTTAAGAGTTTGTCTATAGTTGATGTGTATGATATGTGGCTTACAGGTTGTAGGTGTGTTGTTAGGACTGCTAAT

GCTTTGAGCAGAGCAGTTAACGTACCTACAATACGTAAGTTTATAAAATTTGGTATGACTCTTGTTAGTATACCAATTGA

TTTGTTAAATTTAAGAGAGATTAAGCCTGTTTTTAATGTGGTTAAAGCTGTGCGAAATAAAATTTCTGCATGCTTTAATT

TTATTAAATGGCTTTTTGTCTTATTATTTGGCTGGATTAAAATATCCGCTGATAATAAAGTAATTTACACCACAGAAGTT

GCATCAAAGCTTACGTGTAAGCTTGTAGCTTTAGCTTTTAAAAATGCATTTTTGACATTTAAGTGGAGTGTGGTTGCTAG

AGGTGCTTGCATTATAGCGACTATATTTCTATTGTGGTTTAATTTTATATATGCCAATGTAATTTTTAGTGATTTTTATT

TGCCTAAAATCGGTTTCTTGCCGACTTTTGTTGGTAAGATCGCACAGTGGATTAAGAACACTTTTAGTCTTGTAACTATT

TGTGATCTATATTCCATTCAGGATGTGGGTTTTAAGAATCAGTATTGTAATGGAAGTATCGCATGTCAGTTCTGCTTGGC

AGGATTTGATATGTTAGATAATTATAAAGCCATTGATGTAGTACAGTATGAAGCTGATAGGCGAGCATTTGTTGATTATA

CAGGTGTGTTAAAGATTGTCATTGAATTGATAGTTAGTTACGCCCTGTATACGGCATGGTTTTACCCATTGTTTGCTCTT

ATTAGTATTCAGATCTTGACCACTTGGCTGCCTGAGCTTTTTATGCTTAGTACATTACATTGGAGTGTTAGGTTGCTGGT

GTCTTTAGCTAATATGTTACCAGCACATGTGTTTATGAGGTTTTATATTATTATTGCCTCTTTTATTAAGCTGTTTAGCT

TGTTTAGGCATGTTGCCTATGGTTGTAGTAAATCTGGTTGTTTGTTTTGTTACAAGAGGAATCGTAGTCTACGTGTTAAA

TGTAGTACTATTGTTGGTGGCATGATACGCTATTACGATGTTATGGCTAATGGTGGCACTGGCTTTTGTTCAAAACATCA

ATGGAATTGCATTGATTGTGATTCTTATAAACCAGGTAATACTTTTATTACTGTTGAGGCCGCTCTTGATTTATCTAAGG

AATTGAAACGGCCTATTCAGCCTACAGATGTTGCTTATCATACGGTTACGGATGTTAAGCAAGTTGGTTGTTATATGCGC

TTGTTCTATGATCGTGATGGACAGCGCACATATGATGATGTTAATGCTAGTTTGTTTGTGGATTATAGTAATTTGCTACA

TTCTAAGGTTAAGAGTGTGCCTAATATGCATGTTGTGGTAGTGGAAAATGATGCCGATAAAGCTAATTTTCTTAATGCTG

CTGTATTTTATGCACAGTCTTTGTTTAGACCTATTTTAATGGTTGATAAAAATCTGATAACTACTGCTAATACTGGTACG

TCTGTTACAGAAACTATGTTTGATGTTTATGTGGATACATTTTTGTCTATGTTTGATGTGGATAAAAAGAGTCTTAATGC

TTTAATAGCAACTGCGCATTCTTCTATAAAACAGGGTACGCAGATCTGTAAAGTTTTGGATACCTTTTTAAGCTGTGCTC

GTAAAAGTTGTTCTATTGATTCAGATGTTGATACTAAGTGTTTAGCTGATTCTGTCATGTCTGCTGTATCGGCAGGCCTT

GAATTGACGGATGAAAGTTGTAATAACTTGGTGCCAACATATTTGAAGGGTGATAACATTGTGGCAGCTGATTTAGGTGT

TCTGATTCAAAATTCTGCTAAGCATGTGCAGGGTAATGTTGCTAAAATAGCCGGTGTTTCCTGTATATGGTCTGTGGATG

CTTTTAATCAGCTTAGTTCTGATTTCCAGCATAAATTGAAGAAAGCATGTTGTAAAACTAGTTTGAAACTGAAGCTTACT

TATAATAAGCAGATGGCTAATGTCTCTGTTTTAACTACACCCTTTAGTCTTAAAGGGGGTGCAGTTTTTAGTTATTTTGT

-continued

TTATGTATGTTTTGTGTTGAGTTTGGTTTGTTTTATTGGATTGTGGTGCTTAATGCCCACTTACACAGTACACAAATCAG

ATTTTCAGCTTCCCGTTTATGCCAGTTATAAAGTTTTAGATAATGGTGTTATTAGAGATGTTAGCGTTGAAGATGTTTGT

TTCGCTAACAAATTTGAACAATTTGATCAATGGTATGAGTCTACATTTGGTCTAAGTTATTATAGTAACAGTATGGCTTG

TCCCATTGTTGTTGCTGTAGTAGACCAGGATTTTGGCTCTACTGTGTTTAATGTCCCTACCAAAGTGTTACGATATGGTT

ACCATGTGTTGCACTTTATTACACATGCACTTTCTGCTGATGGAGTGCAGTGTTATACGCCACATAGTCAAATATCGTAT

TCTAATTTTTATGCTAGTGGCTGTGTGCTTTCCTCTGCTTGCACTATGTTTGCAATGGCCGATGGTAGTCCACAACCTTA

TTGTTATACAGATGGGCTTATGCAGAATGCTTCTCTGTATAGTTCATTGGTACCTCATGTGCGGTATAATCTTGCTAATG

CTAAAGGTTTTATCCGTTTTCCAGAAGTGTTGCGAGAAGGACTTGTGCGTATTGTGCGTACTCGTTCTATGTCGTATTGC

AGAGTTGGATTATGTGAGGAAGCTGATGAGGGTATATGCTTTAATTTTAATGGTTCTTGGGTGCTTAATAATGATTATTA

TAGATCATTGCCTGGGACCTTTTGTGGTAGAGATGTTTTTGACTTAATTTATCAGCTGTTTAAAGGTTTAGCACAGCCTG

TGGATTTCTTGGCATTGACTGCTAGTTCCATTGCTGGTGCTATACTTGCTGTAATTGTTGTTTTGGTGTTTTATTACTTA

ATAAAGCTTAAACGTGCTTTTGGTGATTACACCAGTATTGTTTTTGTTAATGTGATTGTGTGGTGTGTAAATTTTATGAT

GCTTTTTGTGTTTCAAGTTTACCCTACACTTTCTTGTGTATATGCTATTTGTTATTTTTATGCCACGCTTTATTTCCCTT

CGGAGATAAGTGTGATAATGCATTTACAATGGCTAGTTATGTATGGCACTATTATGCCTTTATGGTTTTGTTTGCTATAT

ATATCTGTTGTTGTTTCAAATCATGCTTTTTGGGTATTTTCTTACTGCAGACAGCTTGGTACTTCTGTTCGTAGTGATGG

TACATTTGAAGAAATGGCTCTTACTACTTTTATGATTACAAAAGATTCTTATTGTAAGCTTAAGAATTCTTTGTCTGATG

TTGCTTTTAATAGATATTTGAGTTTGTATAATAAATATAGGTATTACAGCGGTAAAATGGATACTGCTGCATATAGGGAG

GCTGCTTGTTCTCAGTTGGCTAAAGCAATGGATACATTTACCAATAATAATGGTAGTGATGTGCTTTACCAACCGCCTAC

TGCTTCCGTTTCAACTTCATTCTTGCAATCTGGTATTGTGAAAATGGTTAATCCTACTTCTAAGGTAGAACCATGTATTG

TCAGTGTTACCTATGGTAATATGACATTGAATGGTTTATGGTTGGATGATAAGGTCTACTGTCCCAGACATGTGATATGT

TCTGCTTCAGATATGACTTATCCAGATTATACAAATTTGTTGTGTAGAGTAACATCAAGTGATTTTACTGTATTGTTTGA

TCGTCTAAGCCTTACAGTGATGTCTTATCAAATGCAGGGTTGTATGCTTGTTCTTACAGTGACCCTGCAAAATTCTCGTA

CGCCAAAATATACATTTGGTGTGGTTAAACCTGGTGAGACTTTTACTGTTTTAGCTGCTTATAACGGCAAACCACAAGGA

GCCTTTCATGTGACTATGCGTAGTAGTTATACCATTAAGGGTTCCTTTTTATGCGGATCTTGTGGATCTGTTGGTTATGT

AATAATGGGTGATTGTGTTAAATTTGTGTATATGCATCAATTGGAGCTTAGTACTGGTTGTCATACTGGTACTGATTTCA

ATGGGGATTTTTATGGTCCTTATAAGGATGCTCAGGTTGTCCAATTGCCCGTTCAGGATTATATACAATCTGTTAATTTT

GTAGCATGGCTTTATGCTGCTATACTTAATAATTGTAATTGGTTTGTACAAAGTGATAAGTGTTCTGTTGAAGATTTTAA

TGTGTGGGCTTTGTCTAATGGGTTTAGCCAAGTTAAGTCTGATCTTGTTATAGATGCTTTAGCTTCTATGACTGGTGTGT

CTTTGGAAACACTATTGGCTGCTATTAAGCGTCTTAAGAATGGTTTTCAAGGACGTCAGATTATGGGTAGTTGCTCCTTT

GAGGATGAATTGACACCTAGCGATGTTTATCAACAACTCGCTGGTATCAAGTTACAATCAAAGCGTACTAGATTGGTTAA

AGGCATTGTTTGTTGGATTATGGCTTCTACATTTTTGTTTAGTTGTATAATTACAGCATTTGTGAAATGGACTATGTTTA

TGTATGTAACTACTAATATGCTTAGTATTACGTTTTGTGCACTTTGTGTTATAAGTTTGGCCATGTTGTTGGTTAAACAT

AAGCATCTTTATTTGACTATGTATATAATTCCTGTGCTTTTTACACTGCTGTATAACAACTATTTGGTTGTGTACAAGCA

GACATTTAGAGGCTATGTTTATGCATGGCTATCATATTATGTTCCATCAGTTGAGTATACTTATACTGATGAAGTAATTT

ATGGCATGTTATTGCTTATAGGAATGGTCTTTGTTACATTACGTAGCATTAACCATGATTTGTTCTCTTTTATAATGTTT

GTTGGTCGTGTGATTTCTGTTGTCTCTTTGTGGTACATGGGTTCTAACTTAGAGGAAGAAATTCTTCTTATGTTGGCTTC

TCTTTTTGGTACTTACACATGGACAACAGCTTTATCTATGGCTGCAGCAAAGGTTATTGCTAAGTGGGTTGCTGTGAATG

TTTTGTATTTCACAGATATACCTCAAATTAAGATAGTGCTTGTATGCTATTTGTTTATAGGTTATATTATTAGCTGTTAT

TGGGGTTTGTTTTCCTTGATGAACAGTTTGTTTAGAATGCCTTTGGGTGTTTATAATTATAAAATTTCAGTACAGGAATT

AAGATATATGAATGCTAATGGATTGCGCCCTCCTAAGAATAGTTTTGAAGCCCTCATGCTTAATTTTAAGCTTTTGGGTA

-continued

TTGGAGGTGTGCCAATTATTGAAGTATCTCAATTTCAATCAAAATTGACTGATGTTAAATGTGCTAATGTTGTCTTGCTT

AATTGCTTGCAACATTTGCATGTTGCTTCTAACTCTAAGTTGTGGCAATATTGTAGCACTTTGCACAATGAAATACTTGC

CACTTCTGATCTGGGTGTTGCTTTTGAAAAGCTTGCTCAGTTGTTAATTGTTTTGTTTGCTAATCCAGCTGCTGTGGATA

GCAAGTGCCTGACTAGTATTGAAGAAGTTTGCGACGATTACGCAAAGGACAATACTGTTTTGCAGGCTTTACAGAGTGAA

TTTGTTAATATGGCTAGCTTCGTTGAATATGAAGTTGCTAAGAAAAATCTTGATGAGGCGTGTTCTAGTGGTTCTGCTAA

TCGACAGCAGTTAAAACAGCTAGAGAAAGCCTGTAATATTGCTAAATCTGCTTATGAACGCGACCGTGCTGTAGCAAGAA

AGTTGGAGCGTATGGCAGATTTGGCTCTCACTAATATGTATAAAGAAGCTAGAATTAATGATAAGAAGAGTAAGGTTGTT

TCTGCCTTGCAAACTATGCTTTTTAGTATGGTGCGTAAGTTAGATAATCAAGCTCTGAATTCAATATTAGATAATGCTGT

GAAGGGTTGTGTACCATTGAATGCAATCCCTTCATTGGCAGCAAATACTCTGACTATAATTGTACCAGATAAAAGTGTTT

ATGATCAGGTAGTTGACAATGTCTATGTTACCTATGCGGGTAATGTATGGCAGATTCAAACTATCCAAGATTCAGATGGT

ACAAATAAGCAGTTGAATGAGATATCTGATGATTGTAACTGGCCACTAGTTATTATTGCAAATCGGCATAATGAGGTATC

TGCTACCGTTTTGCAAAATAATGAATTAATGCCTGCTAAGTTGAAAACTCAGGTTGTTAATAGTGGTCCAGATCAGACTT

GTAATACACCTACTCAATGTTACTATAATAATAGTTACAATGGGAAGATTGTTTATGCTATACTTAGTGATGTTGATGGT

CTTAAGTATACAAAAATTCTTAAAGATGATGGCAATTTTGTTGTTTTGGAGTTAGATCCTCCTTGTAAATTTACTGTTCA

AGATGTTAAAGGTCTTAAAATTAAGTACCTTTATTTTGTAAAAGGTTGTAACACACTAGCAAGAGGCTGGGTTGTTGGTA

CAATTTCTTCTACAGTTAGATTGCAAGCTGGAACTGCTACTGAGTATGCTTCCAACTCATCTATATTATCTTTATGTGCG

TTTTCTGTAGATCCTAAGAAAACGTATTTAGATTTTATACAACAGGGAGGAACACCTATTGCCAATTGTGTTAAAATGTT

GTGTGACCATGCTGGTACCGGTATGGCCATTACTGTTAAACCCGATGCTACCACTAGTCAGGATTCATATGGTGGTGCGT

CTGTTTGTATATATTGCCGCGCACGAGTTGAACACCCAGATGTTGATGGGTTGTGCAAATTACGCGGCAAGTTTGTACAA

GTGCCTGTAGGTATAAAAGATCCTGTGTCTTATGTTTTGACACATGATGTTTGTCAAGTTTGTGGATTTTGGCGGGATGG

AAGCTGTTCATGTGTTAGCACTGACACTACTGTTCAGTCAAAAGATACTAATTTTTTAAACGGGTTCGGGGTACGAGTGT

AGATGCCCGTCTCGTACCCTGTGCCAGTGGTTTATCTACTGATGTACAATTAAGGGCATTTGATATTTGCAATGCTAGTG

TTGCTGGCATTGGTTTACATTTAAAAGTTAATTGCTGCCGTTTTCAGCGTGTTGATGAGAACGGTGATAAATTAGATCAG

TTCTTTGTTGTTAAGAGGACAGATCTGACTATATATAATAGAGAGATGGAATGCTATGAGCGTGTAAAAGATTGTAAGTT

TGTGGCTGAACACGATTTCTTTACATTTGATGTAGAAGGTAGTCGTGTGCCACACATTGTACGCAAGGATTTAACAAAGT

ATACTATGTTGGATCTTTGCTATGCATTGCGACATTTTGATCGCAATGATTGCATGCTGCTTTGTGACATTCTCTCTATA

TATGCTGGTTGTGAACAATCCTACTTTACTAAGAAGGATTGGTATGATTTTGTTGAAAATCCTGATATTATTAATGTTTA

TAAAAAGCTAGGACCTATTTTTAATAGAGCCCTAGTTAGCGCTACTGAGTTTGCAGACAAATTGGTGGAGGTAGGCTTAG

TAGGCATTTTAACACTTGATAACCAAGATTTAAATGGTAAATGGTATGATTTTGGTGACTATGTTATTGCAGCCCCAGGG

TGTGGTGTTGCTATAGCAGACTCTTATTATTCTTATATGATGCCTATGCTGACCATGTGTCATGCATTGGATTGTGAATT

GTATGTGAATAATGCTTATAGACTATTTGATCTTGTACAGTATGATTTTACTGATTACAAGCTCGAATTGTTTAATAAGT

ATTTTAAGCACTGGAGTATGCCATACCATCCTAACACGGTTGATTGTCAGGATGATCGGTGTATCATACATTGTGCTAAT

TTTAACATACTTTTTAGTATGGTTTTACCTAATACATGTTTTGGGCCTCTTGTTAGGCAAATTTTTGTGGATGGTGTGCC

TTTTGTTGTTTCAATTGGCTACCATTATAAAGAACTTGGTATTGTGATGAACATGGATGTGGATACACATCGTTATCGCT

TGTCTTTAAAAGACTTGCTTTTATATGCTGCTGATCCAGCTTTGCATGTAGCTTCTGCTAGTGCATTGTATGATTTACGC

ACTTGCTGTTTTAGTGTTGCGGCTATAACAAGCGGTGTAAAATTTCAAACAGTTAAACCTGGTAATTTTAATCAGGATTT

TTATGATTTTATTTTAAGTAAGGGCCTGCTTAAAGAGGGTAGTTCAGTTGATCTGAAGCACTTTTTCTTTACGCAGGATG

GTAATGCTGCTATTACTGATTATAATTATTATAAGTACAATTTGCCCACCATGGTGGACATTAAGCAGTTGTTGTTTGTT

TTGGAAGTTGTTTATAAGTATTTTGAGATTTATGATGGTGGGTGTATACCGGCATCACAAGTCATTGTTAATAATTATGA

TAAGAGTGCTGGCTATCCATTTAATAAATTTGGAAAAGCCAGGCTCTATTATGAAGCATTATCATTTGAGGAGCAGGATG

AAATTTACGCCTATACTAAGCGCAATGTCCTGCCAACACTTACTCAAATGAATTTGAAATATGCTATTAGTGCTAAGAAT

-continued

AGAGCCCGCACTGTTGCTGGTGTTTCCATACTTAGTACTATGACTGGCAGAATGTTTCATCAAAAATGTTTGAAAAGTAT

AGCAGCTACACGTGGTGTTCCTGTTGTTATAGGCACCACTAAGTTTTATGGCGGCTGGGATGATATGTTACGTCGCCTTA

TTAAAGATGTTGATAATCCTGTACTTATGGGTTGGGATTATCCTAAGTGTGATCGTGCTATGCCAAACATACTACGTATT

GTTAGTAGTCTGGTCTTGGCCCGAAAACATGAGGCATGTTGTTCGCAAAGCGATAGGTTTTATCGACTTGCGAATGAATG

CGCACAAGTTCTGAGTGAAATTGTTATGTGTGGTGGCTGTTATTATGTTAAGCCTGGTGGCACTAGTAGTGGTGATGCAA

CTACTGCTTTTGCTAATTCAGTTTTTAACATATGTCAAGCTGTTTCAGCCAATGTATGTGCTTTAATGTCATGCAATGGT

AATAAGATTGAAGATTTGAGTATACGTGCTCTTCAGAAGCGCTTATACTCACATGTGTATAGAAGTGATATGGTTGATTC

AACCTTTGTCACAGAATATTATGAATTTTTAAATAAGCATTTTAGTATGATGATTTTGAGTGATGATGGCGTTGTGTGTT

ATAATTCTGATTATGCGTCCAAAGGGTATATTGCTAATATAAGTGCCTTTCAACAGGTATTGTATTATCAAAATAACGTT

TTTATGTCAGAATCCAAATGTTGGGTTGAAAATGACATAAACAATGGACCTCATGAATTTTGTTCACAACATACAATGCT

TGTAAAGATGGATGGGGACGATGTCTATCTTCCATATCCTGATCCTAGTCGTATATTAGGAGCTGGATGTTTTGTAGATG

ATTTGTTAAAGACTGATAGTGTTCTTTTAATAGAACGATTTGTAAGTCTTGCAATAGATGCTTATCCACTTGTGTACCAC

GAAAATGAAGAATACCAAAAGGTTTTTCGTGTTTATTTGGAGTATATAAAGAAGTTGTACAATGACCTGGGTAATCAGAT

CTTGGATAGCTACAGTGTTATTTTAAGTACTTGTGATGGACAAAAGTTTACTGATGAGTCCTTTTACAAGAACATGTATT

TAAGAAGTGCAGTTATGCAGAGTGTTGGAGCTTGCGTGGTCTGCTCTTCCCAAACATCATTACGTTGTGGCAGTTGCATC

AGAAAGCCTCTTCTTTGCTGCAAGTGTTGTTACGATCATGTTATGGCAACTGATCATAAATATGTTTTGAGTGTTTCACC

ATATGTGTGTAACGCACCAGGATGTGATGTAAATGATGTTACCAAATTGTATCTAGGTGGTATGTCATATTATTGTGAAG

ATCATAAGCCACAATATTCGTTTAAGTTGGTAATGAATGGTATGGTTTTTGGTCTATATAAACAATCTTGTACAGGATCT

CCGTACATAGATGATTTTAATCGTATAGCTAGTTGTAAATGGACTGATGTTGATGATTACATACTGGCTAATGAATGTAC

AGAGCGCTTGAAATTGTTTGCTGCAGAAACGCAAAAGGCGACTGAGGAAGCCTTTAAGCAGAGTTATGCATCAGCAACAA

TACAAGAGATTGTTAGTGAGCGCGAATTGATCCTCTCTTGGGAGATTGGAAAAGTGAAGCCACCACTTAATAAAAATTAT

GTTTTTACTGGCTACCATTTTACTAAAAATGGCAAGACAGTTTTAGGTGAGTATGTTTTTGATAAGAGTGAGTTGACTAA

TGGTGTGTATTATCGCGCCACAACCACTTATAAGCTATCTGTAGGAGATGTTTTTGTTTTAACCTCTCATTCAGTAGCTA

ATTTAAGTGCTCCTACGCTTGTGCCGCAGGAGAATTATAGTAGTATTAGATTTGCTAGTGTTTATAGTGTGCTTGAGACA

TTTCAGAACAATGTTGTGAACTATCAACACATTGGTATGAAACGTTATTGCACCGTGCAAGGACCTCCTGGTACAGGAAA

GTCACATCTTGCTATTGGTCTTGCTGTATATTATTGTACAGCACGTGTAGTATACACTGCGGCCAGCCATGCAGCTGTTG

ACGCATTGTGTGAAAAAGCATACAAATTTTTGAATATAAATGATTGCACTCGTATTGTTCCTGCCAAGGTCAGGGTGGAG

TGCTATGATAAGTTTAAAATTAATGACACCACTCGTAAGTATGTGTTTACTACTATAAATGCATTACCTGAGATGGTGAC

TGATATTGTTGTTGTAGATGAAGTTAGTATGCTTACCAATTATGAGCTTTCTGTTATTAATGCTCGTATTCGCGCTAAGC

ATTATGTTTATATTGGTGATCCTGCTCAATTGCCAGCACCACGTGTGTTATTGAGCAAGGGTACACTTGAACCTAAATAT

TTTAACACTGTTACTAAGCTTATGTGTTGCTTAGGGCCAGACATTTTTCTTGGTACATGTTATAGATGTCCTAAGGAAAT

CGTTGATACAGTGTCTGCCTTGGTTTATGAAAATAAGCTTAAGGCTAAGAATGAAAGTAGTTCATTGTGTTTTAAGGTCT

ATTATAAAGGCGTTACAACACATGAAAGTTCTAGTGCTGTAAATATGCAGCAGATTTATTTGATTAATAAGTTTTTGAAG

GTTAACCCTTTGTGGCATAAAGCCGTTTTTATTAGCCCATATAATAGTCAGAACTTTGCAGCTAAGCGCGTTTTGGGTTT

GCAAACCCAAACCGTGGATTCTGCGCAAGGTTCTGAATATGATTATGTTATATATTCACAGACTGCAGAAACAGCGCATT

CTGTAAATGTTAATCGCTTCAATGTTGCTATTACTCGAGCCAAGAAAGGTATTCTTTGCGTTATGAGTAATATGCAGTTG

TTTGAAGCATTACAGTTTACTACATTGACCGTAGATAAAGTGCCACAGGCCGTTGAAACGAGAGTTCAATGTAGTACCAA

TTTATTTAAAGATTGTAGCAAGAGTTATAGTGGTTACCACCCAGCTCATGCTCCTTCATTTTTGGCAGTAGATGACAAAT

ATAAGGCAACTGGCGATTTAGCCGTGTGTCTTGGTATTGGAGATTCTGCTGTTACATATTCAAGATTAATATCACTCATG

GGTTTTAAACTGGATGTTACCCTTGATGGGTATTGTAAGCTTTTTATAACTAAAGAAGAAGCTGTTAAACGCGTGCGTGC

-continued

TTGGGTTGGCTTTGATGCTGAAGGTGCTCATGCCACGCGTGATAGCATTGGGACAAATTTCCCACTTCAATTAGGGTTTT

CCACAGGAATTGATTTTGTTGTGGAAGCCACTGGTTTGTTTGCTGATAGAGATGGTTACAGCTTTAAAAAGGCTGTGGCT

AAAGCTCCTCCTGGTGAACAATTTAAGCATCTCATCCCTTTGATGACGAGAGGTCAGCGCTGGGATGTTGTTAGACCTAG

AATAGTACAAATGTTTGCAGATCATTTAATTGATCTGTCTGATTGTGTTGTGCTAGTTACATGGGCAGCCAACTTTGAGC

TCACTTGTCTCCGCTACTTTGCAAAAGTAGGTCGTGAGATCTCTTGTAATGTGTGCACTAAACGTGCCACAGCTTACAAT

TCTAGAACTGGTTACTATGGTTGTTGGCGCCATAGTGTTACATGTGATTACTTGTATAATCCACTTATTGTTGATATTCA

ACAGTGGGGATATATTGGTTCTTTATCAAGTAATCATGATTTATATTGTAGTGTCCATAAAGGAGCACATGTTGCCTCCT

CTGATGCTATAATGACACGGTGTTTGGCCGTTTATGATTGTTTTTGCAATAATATTAATTGGAATGTGGAGTATCCCATC

ATTTCAAATGAGTTAAGTATTAATACCTCTTGTAGGGTCTTGCAGCGTGTTATGCTTAAAGCTGCCATGCTCTGCAACAG

ATATACTTTGTGTTATGATATTGGCAATCCAAAAGCGATTGCCTGTGTCAAAGATTTTGATTTTAAGTTCTATGATGCCC

AACCAATTGTTAAGTCTGTCAAGACTCTTTTGTATTTTTTTGAGGCACATAAGGACTCTTTTAAAGATGGTTTGTGTATG

TTTTGGAACTGTAATGTGGATAAGTATCCACCGAATGCAGTTGTATGTAGATTTGACACGAGAGTGTTGAATAATTTAAA

TCTTCCTGGCTGTAATGGAGGTAGTTTGTATGTTAACAAACATGCATTCCACACTAAACCCTTTTCTAGGGCAGCCTTTG

AGCATTTGAAGCCTATGCCATTTTTCTATTATTCAGATACGCCTTGCGTGTATATGGATGGCATGGATGCTAAGCAGGTT

GATTATGTACCTTTGAAATCCGCCACTTGCATCACAAGATGCAATTTAGGTGGTGCAGTTTGTTTAAAACATGCTGAAGA

GTATCGTGAGTACCTAGAGTCTTACAATACAGCTACTACAGCAGGTTTTACTTTTTGGGTCTATAAGACATTTGATTTTT

ATAATTTGTGGAATACGTTCACCAAGCTACAAAGCTTGGAGAATGTTGTATATAATTTAGTCAAGACTGGTCATTATACA

GGACAGGCTGGTGAAATGCCTTGTGCCATTATAAATGATAAAGTTGTGGCTAAGATCGATAAGGAGGATGTTGTCATTTT

TATTAATAATACAACATATCCTACTAATGTGGCTGTTGAATTATTTGCCAAGCGCAGTATTCGACACCATCCAGAGCTTA

AGCTCTTTAGAAATTTGAATATAGACGTGTGCTGGAAGCACGTCATTTGGGATTATGCTAGAGAAAGTATATTTTGCAGT

AATACCTATGGTGTCTGCATGTATACAGATTTAAAGTTCATTGATAAATTGAATGTCCTTTTTGATGGTCGTGATAATGG

TGCTCTTGAAGCTTTTAAACGCTCTAATAATGGCGTTTACATTTCCACGACAAAAGTTAAGAGTCTTTCGATGATAAGAG

GTCCACCGCGTGCTGAATTAAATGGCGTAGTGGTGGACAAGGTTGGAGACACAGATTGTGTGTTTTATTTTGCTGTGCGT

AAAGAGGGTCAGGATGTCATCTTCAGCCAATTCGACAGCCTGAGAGTCAGCTCTAACCAGAGCCCACAAGGTAATCTGGG

GAGTAATGAACCCGGTAATGTCGGTGGTAATGATGCTCTGGCAACCTCCACTATCTTTACACAAAGCCGTGTTATTAGCT

CTTTTACATGTCGTACTGATATGGAAAAAGATTTTATAGCTTTAGATCAAGATGTGTTTATTCAGAAGTATGGTTTGGAG

GACTATGCCTTTGAACACATTGTTTATGGTAATTTCAACCAGAAGATTATTGGTGGTTTGCATTTGTTAATAGGCTTGTA

CCGAAGACAGCAAACTTCCAATTTGGTTATTCAGGAGTTTGTTTCATACGACTCCAGCATACACTCTTATTTTATCACTG

ATGAGAAGAGTGGTGGTAGTAAGAGTGTTTGCACTGTTATAGATATTTTGTTGGATGATTTTGTGGCTCTTGTCAAGTCA

CTTAATCTTAACTGTGTGAGTAAGGTTGTTAATGTTAATGTTGATTTTAAAGATTTTCAGTTCATGCTTTGGTGTAACGA

TGAGAAAGTTATGACTTTCTATCCTCGTTTGCAAGCTGCATCTGACTGGAAGCCTGGTTATTCTATGCCTGTATTATATA

AGTATTTGAATTCCCCAATGGAAAGAGTTAGTCTCTGGAATTATGGGAAGCCAGTTACTTTGCCTACAGGCTGTATGATG

AATGTTGCTAAGTATACTCAGTTATGTCAATATCTGAATACTACAACATTAGCTGTACCTGTTAATATGCGAGTTTTGCA

TTTAGGTGCAGGTTCAGAAAAAGGAGTAGCACCGGGTTCTGCAGTTCTTAGGCAGTGGTTGCCTGCTGGTACTATTCTTG

TAGATAATGATTTATACCCATTTGTGAGTGACAGTGTCGCTACATATTTTGGGGATTGTATAACCTTACCCTTTGATTGT

CAATGGGATTTGATAATCTCTGATATGTATGACCCTATTACTAAGAACATAGGGGAGTACAATGTAAGTAAAGATGGTTT

CTTTACATACATTTGTCATATGATTCGCGACAAGTTAGCTCTGGGTGGCAGTGTTGCTATAAAAATAACAGAGTTTTCTT

GGAATGCAGAATTATATAAGTTAATGGGGTATTTTGCATTTTGGACGGTTTTCTGCACAAATGCAAATGCTTCTTCTAGT

GAAGGGTTTTTAATTGGCATAAATTATTTGGGTAAGCCCAAGGTTGAGATAGATGGAAATGTTATGCATGCCAATTATTT

GTTTTGGAGAAATTCCACAGTTTGGAACGGGGGTGCTTATAGCCTGTTTGATATGGCTAAATTCCCGCTTAAGTTGGCTG

GTACTGCCGTAATAAATTTAAGAGCAGACCAGATTAATGATATGGTTTATTCCCTTCTTGAAAAGGGTAAACTACTTGTT

-continued

AGAGATACAAATAAAGAAGTTTTTGTTGGTGACAGTATGGTTAATGTAATCTAAACTTTAAGAATGGCAGTTGCTTATGC

AAACAAGCCTAATCACTTTATTAATTTTCCACTTACCCAGTTTGAGGGTTTTGTGTTAAATTATAAAGGTTTACAATTTC

AACTTCTCGATGAAGGAGTGGATTGTAAAATACAAACAGCGCCGCACATTAGTCTTGTTATGCTGGATATTCAGCCTGAA

GACTATAGAAGTGTTGATGTTGCTATTCAAGAAGTTATTGATGACATGCATTGGGGTGAGGGCTTTCAGATTAAATTTGA

TAACCCCCATATCCTAGGAAGATGCATAGTTTTAGATGTTAAAGGTGTAGAAGAATTGCATGATGATTTAGTTAATTACA

TTCGTGATAAAGGTTGTGTTGCTGACCAATCCAGGAAATGGATTGGACATTGCACCATAGCCCAACTCACGGATGCTGCA

CTTTCCATTAAGGAAAATGTTGATTTCATAAACAGCATGCAATTCAATTATAAAATCACTATCAACCCCTCATCACCGGC

TAGACTTGAAATAGTTAAGCTTGGTGCTGAAAAGAAAGATGGTTTTTATGAAACCATAGTTAGCCACTGGATGGGAATTC

GTTTTGAATATAATCCACCCACTGATAAGCTAGCTATGATTATGGGTTATTGTTGTTTAGAAGTGGTGCGTAAAGAGCTA

GAAGAAGGTGATCTTCCCGAGAATGATGATGATGCTTGGTTTAAGCTATCGTACCATTATGAAAACAATTCTTGGTTCTT

TCGACATGTCTACAGGAAAAGTTCTTATTTCCGTAAGTCTTGTCAAAATTTAGATTGTAATTGTTTGGGGTTTTATGAAT

CTCCAGTTGAAGAAGACTAAACTCAGTGAAAATGTTTTTGCTTCTTAGATTTGTTCTAGTTAGCTGCATAATTGGTAGCC

TAGGTTTTGATAACCCTCCTACCAATGTTGTTTCGCATTTAAATGGAGATTGGTTTTTATTTGGTGACAGTCGTTCAGAT

TGTAATCATGTTGTTAATACCAACCCCCGTAATTATTCTTATATGGACCTTAATCCTGCCCTGTGTGATTCTGGTAAAAT

ATCATCTAAAGCTGGCAACTCCATTTTTAGGAGTTTTCACTTTACCGATTTTTATAATTACACAGGCGAAGGTCAACAAA

TTATTTTTTATGAGGGTGTTAATTTTACGCCTTATCATGCCTTTAAATGCACCACTTCTGGTAGTAATGATATTTGGATG

CAGAATAAAGGCTTGTTTTACACTCAGGTTTATAAGAATATGGCTGTGTATCGCAGCCTTACTTTTGTTAATGTACCATA

TGTTTATAATGGCTCTGCACAATCTACAGCTCTTTGTAAATCTGGTAGTTTAGTTCTTAATAACCCTGCATATATAGCTC

GTGAAGCTAATTTTGGGGATTATTATTATAAGGTTGAAGCTGACTTTTATTTGTCAGGTTGTGACGAGTATATCGTACCA

CTTTGTATTTTTAACGGCAAGTTTTTGTCGAATACAAAGTATTATGATGATAGTCAATATTATTTTAATAAAGACACTGG

TGTTATTTATGGTCTCAATTCTACTGAAACCATTACCACTGGTTTTGATTTTAATTGTCATTATTTAGTTTTACCCTCTG

GTAATTATTTAGCCATTTCAAATGAGCTATTGTTAACTGTTCCTACGAAAGCAATCTGTCTTAACAAGCGTAAGGATTTT

ACGCCTGTACAGGTTGTTGATTCACGGTGGAACAATGCCAGGCAGTCTGATAACATGACGGCGGTTGCTTGTCAACCCCC

GTACTGTTATTTTCGTAATTCTACTACCAACTATGTTGGTGTTTATGATATCAATCATGGGGATGCTGGTTTTACTAGCA

TACTCAGTGGTTTGTTATATGATTCACCTTGTTTTTCGCAGCAAGGTGTTTTTAGGTATGATAATGTTAGCAGTGTCTGG

CCTCTCTATTCCTATGGCAGATGCCCTACTGCTGCTGGTATTAATACCCCTGATGTACCTATTTGTGTGTATGATCCGCT

ACCACTTATTTTGCTTGGCATCCTTTTGGGTGTTGCGGTCATAATTATTGTAGTTTTGTTGTTATATTTTATGGTGGATA

ATGGTACTAGGCTGCATGATGCTTAGACCATAATCTAAACATGTTTTTGATACTTTTAATTTCCTTACCAATGGCTTTTG

CTGTTATAGGAGATTTAAAGTGTACTACGGTTGCCATTAATGATGTTGACACCGGTCCTCCTTCTATTAGCACTGATATT

GTCGATGTTACTAATGGTTTAGGTACTTATTATGTTTTAGATCGTGTGTATTTAAATACTACGTTGTTGCTTAATGGTTA

CTACCCTACTTCAGGTTCTACATATCGTAATATGGCACTGAAGGGAACTTTACTATTGAGCAGACTATGGTTTAAACCAC

CTTTTCTTTCTGATTTTATTAATGGTATTTTTGCTAAGGTCAAAAATACCAAGGTTATTAAAAAGGGTGTAATGTATAGT

GAGTTTCCTGCTATAACTATAGGTAGTACTTTTGTAAATACATCCTATAGTGTGGTAGTACAACCACATACTACCAATTT

GGATAATAAATTACAAGGTCTCTTAGAGATCTCTGTTTGCCAGTATACTATGTGCGAGTACCCACATACGATTTGTCATC

CTAATCTGGGTAATCGACGCGTAGAACTATGGCATTGGGATACAGGTGTTGTTTCCTGTTTATATAAGCGTAATTTCACA

TATGATGTGAATGCTGATTACTTGTATTTCCATTTTTATCAAGAAGGTGGTACTTTTTATGCATATTTTACAGACACTGG

TGTTGTTACTAAGTTTCTGTTTAATGTTTATTTAGGCACGGTGCTTTCACATTATTATGTCCTGCCTTTGACTTGTTCTA

GTGCTATGACTTTAGAATATTGGGTTACACCTCTCACTTCTAAACAATATTTACTAGCTTTCAATCAAGATGGTGTTATT

TTTAATGCTGTTGATTGTAAGAGTGATTTTATGAGTGAGATTAAGTGTAAAACACTATCTATAGCACCATCTACTGGTGT

TTATGAATTAAACGGTTACACTGTTCAGCCAATTGCAGATGTTTACCGACGTATACCTAATCTTCCCGATTGTAATATAG

-continued

AGGCTTGGCTTAATGATAAGTCGGTGCCCTCTCCATTAAATTGGGAACGTAAGACCTTTTCAAATTGTAATTTTAATATG

AGCAGCCTGATGTCTTTTATTCAGGCAGACTCATTTACTTGTAATAATATTGATGCTGCTAAGATATATGGTATGTGTTT

TTCCAGCATAACTATAGATAAGTTTGCTATACCCAATGGTAGGAAGGTTGACCTACAATTGGGCAATTTGGGCTATTTGC

AGTCTTTTAACTATAGAATTGATACTACTGCTACAAGTTGTCAGTTGTATTATAATTTACCTGCTGCTAATGTTTCTGTT

AGCAGGTTTAATCCTTCTACTTGGAATAGGAGATTTGGTTTTACAGAACAATCTGTTTTTAAGCCTCAACCTGCAGGTGT

TTTTACTCATCATGATGTTGTTTATGCACAACATTGTTTTAAAGCTCCCACAAATTTCTGTCCGTGTAAATTGGATGGGT

CTTTGTGTGTAGGTAATGGTCCTGGTATAGATGCTGGTTATAAAAATAGTGGTATAGGCACTTGTCCTGCAGGTACTAAT

TATTTAACTTGCCATAATGCTGCCCAATGTGATTGTTTGTGCACTCCCGACCCCATTACATCTAAATCTACAGGGCCTTA

CAAGTGCCCCCAAACTAAATACTTAGTTGGCATAGGTGAGCACTGTTCGGGTCTTGCTATTAAAAGTGATTATTGTGGAG

GTAATCCTTGTACTTGCCAACCACAAGCATTTTTGGGTTGGTCTGCTGACTCTTGTTTACAAGGGGATAGGTGTAATATT

TTTGCTAATTTTATTTTTCATGATGTTAATAGTGGTACTACTTGTTCTACTGATTTACAAAAATCAAACACAGACATAAT

TCTTGGTGTTTGTGTTAATTATGATCTTTATGGTATTATAGGCCAAGGTGTTTTTGTTGAGGTTAATGCGACTTATTATA

ATAGTTGGCAGAACCTTTTATATGATTCTAATGGTAATCTCTATGGTTTTAGAGACTACTTAACAAACAGAACTTTTATG

ATTCGTAGTTGCTATAGCGGTCGTGTTTCAGCGGCCTTTCATGCTAACTCTTCCGAACCAGCATTGCTATTTCGGAATAT

TAAATGCAATTACGTTTTTAATAATATTCTTTCACGACAGCTGCAACCTATTAACTATTTTGATAGTTATCTTGGTTGTG

TTGTCAATGCTGATAATAGTACTTCTAGTGTTGTTCAAACATGTGATCTCACAGTAGGTAGTGGTTACTGTGTGGATTAC

TCTACAAAAAGACGAAGTCGTAGAGCGATTACCACTGGTTATCGGTTTACTAATTTTGAGCCATTTACTGTTAATTCAGT

AAATGATAGTTTAGAACCTGTAGGTGGTTTGTATGAAATTCAAATACCTTCAGAGTTTACTATAGGTAATATGGAGGAGT

TTATTCAAACAAGCTCTCCTAAAGTTACTATTGATTGTTCTGCTTTTGTCTGTGGTGATTATGCAGCATGTAAATCACAG

TTGGTTGAATATGGTAGCTTCTGTGACAATATTAATGCTATACTCACAGAAGTAAATGAACTACTTGACACTACACAGTT

GCAAGTAGCTAATAGTTTAATGAATGGTGTCACTCTTAGCACTAAGCTTAAAGATGGCGTTAATTTCAATGTAGACGACA

TCAATTTTTCCCCTGTATTAGGTTGTTTAGGAAGCGGTTGTAATAAAGGTTCCAGTAGATCTGCTATAGAGGATTTACTT

TTTTCTAAAGTAAAGTTATCTGATGTCGGTTTCGTTGAGGCTTATAATAATTGTACTGGAGGTGCCGAAATTAGGGACCT

CATTTGTGTGCAAAGTTATAATGGTATCAAAGTGTTGCCTCCACTGCTCTCAGTAAATCAGATCAGTGGATACACTTTGG

CTGCCACCTCTGCTAGTCTGTTTCCTCCTTGGTCAGCAGCAGCAGGTGTACCATTTTATTTAAATGTTCAGTATCGTATT

AATGGGCTTGGTGTTACCATGGATGTGTTAAGTCAAAATCAAAAGCTTATTGCTAATGCATTTAACAATGCTCTTGATGC

TATTCAGGAAGGGTTTGATGCTACCAATTCTGCTTTAGTTAAAATTCAAGCTGTTGTTAATGCAAATGCTGAAGCTCTTA

ATAACTTATTGCAACAACTCTCTAATAGATTTGGTGCTATAAGTTCTTCTTTACAAGAAATTCTATCTAGACTGGATGCT

CTTGAAGCGCAAGCTCAGATAGACAGACTTATTAATGGGCGTCTTACCGCTCTTAATGCTTATGTTTCTCAACAGCTTAG

TGATTCTACACTAGTAAAATTTAGTGCAGCACAAGCTATGGAGAAGGTTAATGAATGTGTCAAAAGCCAATCATCTAGGA

TAAATTTTTGTGGTAATGGTAATCATATTATATCATTAGTGCAGAATGCTCCATATGGTTTGTATTTTATCCACTTTAGC

TATGTCCCTACTAAGTATGTCACTGCGAAGGTTAGTCCCGGTCTGTGCATTGCTGGTGATAGAGGTATAGCCCCTAAGAG

TGGTTATTTTGTTAATGTAAATAATACTTGGATGTTCACTGGTAGTGGTTATTACTACCCTGAACCCATAACTGGAAATA

ATGTTGTTGTTATGAGTACCTGTGCTGTTAACTATACTAAAGCGCCGGATGTAATGCTGAACATTTCAACACCCAACCTC

CATGATTTTAAGGAAGAGTTGGATCAATGGTTTAAAAACCAAACATCAGTGGCACCAGATTTGTCACTTGATTATATAAA

TGTTACATTCTTGGACCTACAAGATGAAATGAATAGGTTACAGGAGGCAATAAAAGTTTTAAATCAGAGCTACATCAATC

TCAAGGACATTGGTACATATGAGTATTATGTAAAATGGCCTTGGTATGTATGGCTTTTAATTGGCTTTGCTGGTGTAGCT

ATGCTTGTTTTACTATTCTTCATATGCTGTTGTACAGGATGTGGGACTAGTTGTTTTAAGATATGTGGTGGTTGTTGTGA

TGATTATACTGGACACCAGGAGTTAGTAATTAAAACATTACATGACGACTAAGTTCGTCTTTGATTTATTGGCTCCTGAC

GATATATTACATCCCTTCAATCATGTGAAGCTAATTATAAGACCCATTGAGGTCGAGCATATTATAATAGCTACCACAAT

GCCTGCTGTTTAGTGGGTACTGTGTCTTATATAACTAGTAAACCTGTAATGCCAATGGCTACAACCATTGACGGTACAGA

-continued

TTATACTAATATTATGCCTAGTACTGTTTCTACAACAGTTTATTTAGGCTGTTCTATAGGTATTGACACTAGCACCACTG

GTTTTACCTGTTTTTCACGGTACTAGTTCCAAACCATATTATAATTTAGGTAGACCTTATAACTTTAAGCATTATTGCCA

AAGTTCCTAAGGTCACGCCCTAGTAATGGACATCTGGAGACCTGAGATTAAATATCTCCGTTATATTAACGGTTTTAATG

TCTCAGAATTAGAAGATGCTTGTTTTAAATTTAACTATAAATTTCCTAAAGTAGGATATTGTAGAGTTCCTAGTCATGCT

TGGTGCCGTAATCAAGGTAGCTTTTGTGCTACACTCACTCTTTATGGCAAATCCAAACATTATGATAAATATTTTGGAGT

AATAACTGGTTTTACAGCATTCGCTAATACTGTAGAGGAGGCTGTTAACAAACTGGTTTTCTTAGCTGTTGACTTTATTA

CCTGGCGGAGACAGGAGTTAAATGTTTATGGCTGATGCTTATTTTGCAGACACTGTGTGGTATGTGGGGCAAATAATTTT

TATAGTTGCCATTTGTTTATTGGTTATAATAGTTGTAGTGGCATTTTTGGCAACTTTTAAATTGTGTATTCAACTTTGCG

GTATGTGTAATACCTTAGTACTGTCCCCTTCTATTTATGTGTTTAATAGAGGTAGGCAGTTTTATGAGTTTTACAACGAT

GTAAAACCACCAGTTCTTGATGTGGATGACGTTTAGTTAATCCAAACATTATGAGTAGTGTAACTACACCAGCACCAGTT

TACACCTGGACTGCTGATGAAGCTATTAAATTCCTAAAGGAATGGAACTTTTCTTTGGGTATTATACTACTTTTTATTAC

AATCATATTGCAATTTGGATATACAAGTCGCAGTATGTTTGTTTATGTTATTAAGATGATCATTTTGTGGCTTATGTGGC

CCCTTACTATCATCTTAACTATTTTCAATTGCGTGTATGCGTTGAATAATGTGTATCTTGGCTTTTCTATAGTTTTCACT

ATAGTGGCCATTATCATGTGGATTGTGTATTTTGTGAATAGTATCAGGTTGTTTATTAGAACTGGAAGTTGGTGGAGTTT

CAACCCAGAAACAAACAACTTGATGTGTATAGATATGAAGGGAAGGATGTATGTTAGGCCGATAATTGAGGACTACCATA

CCCTTACGGTCACAATAATACGTGGTCATCTTTACATGCAAGGTATAAAACTAGGTACTGGCTATTCTTTGTCAGATTTG

CCAGCTTATGTGACTGTTGCTAAGGTCTCACACCTGCTCACGTATAAGCGTGGTTTTCTTGACAAGATAGGCGATACTAG

TGGTTTTGCTGTTTATGTTAAGTCCAAAGTCGGTAATTACCGACTGCCATCAACCCAAAAGGGTTCTGGCATGGACACCG

CATTGTTGAGAAATATAATCTAAACTTTAAGGATGTCTTTTACTCCTGGTAAGCAATCCAGTAGTAGAGCGTCCTCTGGA

AATCGTTCTGGTAATGGCATCCTTAAGTGGGCCGATCAGTCCGACCAATCTAGAAATGTTCAAACCAGGGGTAGAAGAGC

TCAACCCAAGCAAACTGCTACTTCTCAGCTACCATCAGGAGGGAATGTTGTACCCTACTATTCTTGGTTCTCTGGAATTA

CTCAGTTTCAAAAAGGAAAGGAGTTTGAATTTGCAGAGGGACAAGGTGTGCCTATTGCACCAGGAGTCCCAGCTACTGAA

GCTAAGGGGTACTGGTACAGACACAACAGACGTTCTTTTAAAACAGCCGATGGCAACCAGCGTCAACTGCTGCCACGATG

GTATTTTTACTATCTTGGAACAGGACCGCATGCCAAAGACCAGTATGGCACCGATATTGACGGTGTCTTCTGGGTCGCTA

GTAACCAGGCTGATGTCAATACCCCGGCTGACATTCTCGATCGGGACCCAAGTAGCGATGAGGCTATTCCGACTAGGTTT

CCGCCTGGCACGGTACTCCCTCAGGGTTACTATATTGAAGGCTCAGGAAGGTCTGCTCCTAATTCCAGATCTACTTCACG

CGCATCCAGTAGAGCCTCTAGTGCAGGATCGCGTAGTAGAGCCAATTCTGGCAACAGAACCCCTACCTCTGGTGTAACAC

CTGATATGGCTGATCAAATTGCTAGTCTTGTTCTGGCAAAACTTGGCAAGGATGCCACTAAGCCACAGCAAGTAACTAAG

CAGACTGCCAAAGAAATCAGACAGAAAATTTTGAATAAGCCCCGCCAGAAGAGGAGCCCCAATAAACAATGCACTGTTCA

GCAGTGTTTTGGGAAGAGAGGCCCCAATCAGAATTTTGGTGGTGGAGAAATGTTAAAACTTGGAACTAGTGACCCACAGT

TCCCCATTCTTGCAGAACTCGCACCCACAGCTGGTGCGTTTTTCTTTGGATCAAGATTAGAGTTGGCCAAAGTGCAGAAT

TTGTCTGGGAATCTTGACGAGCCCCAGAAGGATGTTTATGAATTGCGCTATAATGGTGCAATTAGATTTGACAGTACACT

TTCAGGTTTTGAGACCATAATGAAGGTGTTGAATGAGAATTTGAATGCATATCAACAACAAGATGGTATGATGAATATGA

GTCCAAAACCACAGCGTCAGCGTGGTCAGAAGAATGGACAAGGAGAAAATGATAATATAAGTGTTGCAGCGCCTAAAAGC

CGTGTGCAGCAAAATAAGAGTAGAGAGTTGACTGCAGAGGACATCAGCCTTCTTAAGAAGATGGATGAGCCCTATACTGA

AGACACCTCAGAAATATAAGAGAATGAACCTTATGTCGGCACCTGGTGGTAAGCCCTCGCAGGAAAGTCGGGATAAGGCA

CTCTCTATCAGAATGGATGTCTTGCTGCTATAATAGATAGAGAAGGTTATAGCAGACTATAGATTAATTAGTTGAAAGTT

TTGTGTGGTAATGTATAGTGTTGGAGAAAGTGAAAGACTTGCGGAAGTAATTGCCGACAAGTGCCCAAGGGGAAGAGCCA

GCATGTTAAGTTACCACCCAGTAATTAGTAAATGAATGAAGTTAATTATGGCCAATTGGAAGAATCAC

-continued

Orf1 ab gene (21,284 nucleotides) SEQ ID NO: 11

ATGTCGAAGATCAACAAATACGGTCTCGAACTACACTGGGCTCCAGAATTTCCATGGATGTTTGAGGACGCAGAGGAGAA

GTTGGATAACCCTAGTAGTTCAGAGGTGGATATAGTATGCTCCACCACTGCGCAAAAGCTGGAAACAGGCGGAATTTGTC

CTGAAAATCATGTGATGGTGGATTGTCGCCGACTTCTTAAACAAGAGTGTTGTGTGCAGTCTAGCCTAATACGTGAAATT

GTTATGAATACACGTCCATATGATTTGGAGGTGCTACTTCAAGATGCTTTGCAGTCCTGCGAAGCAGTTTTGGTTACACC

CCCTCTAGGTATGTCTCTGGAGGCATGCTATGTGAGAGGTTGTAATCCTAATGGATGGACCATGGGTTTGTTTCGGCGTA

GAAGTGTGTGTAACACTGGTCGTTGCGCTGTTAACAAGCATGTGGCCTATCAGCTATATATGATTGATCCTGCGGGTGTC

TGTTTTGGTGCAGGTCAATTTGTGGGTTGGGTTATACCCTTAGCCTTTATGCCTGTGCAATCCCGGAAATTTATTGTTCC

TAGGGTTATGTACTTGCGTAAGTGTGGCGAAAAGGGTGCCTACAATAAAGATCATAAACGTGGCGGTTTTGAACACGTTT

ATAATTTTAAAGTTGAGGATGCTTACGACCTGGTTCATGATGAGCCTAAGGGTAAGTTTTCTAAGAAGGCTTATGCTTTA

ATTAGAGGATACCGTGGTGTTAAACCGCTTCTCTATGTAGACCAGTATGGTTGTGATTATACTGGTGGTCTTGCAGATGG

CTTAGAGGCTTATGCTGATAAGACATTGCAAGAAATGAAGGCATTATTTCCTATTTGGAGCCAGGAACTCCCTTTTGATG

TAACTGTGGCATGGCACGTTGTGCGTGATCCACGTTATGTTATGAGACTGCAGAGTGCTTCTACTATACGTAGTGTTGCA

TATGTTGCTAACCCTACTGAAGACTTGTGTGATGGTTCTGTTGTTATAAAGGAACCTGTGCATGTTTATGCGGATGACTC

TATTATTTTACGTCAACATAATTTAGTTGACATTATGAGTTGTTTTTATATGGAGGCAGATGCAGTTGTAAATGCTTTTT

ATGGTGTTGATTTGAAAGATTGTGGTTTTGTTATGCAGTTTGGTTATATTGACTGCGAACAAGACTTGTGTGATTTTAAA

GGTTGGGTTCCTGGTAATATGATAGATGGTTTTGCTTGCACTACTTGTGGTCATGTTTATGAGACAGGTGATTTGCTAGC

ACAATCTTCAGGTGTTTTGCCTGTTAATCCTGTATTGCATACTAAGAGTGCAGCAGGTTATGGTGGTTTTGGTTGTAAGG

ATTCTTTTACCCTGTATGGCCAAACTGTAGTTTATTTTGGAGGTTGTGTGTATTGGAGTCCAGCACGTAATATATGGATT

CCTATATTAAAATCTTCTGTTAAGTCTTATGACGGTTTGGTTTATACTGGAGTTGTAGGTTGCAAGGCTATTGTAAAGGA

AACAAATCTCATTTGCAAAGCGTTGTACCTTGATTATGTTCAACACAAGTGTGGCAATTTACACCAGCGGGAGTTGCTAG

GTGTGTCAGATGTGTGGCATAAACAATTGTTATTAAATAGAGGTGTGTACAAACCTCTTTTAGAGAATATTGATTATTTT

AATATGCGGCGCGCTAAATTTAGTTTAGAAACTTTTACTGTTTGTGCAGATGGTTTTATGCCTTTTCTTTTAGATGATTT

GGTTCCGCGCGCATATTATTTGGCAGTAAGTGGTCAAGCATTTTGTGACTACGCAGGTAAAATCTGCCATGCTGTTGTGT

CTAAGAGTAAAGAGTTACTTGATGTGTCTCTGGATTCTTTAGGTGCAGCTATACATTATTTGAATTCTAAAATTGTTGAT

TTGGCTCAACATTTTAGTGATTTTGGAACAAGTTTCGTTTCTAAAATTGTTCATTTCTTTAAGACTTTTACTACTAGCAC

TGCTCTTGCATTTGCATGGGTTTTATTTCATGTTTTGCATGGTGCTTATATAGTAGTGGAGAGTGATATATATTTTGTTA

AAAACATTCCTCGTTATGCTAGTGCTGTTGCACAAGCATTTCGGAGTGTTGCTAAAGTTGTACTGGACTCTTTAAGAGTT

ACTTTTATTGATGGCCTTTCTTGTTTTAAGATTGGACGTAGAAGAATTTGTCTTTCAGGCAGTAAAATTTATGAAGTTGA

GCGTGGCTTGTTACATTCATCTCAATTGCCATTAGATGTTTATGATTTAACCATGCCTAGTCAAGTTCAGAAAACCAAGC

AAAAACCTATTTATTTAAAAGGTTCTGGTTCTGATTTTTCATTAGCGGATAGTGTAGTTGAAGTTGTTACAACTTCACTT

ACACCATGTGGTTATTCTGAACCACCTAAAGTTGCAGATAAAATTTGCATTGTGGATAATGTTTATATGGCCAAGGCTGG

TGACAAATATTACCCTGTTGTGGTTGATGGTCATGTTGGACTTTTGGATCAAGCATGGAGGGTTCCTTGTGCTGGAAGGC

GTGTTACATTTAAGGAACAGCCTACAGTAAATGAGATTGCAAGCACGCCTAAGACTATTAAAGTTTTTTATGAGCTTGAC

AAAGATTTTAATACTATTTTAAACACTGCATGTGGAGTGTTTGAAGTGGATGATACTGTGGATATGGAGGAATTTTATGC

TGTGGTGATTGATGCCATAGAAGAGAAACTTTCTCCATGTAAGGAGCTTGAAGGTGTAGGTGCTAAAGTTAGTGCCTTTT

TACAGAAATTAGAGGATAATTCCCTATTTTTATTTGATGAGGCTGGTGAGGAAGTTCTTGCTCCTAAATTGTATTGTGCT

TTTACAGCTCCTGAAGATGATGACTTTCTTGAAGAAAGTGGTGTTGAAGAAGATGATGTAGAAGGTGAGGAAACTGATTT

AACTGTCACAAGTGCTGGAGAGCCTTGTGTTGCCAGTGAACAGGAGGAGTCTTCTGAAATCTTAGAGGACACTTTGGATG

ATGGTCCATGTGTGGAGACATCTGATTCACAAGTTGAAGAAGATGTACAAATGTCGGATTTTGTTGATCTTGAATCTGTG

ATTCAGGATTATGAAAATGTTTGTTTTGAGTTTTATACTACAGAACCAGAATTTGTTAAAGTTTTGGATCTGTATGTTCC

-continued

TAAAGCAACTCGCAACAATTGCTGGTTGCGATCAGTTTTGGCAGTGATGCAGAAACTGCCCTGTCAATTTAAAGATAAAA

ATTTGCAGGATCTTTGGGTGTTATATAAGCAACAGTATAGTCAGTTGTTTGTTGATACCTTGGTTAATAAGATACCTGCT

AATATTGTAGTTCCACAAGGTGGTTATGTTGCTGATTTTGCATATTGGTTCTTAACCTTATGTGATTGGCAGTGTGTTGC

ATACTGGAAATGCATTAAATGTGATTTAGCTCTTAAGCTTAAAGGCTTGGATGCTATGTTCTTTTATGGTGATGTTGTCT

CACATGTGTGCAAGTGTGGTGAGTCTATGGTACTTATTGATGTTGATGTGCCATTTACAGCCCACTTTGCTCTTAAAGAT

AAGTTGTTTTGTGCATTTATTACTAAGCGTAGTGTGTATAAAGCAGCTTGTGTTGTGGCTGTTAATGATAGTCATTCTAT

GGCTGTTGTTGATGGTAAACAAATTGATGATCATTGTATCACTAGTATTACTAGTGATAAGTTTGATTTTATTATTGGGC

ATGGTATGTCATTTTCAATGACTACTTTTGAAATTGCCCAATTGTATGGTTCTTGTATAACACCTAATGTATGTTTTGTT

AAAGGTGATATAATTAAAGTTTCTAAGCGTGTTAAAGCAGAAGTCGTTGTAAATCCTGCTAATGGCCATATGGCACATGG

TGGTGGTGTTGCAAAGGCTATTGCAGTAGCAGCTGGACAGCAGTTTGTTAAAGAGACCACCGATATGGTTAAGTCTAAAG

GAGTTTGTGCTACTGGAGATTGTTATGTCTCTACAGGGGGCAAATTATGTAAAACTGTGCTTAATGTTGTTGGACCTGAT

GCGAGGACACAGGGTAAACAAAGTTATGCATTGTTAGAGCGTGTTTATAAACATCTTAACAAATATGATTGTGTTGTTAC

AACTTTGATCTCAGCTGGTATATTTAGTGTGCCTTCTGATGTGTCTTTAACATATCTACTTGGTACTGCTAAGAAACAAG

TTGTTCTTGTTAGCAATAATCAAGAGGATTTTGATCTTATTTCTAAGTGTCAGATAACTGCCGTTGAGGGCACTAAGAAA

TTGGCAGAGCGTCTTTCTTTTAATGTTGGGCGTTCTATCGTTTACGAAACAGATGCTAATAAGTTGATTTTAAGCAATGA

CGTTGCATTTGTTTCGACATTTAATGTCTTACAGGATGTTTTATCCTTAAGACATGATATAGCACTTGATGATGATGCAC

GAACCTTTGTTCAGAGCAATGTTGATGTTGTACCTGAGGGTTGGCGTGTTGTCAATAAGTTTTATCAAATTAATGGTGTT

AGAACCGTTAAGTATTTTGAGTGTCCCGGGGGCATAGATATATGCAGCCAGGATAAAGTTTTTGGTTATGTACAGCAGGG

TAGTTTTAATAAGGCTACTGTTGCTCAAATTAAAGCCTTGTTTTTGGATAAAGTGGACATCTTGCTAACTGTTGATGGTG

TTAATTTCACTAACAGGTTTGTGCCTGTAGGTGAAAGTTTTGGTAAGAGTCTAGGAAATGTGTTTTGTGATGGAGTTAAT

GTCACGAAACATAAGTGTGATATAAATTATAAAGGTAAAGTCTTTTTCCAGTTTGATAATCTTTCTAGTGAAGATTTAAA

GGCTGTAAGAAGTTCTTTTAATTTTGATCAGAAGGAATTGCTTGCCTACTACAACATGCTTGTTAATTGTTCTAAGTGGC

AGGTTGTTTTTAATGGTAAGTATTTCACTTTTAAGCAAGCTAATAACAATTGTTTTGTTAATGTTTCTTGCTTAATGCTC

CAGAGTTTGAATCTGAAATTTAAAATTGTTCAATGGCAGGAGGCGTGGCTTGAATTTCGTTCTGGCCGCCCTGCTAGATT

TGTATCTTTGGTTTTGGCTAAAGGTGGGTTTAAATTTGGGGATCCTGCTGATTCTAGAGATTTCTTGCGTGTTGTGTTTA

GTCAAGTTGATTTGACAGGGGCAATATGTGATTTTGAAATTGCATGTAAATGTGGTGTAAAGCAGGAACAGCGTACTGGT

GTGGACGCTGTTATGCATTTTGGTACATTGAGTCGTGAAGATCTTGAGATTGGTTACACCGTGGATTGTTCTTGCGGTAA

AAAGCTAATTCATTGTGTACGATTTGATGTACCATTTTTAATTTGCAGTAATACACCTGCTAGTGTAAAATTACCTAAGG

GTGTAGGAAGTGCAAATATTTTTAAAGGTGATAAGGTTGGTCATTATGTTCATGTTAAGTGTGAACAGTCTTATCAGCTT

TATGATGCTTCTAATGTTAAGAAGGTTACAGACGTTACTGGCAATTTGTCAGATTGTTTGTATCTTAAAAATTTGAAACA

AACTTTTAAATCGGTGTTAACCACCTATTATTTGGATGATGTTAAGAAAATTGAGTATAAACCTGACTTGTCACAATATT

ATTGTGACGGAGGTAAGTATTATACTCAGCGTATTATTAAAGCCCAATTTAAAACATTTGAGAAAGTAGATGGTGTGTAT

ACTAATTTTAAATTGATAGGACACACCGTCTGTGATATTCTTAATGCTAAGTTGGGTTTTGATAGCTCTAAAGAGTTTGT

TGAATATAAGGTTACTGAGTGGCCAACAGCTACAGGTGATGTGGTGTTGGCTACTGATGATTTGTATGTTAAGAGATATG

AAAGGGGTTGTATTACTTTTGGTAAACCTGTTATATGGTTAAGCCATGAGCAAGCTTCCCTCAATTCTTTAACATATTTT

AATAGACCTTTATTGGTTGATGAGAATAAATTTGATGTTTTAAAAGTGGATGATGTTGACGATGGTGGTGATATCTCAGA

GAGTGATGCTAAAGAACCCAAAGAAATCAACATTATTAAGTTAAGTGGTGTTAAAAAACCATTTAAGGTTGAAGATAGTG

TCATTGTTAATGATGATACTAGTGAAATCAAATATGTTAAGAGTTTGTCTATAGTTGATGTGTATGATATGTGGCTTACA

GGTTGTAGGTGTGTTGTTAGGACTGCTAATGCTTTGAGCAGAGCAGTTAACGTACCTACAATACGTAAGTTTATAAAATT

TGGTATGACTCTTGTTAGTATACCAATTGATTTGTTAAATTTAAGAGAGATTAAGCCTGTTTTTAATGTGGTTAAAGCTG

-continued

TGCGAAATAAAATTTCTGCATGCTTTAATTTTATTAAATGGCTTTTTGTCTTATTATTTGGCTGGATTAAAATATCCGCT

GATAATAAAGTAATTTACACCACAGAAGTTGCATCAAAGCTTACGTGTAAGCTTGTAGCTTTAGCTTTTAAAAATGCATT

TTTGACATTTAAGTGGAGTGTGGTTGCTAGAGGTGCTTGCATTATAGCGACTATATTTCTATTGTGGTTTAATTTTATAT

ATGCCAATGTAATTTTTAGTGATTTTTATTTGCCTAAAATCGGTTTCTTGCCGACTTTTGTTGGTAAGATCGCACAGTGG

ATTAAGAACACTTTTAGTCTTGTAACTATTTGTGATCTATATTCCATTCAGGATGTGGGTTTTAAGAATCAGTATTGTAA

TGGAAGTATCGCATGTCAGTTCTGCTTGGCAGGATTTGATATGTTAGATAATTATAAAGCCATTGATGTAGTACAGTATG

AAGCTGATAGGCGAGCATTTGTTGATTATACAGGTGTGTTAAAGATTGTCATTGAATTGATAGTTAGTTACGCCCTGTAT

ACGGCATGGTTTTACCCATTGTTTGCTCTTATTAGTATTCAGATCTTGACCACTTGGCTGCCTGAGCTTTTTATGCTTAG

TACATTACATTGGAGTGTTAGGTTGCTGGTGTCTTTAGCTAATATGTTACCAGCACATGTGTTTATGAGGTTTTATATTA

TTATTGCCTCTTTTATTAAGCTGTTTAGCTTGTTTAGGCATGTTGCCTATGGTTGTAGTAAATCTGGTTGTTTGTTTTGT

TACAAGAGGAATCGTAGTCTACGTGTTAAATGTAGTACTATTGTTGGTGGCATGATACGCTATTACGATGTTATGGCTAA

TGGTGGCACTGGCTTTTGTTCAAAACATCAATGGAATTGCATTGATTGTGATTCTTATAAACCAGGTAATACTTTTATTA

CTGTTGAGGCCGCTCTTGATTTATCTAAGGAATTGAAACGGCCTATTCAGCCTACAGATGTTGCTTATCATACGGTTACG

GATGTTAAGCAAGTTGGTTGTTATATGCGCTTGTTCTATGATCGTGATGGACAGCGCACATATGATGATGTTAATGCTAG

TTTGTTTGTGGATTATAGTAATTTGCTACATTCTAAGGTTAAGAGTGTGCCTAATATGCATGTTGTGGTAGTGGAAAATG

ATGCCGATAAAGCTAATTTTCTTAATGCTGCTGTATTTTATGCACAGTCTTTGTTTAGACCTATTTTAATGGTTGATAAA

AATCTGATAACTACTGCTAATACTGGTACGTCTGTTACAGAAACTATGTTTGATGTTTATGTGGATACATTTTTGTCTAT

GTTTGATGTGGATAAAAAGAGTCTTAATGCTTTAATAGCAACTGCGCATTCTTCTATAAAACAGGGTACGCAGATCTGTA

AAGTTTTGGATACCTTTTTAAGCTGTGCTCGTAAAAGTTGTTCTATTGATTCAGATGTTGATACTAAGTGTTTAGCTGAT

TCTGTCATGTCTGCTGTATCGGCAGGCCTTGAATTGACGGATGAAAGTTGTAATAACTTGGTGCCAACATATTTGAAGGG

TGATAACATTGTGGCAGCTGATTTAGGTGTTCTGATTCAAAATTCTGCTAAGCATGTGCAGGGTAATGTTGCTAAAATAG

CCGGTGTTTCCTGTATATGGTCTGTGGATGCTTTTAATCAGCTTAGTTCTGATTTCCAGCATAAATTGAAGAAAGCATGT

TGTAAAACTAGTTTGAAACTGAAGCTTACTTATAATAAGCAGATGGCTAATGTCTCTGTTTTAACTACACCCTTTAGTCT

TAAAGGGGGTGCAGTTTTTAGTTATTTTGTTTATGTATGTTTTGTGTTGAGTTTGGTTTGTTTTATTGGATTGTGGTGCT

TAATGCCCACTTACACAGTACACAAATCAGATTTTCAGCTTCCCGTTTATGCCAGTTATAAAGTTTTAGATAATGGTGTT

ATTAGAGATGTTAGCGTTGAAGATGTTTGTTTCGCTAACAAATTTGAACAATTTGATCAATGGTATGAGTCTACATTTGG

TCTAAGTTATTATAGTAACAGTATGGCTTGTCCCATTGTTGTTGCTGTAGTAGACCAGGATTTTGGCTCTACTGTGTTTA

ATGTCCCTACCAAAGTGTTACGATATGGTTACCATGTGTTGCACTTTATTACACATGCACTTTCTGCTGATGGAGTGCAG

TGTTATACGCCACATAGTCAAATATCGTATTCTAATTTTTATGCTAGTGGCTGTGTGCTTTCCTCTGCTTGCACTATGTT

TGCAATGGCCGATGGTAGTCCACAACCTTATTGTTATACAGATGGGCTTATGCAGAATGCTTCTCTGTATAGTTCATTGG

TACCTCATGTGCGGTATAATCTTGCTAATGCTAAAGGTTTTATCCGTTTTCCAGAAGTGTTGCGAGAAGGACTTGTGCGT

ATTGTGCGTACTCGTTCTATGTCGTATTGCAGAGTTGGATTATGTGAGGAAGCTGATGAGGGTATATGCTTTAATTTTAA

TGGTTCTTGGGTGCTTAATAATGATTATTATAGATCATTGCCTGGGACCTTTTGTGGTAGAGATGTTTTTGACTTAATTT

ATCAGCTGTTTAAAGGTTTAGCACAGCCTGTGGATTTCTTGGCATTGACTGCTAGTTCCATTGCTGGTGCTATACTTGCT

GTAATTGTTGTTTTGGTGTTTTATTACTTAATAAAGCTTAAACGTGCTTTTGGTGATTACACCAGTATTGTTTTTGTTAA

TGTGATTGTGTGGTGTGTAAATTTTATGATGCTTTTTGTGTTTCAAGTTTACCCTACACTTTCTTGTGTATATGCTATTT

GTTATTTTTATGCCACGCTTTATTTCCCTTCGGAGATAAGTGTGATAATGCATTTACAATGGCTAGTTATGTATGGCACT

ATTATGCCTTTATGGTTTTGTTTGCTATATATATCTGTTGTTGTTTCAAATCATGCTTTTTGGGTATTTTCTTACTGCAG

ACAGCTTGGTACTTCTGTTCGTAGTGATGGTACATTTGAAGAAATGGCTCTTACTACTTTTATGATTACAAAAGATTCTT

ATTGTAAGCTTAAGAATTCTTTGTCTGATGTTGCTTTTAATAGATATTTGAGTTTGTATAATAAATATAGGTATTACAGC

GGTAAAATGGATACTGCTGCATATAGGGAGGCTGCTTGTTCTCAGTTGGCTAAAGCAATGGATACATTTACCAATAATAA

-continued

TGGTAGTGATGTGCTTTACCAACCGCCTACTGCTTCCGTTTCAACTTCATTCTTGCAATCTGGTATTGTGAAAATGGTTA

ATCCTACTTCTAAGGTAGAACCATGTATTGTCAGTGTTACCTATGGTAATATGACATTGAATGGTTTATGGTTGGATGAT

AAGGTCTACTGTCCCAGACATGTGATATGTTCTGCTTCAGATATGACTTATCCAGATTATACAAATTTGTTGTGTAGAGT

AACATCAAGTGATTTTACTGTATTGTTTGATCGTCTAAGCCTTACAGTGATGTCTTATCAAATGCAGGGTTGTATGCTTG

TTCTTACAGTGACCCTGCAAAATTCTCGTACGCCAAAATATACATTTGGTGTGGTTAAACCTGGTGAGACTTTTACTGTT

TTAGCTGCTTATAACGGCAAACCACAAGGAGCCTTTCATGTGACTATGCGTAGTAGTTATACCATTAAGGGTTCCTTTTT

ATGCGGATCTTGTGGATCTGTTGGTTATGTAATAATGGGTGATTGTGTTAAATTTGTGTATATGCATCAATTGGAGCTTA

GTACTGGTTGTCATACTGGTACTGATTTCAATGGGGATTTTTATGGTCCTTATAAGGATGCTCAGGTTGTCCAATTGCCC

GTTCAGGATTATATACAATCTGTTAATTTTGTAGCATGGCTTTATGCTGCTATACTTAATAATTGTAATTGGTTTGTACA

AAGTGATAAGTGTTCTGTTGAAGATTTTAATGTGTGGGCTTTGTCTAATGGGTTTAGCCAAGTTAAGTCTGATCTTGTTA

TAGATGCTTTAGCTTCTATGACTGGTGTGTCTTTGGAAACACTATTGGCTGCTATTAAGCGTCTTAAGAATGGTTTTCAA

GGACGTCAGATTATGGGTAGTTGCTCCTTTGAGGATGAATTGACACCTAGCGATGTTTATCAACAACTCGCTGGTATCAA

GTTACAATCAAAGCGTACTAGATTGGTTAAAGGCATTGTTTGTTGGATTATGGCTTCTACATTTTTGTTTAGTTGTATAA

TTACAGCATTTGTGAAATGGACTATGTTTATGTATGTAACTACTAATATGCTTAGTATTACGTTTTGTGCACTTTGTGTT

ATAAGTTTGGCCATGTTGTTGGTTAAACATAAGCATCTTTATTTGACTATGTATATAATTCCTGTGCTTTTTACACTGCT

GTATAACAACTATTTGGTTGTGTACAAGCAGACATTTAGAGGCTATGTTTATGCATGGCTATCATATTATGTTCCATCAG

TTGAGTATACTTATACTGATGAAGTAATTTATGGCATGTTATTGCTTATAGGAATGGTCTTTGTTACATTACGTAGCATT

AACCATGATTTGTTCTCTTTTATAATGTTTGTTGGTCGTGTGATTTCTGTTGTCTCTTTGTGGTACATGGGTTCTAACTT

AGAGGAAGAAATTCTTCTTATGTTGGCTTCTCTTTTTGGTACTTACACATGGACAACAGCTTTATCTATGGCTGCAGCAA

AGGTTATTGCTAAGTGGGTTGCTGTGAATGTTTTGTATTTCACAGATATACCTCAAATTAAGATAGTGCTTGTATGCTAT

TTGTTTATAGGTTATATTATTAGCTGTTATTGGGGTTTGTTTTCCTTGATGAACAGTTTGTTTAGAATGCCTTTGGGTGT

TTATAATTATAAAATTTCAGTACAGGAATTAAGATATATGAATGCTAATGGATTGCGCCCTCCTAAGAATAGTTTTGAAG

CCCTCATGCTTAATTTTAAGCTTTTGGGTATTGGAGGTGTGCCAATTATTGAAGTATCTCAATTTCAATCAAAATTGACT

GATGTTAAATGTGCTAATGTTGTCTTGCTTAATTGCTTGCAACATTTGCATGTTGCTTCTAACTCTAAGTTGTGGCAATA

TTGTAGCACTTTGCACAATGAAATACTTGCCACTTCTGATCTGGGTGTTGCTTTTGAAAAGCTTGCTCAGTTGTTAATTG

TTTTGTTTGCTAATCCAGCTGCTGTGGATAGCAAGTGCCTGACTAGTATTGAAGAAGTTTGCGACGATTACGCAAAGGAC

AATACTGTTTTGCAGGCTTTACAGAGTGAATTTGTTAATATGGCTAGCTTCGTTGAATATGAAGTTGCTAAGAAAAATCT

TGATGAGGCGTGTTCTAGTGGTTCTGCTAATCGACAGCAGTTAAAACAGCTAGAGAAAGCCTGTAATATTGCTAAATCTG

CTTATGAACGCGACCGTGCTGTAGCAAGAAAGTTGGAGCGTATGGCAGATTTGGCTCTCACTAATATGTATAAAGAAGCT

AGAATTAATGATAAGAAGAGTAAGGTTGTTTCTGCCTTGCAAACTATGCTTTTTAGTATGGTGCGTAAGTTAGATAATCA

AGCTCTGAATTCAATATTAGATAATGCTGTGAAGGGTTGTGTACCATTGAATGCAATCCCTTCATTGGCAGCAAATACTC

TGACTATAATTGTACCAGATAAAAGTGTTTATGATCAGGTAGTTGACAATGTCTATGTTACCTATGCGGGTAATGTATGG

CAGATTCAAACTATCCAAGATTCAGATGGTACAAATAAGCAGTTGAATGAGATATCTGATGATTGTAACTGGCCACTAGT

TATTATTGCAAATCGGCATAATGAGGTATCTGCTACCGTTTTGCAAAATAATGAATTAATGCCTGCTAAGTTGAAAACTC

AGGTTGTTAATAGTGGTCCAGATCAGACTTGTAATACACCTACTCAATGTTACTATAATAATAGTTACAATGGGAAGATT

GTTTATGCTATACTTAGTGATGTTGATGGTCTTAAGTATACAAAAATTCTTAAAGATGATGGCAATTTTGTTGTTTTGGA

GTTAGATCCTCCTTGTAAATTTACTGTTCAAGATGTTAAAGGTCTTAAAATTAAGTACCTTTATTTTGTAAAAGGTTGTA

ACACACTAGCAAGAGGCTGGGTTGTTGGTACAATTTCTTCTACAGTTAGATTGCAAGCTGGAACTGCTACTGAGTATGCT

TCCAACTCATCTATATTATCTTTATGTGCGTTTTCTGTAGATCCTAAGAAAACGTATTTAGATTTTATACAACAGGGAGG

AACACCTATTGCCAATTGTGTTAAAATGTTGTGTGACCATGCTGGTACCGGTATGGCCATTACTGTTAAACCCGATGCTA

-continued

CCACTAGTCAGGATTCATATGGTGGTGCGTCTGTTTGTATATATTGCCGCGCACGAGTTGAACACCCAGATGTTGATGGG

TTGTGCAAATTACGCGGCAAGTTTGTACAAGTGCCTGTAGGTATAAAAGATCCTGTGTCTTATGTTTTGACACATGATGT

TTGTCAAGTTTGTGGATTTTGGCGGGATGGAAGCTGTTCATGTGTTAGCACTGACACTACTGTTCAGTCAAAAGATACTA

ATTTTTTAAACGGGTTCGGGGTACGAGTGTAGATGCCCGTCTCGTACCCTGTGCCAGTGGTTTATCTACTGATGTACAAT

TAAGGGCATTTGATATTTGCAATGCTAGTGTTGCTGGCATTGGTTTACATTTAAAAGTTAATTGCTGCCGTTTTCAGCGT

GTTGATGAGAACGGTGATAAATTAGATCAGTTCTTTGTTGTTAAGAGGACAGATCTGACTATATATAATAGAGAGATGGA

ATGCTATGAGCGTGTAAAAGATTGTAAGTTTGTGGCTGAACACGATTTCTTTACATTTGATGTAGAAGGTAGTCGTGTGC

CACACATTGTACGCAAGGATTTAACAAAGTATACTATGTTGGATCTTTGCTATGCATTGCGACATTTTGATCGCAATGAT

TGCATGCTGCTTTGTGACATTCTCTCTATATATGCTGGTTGTGAACAATCCTACTTTACTAAGAAGGATTGGTATGATTT

TGTTGAAAATCCTGATATTATTAATGTTTATAAAAAGCTAGGACCTATTTTTAATAGAGCCCTAGTTAGCGCTACTGAGT

TTGCAGACAAATTGGTGGAGGTAGGCTTAGTAGGCATTTTAACACTTGATAACCAAGATTTAAATGGTAAATGGTATGAT

TTTGGTGACTATGTTATTGCAGCCCCAGGGTGTGGTGTTGCTATAGCAGACTCTTATTATTCTTATATGATGCCTATGCT

GACCATGTGTCATGCATTGGATTGTGAATTGTATGTGAATAATGCTTATAGACTATTTGATCTTGTACAGTATGATTTTA

CTGATTACAAGCTCGAATTGTTTAATAAGTATTTTAAGCACTGGAGTATGCCATACCATCCTAACACGGTTGATTGTCAG

GATGATCGGTGTATCATACATTGTGCTAATTTTAACATACTTTTTAGTATGGTTTTACCTAATACATGTTTTGGGCCTCT

TGTTAGGCAAATTTTTGTGGATGGTGTGCCTTTTGTTGTTTCAATTGGCTACCATTATAAAGAACTTGGTATTGTGATGA

ACATGGATGTGGATACACATCGTTATCGCTTGTCTTTAAAAGACTTGCTTTTATATGCTGCTGATCCAGCTTTGCATGTA

GCTTCTGCTAGTGCATTGTATGATTTACGCACTTGCTGTTTTAGTGTTGCGGCTATAACAAGCGGTGTAAAATTTCAAAC

AGTTAAACCTGGTAATTTTAATCAGGATTTTTATGATTTTATTTTAAGTAAGGGCCTGCTTAAAGAGGGTAGTTCAGTTG

ATCTGAAGCACTTTTTCTTTACGCAGGATGGTAATGCTGCTATTACTGATTATAATTATTATAAGTACAATTTGCCCACC

ATGGTGGACATTAAGCAGTTGTTGTTTGTTTTGGAAGTTGTTTATAAGTATTTTGAGATTTATGATGGTGGGTGTATACC

GGCATCACAAGTCATTGTTAATAATTATGATAAGAGTGCTGGCTATCCATTTAATAAATTTGGAAAAGCCAGGCTCTATT

ATGAAGCATTATCATTTGAGGAGCAGGATGAAATTTACGCCTATACTAAGCGCAATGTCCTGCCAACACTTACTCAAATG

AATTTGAAATATGCTATTAGTGCTAAGAATAGAGCCCGCACTGTTGCTGGTGTTTCCATACTTAGTACTATGACTGGCAG

AATGTTTCATCAAAAATGTTTGAAAAGTATAGCAGCTACACGTGGTGTTCCTGTTGTTATAGGCACCACTAAGTTTTATG

GCGGCTGGGATGATATGTTACGTCGCCTTATTAAAGATGTTGATAATCCTGTACTTATGGGTTGGGATTATCCTAAGTGT

GATCGTGCTATGCCAAACATACTACGTATTGTTAGTAGTCTGGTCTTGGCCCGAAAACATGAGGCATGTTGTTCGCAAAG

CGATAGGTTTTATCGACTTGCGAATGAATGCGCACAAGTTCTGAGTGAAATTGTTATGTGTGGTGGCTGTTATTATGTTA

AGCCTGGTGGCACTAGTAGTGGTGATGCAACTACTGCTTTTGCTAATTCAGTTTTTAACATATGTCAAGCTGTTTCAGCC

AATGTATGTGCTTTAATGTCATGCAATGGTAATAAGATTGAAGATTTGAGTATACGTGCTCTTCAGAAGCGCTTATACTC

ACATGTGTATAGAAGTGATATGGTTGATTCAACCTTTGTCACAGAATATTATGAATTTTTAAATAAGCATTTTAGTATGA

TGATTTTGAGTGATGATGGCGTTGTGTGTTATAATTCTGATTATGCGTCCAAAGGGTATATTGCTAATATAAGTGCCTTT

CAACAGGTATTGTATTATCAAAATAACGTTTTTATGTCAGAATCCAAATGTTGGGTTGAAAATGACATAAACAATGGACC

TCATGAATTTTGTTCACAACATACAATGCTTGTAAAGATGGATGGGGACGATGTCTATCTTCCATATCCTGATCCTAGTC

GTATATTAGGAGCTGGATGTTTTGTAGATGATTTGTTAAAGACTGATAGTGTTCTTTTAATAGAACGATTTGTAAGTCTT

GCAATAGATGCTTATCCACTTGTGTACCACGAAAATGAAGAATACCAAAAGGTTTTTCGTGTTTATTTGGAGTATATAAA

GAAGTTGTACAATGACCTGGGTAATCAGATCTTGGATAGCTACAGTGTTATTTTAAGTACTTGTGATGGACAAAAGTTTA

CTGATGAGTCCTTTTACAAGAACATGTATTTAAGAAGTGCAGTTATGCAGAGTGTTGGAGCTTGCGTGGTCTGCTCTTCC

CAAACATCATTACGTTGTGGCAGTTGCATCAGAAAGCCTCTTCTTTGCTGCAAGTGTTGTTACGATCATGTTATGGCAAC

TGATCATAAATATGTTTTGAGTGTTTCACCATATGTGTGTAACGCACCAGGATGTGATGTAAATGATGTTACCAAATTGT

ATCTAGGTGGTATGTCATATTATTGTGAAGATCATAAGCCACAATATTCGTTTAAGTTGGTAATGAATGGTATGGTTTTT

-continued

GGTCTATATAAACAATCTTGTACAGGATCTCCGTACATAGATGATTTTAATCGTATAGCTAGTTGTAAATGGACTGATGT

TGATGATTACATACTGGCTAATGAATGTACAGAGCGCTTGAAATTGTTTGCTGCAGAAACGCAAAAGGCGACTGAGGAAG

CCTTTAAGCAGAGTTATGCATCAGCAACAATACAAGAGATTGTTAGTGAGCGCGAATTGATCCTCTCTTGGGAGATTGGA

AAAGTGAAGCCACCACTTAATAAAAATTATGTTTTTACTGGCTACCATTTTACTAAAAATGGCAAGACAGTTTTAGGTGA

GTATGTTTTTGATAAGAGTGAGTTGACTAATGGTGTGTATTATCGCGCCACAACCACTTATAAGCTATCTGTAGGAGATG

TTTTTGTTTTAACCTCTCATTCAGTAGCTAATTTAAGTGCTCCTACGCTTGTGCCGCAGGAGAATTATAGTAGTATTAGA

TTTGCTAGTGTTTATAGTGTGCTTGAGACATTTCAGAACAATGTTGTGAACTATCAACACATTGGTATGAAACGTTATTG

CACCGTGCAAGGACCTCCTGGTACAGGAAAGTCACATCTTGCTATTGGTCTTGCTGTATATTATTGTACAGCACGTGTAG

TATACACTGCGGCCAGCCATGCAGCTGTTGACGCATTGTGTGAAAAAGCATACAAATTTTTGAATATAAATGATTGCACT

CGTATTGTTCCTGCCAAGGTCAGGGTGGAGTGCTATGATAAGTTTAAAATTAATGACACCACTCGTAAGTATGTGTTTAC

TACTATAAATGCATTACCTGAGATGGTGACTGATATTGTTGTTGTAGATGAAGTTAGTATGCTTACCAATTATGAGCTTT

CTGTTATTAATGCTCGTATTCGCGCTAAGCATTATGTTTATATTGGTGATCCTGCTCAATTGCCAGCACCACGTGTGTTA

TTGAGCAAGGGTACACTTGAACCTAAATATTTTAACACTGTTACTAAGCTTATGTGTTGCTTAGGGCCAGACATTTTTCT

TGGTACATGTTATAGATGTCCTAAGGAAATCGTTGATACAGTGTCTGCCTTGGTTTATGAAAATAAGCTTAAGGCTAAGA

ATGAAAGTAGTTCATTGTGTTTTAAGGTCTATTATAAAGGCGTTACAACACATGAAAGTTCTAGTGCTGTAAATATGCAG

CAGATTTATTTGATTAATAAGTTTTTGAAGGTTAACCCTTTGTGGCATAAAGCCGTTTTTATTAGCCCATATAATAGTCA

GAACTTTGCAGCTAAGCGCGTTTTGGGTTTGCAAACCCAAACCGTGGATTCTGCGCAAGGTTCTGAATATGATTATGTTA

TATATTCACAGACTGCAGAAACAGCGCATTCTGTAAATGTTAATCGCTTCAATGTTGCTATTACTCGAGCCAAGAAAGGT

ATTCTTTGCGTTATGAGTAATATGCAGTTGTTTGAAGCATTACAGTTTACTACATTGACCGTAGATAAAGTGCCACAGGC

CGTTGAAACGAGAGTTCAATGTAGTACCAATTTATTTAAAGATTGTAGCAAGAGTTATAGTGGTTACCACCCAGCTCATG

CTCCTTCATTTTTGGCAGTAGATGACAAATATAAGGCAACTGGCGATTTAGCCGTGTGTCTTGGTATTGGAGATTCTGCT

GTTACATATTCAAGATTAATATCACTCATGGGTTTTAAACTGGATGTTACCCTTGATGGGTATTGTAAGCTTTTTATAAC

TAAAGAAGAAGCTGTTAAACGCGTGCGTGCTTGGGTTGGCTTTGATGCTGAAGGTGCTCATGCCACGCGTGATAGCATTG

GGACAAATTTCCCACTTCAATTAGGGTTTTCCACAGGAATTGATTTTGTTGTGGAAGCCACTGGTTTGTTTGCTGATAGA

GATGGTTACAGCTTTAAAAAGGCTGTGGCTAAAGCTCCTCCTGGTGAACAATTTAAGCATCTCATCCCTTTGATGACGAG

AGGTCAGCGCTGGGATGTTGTTAGACCTAGAATAGTACAAATGTTTGCAGATCATTTAATTGATCTGTCTGATTGTGTTG

TGCTAGTTACATGGGCAGCCAACTTTGAGCTCACTTGTCTCCGCTACTTTGCAAAAGTAGGTCGTGAGATCTCTTGTAAT

GTGTGCACTAAACGTGCCACAGCTTACAATTCTAGAACTGGTTACTATGGTTGTTGGCGCCATAGTGTTACATGTGATTA

CTTGTATAATCCACTTATTGTTGATATTCAACAGTGGGGATATATTGGTTCTTTATCAAGTAATCATGATTTATATTGTA

GTGTCCATAAAGGAGCACATGTTGCCTCCTCTGATGCTATAATGACACGGTGTTTGGCCGTTTATGATTGTTTTTGCAAT

AATATTAATTGGAATGTGGAGTATCCCATCATTTCAAATGAGTTAAGTATTAATACCTCTTGTAGGGTCTTGCAGCGTGT

TATGCTTAAAGCTGCCATGCTCTGCAACAGATATACTTTGTGTTATGATATTGGCAATCCAAAAGCGATTGCCTGTGTCA

AAGATTTTGATTTTAAGTTCTATGATGCCCAACCAATTGTTAAGTCTGTCAAGACTCTTTTGTATTTTTTTGAGGCACAT

AAGGACTCTTTTAAAGATGGTTTGTGTATGTTTTGGAACTGTAATGTGGATAAGTATCCACCGAATGCAGTTGTATGTAG

ATTTGACACGAGAGTGTTGAATAATTTAAATCTTCCTGGCTGTAATGGAGGTAGTTTGTATGTTAACAAACATGCATTCC

ACACTAAACCCTTTTCTAGGGCAGCCTTTGAGCATTTGAAGCCTATGCCATTTTTCTATTATTCAGATACGCCTTGCGTG

TATATGGATGGCATGGATGCTAAGCAGGTTGATTATGTACCTTTGAAATCCGCCACTTGCATCACAAGATGCAATTTAGG

TGGTGCAGTTTGTTTAAAACATGCTGAAGAGTATCGTGAGTACCTAGAGTCTTACAATACAGCTACTACAGCAGGTTTTA

CTTTTTGGGTCTATAAGACATTTGATTTTTATAATTTGTGGAATACGTTCACCAAGCTACAAAGCTTGGAGAATGTTGTA

TATAATTTAGTCAAGACTGGTCATTATACAGGACAGGCTGGTGAAATGCCTTGTGCCATTATAAATGATAAAGTTGTGGC

-continued

TAAGATCGATAAGGAGGATGTTGTCATTTTTATTAATAATACAACATATCCTACTAATGTGGCTGTTGAATTATTTGCCA

AGCGCAGTATTCGACACCATCCAGAGCTTAAGCTCTTTAGAAATTTGAATATAGACGTGTGCTGGAAGCACGTCATTTGG

GATTATGCTAGAGAAAGTATATTTTGCAGTAATACCTATGGTGTCTGCATGTATACAGATTTAAAGTTCATTGATAAATT

GAATGTCCTTTTTGATGGTCGTGATAATGGTGCTCTTGAAGCTTTTAAACGCTCTAATAATGGCGTTTACATTTCCACGA

CAAAAGTTAAGAGTCTTTCGATGATAAGAGGTCCACCGCGTGCTGAATTAAATGGCGTAGTGGTGGACAAGGTTGGAGAC

ACAGATTGTGTGTTTTATTTTGCTGTGCGTAAAGAGGGTCAGGATGTCATCTTCAGCCAATTCGACAGCCTGAGAGTCAG

CTCTAACCAGAGCCCACAAGGTAATCTGGGGAGTAATGAACCCGGTAATGTCGGTGGTAATGATGCTCTGGCAACCTCCA

CTATCTTTACACAAAGCCGTGTTATTAGCTCTTTTACATGTCGTACTGATATGGAAAAAGATTTTATAGCTTTAGATCAA

GATGTGTTTATTCAGAAGTATGGTTTGGAGGACTATGCCTTTGAACACATTGTTTATGGTAATTTCAACCAGAAGATTAT

TGGTGGTTTGCATTTGTTAATAGGCTTGTACCGAAGACAGCAAACTTCCAATTTGGTTATTCAGGAGTTTGTTTCATACG

ACTCCAGCATACACTCTTATTTTATCACTGATGAGAAGAGTGGTGGTAGTAAGAGTGTTTGCACTGTTATAGATATTTTG

TTGGATGATTTTGTGGCTCTTGTCAAGTCACTTAATCTTAACTGTGTGAGTAAGGTTGTTAATGTTAATGTTGATTTTAA

AGATTTTCAGTTCATGCTTTGGTGTAACGATGAGAAAGTTATGACTTTCTATCCTCGTTTGCAAGCTGCATCTGACTGGA

AGCCTGGTTATTCTATGCCTGTATTATATAAGTATTTGAATTCCCCAATGGAAAGAGTTAGTCTCTGGAATTATGGGAAG

CCAGTTACTTTGCCTACAGGCTGTATGATGAATGTTGCTAAGTATACTCAGTTATGTCAATATCTGAATACTACAACATT

AGCTGTACCTGTTAATATGCGAGTTTTGCATTTAGGTGCAGGTTCAGAAAAAGGAGTAGCACCGGGTTCTGCAGTTCTTA

GGCAGTGGTTGCCTGCTGGTACTATTCTTGTAGATAATGATTTATACCCATTTGTGAGTGACAGTGTCGCTACATATTTT

GGGGATTGTATAACCTTACCCTTTGATTGTCAATGGGATTTGATAATCTCTGATATGTATGACCCTATTACTAAGAACAT

AGGGGAGTACAATGTAAGTAAAGATGGTTTCTTTACATACATTTGTCATATGATTCGCGACAAGTTAGCTCTGGGTGGCA

GTGTTGCTATAAAAATAACAGAGTTTTCTTGGAATGCAGAATTATATAAGTTAATGGGGTATTTTGCATTTTGGACGGTT

TTCTGCACAAATGCAAATGCTTCTTCTAGTGAAGGGTTTTTAATTGGCATAAATTATTTGGGTAAGCCCAAGGTTGAGAT

AGATGGAAATGTTATGCATGCCAATTATTTGTTTTGGAGAAATTCCACAGTTTGGAACGGGGGTGCTTATAGCCTGTTTG

ATATGGCTAAATTCCCGCTTAAGTTGGCTGGTACTGCCGTAATAAATTTAAGAGCAGACCAGATTAATGATATGGTTTAT

TCCCTTCTTGAAAAGGGTAAACTACTTGTTAGAGATACAAATAAAGAAGTTTTTGTTGGTGACAGTATGGTTAATGTAAT

CTAA

Orf1ab polyprotein (7094 amino acids) SEQ ID NO: 12
MSKINKYGLELHWAPEFPWMFEDAEEKLDNPSSSEVDIVCSTTAQKLETGGICPENHVMVDCRRLLKQECCVQSSLIREI

VMNTRPYDLEVLLQDALQSCEAVLVTPPLGMSLEACYVRGCNPNGWTMGLFRRRSVCNTGRCAVNKHVAYQLYMIDPAGV

CFGAGQFVGWVIPLAFMPVQSRKFIVPRVMYLRKCGEKGAYNKDHKRGGFEHVYNFKVEDAYDLVHDEPKGKFSKKAYAL

IRGYRGVKPLLYVDQYGCDYTGGLADGLEAYADKTLQEMKALFPIWSQELPFDVTVAWHVVRDPRYVMRLQSASTIRSVA

YVANPTEDLCDGSVVIKEPVHVYADDSIILRQHNLVDIMSCFYMEADAVVNAFYGVDLKDCGFVMQFGYIDCEQDLCDFK

GWVPGNMIDGFACTTCGHVYETGDLLAQSSGVLPVNPVLHTKSAAGYGGFGCKDSFTLYGQTVVYFGGCVYWSPARNIWI

PILKSSVKSYDGLVYTGVVGCKAIVKETNLICKALYLDYVQHKCGNLHQRELLGVSDVWHKQLLLNRGVYKPLLENIDYF

NMRRAKFSLETFTVCADGFMPFLLDDLVPRAYYLAVSGQAFCDYAGKICHAVVSKSKELLDVSLDSLGAAIHYLNSKIVD

LAQHFSDFGTSFVSKIVHFFKTFTTSTALAFAWVLFHVLHGAYIVVESDIYFVKNIPRYASAVAQAFRSVAKVVLDSLRV

TFIDGLSCFKIGRRRICLSGSKIYEVERGLLHSSQLPLDVYDLTMPSQVQKTKQKPIYLKGSGSDFSLADSVVEVVTTSL

TPCGYSEPPKVADKICIVDNVYMAKAGDKYYPVVVDGHVGLLDQAWRVPCAGRRVTFKEQPTVNEIASTPKTIKVFYELD

KDFNTILNTACGVFEVDDTVDMEEFYAVVIDAIEEKLSPCKELEGVGAKVSAFLQKLEDNSLFLFDEAGEEVLAPKLYCA

FTAPEDDDFLEESGVEEDDVEGEETDLTVTSAGEPCVASEQEESSEILEDTLDDGPCVETSDSQVEEDVQMSDFVDLESV

IQDYENVCFEFYTTEPEFVKVLDLYVPKATRNNCWLRSVLAVMQKLPCQFKDKNLQDLWVLYKQQYSQLFVDTLVNKIPA

NIVVPQGGYVADFAYWFLTLCDWQCVAYWKCIKCDLALKLKGLDAMFFYGDVVSHVCKCGESMVLIDVDVPFTAHFALKD

-continued

KLFCAFITKRSVYKAACVVAVNDSHSMAVVDGKQIDDHCITSITSDKFDFIIGHGMSFSMTTFEIAQLYGSCITPNVCFV

KGDIIKVSKRVKAEVVVNPANGHMAHGGGVAKAIAVAAGQQFVKETTDMVKSKGVCATGDCYVSTGGKLCKTVLNVVGPD

ARTQGKQSYALLERVYKHLNKYDCVVTTLISAGIFSVPSDVSLTYLLGTAKKQVVLVSNNQEDFDLISKCQITAVEGTKK

LAERLSFNVGRSIVYETDANKLILSNDVAFVSTFNVLQDVLSLRHDIALDDDARTFVQSNVDVVPEGWRVVNKFYQINGV

RTVKYFECPGGIDICSQDKVFGYVQQGSFNKATVAQIKALFLDKVDILLTVDGVNFTNRFVPVGESFGKSLGNVFCDGVN

VTKHKCDINYKGKVFFQFDNLSSEDLKAVRSSFNFDQKELLAYYNMLVNCSKWQVVFNGKYFTFKQANNNCFVNVSCLML

QSLNLKFKIVQWQEAWLEFRSGRPARFVSLVLAKGGFKFGDPADSRDFLRVVFSQVDLTGAICDFEIACKCGVKQEQRTG

VDAVMHFGTLSREDLEIGYTVDCSCGKKLIHCVRFDVPFLICSNTPASVKLPKGVGSANIFKGDKVGHYVHVKCEQSYQL

YDASNVKKVTDVTGNLSDCLYLKNLKQTFKSVLTTYYLDDVKKIEYKPDLSQYYCDGGKYYTQRIIKAQFKTFEKVDGVY

TNFKLIGHTVCDILNAKLGFDSSKEFVEYKVTEWPTATGDVVLATDDLYVKRYERGCITFGKPVIWLSHEQASLNSLTYF

NRPLLVDENKFDVLKVDDVDDGGDISESDAKEPKEINIIKLSGVKKPFKVEDSVIVNDDTSEIKYVKSLSIVDVYDMWLT

GCRCVVRTANALSRAVNVPTIRKFIKFGMTLVSIPIDLLNLREIKPVFNVVKAVRNKISACFNFIKWLFVLLFGWIKISA

DNKVIYTTEVASKLTCKLVALAFKNAFLTFKWSVVARGACIIATIFLLWFNFIYANVIFSDFYLPKIGFLPTFVGKIAQW

IKNTFSLVTICDLYSIQDVGFKNQYCNGSIACQFCLAGFDMLDNYKAIDVVQYEADRRAFVDYTGVLKIVIELIVSYALY

TAWFYPLFALISIQILTTWLPELFMLSTLHWSVRLLVSLANMLPAHVFMRFYIIIASFIKLFSLFRHVAYGCSKSGCLFC

YKRNRSLRVKCSTIVGGMIRYYDVMANGGTGFCSKHQWNCIDCDSYKPGNTFITVEAALDLSKELKRPIQPTDVAYHTVT

DVKQVGCYMRLFYDRDGQRTYDDVNASLFVDYSNLLHSKVKSVPNMHVVVVENDADKANFLNAAVFYAQSLFRPILMVDK

NLITTANTGTSVTETMFDVYVDTFLSMFDVDKKSLNALIATAHSSIKQGTQICKVLDTFLSCARKSCSIDSDVDTKCLAD

SVMSAVSAGLELTDESCNNLVPTYLKGDNIVAADLGVLIQNSAKHVQGNVAKIAGVSCIWSVDAFNQLSSDFQHKLKKAC

CKTSLKLKLTYNKQMANVSVLTTPFSLKGGAVFSYFVYVCFVLSLVCFIGLWCLMPTYTVHKSDFQLPVYASYKVLDNGV

IRDVSVEDVCFANKFEQFDQWYESTFGLSYYSNSMACPIVVAVVDQDFGSTVFNVPTKVLRYGYHVLHFITHALSADGVQ

CYTPHSQISYSNFYASGCVLSSACTMFAMADGSPQPYCYTDGLMQNASLYSSLVPHVRYNLANAKGFIRFPEVLREGLVR

IVRTRSMSYCRVGLCEEADEGICFNFNGSWVLNNDYYRSLPGTFCGRDVFDLIYQLFKGLAQPVDFLALTASSIAGAILA

VIVVLVFYYLIKLKRAFGDYTSIVFVNVIVWCVNFMMLFVFQVYPTLSCVYAICYFYATLYFPSEISVIMHLQWLVMYGT

IMPLWFCLLYISVVVSNHAFWVFSYCRQLGTSVRSDGTFEEMALTTFMITKDSYCKLKNSLSDVAFNRYLSLYNKYRYYS

GKMDTAAYREAACSQLAKAMDTFTNNNGSDVLYQPPTASVSTSFLQSGIVKMVNPTSKVEPCIVSVTYGNMTLNGLWLDD

KVYCPRHVICSASDMTYPDYTNLLCRVTSSDFTVLFDRLSLTVMSYQMQGCMLVLTVTLQNSRTPKYTFGVVKPGETFTV

LAAYNGKPQGAFHVTMRSSYTIKGSFLCGSCGSVGYVIMGDCVKFVYMHQLELSTGCHTGTDFNGDFYGPYKDAQVVQLP

VQDYIQSVNFVAWLYAAILNNCNWFVQSDKCSVEDFNVWALSNGFSQVKSDLVIDALASMTGVSLETLLAAIKRLKNGFQ

GRQIMGSCSFEDELTPSDVYQQLAGIKLQSKRTRLVKGIVCWIMASTFLFSCIITAFVKWTMFMYVTTNMLSITFCALCV

ISLAMLLVKHKHLYLTMYIIPVLFTLLYNNYLVVYKQTFRGYVYAWLSYYVPSVEYTYTDEVIYGMLLLIGMVFVTLRSI

NHDLFSFIMFVGRVISVVSLWYMGSNLEEEILLMLASLFGTYTWTTALSMAAAKVIAKWVAVNVLYFTDIPQIKIVLVCY

LFIGYIISCYWGLFSLMNSLFRMPLGVYNYKISVQELRYMNANGLRPPKNSFEALMLNFKLLGIGGVPIIEVSQFQSKLT

DVKCANVVLLNCLQHLHVASNSKLWQYCSTLHNEILATSDLGVAFEKLAQLLIVLFANPAAVDSKCLTSIEEVCDDYAKD

NTVLQALQSEFVNMASFVEYEVAKKNLDEACSSGSANRQQLKQLEKACNIAKSAYERDRAVARKLERMADLALTNMYKEA

RINDKKSKVVSALQTMLFSMVRKLDNQALNSILDNAVKGCVPLNAIPSLAANTLTIIVPDKSVYDQVVDNVYVTYAGNVW

QIQTIQDSDGTNKQLNEISDDCNWPLVIIANRHNEVSATVLQNNELMPAKLKTQVVNSGPDQTCNTPTQCYYNNSYNGKI

VYAILSDVDGLKYTKILKDDGNFVVLELDPPCKFTVQDVKGLKIKYLYFVKGCNTLARGWVVGTISSTVRLQAGTATEYA

SNSSILSLCAFSVDPKKTYLDFIQQGGTPIANCVKMLCDHAGTGMAITVKPDATTSQDSYGGASVCIYCRARVEHPDVDG

LCKLRGKFVQVPVGIKDPVSYVLTHDVCQVCGFWRDGSCSCVSTDTTVQSKDTNFLNRVRGTSVDARLVPCASGLSTDVQ

LRAFDICNASVAGIGLHLKVNCCRFQRVDENGDKLDQFFVVKRTDLTIYNREMECYERVKDCKFVAEHDFFTFDVEGSRV

-continued

PHIVRKDLTKYTMLDLCYALRHFDRNDCMLLCDILSIYAGCEQSYFTKKDWYDFVENPDIINVYKKLGPIFNRALVSATE

FADKLVEVGLVGILTLDNQDLNGKWYDFGDYVIAAPGCGVAIADSYYSYMMPMLTMCHALDCELYVNNAYRLFDLVQYDF

TDYKLELFNKYFKHWSMPYHPNTVDCQDDRCIIHCANFNILFSMVLPNTCFGPLVRQIFVDGVPFVVSIGYHYKELGIVM

NMDVDTHRYRLSLKDLLLYAADPALHVASASALYDLRTCCFSVAAITSGVKFQTVKPGNFNQDFYDFILSKGLLKEGSSV

DLKHFFFTQDGNAAITDYNYYKYNLPTMVDIKQLLFVLEVVYKYFEIYDGGCIPASQVIVNNYDKSAGYPFNKFGKARLY

YEALSFEEQDEIYAYTKRNVLPTLTQMNLKYAISAKNRARTVAGVSILSTMTGRMFHQKCLKSIAATRGVPVVIGTTKFY

GGWDDMLRRLIKDVDNPVLMGWDYPKCDRAMPNILRIVSSLVLARKHEACCSQSDRFYRLANECAQVLSEIVMCGGCYYV

KPGGTSSGDATTAFANSVFNICQAVSANVCALMSCNGNKIEDLSIRALQKRLYSHVYRSDMVDSTFVTEYYEFLNKHFSM

MILSDDGVVCYNSDYASKGYIANISAFQQVLYYQNNVFMSESKCWVENDINNGPHEFCSQHTMLVKMDGDDVYLPYPDPS

RILGAGCFVDDLLKTDSVLLIERFVSLAIDAYPLVYHENEEYQKVFRVYLEYIKKLYNDLGNQILDSYSVILSTCDGQKF

TDESFYKNMYLRSAVMQSVGACVVCSSQTSLRCGSCIRKPLLCCKCCYDHVMATDHKYVLSVSPYVCNAPGCDVNDVTKL

YLGGMSYYCEDHKPQYSFKLVMNGMVFGLYKQSCTGSPYIDDFNRIASCKWTDVDDYILANECTERLKLFAAETQKATEE

AFKQSYASATIQEIVSERELILSWEIGKVKPPLNKNYVFTGYHFTKNGKTVLGEYVFDKSELTNGVYYRATTTYKLSVGD

VFVLTSHSVANLSAPTLVPQENYSSIRFASVYSVLETFQNNVVNYQHIGMKRYCTVQGPPGTGKSHLAIGLAVYYCTARV

VYTAASHAAVDALCEKAYKFLNINDCTRIVPAKVRVECYDKFKINDTTRKYVFTTINALPEMVTDIVVVDEVSMLTNYEL

SVINARIRAKHYVYIGDPAQLPAPRVLLSKGTLEPKYFNTVTKLMCCLGPDIFLGTCYRCPKEIVDTVSALVYENKLKAK

NESSSLCFKVYYKGVTTHESSSAVNMQQIYLINKFLKVNPLWHKAVFISPYNSQNFAAKRVLGLQTQTVDSAQGSEYDYV

IYSQTAETAHSVNVNRFNVAITRAKKGILCVMSNMQLFEALQFTTLTVDKVPQAVETRVQCSTNLFKDCSKSYSGYHPAH

APSFLAVDDKYKATGDLAVCLGIGDSAVTYSRLISLMGFKLDVTLDGYCKLFITKEEAVKRVRAWVGFDAEGAHATRDSI

GTNFPLQLGFSTGIDFVVEATGLFADRDGYSFKKAVAKAPPGEQFKHLIPLMTRGQRWDVVRPRIVQMFADHLIDLSDCV

VLVTWAANFELTCLRYFAKVGREISCNVCTKRATAYNSRTGYYGCWRHSVTCDYLYNPLIVDIQQWGYIGSLSSNHDLYC

SVHKGAHVASSDAIMTRCLAVYDCFCNNINWNVEYPIISNELSINTSCRVLQRVMLKAAMLCNRYTLCYDIGNPKAIACV

KDFDFKFYDAQPIVKSVKTLLYFFEAHKDSFKDGLCMFWNCNVDKYPPNAVVCRFDTRVLNNLNLPGCNGGSLYVNKHAF

HTKPFSRAAFEHLKPMPFFYYSDTPCVYMDGMDAKQVDYVPLKSATCITRCNLGGAVCLKHAEEYREYLESYNTATTAGF

TFWVYKTFDFYNLWNTFTKLQSLENVVYNLVKTGHYTGQAGEMPCAIINDKVVAKIDKEDVVIFINNTTYPTNVAVELFA

KRSIRHHPELKLFRNLNIDVCWKHVIWDYARESIFCSNTYGVCMYTDLKFIDKLNVLFDGRDNGALEAFKRSNNGVYIST

TKVKSLSMIRGPPRAELNGVVVDKVGDTDCVFYFAVRKEGQDVIFSQFDSLRVSSNQSPQGNLGSNEPGNVGGNDALATS

TIFTQSRVISSFTCRTDMEKDFIALDQDVFIQKYGLEDYAFEHIVYGNFNQKIIGGLHLLIGLYRRQQTSNLVIQEFVSY

DSSIHSYFITDEKSGGSKSVCTVIDILLDDFVALVKSLNLNCVSKVVNVNVDFKDFQFMLWCNDEKVMTFYPRLQAASDW

KPGYSMPVLYKYLNSPMERVSLWNYGKPVTLPTGCMMNVAKYTQLCQYLNTTTLAVPVNMRVLHLGAGSEKGVAPGSAVL

RQWLPAGTILVDNDLYPFVSDSVATYFGDCITLPFDCQWDLIISDMYDPITKNIGEYNVSKDGFFTYICHMIRDKLALGG

SVAIKITEFSWNAELYKLMGYFAFWTVFCTNANASSSEGFLIGINYLGKPKVEIDGNVMHANYLFWRNSTVWNGGAYSLF

DMAKFPLKLAGTAVINLRADQINDMVYSLLEKGKLLVRDTNKEVFVGDSMVNVI 32 kDa gene (837 nucleotides): SEQ ID NO: 13

ATGGCAGTTGCTTATGCAAACAAGCCTAATCACTTTATTAATTTTCCACTTACCCAGTTTGAGGGTTTTGTGTTAAATTA

TAAAGGTTTACAATTTCAACTTCTCGATGAAGGAGTGGATTGTAAAATACAAACAGCGCCGCACATTAGTCTTGTTATGC

TGGATATTCAGCCTGAAGACTATAGAAGTGTTGATGTTGCTATTCAAGAAGTTATTGATGACATGCATTGGGGTGAGGGC

TTTCAGATTAAATTTGATAACCCCCATATCCTAGGAAGATGCATAGTTTTAGATGTTAAAGGTGTAGAAGAATTGCATGA

TGATTTAGTTAATTACATTCGTGATAAAGGTTGTGTTGCTGACCAATCCAGGAAATGGATTGGACATTGCACCATAGCCC

AACTCACGGATGCTGCACTTTCCATTAAGGAAAATGTTGATTTCATAAACAGCATGCAATTCAATTATAAAATCACTATC

AACCCCTCATCACCGGCTAGACTTGAAATAGTTAAGCTTGGTGCTGAAAAGAAAGATGGTTTTTATGAAACCATAGTTAG

-continued

CCACTGGATGGGAATTCGTTTTGAATATAATCCACCCACTGATAAGCTAGCTATGATTATGGGTTATTGTTGTTTAGAAG

TGGTGCGTAAAGAGCTAGAAGAAGGTGATCTTCCCGAGAATGATGATGATGCTTGGTTTAAGCTATCGTACCATTATGAA

AACAATTCTTGGTTCTTTCGACATGTCTACAGGAAAAGTTCTTATTTCCGTAAGTCTTGTCAAAATTTAGATTGTAATTG

TTTGGGGTTTTATGAATCTCCAGTTGAAGAAGACTAA 32 kDa protein (278 amino acids) SEQ ID NO: 14
MAVAYANKPNHFINFPLTQFEGFVLNYKGLQFQLLDEGVDCKIQTAPHISLVMLDIQPEDYRSVDVAIQEVIDDMHWGEG

FQIKFDNPHILGRCIVLDVKGVEELHDDLVNYIRDKGCVADQSRKWIGHCTIAQLTDAALSIKENVDFINSMQFNYKITI

NPSSPARLEIVKLGAEKKDGFYETIVSHWMGIRFEYNPPTDKLAMIMGYCCLEVVRKELEEGDLPENDDDAWFKLSYHYE

NNSWFFRHVYRKSSYFRKSCQNLDCNCLGFYESPVEED

Hemagglutinin-esterase precursor gene (HE: 1275 nucleotides) SEQ ID NO: 3 without signal sequence; SEQ ID NO: 23 with the signal sequence; the signal sequence is in bold:
ATGTTTTTGCTTCTTAGATTTGTTCTAGTTAGCTGCATAATTGGTAGCCTAGGTTTTGATAACCCTCCTACCAATGTTGT

TTCGCATTTAAATGGAGATTGGTTTTTATTTGGTGACAGTCGTTCAGATTGTAATCATGTTGTTAATACCAACCCCCGTA

ATTATTCTTATATGGACCTTAATCCTGCCCTGTGTGATTCTGGTAAAATATCATCTAAAGCTGGCAACTCCATTTTTAGG

AGTTTTCACTTTACCGATTTTTATAATTACACAGGCGAAGGTCAACAAATTATTTTTTATGAGGGTGTTAATTTTACGCC

TTATCATGCCTTTAAATGCACCACTTCTGGTAGTAATGATATTTGGATGCAGAATAAAGGCTTGTTTTACACTCAGGTTT

ATAAGAATATGGCTGTGTATCGCAGCCTTACTTTTGTTAATGTACCATATGTTTATAATGGCTCTGCACAATCTACAGCT

CTTTGTAAATCTGGTAGTTTAGTTCTTAATAACCCTGCATATATAGCTCGTGAAGCTAATTTTGGGGATTATTATTATAA

GGTTGAAGCTGACTTTTATTTGTCAGGTTGTGACGAGTATATCGTACCACTTTGTATTTTTAACGGCAAGTTTTTGTCGA

ATACAAAGTATTATGATGATAGTCAATATTATTTTAATAAAGACACTGGTGTTATTTATGGTCTCAATTCTACTGAAACC

ATTACCACTGGTTTTGATTTTAATTGTCATTATTTAGTTTTACCCTCTGGTAATTATTTAGCCATTTCAAATGAGCTATT

GTTAACTGTTCCTACGAAAGCAATCTGTCTTAACAAGCGTAAGGATTTTACGCCTGTACAGGTTGTTGATTCACGGTGGA

ACAATGCCAGGCAGTCTGATAACATGACGGCGGTTGCTTGTCAACCCCCGTACTGTTATTTTCGTAATTCTACTACCAAC

TATGTTGGTGTTTATGATATCAATCATGGGGATGCTGGTTTTACTAGCATACTCAGTGGTTTGTTATATGATTCACCTTG

TTTTTCGCAGCAAGGTGTTTTTAGGTATGATAATGTTAGCAGTGTCTGGCCTCTCTATTCCTATGGCAGATGCCCTACTG

CTGCTGGTATTAATACCCCTGATGTACCTATTTGTGTGTATGATCCGCTACCACTTATTTTGCTTGGCATCCTTTTGGGT

GTTGCGGTCATAATTATTGTAGTTTTGTTGTTATATTTTATGGTGGATAATGGTACTAGGCTGCATGATGCTTAG

Hemagglutinin-esterase precursor protein (HE: 424 amino acids) SEQ ID NO: 4 without signal sequence; SEQ ID NO: 24 with the signal sequence; the signal sequence is in bold:
MFLLLRFVLVSCIIGSLGFDNPPTNVVSHLNGDWFLFGDSRSDCNHVVNTNPRNYSYMDLNPALCDSGKISSKAGNSIFR

SFHFTDFYNYTGEGQQIIFYEGVNFTPYHAFKCTTSGSNDIWMQNKGLFYTQVYKNMAVYRSLTFVNVPYVYNGSAQSTA

LCKSGSLVLNNPAYIAREANFGDYYYKVEADFYLSGCDEYIVPLCIFNGKFLSNTKYYDDSQYYFNKDTGVIYGLNSTET

ITTGFDFNCHYLVLPSGNYLAISNELLLTVPTKAICLNKRKDFTPVQVVDSRWNNARQSDNMTAVACQPPYCYFRNSTTN

YVGVYDINHGDAGFTSILSGLLYDSPCFSQQGVFRYDNVSSVWPLYSYGRCPTAAGINTPDVPICVYDPLPLILLGILLG

VAVIIIVVLLLYFMVDNGTRLHDA

Spike protein precursor gene (4092 nucleotides) SEQ ID NO: 1 without signal sequence; SEQ ID NO: 21 with the signal sequence; the signal sequence is in bold:
ATGTTTTTGATACTTTTAATTTCCTTACCAATGGCTTTTGCTGTTATAGGAGATTTAAAGTGTACTACGGTTGCCATTAA

TGATGTTGACACCGGTCCTCCTTCTATTAGCACTGATATTGTCGATGTTACTAATGGTTTAGGTACTTATTATGTTTTAG

ATCGTGTGTATTTAAATACTACGTTGTTGCTTAATGGTTACTACCCTACTTCAGGTTCTACATATCGTAATATGGCACTG

AAGGGAACTTTACTATTGAGCAGACTATGGTTTAAACCACCTTTTCTTTCTGATTTTATTAATGGTATTTTTGCTAAGGT

CAAAAATACCAAGGTTATTAAAAAGGGTGTAATGTATAGTGAGTTTCCTGCTATAACTATAGGTAGTACTTTTGTAAATA

CATCCTATAGTGTGGTAGTACAACCACATACTACCAATTTGGATAATAAATTACAAGGTCTCTTAGAGATCTCTGTTTGC

-continued

CAGTATACTATGTGCGAGTACCCACATACGATTTGTCATCCTAATCTGGGTAATCGACGCGTAGAACTATGGCATTGGGA

TACAGGTGTTGTTTCCTGTTTATATAAGCGTAATTTCACATATGATGTGAATGCTGATTACTTGTATTTCCATTTTTATC

AAGAAGGTGGTACTTTTTATGCATATTTTACAGACACTGGTGTTGTTACTAAGTTTCTGTTTAATGTTTATTTAGGCACG

GTGCTTTCACATTATTATGTCCTGCCTTTGACTTGTTCTAGTGCTATGACTTTAGAATATTGGGTTACACCTCTCACTTC

TAAACAATATTTACTAGCTTTCAATCAAGATGGTGTTATTTTTAATGCTGTTGATTGTAAGAGTGATTTTATGAGTGAGA

TTAAGTGTAAAACACTATCTATAGCACCATCTACTGGTGTTTATGAATTAAACGGTTACACTGTTCAGCCAATTGCAGAT

GTTTACCGACGTATACCTAATCTTCCCGATTGTAATATAGAGGCTTGGCTTAATGATAAGTCGGTGCCCTCTCCATTAAA

TTGGGAACGTAAGACCTTTTCAAATTGTAATTTTAATATGAGCAGCCTGATGTCTTTTATTCAGGCAGACTCATTTACTT

GTAATAATATTGATGCTGCTAAGATATATGGTATGTGTTTTTCCAGCATAACTATAGATAAGTTTGCTATACCCAATGGT

AGGAAGGTTGACCTACAATTGGGCAATTTGGGCTATTTGCAGTCTTTTAACTATAGAATTGATACTACTGCTACAAGTTG

TCAGTTGTATTATAATTTACCTGCTGCTAATGTTTCTGTTAGCAGGTTTAATCCTTCTACTTGGAATAGGAGATTTGGTT

TTACAGAACAATCTGTTTTTAAGCCTCAACCTGCAGGTGTTTTTACTCATCATGATGTTGTTTATGCACAACATTGTTTT

AAAGCTCCCACAAATTTCTGTCCGTGTAAATTGGATGGGTCTTTGTGTGTAGGTAATGGTCCTGGTATAGATGCTGGTTA

TAAAAATAGTGGTATAGGCACTTGTCCTGCAGGTACTAATTATTTAACTTGCCATAATGCTGCCCAATGTGATTGTTTGT

GCACTCCCGACCCCATTACATCTAAATCTACAGGGCCTTACAAGTGCCCCCAAACTAAATACTTAGTTGGCATAGGTGAG

CACTGTTCGGGTCTTGCTATTAAAAGTGATTATTGTGGAGGTAATCCTTGTACTTGCCAACCACAAGCATTTTTGGGTTG

GTCTGCTGACTCTTGTTTACAAGGGGATAGGTGTAATATTTTTGCTAATTTTATTTTTCATGATGTTAATAGTGGTACTA

CTTGTTCTACTGATTTACAAAAATCAAACACAGACATAATTCTTGGTGTTTGTGTTAATTATGATCTTTATGGTATTATA

GGCCAAGGTGTTTTTGTTGAGGTTAATGCGACTTATTATAATAGTTGGCAGAACCTTTTATATGATTCTAATGGTAATCT

CTATGGTTTTAGAGACTACTTAACAAACAGAACTTTTATGATTCGTAGTTGCTATAGCGGTCGTGTTTCAGCGGCCTTTC

ATGCTAACTCTTCCGAACCAGCATTGCTATTTCGGAATATTAAATGCAATTACGTTTTTAATAATATTCTTTCACGACAG

CTGCAACCTATTAACTATTTTGATAGTTATCTTGGTTGTGTTGTCAATGCTGATAATAGTACTTCTAGTGTTGTTCAAAC

ATGTGATCTCACAGTAGGTAGTGGTTACTGTGTGGATTACTCTACAAAAAGACGAAGTCGTAGAGCGATTACCACTGGTT

ATCGGTTTACTAATTTTGAGCCATTTACTGTTAATTCAGTAAATGATAGTTTAGAACCTGTAGGTGGTTTGTATGAAATT

CAAATACCTTCAGAGTTTACTATAGGTAATATGGAGGAGTTTATTCAAACAAGCTCTCCTAAAGTTACTATTGATTGTTC

TGCTTTTGTCTGTGGTGATTATGCAGCATGTAAATCACAGTTGGTTGAATATGGTAGCTTCTGTGACAATATTAATGCTA

TACTCACAGAAGTAAATGAACTACTTGACACTACACAGTTGCAAGTAGCTAATAGTTTAATGAATGGTGTCACTCTTAGC

ACTAAGCTTAAAGATGGCGTTAATTTCAATGTAGACGACATCAATTTTTCCCCTGTATTAGGTTGTTTAGGAAGCGGTTG

TAATAAAGGTTCCAGTAGATCTGCTATAGAGGATTTACTTTTTTCTAAAGTAAAGTTATCTGATGTCGGTTTCGTTGAGG

CTTATAATAATTGTACTGGAGGTGCCGAAATTAGGGACCTCATTTGTGTGCAAAGTTATAATGGTATCAAAGTGTTGCCT

CCACTGCTCTCAGTAAATCAGATCAGTGGATACACTTTGGCTGCCACCTCTGCTAGTCTGTTTCCTCCTTGGTCAGCAGC

AGCAGGTGTACCATTTTATTTAAATGTTCAGTATCGTATTAATGGGCTTGGTGTTACCATGGATGTGTTAAGTCAAAATC

AAAAGCTTATTGCTAATGCATTTAACAATGCTCTTGATGCTATTCAGGAAGGGTTTGATGCTACCAATTCTGCTTTAGTT

AAAATTCAAGCTGTTGTTAATGCAAATGCTGAAGCTCTTAATAACTTATTGCAACAACTCTCTAATAGATTTGGTGCTAT

AAGTTCTTCTTTACAAGAAATTCTATCTAGACTGGATGCTCTTGAAGCGCAAGCTCAGATAGACAGACTTATTAATGGGC

GTCTTACCGCTCTTAATGCTTATGTTTCTCAACAGCTTAGTGATTCTACACTAGTAAAATTTAGTGCAGCACAAGCTATG

GAGAAGGTTAATGAATGTGTCAAAAGCCAATCATCTAGGATAAATTTTTGTGGTAATGGTAATCATATTATATCATTAGT

GCAGAATGCTCCATATGGTTTGTATTTTATCCACTTTAGCTATGTCCCTACTAAGTATGTCACTGCGAAGGTTAGTCCCG

GTCTGTGCATTGCTGGTGATAGAGGTATAGCCCCTAAGAGTGGTTATTTTGTTAATGTAAATAATACTTGGATGTTCACT

GGTAGTGGTTATTACTACCCTGAACCCATAACTGGAAATAATGTTGTTGTTATGAGTACCTGTGCTGTTAACTATACTAA

-continued

AGCGCCGGATGTAATGCTGAACATTTCAACACCCAACCTCCATGATTTTAAGGAAGAGTTGGATCAATGGTTTAAAAACC

AAACATCAGTGGCACCAGATTTGTCACTTGATTATATAAATGTTACATTCTTGGACCTACAAGATGAAATGAATAGGTTA

CAGGAGGCAATAAAAGTTTTAAATCAGAGCTACATCAATCTCAAGGACATTGGTACATATGAGTATTATGTAAAATGGCC

TTGGTATGTATGGCTTTTAATTGGCTTTGCTGGTGTAGCTATGCTTGTTTTACTATTCTTCATATGCTGTTGTACAGGAT

GTGGGACTAGTTGTTTTAAGATATGTGGTGGTTGTTGTGATGATTATACTGGACACCAGGAGTTAGTAATTAAAACATTA

CATGACGACTAA

Spike protein precursor protein (1363 amino acids) SEQ ID NO: 2 without signal sequence; SEQ ID NO: 22 with the signal sequence; the signal sequence is in bold:

MFLILLISLPMAFAVIGDLKCTTVAINDVDTGPPSISTDIVDVTNGLGTYYVLDRVYLNTTLLLNGYYPTSGSTYRNMAL

KGTLLLSRLWFKPPFLSDFINGIFAKVKNTKVIKKGVMYSEFPAITIGSTFVNTSYSVVVQPHTTNLDNKLQGLLEISVC

QYTMCEYPHTICHPNLGNRRVELWHWDTGVVSCLYKRNFTYDVNADYLYFHFYQEGGTFYAYFTDTGVVTKFLFNVYLGT

VLSHYYVLPLTCSSAMTLEYWVTPLTSKQYLLAFNQDGVIFNAVDCKSDFMSEIKCKTLSIAPSTGVYELNGYTVQPIAD

VYRRIPNLPDCNIEAWLNDKSVPSPLNWERKTFSNCNFNMSSLMSFIQADSFTCNNIDAAKIYGMCFSSITIDKFAIPNG

RKVDLQLGNLGYLQSFNYRIDTTATSCQLYYNLPAANVSVSRFNPSTWNRRFGFTEQSVFKPQPAGVFTHHDVVYAQHCF

KAPTNFCPCKLDGSLCVGNGPGIDAGYKNSGIGTCPAGTNYLTCHNAAQCDCLCTPDPITSKSTGPYKCPQTKYLVGIGE

HCSGLAIKSDYCGGNPCTCQPQAFLGWSADSCLQGDRCNIFANFIFHDVNSGTTCSTDLQKSNTDIILGVCVNYDLYGII

GQGVFVEVNATYYNSWQNLLYDSNGNLYGFRDYLTNRTFMIRSCYSGRVSAAFHANSSEPALLFRNIKCNYVFNNILSRQ

LQPINYFDSYLGCVVNADNSTSSVVQTCDLTVGSGYCVDYSTKRRSRRAITTGYRFTNFEPFTVNSVNDSLEPVGGLYEI

QIPSEFTIGNMEEFIQTSSPKVTIDCSAFVCGDYAACKSQLVEYGSFCDNINAILTEVNELLDTTQLQVANSLMNGVTLS

TKLKDGVNFNVDDINFSPVLGCLGSGCNKGSSRSAIEDLLFSKVKLSDVGFVEAYNNCTGGAEIRDLICVQSYNGIKVLP

PLLSVNQISGYTLAATSASLFPPWSAAAGVPFYLNVQYRINGLGVTMDVLSQNQKLIANAFNNALDAIQEGFDATNSALV

KIQAVVNANAEALNNLLQQLSNRFGAISSSLQEILSRLDALEAQAQIDRLINGRLTALNAYVSQQLSDSTLVKFSAAQAM

EKVNECVKSQSSRINFCGNGNHIISLVQNAPYGLYFIHFSYVPTKYVTAKVSPGLCIAGDRGIAPKSGYFVNVNNTWMFT

GSGYYYPEPITGNNVVVMSTCAVNYTKAPDVMLNISTPNLHDFKEELDQWFKNQTSVAPDLSLDYINVTFLDLQDEMNRL

QEAIKVLNQSYINLKDIGTYEYYVKWPWYVWLLIGFAGVAMLVLLFFICCCTGCGTSCFKICGGCCDDYTGHQELVIKTL

HDD 4.9 kDA gene (132 nucleotides) SEQ ID NO: 15
ATGACGACTAAGTTCGTCTTTGATTTATTGGCTCCTGACGATATATTACATCCCTTCAATCATGTGAAGCTAATTATAAG

ACCCATTGAGGTCGAGCATATTATAATAGCTACCACAATGCCTGCTGTTTAG 4.9 kDA protein (43 amino acids) SEQ ID NO: 16
MTTKFVFDLLAPDDILHPFNHVKLIIRPIEVEHIIIATTMPAV 4.8 kDA gene (138 nucleotides) SEQ ID NO: 17
ATGCCAATGGCTACAACCATTGACGGTACAGATTATACTAATATTATGCCTAGTACTGTTTCTACAACAGTTTATTTAGG

CTGTTCTATAGGTATTGACACTAGCACCACTGGTTTTACCTGTTTTTCACGGTACTAG 4.8 kDA protein (45 amino acids) SEQ ID NO: 18
MPMATTIDGTDYTNIMPSTVSTTVYLGCSIGIDTSTTGFTCFSRY 12.7 kDa gene (330 nucleotides) SEQ ID NO: 19
ATGGACATCTGGAGACCTGAGATTAAATATCTCCGTTATATTAACGGTTTTAATGTCTCAGAATTAGAAGATGCTTGTTT

TAAATTTAACTATAAATTTCCTAAAGTAGGATATTGTAGAGTTCCTAGTCATGCTTGGTGCCGTAATCAAGGTAGCTTTT

GTGCTACACTCACTCTTTATGGCAAATCCAAACATTATGATAAATATTTTGGAGTAATAACTGGTTTTACAGCATTCGCT

AATACTGTAGAGGAGGCTGTTAACAAACTGGTTTTCTTAGCTGTTGACTTTATTACCTGGCGGAGACAGGAGTTAAATGT

TTATGGCTGA

-continued 12.7 kDa protein (109 amino acids) SEQ ID NO: 20
MDIWRPEIKYLRYINGFNVSELEDACFKFNYKFPKVGYCRVPSHAWCRNQGSFCATLTLYGKSKHYDKYFGVITGFTAFA

NTVEEAVNKLVFLAVDFITWRRQELNVYG

Small envelope protein (E gene) (255 nucleotides) SEQ ID NO: 7
ATGTTTATGGCTGATGCTTATTTTGCAGACACTGTGTGGTATGTGGGGCAAATAATTTTTATAGTTGCCATTTGTTTATT

GGTTATAATAGTTGTAGTGGCATTTTTGGCAACTTTTAAATTGTGTATTCAACTTTGCGGTATGTGTAATACCTTAGTAC

TGTCCCCTTCTATTTATGTGTTTAATAGAGGTAGGCAGTTTTATGAGTTTTACAACGATGTAAAACCACCAGTTCTTGAT

GTGGATGACGTTTAG

Small envelope protein (E gene) (84 amino acids) SEQ ID NO: 8
MFMADAYFADTVWYVGQIIFIVAICLLVIIVVVAFLATFKLCIQLCGMCNTLVLSPSIYVFNRGRQFYEFYNDVKPPVLD

VDDV

Multispanning envelope protein (M gene) (693 nucleotides) SEQ ID NO: 5
ATGAGTAGTGTAACTACACCAGCACCAGTTTACACCTGGACTGCTGATGAAGCTATTAAATTCCTAAAGGAATGGAACTT

TTCTTTGGGTATTATACTACTTTTTATTACAATCATATTGCAATTTGGATATACAAGTCGCAGTATGTTTGTTTATGTTA

TTAAGATGATCATTTTGTGGCTTATGTGGCCCCTTACTATCATCTTAACTATTTTCAATTGCGTGTATGCGTTGAATAAT

GTGTATCTTGGCTTTTCTATAGTTTTCACTATAGTGGCCATTATCATGTGGATTGTGTATTTTGTGAATAGTATCAGGTT

GTTTATTAGAACTGGAAGTTGGTGGAGTTTCAACCCAGAAACAAACAACTTGATGTGTATAGATATGAAGGGAAGGATGT

ATGTTAGGCCGATAATTGAGGACTACCATACCCTTACGGTCACAATAATACGTGGTCATCTTTACATGCAAGGTATAAAA

CTAGGTACTGGCTATTCTTTGTCAGATTTGCCAGCTTATGTGACTGTTGCTAAGGTCTCACACCTGCTCACGTATAAGCG

TGGTTTTCTTGACAAGATAGGCGATACTAGTGGTTTTGCTGTTTATGTTAAGTCCAAAGTCGGTAATTACCGACTGCCAT

CAACCCAAAAGGGTTCTGGCATGGACACCGCATTGTTGAGAAATATAATCTAA

Multispanning envelope protein (14 gene) (230 amino acids) SEQ ID NO: 6
MSSVTTPAPVYTWTADEAIKFLKEWNFSLGIILLFITIILQFGYTSRSMFVYVIKMIILWLMWPLTIILTIFNCVYALNN

VYLGFSIVFTIVAIIMWIVYFVNSIRLFIRTGSWWSFNPETNNLMCIDMKGRMYVRPIIEDYHTLTVTIIRGHLYMQGIK

LGTGYSLSDLPAYVTVAKVSHLLTYKRGFLDKIGDTSGFAVYVKSKVGNYRLPSTQKGSGMDTALLRNII

Nucleocapsid protein (N gene) (1347 nucleotides) SEQ ID NO: 9
ATGTCTTTTACTCCTGGTAAGCAATCCAGTAGTAGAGCGTCCTCTGGAAATCGTTCTGGTAATGGCATCCTTAAGTGGGC

CGATCAGTCCGACCAATCTAGAAATGTTCAAACCAGGGGTAGAAGAGCTCAACCCAAGCAAACTGCTACTTCTCAGCTAC

CATCAGGAGGGAATGTTGTACCCTACTATTCTTGGTTCTCTGGAATTACTCAGTTTCAAAAAGGAAAGGAGTTTGAATTT

GCAGAGGGACAAGGTGTGCCTATTGCACCAGGAGTCCCAGCTACTGAAGCTAAGGGGTACTGGTACAGACACAACAGACG

TTCTTTTAAAACAGCCGATGGCAACCAGCGTCAACTGCTGCCACGATGGTATTTTTACTATCTTGGAACAGGACCGCATG

CCAAAGACCAGTATGGCACCGATATTGACGGTGTCTTCTGGGTCGCTAGTAACCAGGCTGATGTCAATACCCCGGCTGAC

ATTCTCGATCGGGACCCAAGTAGCGATGAGGCTATTCCGACTAGGTTTCCGCCTGGCACGGTACTCCCTCAGGGTTACTA

TATTGAAGGCTCAGGAAGGTCTGCTCCTAATTCCAGATCTACTTCACGCGCATCCAGTAGAGCCTCTAGTGCAGGATCGC

GTAGTAGAGCCAATTCTGGCAACAGAACCCCTACCTCTGGTGTAACACCTGATATGGCTGATCAAATTGCTAGTCTTGTT

CTGGCAAAACTTGGCAAGGATGCCACTAAGCCACAGCAAGTAACTAAGCAGACTGCCAAAGAAATCAGACAGAAAATTTT

GAATAAGCCCCGCCAGAAGAGGAGCCCCAATAAACAATGCACTGTTCAGCAGTGTTTTGGGAAGAGAGGCCCCAATCAGA

ATTTTGGTGGTGGAGAAATGTTAAAACTTGGAACTAGTGACCCACAGTTCCCCATTCTTGCAGAACTCGCACCCACAGCT

GGTGCGTTTTTCTTTGGATCAAGATTAGAGTTGGCCAAAGTGCAGAATTTGTCTGGGAATCTTGACGAGCCCCAGAAGGA

TGTTTATGAATTGCGCTATAATGGTGCAATTAGATTTGACAGTACACTTTCAGGTTTTGAGACCATAATGAAGGTGTTGA

ATGAGAATTTGAATGCATATCAACAACAAGATGGTATGATGAATATGAGTCCAAAACCACAGCGTCAGCGTGGTCAGAAG

AATGGACAAGGAGAAAATGATAATATAAGTGTTGCAGCGCCTAAAAGCCGTGTGCAGCAAAATAAGAGTAGAGAGTTGAC

TGCAGAGGACATCAGCCTTCTTAAGAAGATGGATGAGCCCTATACTGAAGACACCTCAGAAATATAA

-continued

Nucleocapsid protein (N gene) (448 amino acids) SEQ ID NO: 10

MSFTPGKQSSSRASSGNRSGNGILKWADQSDQSRNVQTRGRRAQPKQTATSQLPSGGNVVPYYSWFSGITQFQKGKEFEF

AEGQGVPIAPGVPATEAKGYWYRHNRRSFKTADGNQRQLLPRWYFYYLGTGPHAKDQYGTDIDGVFWVASNQADVNTPAD

ILDRDPSSDEAIPTRFPPGTVLPQGYYIEGSGRSAPNSRSTSRASSRASSAGSRSRANSGNRTPTSGVTPDMADQIASLV

LAKLGKDATKPQQVTKQTAKEIRQKILNKPRQKRSPNKQCTVQQCFGKRGPNQNFGGGEMLKLGTSDPQFPILAELAPTA

GAFFFGSRLELAKVQNLSGNLDEPQKDVYELRYNGAIRFDSTLSGFETIMKVLNENLNAYQQQDGMMNMSPKPQRQRGQK

NGQGENDNISVAAPKSRVQQNKSRELTAEDISLLKKMDEPYTEDTSEI

Example 3

Detection of Bovine Coronavirus in Respiratory and Enteric Tissues

A study was performed using nineteen (19) colostrum deprived calves, three to four days of age. Two (2) of the calves were necropsied prior to the challenge to collect negative control tissues. On the same day, the remaining seventeen (17) calves were challenged by the oral and intranasal route with virulent BCV strain MN-1988. The calves were challenged again on the following day with the same dose of challenge virus, but only by the intranasal route. Calves were observed daily, for clinical signs associated with BCV infection. Nasal and fecal swabs were collected daily, and blood samples for serology were collected prior to challenge and on the day of necropsy. On each of study days 4, 6, 8, 11, and 13 post-challenge, selected calves were euthanized and a necropsy performed. The calves were examined for gross pathology, and respiratory and enteric tissues were collected. The tissues were sent to an independent laboratory for histopathology and immunohistochemistry (IHC), and for testing by real-time quantitative PCR for the presence of BCV.

Moderate and severe nasal discharge was observed in 13 of 17 calves post challenge with BCV. The peak period of disease was at three to eight days post challenge, and BCV was detected in nasal swabs during this peak period of clinical signs. BCV was detected by PCR in the upper respiratory tissues of turbinates, trachea, tonsil, bronchia, and bronchial lymph nodes from 12 of 17 calves post challenge, but was detected in lung tissues from only 4 of the 17 calves. The peak period of BCV detection in respiratory tissues was four through six days post challenge, but BCV was not detected after day eight. Minor gross lesions and histopathology were observed in respiratory tissues from 7 of 17 calves, but respiratory tissue from only one of these 7 calves was IHC positive for BCV. Moderate and severe diarrhea was observed in 11 of 17 calves on days three through six post challenge. BCV was detected by PCR in fecal swabs and intestinal tissues during these same days and persisted in these samples through day 11 post challenge. Gross and microscopic lesions and histopathology were observed in intestinal tissues from 7 of 17 calves on days 4 and 6 post challenge, and these tissues were positive by IHC. This study demonstrated BCV is detected primarily in upper respiratory tissues, compared to lower respiratory tissues, and the detection of BCV correlates with respiratory disease. BCV colonizes upper respiratory tissues, but causes little to no pathology.

CONCLUSIONS

- BCV colonizes primarily upper respiratory tissues compared to lower respiratory tissues, as detected by PCR, and is detected optimally within six days post BCV challenge.
- Infection of respiratory tissues by BCV produces little to no gross or microscopic lesions and is infrequently detected in respiratory tissues by IHC.
- BCV is optimally detected by PCR in intestinal tissues out through day 11 post BCV challenge.
- BCV infection of intestinal tissues by BCV produces gross and microscopic lesions and BCV is associated with lesions and histopathology of enteric tissues as determined by IHC.

It is to be understood that all base sizes or amino acid sizes, and all molecular weight or molecular mass values, provided to describe nucleic acids and polypeptides according to the invention are approximate within conventional measurement variations.

What is claimed is:

1. An attenuated bovine coronavirus (BCoV) that comprises a genome that encodes a spike protein that has greater than 99% identity with the amino acid sequence of SEQ ID NO: 2;

a hemagglutinin-esterase glycoprotein (HE) that has 98% or greater identity with the amino acid sequence of SEQ ID NO: 4;

an integral membrane protein (M) that has 98% or greater identity with the amino acid sequence of SEQ ID NO: 6; and a nucleocapsid protein (N) that has 98% or greater identity with the amino acid sequence of SEQ ID NO: 10.

2. The attenuated bovine coronavirus (BCoV) of claim 1 that comprises a nucleotide sequence selected from the group consisting of SEQ ID NO: 1, SEQ ID NO: 3, SEQ ID NO: 5, SEQ ID NO: 9, SEQ ID NO: 11, and any combination thereof.

3. The BCoV of claim 1 that further encodes one or more of following proteins selected from the group consisting of:

an Orf 1 ab protein that has 98% or greater identity with the amino acid sequence of SEQ ID NO: 12, an Orf 2a protein that has 98% or greater identity with the amino acid sequence of SEQ ID NO: 14, and a 4.9 kDa protein that has 98% or greater identity with the amino acid sequence of SEQ ID NO: 16.

4. The BCoV of claim 1 that further encodes a small membrane protein (E) that has 98% or greater identity with the amino acid sequence of SEQ ID NO: 8.

5. The BCoV of claim 2 that further comprises the nucleotide sequence of SEQ ID NO: 7.

6. An attenuated bovine coronavirus (BCoV) comprising the immunogenic properties of the bovine coronavirus having the ATCC deposit number PTA-121515 or is the progeny of said BCoV.

7. A vaccine comprising the BCoV of claim 1.

8. The vaccine of claim 7, wherein the attenuated BCoV is live.

9. The vaccine of claim 8 that is stored as a liquid stable vaccine.

10. The vaccine of claim 7 further comprising one or more additional viruses selected from the group consisting of a bovine viral diarrhea virus (BVDV), infectious bovine rinotracheitis virus (IBR), parainfluenza type 3 virus (PI3), bovine respiratory syncytial virus (BRSV), Rift Valley fever virus (RVFV), and any combination thereof.

11. The vaccine of claim 7 further comprising one or more bacteria selected from the group consisting of a *Pasteurella multocida*, a *Mannheimia haemolytica*, a *Histophilus somni*, a *Mycoplasma bovis*, and any combination thereof.

12. The vaccine of claim 11 wherein said one or more bacteria are live attenuated bacteria.

13. A method of vaccinating a bovine comprising administering the vaccine of claim 7.

14. The method of claim 13 wherein said administering is performed intranasally.

15. The attenuated (BCoV) of claim 1 that comprises a genome that encodes a spike protein that comprises the amino acid sequence of SEQ ID NO: 2;

a hemagglutinin-esterase glycoprotein (HE) that comprises the amino acid sequence of SEQ ID NO: 4;

an integral membrane protein (M) that comprises the amino acid sequence of SEQ ID NO: 6; and a nucleocapsid protein (N) that comprises the amino acid sequence of SEQ ID NO: 10.

16. The BCoV of claim 15 that further encodes one or more of following proteins selected from the group consisting of:

an Orf 1 ab protein that has 98% or greater identity with the amino acid sequence of SEQ ID NO: 12, an Orf 2a protein that has 98% or greater identity with the amino acid sequence of SEQ ID NO: 14, and a 4.9 kDa protein that has 98% or greater identity with the amino acid sequence of SEQ ID NO: 16.

17. A vaccine comprising the BCoV of claim 16.

18. An attenuated bovine coronavirus (BCoV) having the ATCC deposit number PTA-121515.

19. A vaccine comprising the BCoV of claim 18.

20. The vaccine of claim 19, wherein the attenuated BCoV is live.

* * * * *